(12) United States Patent
Alexandrov et al.

US009914935B2

(10) Patent No.: US 9,914,935 B2
(45) Date of Patent: Mar. 13, 2018

(54) NUCLEOTIDE SEQUENCES AND CORRESPONDING POLYPEPTIDES CONFERRING MODULATED PLANT GROWTH RATE AND BIOMASS IN PLANTS

(75) Inventors: Nickolai Alexandrov, Thousand Oaks, CA (US); Vyacheslav Brover, Simi Valley, CA (US); Peter Mascia, Thousand Oaks, CA (US); Kenneth Feldmann, Newbury Park, CA (US); Cory Christensen, Simi Valley, CA (US); Greg Nadzan, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 442 days.

(21) Appl. No.: 12/911,698

(22) Filed: Oct. 25, 2010

(65) Prior Publication Data

US 2012/0005781 A1 Jan. 5, 2012

Related U.S. Application Data

(60) Division of application No. 11/324,098, filed on Dec. 29, 2005, now Pat. No. 7,884,261, which is a continuation-in-part of application No. 11/172,740, filed on Jun. 30, 2005, now Pat. No. 7,396,979.

(60) Provisional application No. 60/583,621, filed on Jun. 30, 2004, provisional application No. 60/584,800, filed on Jun. 30, 2004, provisional application No. 60/584,829, filed on Jun. 30, 2004.

(51) Int. Cl.
*C12N 15/82* (2006.01)
*A01H 5/10* (2006.01)
*C07K 14/415* (2006.01)

(52) U.S. Cl.
CPC ........ *C12N 15/8261* (2013.01); *C07K 14/415* (2013.01); *C12N 15/827* (2013.01); *C12N 15/8291* (2013.01)

(58) Field of Classification Search
None
See application file for complete search history.

(56) References Cited

U.S. PATENT DOCUMENTS

| | | | |
|---|---|---|---|
| 7,109,033 B2 | 9/2006 | Harper et al. | |
| 7,396,979 B2 | 7/2008 | Alexandrov et al. | |
| 7,803,983 B2 | 9/2010 | Alexandrov et al. | |
| 7,868,155 B2* | 1/2011 | Lu ..................... | C12N 15/8216 435/320.1 |
| 7,884,261 B2* | 2/2011 | Alexandrov ......... | C07K 14/415 435/468 |
| 2002/0040490 A1 | 4/2002 | Gorlach et al. | |
| 2002/0053095 A1* | 5/2002 | Brown et al. .................. | 800/278 |
| 2003/0150025 A1 | 8/2003 | Chory et al. | |
| 2003/0167537 A1* | 9/2003 | Jiang .............................. | 800/290 |
| 2003/0226173 A1 | 12/2003 | Ratcliffe et al. | |
| 2004/0019927 A1 | 1/2004 | Sherman et al. | |
| 2004/0025263 A1 | 2/2004 | Laurie et al. | |
| 2004/0031072 A1 | 2/2004 | La Rosa et al. | |
| 2004/0034888 A1 | 2/2004 | Liu et al. | |
| 2004/0045051 A1* | 3/2004 | Norris et al. .................. | 800/278 |
| 2004/0054049 A1 | 3/2004 | Tavares | |
| 2004/0214272 A1 | 10/2004 | La Rosa et al. | |
| 2004/0216182 A1 | 10/2004 | Federspiel et al. | |
| 2005/0108791 A1 | 5/2005 | Edgerton | |
| 2005/0160493 A9 | 7/2005 | Ratcliffe et al. | |
| 2005/0257293 A1 | 11/2005 | Mascia | |
| 2006/0008816 A1 | 1/2006 | Lu et al. | |
| 2006/0041952 A1* | 2/2006 | Cook ............................ | 800/278 |
| 2006/0123505 A1* | 6/2006 | Kikuchi et al. | |
| 2006/0168696 A1 | 7/2006 | Feldmann et al. | |
| 2007/0044171 A1 | 2/2007 | Kovalic et al. | |
| 2009/0136925 A1 | 5/2009 | Park et al. | |
| 2009/0183270 A1 | 7/2009 | Adams et al. | |

FOREIGN PATENT DOCUMENTS

| | | |
|---|---|---|
| CN | 1474872 A | 2/2004 |
| EP | 1 033 405 A2 | 9/2000 |
| JP | 2003334089 | 11/2003 |
| JP | 2004350553 | 12/2004 |
| JP | 2005052114 | 3/2005 |
| WO | WO 97/13843 A1 | 4/1997 |
| WO | WO 01/96580 A2 | 12/2001 |
| WO | WO 02/16655 A2 | 2/2002 |
| WO | WO 02/22675 A2 | 3/2002 |
| WO | WO 02/052012 A2 | 7/2002 |
| WO | WO 2002/079403 | 10/2002 |

(Continued)

OTHER PUBLICATIONS

McElroy et al (The Plant Cell, vol. 2, 163-171, Feb. 1990).*
Guo et al (PNAS 2004 (101)25,9205-9210).*
Thornton et al (Nature structural biology, structural genomics supplement, Nov. 2000, pp. 991-994).*
Cornego et al (Plant Molecular Biology (1993) 23: 567-581).*
Hedden (Trends in Genetics, vol. 19, Issue 1, Jan. 2003, pp. 5-9).*
Okamuro et al (Proc. Natl. Acad. Sci. vol. 94, pp. 7076-7081, Jun. 1997).*
Dubouzet et al (The Plant Journal (2003) 33, 751-763).*
Friedberg (Brief. Bioinformatics (2006) 7: 225-242).*
English Translation of Japanese Office Action dated May 10, 2011.
Town CD et al., "*Arabidopsis thaliana* AP2 domain transcription factor, putative", GenBank Accession: NM_119606.2, Sep. 16, 2003 (Sep. 16, 2003).

(Continued)

*Primary Examiner* — Lee A Visone
(74) *Attorney, Agent, or Firm* — Dentons US LLP

(57) ABSTRACT

The present invention relates to isolated nucleic acid molecules and their corresponding encoded polypeptides able confer the trait of modulated plant size, vegetative growth, organ number, plant architecture, growth rate, seedling vigor, growth rate, fruit and seed yield, tillering and/or biomass in plants. The present invention further relates to the use of these nucleic acid molecules and polypeptides in making transgenic plants, plant cells, plant materials or seeds of a plant having plant size, vegetative growth, organ number, plant architecture, growth rate, seedling vigor and/or biomass that are altered with respect to wild type plants grown under similar conditions.

21 Claims, 9 Drawing Sheets

(56) References Cited

FOREIGN PATENT DOCUMENTS

| WO | WO 03/008540 A2 | 1/2003 |
|---|---|---|
| WO | WO 03/013227 A2 | 2/2003 |
| WO | WO 2004/058963 A2 | 7/2004 |
| WO | WO 2006/004955 A2 | 1/2006 |

OTHER PUBLICATIONS

Canadian Office Action issued in corresponding Canadian Application No. 2,632,947 dated Feb. 23, 2012.
Bock et al., "Taming plastids for a green future", Trends in Biotechnology, vol. 22, No. 6, Jun. 2004, pp. 311-318, XP-002385212.
Bork et al., "Go hunting in sequence databases but watch out for the traps", TIG, vol. 12, No. 10, Oct. 1996, pp. 425-427.
Buell, "Direct Submission", Database NCBI, Database Accession No. ABB47567, BT004686, At1g26946, [*Oryza sativa* (japonica cuoivar-group)], Dec. 19, 2005, 2 pages, XP0002389148.
Buell, et al., "Direct Submission", Database Accession No. AE016959, *Oryza sativa* (japonica cuoivar-group) chromosome 10, complete sequence, Dec. 19, 2005, 3 pages.
Bustos et al., "Regulation of β-glucuronidase Expression in Transgenic Tobacco Plants by an A/T Rich, cis-Acting Sequence Found Upstream of a French Bean β-Phaseolin Gene", Plant Cell, vol. 1, No. 9, Sep. 1989, pp. 839-853.
Canadian Examiner's Report, dated Jan. 14, 2011, for Canadian Application No. 2,632,961.
Canadian Examiner's Report, dated Mar. 21, 2013, for Canadian Application No. 2,632,947.
Dai et al., "The Rice YABBY1 Gene Is Involved in the Feeback Regulation of Gibberellin Metabolism", Plant Physiology, vol. 144, 2007 (Published online Mar. 16, 2007), pp. 121-133, Abstract only provided.
Database EMBL, "*Arabidopsis thaliana* clone 40252 mRNA, complete sequence," Database Accession No. AY087999, Jun. 14, 2002, 2 pages, XP-002385217.
Database EMBL, "Triticum aestivum cDNA clone:whr24p13, 3'end, single read," Database Accession No. BJ287183, Apr. 3, 2002, 2 pages, XP002388818.
Database EMBL, "Triticum aestivum cDNA clone:whr24p13, 5'end, single read," Database Accession No. BJ282051, Apr. 3, 2002, 2 pages, XP002388617.
Database EMBL, "wle1n.pk0058.d12 wle1n Triticum aestivum cDNA clone wle1n.pk0058.d12 5'end, mRNA sequence," Database Accession No. CA632062, Nov. 25, 2002, 2 pages.
Database Geneseq, "*Arabidopsis thaliana* DNA fragment SEQ ID No. 71025," Database Accession No. AAC52337, Oct. 18, 2000, 6 pages, XP-002385219.
Database Geneseq, "*Arabidopsis thaliana* protein fragment SEQ ID No. 71026," Database Accession No. AAG55399, Oct. 18, 2000, 6 pages, XP-00238220.
Database Geneseq, Accession No. ADX87410, Seq ID No. 50074, Apr. 21, 2005, 1 page.
Database UniProt "Hypothetical protein," Database Accession No. Q8LA65, Oct. 1, 2002, 2 pages, XP002385218.
Dewaele et al., "Metabolic engineering of a complex biochemical pathway: The lysine and threonine biosynthesis as an example", Phyochemistry Reviews, vol. 1, 2002, pp 125-133, XP-002385209.
Doerks et al., "Protein annotation: detective work for function prediction", TIG, vol. 14, No. 6, Jun. 1998, pp. 248-250.
Eriksson et al., "Increased gibberellin biosynthesis in transgenic trees promote growth, biomass production and xylem fiber length", Nature Biotechnology, vol. 18, Jul. 2000, pp. 784-788, XP-002956005.
Hanzawa et al., "A single amino acid converts a repressor to an activator of flowering", PNAS, vol. 102, No. 21, May 24, 2005, pp. 7748-7753.
Indian First Examination Report, dated Oct. 16, 2012, for Indian Application No. 5783/DELNP/2008.
Indian First Examination Report, dated Jun. 19, 2013, for Indian Application No. 2707/KOLNP/2008.

International Search Report dated Aug. 21, 2007, for International Application No. PCT/US2005/047423.
International Search Report, dated Nov. 10. 2006, for International Application No. PCT/US2005/023326.
International Search Report, dated Sep. 12, 2006, for International Application No. PCT/US2005/047422.
Jeanneau et al., "Manipulating PEPC levels in plants", Journal of Experimental Botany, vol. 53, No. 376, Sep. 2002, pp. 1837-1845, XP008013190.
Kasuga et al., "Improving plant drought, salt, and freezing tolerance by gene transfer of a single stress-inducible transcription factor", Nature Biotechnology, vol. 17, Mar. 1999, pp. 287-291, XP-002173128.
Kaufmann et al., "MIKC-type MADS-dornain proteins: structural modularity, protein interactions and network evolution in lard plants", Gene, vol. 347, 2005, pp. 183-198.
Kawaura et al., "Expression Profile of Two Storage-Protein Gene Families in Hexaploid Wheat Revealed by Large-Scale Analysis of Expressed Sequence Tags", Plant Physiology, vol. 139, No. 4, Dec. 2005, pp. 1870-1880.
Keskin et al., "A new, structurally nonredundant, diverse data set of protein-protein interfaces and its implications", Protein Science, vol. 13, 2004, pp. 1043-1055.
Mitra et al., "Genetics and genetic improvement of drought resistance in crop plants", Current Science, vol. 80, No. 6, Mar. 25, 2001, pp. 758-763, XP008025694.
Mundree et al., "Physioiogical and molecular insights into drought tolerance", African Journal of Biotechnology, vol. 1, No. 2, Dec. 2002, pp. 28-36, XP-002378439.
Murphy, "Engineering oil production in rapeseed and other oil crops", Tibtech, vol. 14, Jun. 1996, pp. 206-213, XP-002385211.
Nakamura et al., "*Arabidopsis thaliana* genomic DNA, chromosome 3, P1 clone: MGD6, complete sequence", GenBank Accession No. A902216, Jul. 15, 2000, 31 pages.
Nam, "The molecular genetic analysis of leaf senescence", Current Opinion in Biotechnology, vol. 8; 1997, pp. 200-207, XP-002385210.
Ngo et al., "Computational Complexity, Protein Structure Prediction, and the Levinthal Paradox", The Protein Folding Problem and Tertiary Structure, Chapter 14, 1994, pp. 492-495.
Roy et al., "Arginine decarboxyiase transgene expression and analysis of enviromental stress tolerance in transgenic rice", Plant Science, vol. 160, 2001, pp. 869-875, XP002907948.
Sasaki et al., "Ethylene-binding protein-like [*Oryza sativa* Japonica Group]", Database NCBI, GenBank Accession No. BAD38371, Aug. 25, 2004.
Seki et al., "*Arabidopsis thaliana* At5g58920 mRNA for unknown protein, complete cds, clone: RAFL21-12-P09", Accession No. AK118796, Dec. 13, 2002, 2 pages, XP-002378432.
Sinha et al., "Overexpression of the maize homeo box gene, KNOTTED-1, causes a switch from determinate to indeterminate cell fates", Gene & Development, vol. 7, 1993, pp. 787-795, Abstract only.
Sivamani et al., "Improved biomass productivity and water use efficiency under water deficit conditions in transgenic wheat constitutively expressing the barley HVA1 gene", Plant Science, vol. 155, 2000, pp. 1-9, XP-000983688.
Smith et al., "The challenges of genome sequence annotation or 'The devil is in the details'", Nature Biotechnology, vol. 15, Nov. 1997, pp. 1222-1223.
U.S. Office Action, dated Apr. 12, 2007, for U.S. Appl. No. 11/172,740.
U.S. Office Action, dated Aug. 22, 2006, for U.S. Appl. No. 11/172,740.
U.S. Office Action, dated Aug. 27, 2007, for U.S. Appl. No. 11/172,740.
U.S. Office Action, dated Dec. 12, 2007, for U.S. Appl. No. 11/324,098.
U.S. Office Action, dated Jul. 22, 2008, for U.S. Appl. No. 11/324,098.

(56) References Cited

OTHER PUBLICATIONS

U.S. Office Action, dated Mar. 18, 2009, for U.S. Appl. No. 11/317,789.
U.S. Office Action, dated Mar. 18, 2009, for U.S. Appl. No. 11/324,098.
U.S. Office Action, dated May 11, 2011, for U.S. Appl. No. 12/139,269.
U.S. Office Action, dated May 16, 2012, for U.S. Appl. No. 12/139,269.
U.S. Office Action, dated Nov. 17, 2011, for U.S. Appl. No. 12/139,269.
U.S. Office Action, dated Oct. 23, 2009, for U.S. Appl. No. 11/324,098.
U.S. Office Action, dated Oct. 9, 2008, for U.S. Appl. No. 11/241,607.
U.S. Office Action, dated Sep. 19, 2007, for U.S. Appl. No. 11/241,607.
Wang et al., "Plant responses to drought, salinity and extreme temperatures: towards genetic engineering for stress tolerance", Planta, vol. 218, 2003 (Published online Sep. 26, 2003), pp. 1-14. XP-002378470.
Wells, "Additivity of Mutational Effects in Proteins", Biochemistry, vol. 29, No. 37, Sep. 16, 1990, pp. 8509-8517.
Yamamoto et al., "The Promoter of a Pine Photosynthetic Gene Allows Expression of a β-Glucuronidase Reporter Gene in Transgenic Rice Plants in a Light-Independent but Tissue-Specific Manne", Plant and Cell Physiology, vol. 35, No. 5, 1994, pp. 773-778, Abstract only provided.
Yang et al., "Expression of the REB transcriptional activator in rice grains improves the yield of recombinant proteins whose genes are controlled by a Reb-responsive promoter", PNAS, vol. 98, No. 20, Sep. 25, 2001, pp. 11438-11443.
"*Arabidopsis thaliana* ethylene-responsive transcription factor ERF109 mRNA, complete cds," NCBI Reference Sequence: NM_199606, GENBANK, Town C.E., (May 13, 2003).
Office Action dated Jan. 21, 2015, in Chinese Patent Application No. 200580052564.9, with English translation.
Kumar, Prateek, et al., "Predicting the effects of coding non-synonymous variants on protein function using the SIFT algorithm," Nature Publishing Group, 2009, pp. 1073-1082.
Reva, Boris, et al., "Predicting the functional impact of protein mutations: application to cancer genomics," Nucleic Acids Research, 2011, vol. 39, No. 17, pp. 1-14.
Ng, Pauline C., et al., "Predicting the Effects off Amino Acid Substitutions on Protein Function," Annu. Rev. Genomics Hum. Genet. 2006, pp. 61-80.
Guerois, Raphael, "Predicting Changes in the Stability of Proteins and Protein Complexes: A Study of More Than 1000 Mutations," *J. Mol. Biol.* (2002) 320, 369-387.
NCBI Accession No. NP_195167.1, dated Nov. 4, 2005.
Guerois et al., "Predicting changes in the stability of proteins and protein complexes: A study of more than 1000 mutations", *J. Mol. Biol.*; 320; 369-287; 2002.
Kumar et al., "Predicting the effects of coding non-synonymous variants on protein function using the SIFT algorithm," www.nature.com/natureprotocols; *Nature Protocols*; vol. 4 No. 8; 2009.
Ng et al., Predicting the effects of amino acid substitutions on protein function, *Annual Review Genom. Hum. Genet*; 7:61-80; 2006.
Reva et al., Predicting the functional impact of protein mutations: application to cancer genomics,: *Nucleic Acids Research*; vol. 39. No. 17.; e118; Jul. 2011.
Rivera et al., Genomic evidence for two functionally distinct gene classes, *Proc. Natl. Acad. Sci.*; vol. 95; 6239-6244; May 1998.
Sandhya et al., "CUSP: an algorithm to distinguish structurally conserved and unconserved regions in protein domain alignments and its application in the study of large length variations," *BMC Structural Biol*; 8:28; May 2008.
Zhang et al. "Inferring protein function by domain context similarities in protein-protein interaction networks," *BMC Bioinformatics*; 10-395;2009.
Ratcliffe et al., "Regulation of Flowering in *Arabidopsis* by an FLC Homologue," *Plant Physiol.*, 12:122-132, 2001.
Scortecci et al., "Identification of a MADS-box gene, *Flowering Locus M*, that represses flowering," *The Plant Journal* 26(2):229-236, 2001.

* cited by examiner

| | | | | | | | |
|---|---|---|---|---|---|---|---|
| gi\|50941583 | M A D A A E Q H R | Q E E T A A A T T T | P Q Q M M M R R R R | A R A S S E Y L G V | R R R P W G R Y A A | 50 |
| Lead-clone679923-Taxonomy-3847 | M E N L S P L L Y K | N P - - - - - - - - | - - - - - - - R R T | S R R S T M Y L G V | R K R P W G R Y A A | 36 |
| CeresGdna:1479788 | M E N F P P L L Y R | N P - - - - - - - - | - - - - - - - K R S | S R Q S S R Y L G V | R R R P W G R Y A A | 35 |
| CeresGdna:1533259 | M E N F P P L L Y R | N P - - - - - - - - | - - - - - - - K R S | S R Q S S R Y L G V | R R R P W G R Y A A | 35 |
| Consensus | M E N F - P L L Y R | N P - - - - - - - - | - - - - - - - - R S | S R Q S S R Y L G V | R R R P W G R Y A A | 50 |
| | | | | | | | |
| gi\|50941583 | E I R N P Y T K E R | H W L G T F D T A E | E A A V A Y D L S A | S I S G A A A A R | T N F L Y P D M H H | 100 |
| Lead-clone679923-Taxonomy-3847 | E I R N P Y T K E R | H W L G T F D T A E | E A A I A Y D L S S | K C G I N - A R | T N F H Y P - - F V | 83 |
| CeresGdna:1479788 | E I R N P Y T K E R | H W L G T F D T A E | E A A V A Y D L S S | S F S G I E R A R | T N F Y Y P - - F F | 83 |
| CeresGdna:1533259 | E I R N P Y T K E R | H W L G T F D T A E | E A A V A Y D L S S | S F S G I E R A R | T N F Y Y P - - F F | 83 |
| Consensus | E I R N P Y T K E R | H W L G T F D T A E | E A A V A Y D L S S | I S - S G I E R A R | T N F Y Y P - - F F | 100 |
| | | | | | | | |
| gi\|50941583 | H H P S P P Q H A L | S P A V P P P P P P | P P S P L Y D D D | Y L S P A A A E E E | V E A G D D E S L T | 150 |
| Lead-clone679923-Taxonomy-3847 | S L P P L P M S S L | - - - - - P P P P P | P P I T P E L D P S V | E V C L E M M N A A | S Y D G D D E S L V | 128 |
| CeresGdna:1479788 | A H P S P S Q E A - | - - - - - - P P P P L | P P P - E M E K G D | Q L G - - - D G N A | - - - D D E S L V | 118 |
| CeresGdna:1533259 | A H P S P S Q E A - | - - - - - - P P P P L | P P P - E M E K G D | Q L G - - - M E D V | G T T Q D D E S I V | 123 |
| Consensus | A H P S P - Q E A L | - - - - - - P P P P - | P P P - E - E K G D | Q L G - - - M E D V | - - - G D D E S L V | 150 |
| | | | | | | | |
| gi\|50941583 | A T I L Q S F Q Y | Q Q S V P P A S S G | S M F Y Y - - - - | 175 | | | |
| Lead-clone679923-Taxonomy-3847 | A S I L Q S F - - | - - - - - S N S G | N C S F - - - - - | 144 | | | |
| CeresGdna:1479788 | L E I L L K - - - | - - - - - A G N G | K - - - - - - - - | 129 | | | |
| CeresGdna:1533259 | A S I L Q S F - - | - - - - - C Q S T | S Y S F H P Q I | 143 | | | |
| Consensus | I A S I L Q S F - - | - - - - - - A - S G | S - S F - - - - - | 178 | | | |

Fig. 2

```
gi|31580813              MGRKKLEIKRI   ENKSSRQVT   FSKRRNGLIE   KARQLSVLCD   ASVALLVVSA    50
gi|34591565              MGRKKLEIKRI   ENKSSRQVT   FSKRRNGLIE   KARQLSVLCD   ASVALLVVSA    50
gi|71834745              MGRRKVEIKL    ENKSSRQVT   FSKRRIGLIE   KARQLSVLCE   SSVAVLVVSA    50
Lead-Peptide-Clone-CeresClone-  MGRRKIEIKR   ENKSSRQVT   FSKRRNGLID   KARQLSILCE   SSVAVVVVSA  50

Consensus                MGR-KLEIKR   IENKSSRQVT  FSKRRNGLIE   KARQLSVLC-   -SVA-LVVSA    50 gi|31580813              SGKLYNFSAGI  DNLVKILDRY  GKQHA-DDLK   ALDLQSKAPK   YGSHHELLEL    99
gi|34591565              SGKLYNFSAGI  DDLVKVIDRY  GEQHADDDRK   ALDLQSEAPK   YGSHHELLEL   100
gi|71834745              SGKLYNSSSSG  DNMTNVDRY   EIQHA-GELR   SLDLAEKTRN   YLPHKELLES   99
Lead-Peptide-Clone-CeresClone-  SGKLYDSSSSG  DDISKIIDRY  ALDLEEKIQN  ALDLEEKIQN  YLPHKELLET   99

Consensus                SGKLYN-S-G   D-L-KIIDRY  --QHA-D-L-   ALDLQ-KA--   Y---H-ELLE-  100 gi|31580813              VESKLVESNS   D-VSVDSLVQ  LEDHLETALS   VTRARKTELM   LKLVDSLKEK   148
gi|34591565              VESKLVESNS   D-VSVDSLVQ  LENHLETALS   VTRARKTELL   LKLVDSLKEK   149
gi|71834745              VKSNEEPNV    DSVSVDSLIS  LEDQLETALS   ATRARKTELT   MEFVKMLQEK   149
Lead-Peptide-Clone-CeresClone-  VQSKLEEPNV  DNVSVDSLIS  LEEQLETALS   VSRARKAELM   MEYIESLKEK  149

Consensus                VESKL-E-N-   D-VSVDSL--  LED-LETALS   VTRARKTEL-M  ---VDSLKEK   150 gi|31580813              EKLLKEENQG   LASQMEKNNL  AGAEADKMEM   SPGQISDINR   PVTLRLLY--   196
gi|34591565              EKLLKEENQG   LASQMEKNNL  AGAEADKMEV   SPGQISDINC   PVTLPLLY--   197
gi|71834745              EELLREENLV   LVSQIGTTNG  R-RENNS---   -PVNSSGINP   PETLPLLKVT   194
Lead-Peptide-Clone-CeresClone-  EKLLREENQV  LASQMGKNTL  L-ATDDERGM  FPGSSSGNKI  PETLPLLNPP  198

Consensus                EKLL-EENQ-   LASQM-KNNL  AGAE-DKMEM   SPG---S-IN-  P-TLPLLY--   200 gi|31580813                                                                              196
gi|34591565                                                                              197
gi|71834745              SVIQRLS-                                                        201
Lead-Peptide-Clone-CeresClone-  SSTAEFSP                                                 206

Consensus                S------S-                                                       208
```

| | | | | |
|---|---|---|---|---|
| Lead-ME04012 | AL GRKHS------ | --EDET ARDL | KKRVRQI MEL | LG-EFPI GDY | VPA-AWI DR- | 237
| gi\|3582021 | TL GKKYGGG--- | --NGSEEVDKL | KEMLTEI QNL | MG- I -SPVWEF | PWLNMTRRF | 235
| gi\|46947673 | SVG--------- | --SGDKVDSY | KI LI LEI MDM | LGYSRSI EDF | FPLLGWVDW | 230
| gi\|25282608 | AFGKKYEG---- | --EEERKNKF | ADLATELTTL | MG--AFFVGDY | FPSFAWVDVL | 230
| gi\|34904242 | VF GDESARGL | YGDVDRGRVL | RKLFDDFFVEL | LG-QEPMGEL | PWLGWVDAL | 245
| CeresClone:703961 | AF GDDSARGL | YEEGNKEREL | RKVFNDFQEL | LG-TAPLGEL | PWLGWLDAV | 242

Consensus          A--GKKYA--G-   --E-E----L   KKI---EI MEL   LG-----P-G--   I PWLGWVD--L   250

| | | | | |
|---|---|---|---|---|
| Lead-ME04012 | NGFNARI KEV | SQGFSDLMDK | VVQEHLE--- | --------A | GNHKEDFVDI | 275
| gi\|3582021 | DGVDQRVDRI | VKAFDGFLES | VI QEHKERDG | DKDG----- | GDGAL DFVDI | 280
| gi\|46947673 | TGLRGKVAEA | AKGVDTFLEG | VLKEHLST-- | --------T | GSKYNDFVSI | 269
| gi\|25282608 | TGMDARLKRN | HGEL DAFVDH | VI DDHLL SRK | --------D | GVEQKDL VDV | 275
| gi\|34904242 | NGMEVKVQRT | FEAL DGI LEK | VI DDHRRRRR | ANGS----- | GGDHRDFVDV | 295
| CeresClone:703961 | RGMEGKI RRT | FKAL DGVLEK | VI GDHRRRRQ | AGQQTGD-- | GGDHRDFVDV | 290

Consensus          NGM----I KR-   -KAL DG-LEK   VI Q-H--RR-   -------D     G---H-DFVD-   300

| | | | | |
|---|---|---|---|---|
| Lead-ME04012 | LLSL-ESEKS | I GFQAQRDDI | KFMI LDMFL G | GTSI SSTL LE | WL MI ELI RNP | 324
| gi\|3582021 | LLQF-QRENK | NRSPVEDDTV | KSLI LDMFVA | GTDTTATALE | WAVAELI KNP | 329
| gi\|46947673 | LL EI--QEAD | AGSSMDNECI | MDMLGA | GTETSTALE | MTLAALI KNP | 317
| gi\|25282608 | LLHL-QKDSS | LGVHL NRNNL | KAVI LDMFSG | GTDTTAVTLE | WAMAELI K-P | 324
| gi\|34904242 | LLDVNETDMD | AGVQLGTI EI | KAI I LDMFAA | GTDTTTMI E | WAMAELI THP | 345
| CeresClone:703961 | LLDVSDTDDE | AGMRL STTE I | KAI I LDMFAA | GTDTSTAME | WAMAEVI THP | 340

Consensus          LL--------   AGMQL--D-I   KA-I LDMFAA   GTDTTSTALE   WAMAELI K-P   350

| | | | | |
|---|---|---|---|---|
| Lead-ME04012 | NVMKKL QDEI | RSTI RPHGSY | I KEKDVENMK | YLKAVI KEVF | RVHPPLPL I L | 374
| gi\|3582021 | RAMKRL QNEV | REVAGSKAE- | EEEDLEKMP | YLKASI KESL | RLHVPVML LV | 378
| gi\|46947673 | DAMFKL QNEV | REI GKCKSK- | SEADLVKMN | YLQAVMKESM | RLYF-APLLV | 366
| gi\|25282608 | DVMEKAQQEV | RRVVGKKAK- | VEEEDLHQLH | YLKL I KETL | RLHPVAPLLV | 373
| gi\|34904242 | DAMRNAQDEI | KAVVGI TSH- | TEDHL DRLF | YLKAVLKETL | RLHPPLPLLV | 394
| CeresClone:703961 | DSMRKLQDEI | RAAVGSGHV | TEDHI DKLH | YLKAVVKETL | RLHPPI PLLV | 390

Consensus          DAM-KL QDEI    RAVVG-K-K-   I -E-DL-K-H   YLKAVI KETL   RLHPPLFLLV   400

Fig. 4
(Continued)

```
Lead:ME04012      PRLLSEDVKV  KGYNIAAGTE  VLINAWAIQR  DPAIWGPIDAE  EFKPERHLDS   424
gi|3582021        PRESTRDINM  LGYDIASGTR  VLINAWAIAR  DPSVW-ENPE   EFLPERFLDS   427
gi|46947673       PREARQDIKF  MGYDISSGTQ  VLINAWAIAR  DPLLW-DKPE   EFRPERFLNS   415
gi|25282608       PRESTRDVMI  RGYHIPAKTR  VFINAWAIGR  DPKSW-ENAE   EFLPERFVNN   422
gi|34904242       PHEPSSDITKI LGYSIPACTR  IVINAWTIGR  DQATWGEHAE   EFIPERFLES   444
CeresClone:703961 PREPQDDAEI  LGHHVPAGTR  VVINAWAVGR  DPAAW-ERAE   EFVPERFLDG   439

Consensus         PRES--DVKI  LGY-I-AGTR  V-INAWAIGR  DPA-W-ENAE   EFLPERFLDS   450

Lead:ME04012      TLDYHGKDLN  FIPFGSGRRI  CPGINLALGL  VEVIVANLVG   RFDWRAEAGP   474
gi|3582021        SIDYKGLHFE  LLPFGAGRRG  CPGATFAVAI  DELALAKLVH   KFDFGLPNCA   477
gi|46947673       PIDYKGFHYE  FLPFGAGRRG  CPGIQFAMCL  NELVVANLVH   KFNFELPDGK   465
gi|25282608       SVDFKGQDFQ  LVPFGAGRRG  CPGIAFGISS  VEISLANLLY   WFNWELPGDL   472
gi|34904242       GLDYLGQDFV  LVPFGAGRRG  CPGVGFAVQA  MEMALASLLY   NFDWEIRVVD   494
CeresClone:703961 AVDYKGQDFQ  LIPFGAGRRG  CPGVGFAAAT  VEMALASLMY   HFDWE-PAGA   488

Consensus         S-DYKGQDF-  LIPFGAGRRG  CPGI-FAVA-  VE-ALANLVY   KFDWELP-G-   500

Lead:ME04012      NGDQ------  DLTEAFGLDV  CRKFPLTAFP  SSVI------                503
gi|3582021        RMEE------P DMSEITSGMTV HKKSPLLLLP  LPHHAAP---                509
gi|46947673       RLED------  DMTAASGITL  RKKSPLVVA   RPHV------                494
gi|25282608       TKED------L DMSEAVGITV  HMKFPLQLVA  KRHLS-----                502
gi|34904242       RRSEFGTSSL  DMSEMNGLSV  RLKYGLPLIA  ISRFP-----                529
CeresClone:703961 S---------  DMREVNGLAM  HLKSGLPLVA  KLRFR-----                515

Consensus         --E-------L DMSEA-GLTV  H-K-PLLLVA  K-H-------                537
```

Fig. 4
(Continued)

| | | | | | | |
|---|---|---|---|---|---|---|
| Lead-clone691319 | MSLLTVAHQR | -GSGEFIRFT | ESHGGGDDV | SGDCEHCCGH | DDGSGAGGSL | 49 |
| CeresGdna:1443093 | MGYSSSSTEMS | -MVSELTHVV | SGQRGSTSDW | GSYGAVGLG- | ---------- | 38 |
| CeresGdna:1452324 | MGYSSSSAEMS | AMVSALTHVV | SGHRGSTSDW | GSYGASGLG- | ---------- | 39 |
| Consensus | MGYSSSAEMS | -MVSELTHVV | SGHRGSTSDW | GSYGA-GLG- | | 50 |
| | | | | | | |
| Lead-clone691319 | GLNFNQVMQQ | GEVTMQQGSL | VSGYNRGDPE | SAFSSSSPSP | VVSSGSGQRS | 99 |
| CeresGdna:1443093 | ---------- | ----GATI-- | TSNFGQAAP- | SAYSSSTSGS- | -----GSNT- | 55 |
| CeresGdna:1452324 | ---------- | ----GATI-- | TSTIVQAAP- | SAYSSSTSGS- | -----GSNT- | 56 |
| Consensus | ---------- | ------GATI | TS----QAAP | ---------- | -----GSNT- | 100 |
| | | | | | | |
| Lead-clone691319 | TELTQQSGFP | MMSASSLSRL | SAFSSSSPSP | SSGASWVGHK | RGREEEENST | 149 |
| CeresGdna:1443093 | ---------- | --STPASPPL | SAYSSSTSGS- | --GLWIGQK | RGREEEAGAA | 89 |
| CeresGdna:1452324 | ---------- | --SPASPSL | SAYSSSTSGS- | --GSWIGQK | RGREKEAGAA | 89 |
| Consensus | ---------- | ---S-PASP-L | SAYSSTSGS- | ----GSWIGQK | RGREEEAGAA | 150 |
| | | | | | | |
| Lead-clone691319 | SHNLMQQQQL | SAPRLFRNLG | DFMVPSQGDS | SSI----VITEE | APTST----T | 191 |
| CeresGdna:1443093 | A------QLME | SLPRVYRGFN | DFR--SSQGDS | SSSGATATEE | VSASTIVIPT | 133 |
| CeresGdna:1452324 | A------QLKE | SLPRVHRGFD | DFR--SSLGDS | PSSGATATEE | VSASTLVFST | 133 |
| Consensus | A------QL-E | SLPRV-RGF- | DFR--SSQGDS | SSSGATATEE | VSAST-V--T | 200 |
| | | | | | | |
| Lead-clone691319 | TTVIAMTENP | PGG--ASLEET | GERRRKYRGV | RQRPWGKWAA | EIRDPHKAAR | 234 |
| CeresGdna:1443093 | TTTPSTTATP | SSEIASLEET | GEQRRYRGV | RQRPWGKWAA | EIRDPHKAAR | 183 |
| CeresGdna:1452324 | TALPSTTATP | SSEIASLGET | GERKRYRGV | RQRPWGKWAA | EIRDPHKAAR | 183 |
| Consensus | TTTPSTTATP | SSE--ASL-ET | GERRRYRGV | RQRPWGKWAA | EIRDPHKAAR | 250 |
| | | | | | | |
| Lead-clone691319 | VWLGTFDTEE | AAARAYDEAA | LRFRGNRAKL | NFPENVRAVP | PIQPFQAITR | 284 |
| CeresGdna:1443093 | VWLGTFDTAE | AAARAYDDAA | LRFRGNRAKL | NFPENVRLLP | AQTQNVTASQ | 233 |
| CeresGdna:1452324 | VWLGTFETAE | AAARAYDEAA | LRFRGSRAKL | NFPENARLLP | AQMQNVTASQ | 233 |
| Consensus | VWLGTFDTAE | AAARAYDEAA | LRFRGNRAKL | NFPENVRLLP | AQ-QNVTASQ | 300 |

```
Lead-clone691319   LTIVSDSTTSQ FRPLSAVAPP -----FIQQPQI-    ----QGSSD   IIRDYLQYSQ   326
CeresGdna:1443093  VPISHSQLSS  HLQLQPISSP RQQAQRPQAP       APALFQSQAD  IIRDYWEYSQ   283
CeresGdna:1452324  VPISRSQLPS  HHQLQSISSP RQQAQRPQVP       APALFQSQPD  IIRDYWEYSQ   283

Consensus          VPIS-SQLSS  H-QLQ-ISSP RQQAQRPQ-P       APALFQSQ-D  IIRDYWEYSQ   350

Lead-clone691319   LLQSDFQQQQ  IQQQQQQQRQ QQQRQRQRQ        QQQQQQQQPS  SLLQQLYYNA   376
CeresGdna:1443093  LLQSS------ ---------- ---GEFHHHQ       QQQQQQQQPS  SLLQPMFYNP   315
CeresGdna:1452324  LLQSS------ ---------- ---GDFH----      ---GQQQPPPS NLLEQMFYNP   310

Consensus          LLQSS-----  ---------- ---G-FH---Q      QQQQQQQQPS  SLLQQMFYNP   400

Lead-clone691319   QFASLQSPSM  --LSSSPSFS S-----SVSPA      PFPLFTITSAS FPLLFSSQQM   419
CeresGdna:1443093  QVASLQSSAL  TSLSSSTSVS SLAAISSGGS        PSTFSPSASS  FPLLFAGQQL   365
CeresGdna:1452324  QLASLQSSTL  SSLPSSTSGS SFAAIPSGSI       SSTLSPSASS  FPLLFAGQQL   360

Consensus          Q-ASLQSS-L  -SLSSSTS-S S-AAISSGS-       PSTLSPSASS  FPLLFAGQQL   450

Lead-clone691319   GYFQPPESRN  PAGGVPEFPL STWSDTSSQP       PPSG        453
CeresGdna:1443093  GYFRPPQNQN  PASG-SDFPV PPWTDSSHNP       SSSG        398
CeresGdna:1452324  GYFRPPENQN  PAAG-SDFPV PPWTDCSRRP       SSTG        393

Consensus          GYFRPPENQN  PA-G-SDFPV PPWTD-S--P       SSSG        484
```

NUCLEOTIDE SEQUENCES AND CORRESPONDING POLYPEPTIDES CONFERRING MODULATED PLANT GROWTH RATE AND BIOMASS IN PLANTS

CROSS-REFERENCE TO RELATED APPLICATION

This application is a Divisional of co-pending application Ser. No. 11/324,098 filed on Dec. 29, 2005, and for which priority is claimed under 35 U.S.C. § 120; which is a Continuation-in-part of application Ser. No. 11/172,740 filed on Jun. 30, 2005, the entire contents of which are hereby incorporated by reference and which claims priority to Application Nos. 60/583,621, 60/584,800, and 60/584,829 all of which were filed on Jun. 30, 2004 under 35 U.S.C. § 119.

FIELD OF THE INVENTION

The present invention relates to isolated nucleic acid molecules and their corresponding encoded polypeptides able to modulate plant growth rate, vegetative growth, organ size, architecture seedling vigor and/or biomass in plants. The present invention further relates to using the nucleic acid molecules and polypeptides to make transgenic plants, plant cells, plant materials or seeds of a plant having modulated growth rate, vegetative growth, organ number, architecture, seedling vigor and/or biomass as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from modulating the size of a plant as a whole or of any of its organs or the number of any of its organs.

Similarly, modulation of the size and stature of an entire plant, or a particular portion of a plant, or growth rate, or seedling vigor allows production of plants better suited for a particular industry. For example, reductions in the height of specific crops and tree species can be beneficial by allowing easier harvesting. Alternatively, increasing height, thickness or organ size, organ number may be beneficial by providing more biomass useful for processing into food, feed, fuels and/or chemicals (see the US Department of Energy website for Energy Efficiency and Renewable Energy). Other examples of commercially desirable traits include increasing the length of the floral stems of cut flowers, increasing or altering leaf size and shape or enhancing the size of seeds and/or fruits. Changes in organ size, organ number and biomass also result in changes in the mass of constituent molecules such as secondary products and convert the plants into factories for these compounds.

Availability and maintenance of a reproducible stream of food and animal feed to feed animals and people has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed, chemicals and energy for the population.

Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, great progress has been made in using molecular genetics approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (Zhang et al. (2004) *Plant Physiol.* 135:615).

Despite this progress, today there continues to be a great need for generally applicable processes that improve forest or agricultural plant growth to suit particular needs depending on specific environmental conditions. To this end, the present invention is directed to advantageously manipulating plant size, organ number, plant growth rate, plant architecture and/or biomass to maximize the benefits of various crops depending on the benefit sought and the particular environment in which the crop must grow, characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having life cycles, particularly plant size, vegetative growth, plant growth rate, organ number, plant architecture and/or biomass, that are altered with respect to wild-type plants grown under similar or identical conditions.

Unless otherwise defined, all technical and scientific terms used herein have the same meaning as commonly understood by one of ordinary skill in the art to which this invention belongs.

BRIEF DESCRIPTION OF THE FIGURES

Figure 1:
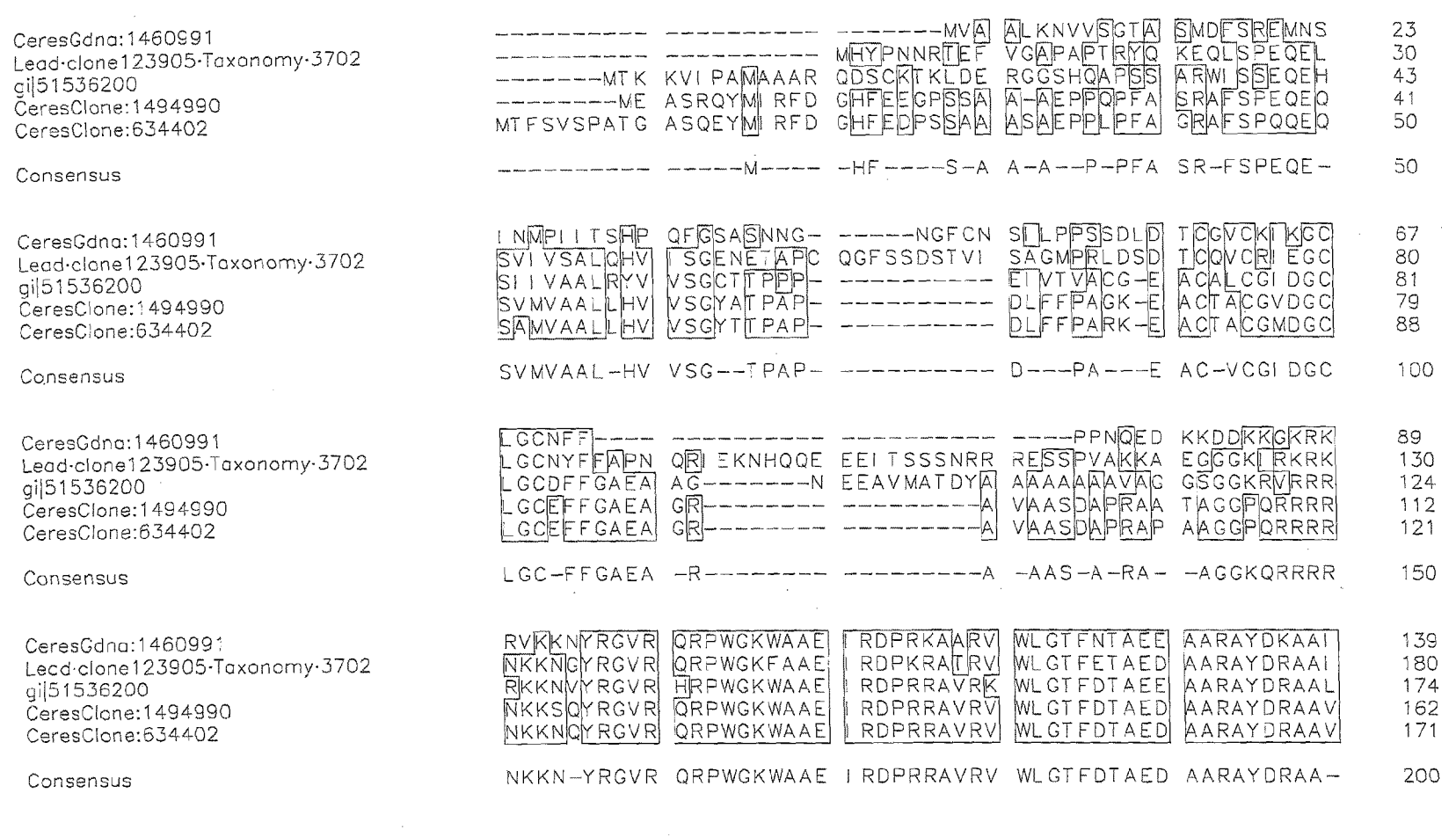
Figure 1:
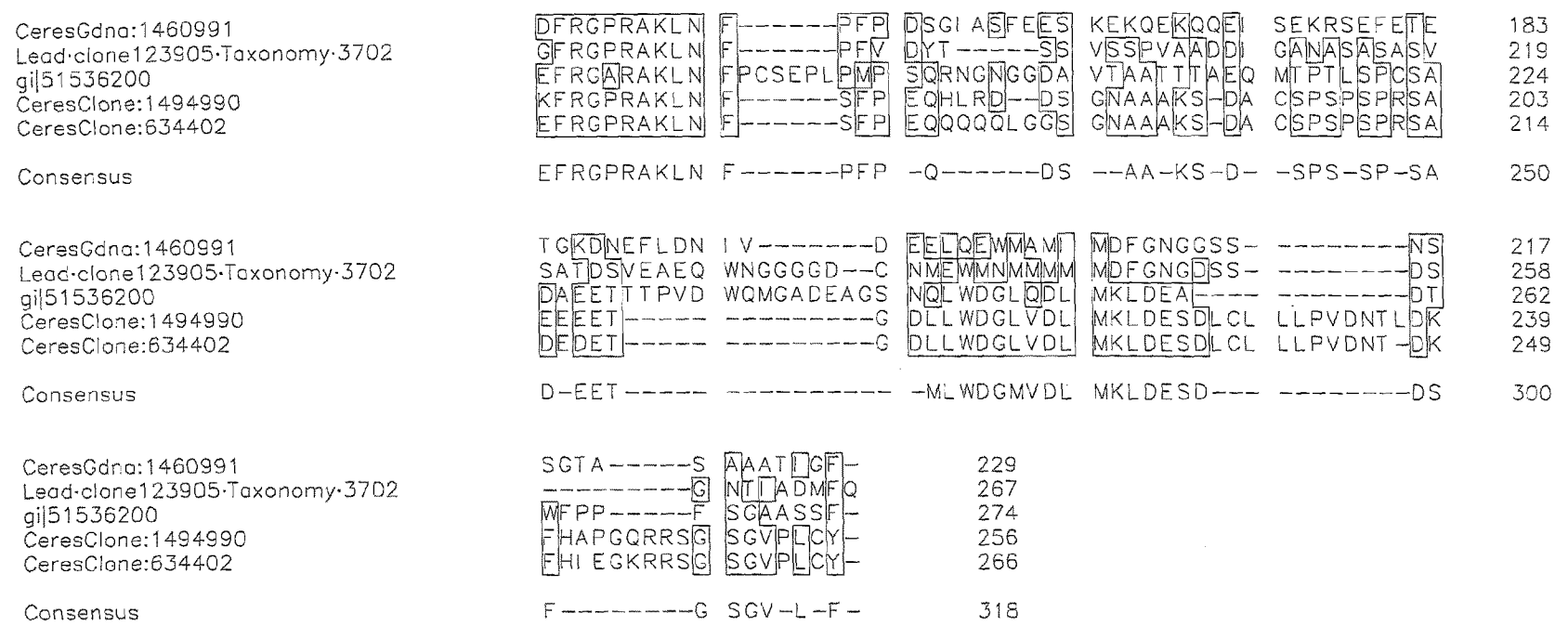

FIG. 1. Amino acid sequence alignment of homologues of Lead 29 (ME04717), SEQ ID NO. 93; Ceres Gdna 1460991, SEQ ID NO: 94; Lead clone 123905, SEQ ID NO: 93; giI51536200, SEQ ID NO: 97; CeresClone 1494990, SEQ ID NO: 95; CeresClone 634402, SEQ ID NO: 96. Conserved regions are enclosed in a box. A consensus sequence, comprised of SEQ ID NOs. 122-134, is shown below the alignment.

FIG. 2. Amino acid sequence alignment of homologues of Lead 36 (ME03195), SEQ ID NO. 99: giI50941583, SEQ ID NO: 102; Lead clone 679923, SEQ ID NO: 99; Ceres Gdna 14719788, SEQ. ID NO: 100; Ceres Gdna 1533259, SEQ ID NO: 101. Conserved regions are enclosed in a box. A consensus sequence, comprised of SEQ ID NOs. 135-144, is shown below the alignment.

FIG. 3. Amino acid sequence alignment of homologues of Lead 15 (ME04077), SEQ ID NO. 81; gi|31580813, SEQ ID NO: 83; gi|134591565, SEQ ID NO: 84; gi|71834745, SEQ ID NO: 82. Conserved regions are enclosed in a box. A consensus sequence, comprised of SEQ ID NOs. 145-158, is shown below the alignment.

FIG. 4. Amino acid sequence alignment of homologues of Lead ME04012, SEQ ID NO. 110; ME04012, SEQ ID NO: 110; gi|3582021, SEQ ID NO: 115; gi|46947673, SEQ, ID NO: 116; gi|25282608, SEQ ID NO: 121 gi|34904242, SEQ ID NO: 118. Conserved regions are enclosed in a box. A consensus sequence, compromised of SEQ ID NOs. 159-198, is shown below the alignment.

FIG. 5. Amino acid sequence alignment of homologues of Lead Clone 691319, SEQ ID NO. 104; Lead clone 691319, SEQ ID NO: 104; Ceres Gdna 1443093, SEQ ID NO: 105; and Ceres Gdna 1452324, SEQ ID NO: 106. Conserved regions are enclosed in a box. A consensus sequence, comprised of SEQ ID Nos. 199-222, is shown below the alignment.

DETAILED DESCRIPTION OF THE INVENTION

1. The Invention

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of Leads 15, 28, 29, 36, ME04012 and Clone 691319, corresponding to SEQ ID Nos. 80, 90, 92, 98, 109, and 103, respectively, (b) a nucleotide sequence that is complementary to any one of the nucleotide sequences according to (a), (c) a nucleotide sequence according to any one of SEQ ID Nos. 80, 90, 92, 98, 109, and 103, (d) a nucleotide sequence that is in reverse order of any one of the nucleotide sequences according to (c) when read in the 5' to 3' direction, (e) a nucleotide sequence able to interfere with any one of the nucleotide sequences according to (a), (f) a nucleotide sequence able to form a hybridized nucleic acid duplex with the nucleic acid according to any one of paragraphs (a)-(e) at a temperature from about 40° C. to about 48° C. below a melting temperature of the hybridized nucleic acid duplex, and (g) a nucleotide sequence encoding any one of amino acid sequences of Leads 15, 28, 29, 36, ME04012 and Clone 691319 corresponding to SEQ ID Nos. 81, 91, 93, 99, 110, and 104, respectively.

Additional embodiments of the present invention include those polypeptide and nucleic acid molecule sequences disclosed in SEQ ID Nos. 80, 81, 90, 91, 92, 93, 98, 99, 109, 110, 103 and 104.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of Leads 15, 28, 29, 36, ME04012 and Clone 691319, corresponding to SEQ ID Nos. 81, 91, 93, 99, 110, and 104, respectively.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth, increased organ number and/or increased biomass (sometimes hereinafter collectively referred to as increased biomass), lethality, sterility or ornamental characteristics as compared to a wild-type plant cultivated under identical conditions. Furthermore, the transgenic plant may comprise a first isolated nucleic acid molecule of the present invention, which encodes a protein involved in modulating growth and phenotype characteristics, and a second isolated nucleic acid molecule which encodes a promoter capable of driving expression in plants, wherein the growth and phenotype modulating component and the promoter are operably linked. More preferably, the first isolated nucleic acid may be mis-expressed in the transgenic plant of the present invention, and the transgenic plant exhibits modulated characteristics as compared to a progenitor plant devoid of the gene, when the transgenic plant and the progenitor plant are cultivated under identical environmental conditions. In another embodiment of the present invention the modulated growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the modulated growth and phenotype characteristics as compared to a wild-type plant cultivated under identical conditions.

The polynucleotide conferring increased biomass or vigor may be mis-expressed in the transgenic plant of the present invention, and the transgenic plant exhibits an increased biomass or vigor as compared to a progenitor plant devoid of the polynucleotide, when the transgenic plant and the progenitor plant are cultivated under identical environmental conditions. In another embodiment of the present invention increased biomass or vigor phenotype may be due to the inactivation of a particular sequence, using for example an interfering RNA.

Another embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased biomass or vigor as compared to a wild-type plant cultivated under identical conditions.

Another embodiment of the present invention includes methods of enhancing biomass or vigor in plants. More particularly, these methods comprise transforming a plant with an isolated nucleic acid molecule according to the present invention. Preferably, the method is a method of enhancing biomass or vigor in the transformed plant, whereby the plant is transformed with a nucleic acid molecule encoding the polypeptide of the present invention.

Figure 4:
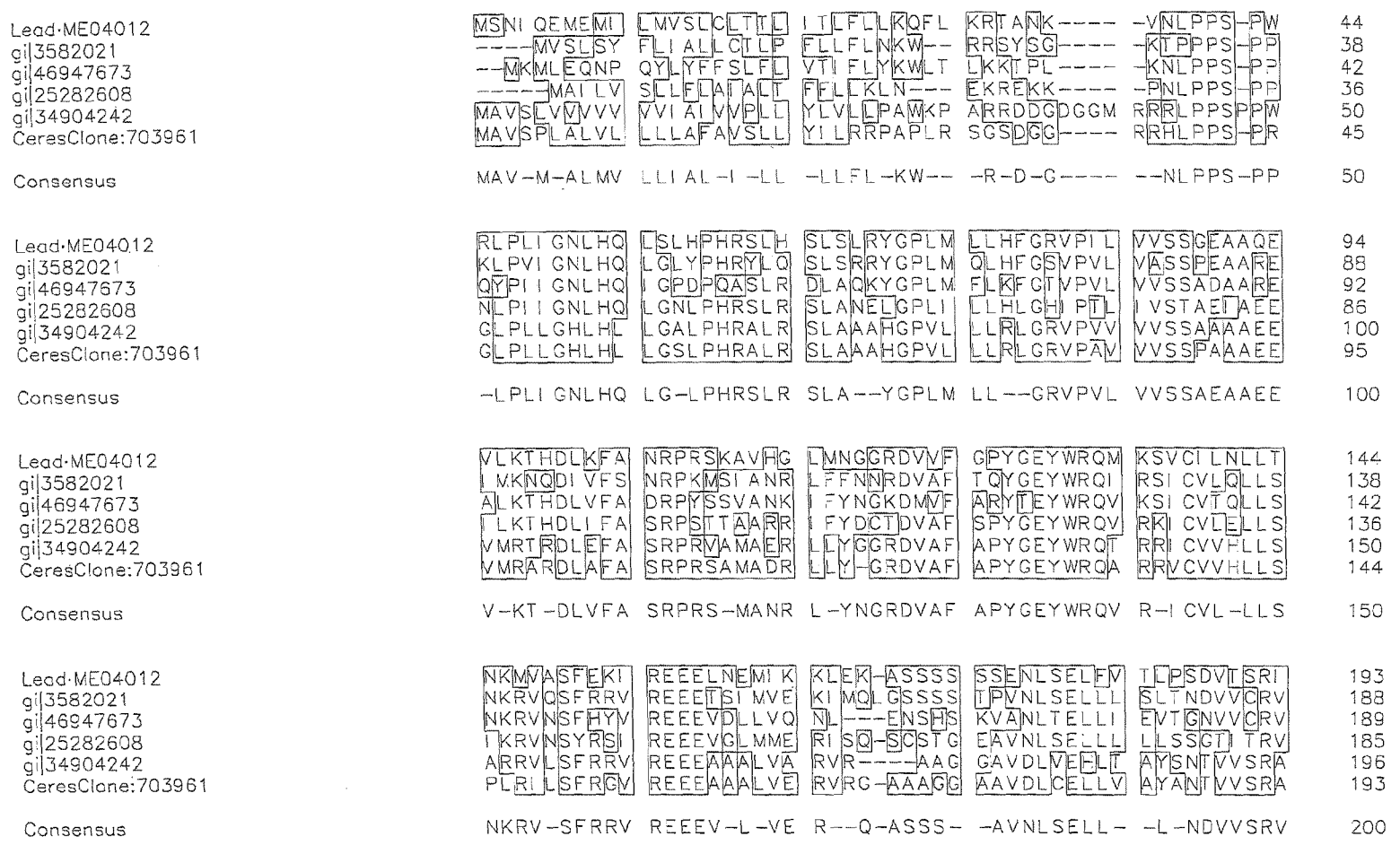

Polypeptides of the present invention include consensus sequences. The consensus sequences are those as shown in FIGS. 1-5.

2. Definitions

The following terms are utilized throughout this application:

Biomass: As used herein, "biomass" refers to useful biological material including a product of interest, which material is to be collected and is intended for further processing to isolate or concentrate the product of interest. "Biomass" may comprise the fruit or parts of it or seeds, leaves, or stems or roots where these are the parts of the plant that are of particular interest for the industrial purpose. "Biomass", as it refers to plant material, includes any structure or structures of a plant that contain or represent the product of interest.

Transformation: Examples of means by which this can be accomplished are described below and include *Agrobacterium*-mediated transformation (of dicots (Needleman and Wunsch (1970) *J. Mol. Biol.* 48:443; Pearson and Lipman (1988) *Proc. Natl. Acad. Sci.* (*USA*) 85: 2444), of monocots (Yamauchi et al. (1996) *Plant Mol Biol.* 30:321-9; Xu et al. (1995) *Plant Mol. Biol.* 27:237; Yamamoto et al. (1991) *Plant Cell* 3:371), and biolistic methods (P. Tijessen, "Hybridization with Nucleic Acid Probes" In Laboratory Techniques in Biochemistry and Molecular Biology, P. C. vand der Vliet, ed., c. 1993 by Elsevier, Amsterdam), electroporation, in planta techniques, and the like. Such a plant containing the exogenous nucleic acid is referred to here as a $T_0$ for the primary transgenic plant and $T_1$ for the first generation.

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functionally comparable proteins share some sequence similarity or at least one biochemical. Within this definition, analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. MoL Biol.* 48:443 (1970), by the search for similarity method of Pearson and Lipman *Proc. Nall. Acad. Sci.* (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

In case of the functional homolog searches, to ensure a subject sequence having the same function as the query sequence, the alignment has to be along at least 80% of the length of the query sequence so that the majority of the query sequence is covered by the subject sequence. To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Seedling vigor: As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship between hybridization conditions and $T_m$ (in ° C.) is expressed in the mathematical equation:

$$T_m = 81.5 - 16.6(\log_{10}[\text{Na}^+]) + 0.41(\%G+C) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log \{[\text{Na}^+]/(1+0.7[\text{Na}^+])\} + 0.41(\%G+C) - 500/L - 0.63(\%\text{formamide}) \quad (II)$$

where L represents the number of nucleotides in the probe in the hybrid (21). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol,* 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

3. Important Characteristics of the Polynuceotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit modulated biomass, growth rate, or seedling vigor as compared to wild-type plants, as evidenced by the results of various experiments disclosed below. This trait can be used to exploit or maximize plant products. For example, the nucleic acid molecules and polypeptides of the present invention are used to increase the expression of genes that cause the plant to have modulated biomass, growth rate or seedling vigor.

Because the disclosed sequences and methods increase vegetative growth, and growth rate, the disclosed methods can be used to enhance biomass production. For example, plants that grow vegetatively have an increase biomass production, compared to a plant of the same species that is not genetically modified for substantial vegetative growth. Examples of increases in biomass production include increases of at least 5%, at least 20%, or even at least 50%, when compared to an amount of biomass production by a plant of the same species not growing vegetatively.

The sequence of Lead 36 of the present invention and its functional homologs in particular provide transformed plants with enhanced yield, including fruit yield and yield per acre, somewhat early maturity, and a more compact stature (20%, 30%, 40% or 60% more compact) with shorter stems, but without proportionally reduced biomass. In tomatoes, this results in plants with increased fruit yield on more compact plants. In rice, this results in plants with an increase number of tillers. The sequence of Lead 29 of the present invention and its functional homologs in particular provide transformed plants with enhanced yield, including fruit yield and yield per acre, somewhat early maturity, and a more compact stature (20%, 30%, 40% or 60% more compact) with shorter stems. In tomatoes, this results in plants with increased fruit yield on more compact plants. In rice, this results in plants with an increase number of tillers. The sequences of Leads 15 and 28 of the present invention and their functional homologs in particular provide transformed plants with enhanced yield, including fruit yield and yield per acre. In tomatoes, this results in plants with increased fruit yield on more compact plants. In rice, this results in plants with an increase number of tillers.

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase (Xu et al. (1995) *Plant Mol. Biol.* 27:237) where the floral organs are produced. If the appropriate environmental and developmental signals the plant switches to floral, or reproductive, growth are disrupted, the plant will not be able to enter reproductive growth, therefore maintaining vegetative growth.

Seed or seedling vigor is an important characteristic that can greatly influence successful growth of a plant, such as crop plants. Adverse environmental conditions, such as dry, wet, cold or hot conditions, can affect a plant growth cycle, and the vigor of seeds (i.e. vitality and strength under such conditions can differentiate between successful and failed crop growth). Seedling vigor has often been defined to comprise the seed properties that determine "the potential for rapid, uniform emergence and development of normal seedlings under a wide range of field conditions". Hence, it would be advantageous to develop plant seeds with increased vigor.

For example, increased seedling vigor would be advantageous for cereal plants such as rice, maize, wheat, etc. production. For these crops, growth can often be slowed or stopped by cool environmental temperatures during the planting season. In addition, rapid emergence and tillering of rice would permit growers to initiate earlier flood irrigation which can save water and suppress weak growth. Genes associated with increased seed vigor and/or cold tolerance in rice, have therefore been sought for producing improve rice varieties. See e.g., Pinson, S., "Molecular Mapping of Seedling Vigor QTLs in Tropical Rice", USDA Agricultural Research Service, Dec. 16, 2000.

Seedling vigor has been measured by different tests and assays, including most typically a cold tolerance test and an accelerated aging test.

Some of the nucleotide sequences of the invention code for basic-helix-loop (bHCH) transcription factors. It is known that transcription factors often control the expression of multiple genes in a pathway. The basic/helix-loop-helix (BHLH) proteins are a superfamily of transcription factors that bind as dimers to specific DNA target sites. The bHLH transcription factors have been well characterized in non-plant eukaryotes and have been identified as important regulatory components in diverse biological processes. Many different functions have been identified for those proteins in animals, including the control of cell proliferation and transcription often involves homo- or hetero-dimerization. Members of the R/B basic helix-loop-helix (bHLH) family of plant transcription factors are involved in a variety of growth and differentiation processes.

A basic-helix-loop-helix (bHLH) is a protein structural motif that characterizes a family of transcription factors. The motif is characterized by two α helices connected by a loop. Transcription factors of this type are typically dimeric, each with one helix containing basic amino acid residues that facilitate DNA binding. One helix is typically smaller and due to the flexibility of the loop allows dimerization by folding and packing against another helix. The larger helix typically contains the DNA binding regions. bHLH proteins typically bind to a consensus sequence called an E-box, CANNTG. The canonical E-box is CACGTG, however some bHLH transcription factors bind to different sequences, which are often similar to the E-box. bHLH transcription factors are often important in development or cell activity.

4. The Polynucleotides/Polypeptides of the Invention

The polynucleotides of the present invention and the proteins expressed via translation of these polynucleotides are set forth in the Sequence Listing, specifically SEQ ID NOS. 80, 81, 90, 91, 92, 93, 98, 99, 109, 110, 103, and 104. The Sequence Listing also consists of functionally comparable proteins. Polypeptides comprised of a sequence within and defined by one of the consensus sequences can be utilized for the purposes of the invention, namely to make transgenic plants with modulated biomass, growth rate and/or seedling vigor.

5. Use of the Polypeptides to Make Transgenic Plants

To use the sequences of the present invention or a combination of them or parts and/or mutants and/or fusions andior variants of them, recombinant DNA constructs are prepared that comprise the polynucleotide sequences of the invention inserted into a vector and that are suitable for transformation of plant cells. The construct can be made using standard recombinant DNA techniques (see, Sambrook et al., Molecular Cloning: A Laboratory Manual, Second Edition, Cold Spring Harbor Laboratory Press, 1989, New York.) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lambda phage vectors, T-DNA fusion vectors and plasmid vectors (see, Shizuya et al. (1992) *Proc. Natl. Acad. Sci. USA*, 89: 8794-8797; Hamilton et al. (1996) *Proc. Natl. Acad. Sci. USA*, 93: 9975-9979; Burke et al. (1987) *Science*, 236:806-812; Sternberg N. et al. (1990) *Proc Natl Acad Sci USA.*, 87:103-7; Bradshaw et al. (1995) *Nucl Acids Res,* 23: 4850-4856; Frischauf et al. (1983) *J. Mol Biol,* 170: 827-842; Huynh et al., Glover N M (ed) DNA Cloning: A practical Approach, Vol. 1 Oxford: IRL Press (1985); Walden et al. (1990) *Mol Cell Biol* 1: 175-194).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell* 1:977-984 (1989).

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell,* 1:855-866 (1989); Bustos, et al., *Plant Cell,* 1:839-854 (1989); Green, et al., *EMBO J.* 7, 4035-4044 (1988); Meier, et al., *Plant Cell,* 3, 309-316 (1991); and Zhang, et al., *Plant Physiology* 110: 1069-1079 (1996).

Examples of various classes of promoters are described below. Some of the promoters indicated below are described in more detail in U.S. patent application Ser. Nos. 60/505,689 (expired); 60/518,075 (expired); 60/544,771 (expired); 60/558,869 (expired); 60/583,691 (expired); 60/619,181 (expired); 60/637,140 (expired); Ser No. 10/950,321 (U.S. Pat. No, 7,173,121); Ser No. 10/957,569 (issued as U.S. Pat. No. 7,402,667); Ser No. 11/058,689 (abandoned); Ser No. 11/172,703 (issued as U.S. Pat. No. 7,173,121); Ser No. 11/208,308 (abandoned); and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the genes of the present invention. Nucleotide sequences of such promoters are set forth in SEQ ID NOS: 1-79. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), and PT0633 (SEQ ID NO: 7). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 52), YP0275 (SEQ ID NO: 63), PT0625 (SEQ ID NO: 6), PT0660 (SEQ ID NO: 9), PT0683 (SEQ ID NO: 14), and PT0758 (SEQ ID NO: 22). Other root-preferential promoters include the PT0613 (SEQ ID NO: 5), PT0672 (SEQ ID NO: 11), PT0688 (SEQ ID NO: 15), and PT0837 (SEQ ID NO: 24), which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA* 86:7890-7894 (1989)), root cell specific promoters reported by Conkling et al., *Plant Physiol.* 93:1203-1211 (1990), and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al. (1989) *Plant Cell* 1(9):839-853), the soybean trypsin inhibitor promoter (Riggs et al. (1989) *Plant Cell* 1(6):609-621), the ACP promoter (Baerson et al. (1993) *Plant Mol Biol*, 22(2):255-267), the stearoyl-ACP desaturase gene (Slocombe et al. (1994) *Plant Physiol* 104(4):167-176), the soybean α' subunit of β-conglycinin promoter (Chen et al. (1986) *Proc Natl Acad Sci USA* 83:8560-8564), the oleosin promoter (Hong et al. (1997) *Plant Mol Biol* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.* 13:5829-5842), the beta-amylase gene promoter, and the barley hordein gene promoter. Other maturing endosperm promoters include the YP0092 (SEQ ID NO: 38), PT0676 (SEQ ID NO: 12), and PT0708 (SEQ ID NO: 17).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 30), YP0111 (SEQ ID NO: 46), YP0092 (SEQ ID NO: 38), YP0103 (SEQ ID NO: 43), YP0028 (SEQ ID NO: 33), YP0121 (SEQ ID NO: 51), YP0008 (SEQ ID NO: 31), YP0039 (SEQ ID NO: 34), YP0115 (SEQ ID NO: 47), YP0119 (SEQ ID NO: 49), YP0120 (SEQ ID NO: 50) and YP0374 (SEQ ID NO: 68).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039 (SEQ ID NO: 34), YP0101 (SEQ ID NO: 41), YP0102 (SEQ ID NO: 42), YP0110 (SEQ ID NO: 45), YP0117 (SEQ ID NO: 48), YP0119 (SEQ ID NO: 49), YP0137 (SEQ ID NO: 53), DME, YP0285 (SEQ ID NO: 64), and YP0212 (SEQ ID NO: 60). Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 40), YP0107 (SEQ ID NO: 44), YP0088 (SEQ ID NO: 37), YP0143 (SEQ ID NO: 54), YP0156 (SEQ ID NO: 56), PT0650 (SEQ ID NO: 8), PT0695 (SEQ ID NO: 16), PT0723 (SEQ ID NO: 19), PT0838 (SEQ ID NO: 25), PT0879 (SEQ ID NO: 28) and PT0740 (SEQ ID NO: 20).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1,5-bisphosphate carboxylase (RbcS) promoters such as the RbcS promoter from eastern larch (9*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad. Sci USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 3), PT0668 (SEQ ID NO: 2), PT0886 (SEQ ID NO: 29), PR0924 (SEQ ID NO: 78), YP0144 (SEQ ID NO: 55), YP0380 (SEQ ID NO: 70) and PT0585 (SEQ ID NO: 4).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inedible promoters are YP0380 (SEQ ID NO: 70), PT0848 (SEQ ID NO: 26), YP0381 (SEQ ID NO: 71), YP0337 (SEQ ID NO: 66), YP0337 (SEQ ID NO: 66), PT0633 (SEQ ID NO: 7), YP0374 (SEQ ID NO: 68), PT0710 (SEQ ID NO: 18), YP0356 (SEQ ID NO: 67), YP0385 (SEQ ID NO: 73), YP0396 (SEQ ID NO: 74), YP0384 (SEQ ID NO: 72), YP0384 (SEQ ID NO: 72), PT0688 (SEQ ID NO: 15), YP0286 (SEQ ID NO: 65), YP0377 (SEQ ID NO: 69), and PD1367 (SEQ ID NO: 79). Examples of promoters induced by nitrogen are PT0863 (SEQ ID NO: 27), PT0829 (SEQ ID NO: 23), PT0665 (SEQ ID NO: 10) and PT0886 (SEQ ID NO: 29). An example of a shade inducible promoter is PR0924 (SEQ ID NO: 78).

Other Promoters: Other classes of promoters include, but are not limited to, leaf-preferential, stem/shoot-preferential, callus-preferential, guard cell-preferential, such as PT0678 (SEQ ID NO: 13), and senescence-preferential promoters. Promoters designated YP0086 (SEQ ID NO: 36), YP0188 (SEQ ID NO: 58), YP0263 (SEQ ID NO: 62), PT0758 (SEQ ID NO: 22), PT0743 (SEQ ID NO: 21), PT0829 (SEQ ID NO: 23), YP0119 (SEQ ID NO: 49), and YP0096 (SEQ ID NO: 39), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a biomass or vigor-modulating polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a biomass-modulating polypeptide. A nucleic acid that decreases the level of a transcription or translation product of a gene encoding a biomass-modulating polypeptide is transcribed into an antisense nucleic acid similar or identical to the sense coding sequence of the biomass- or growth rate-modulating polypeptide. Alternatively, the transcription product of an isolated nucleic acid can be similar or identical to the sense coding sequence of a biomass growth rate-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in Tetrahymena thermophila, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., Weising et al. (1988) *Ann. Rev. Genet.*, 22:421 and Christou (1995) *Euphytica*, 85:13-27).

A variety of techniques known in the art are available for the introduction of DNA into a plant host cell. These techniques include transformation of plant cells by injection (Newell (2000)), microinjection (Griesbach (1987) *Plant Sci*. 50:69-77), electroporation of DNA (Fromm et al. (1985) *Proc. Natl. Acad. Sci. USA* 82:5824), PEG (Paszkowski et al. (1984) *EMBO J.* 3:2717), use of biolistics (Klein et al. (1987) *Nature* 327:773), fusion of cells or protoplasts (Willmilzer, L. (1993) *Transgenic Plants. In: Iotechnology*, A Multi-Volume Comprehensive treatise (H. J. Rehm, G. Reed, A. Püler, P. Stadler, eds., Vol. 2, 627-659, VCH Weinheim-New York-Basel-Cambridge), and via T-DNA using *Agrobacterium tumefaciens* (*Crit. Rev. Plant. Sci*. 4:1-46; Fromm et al. (1990) *Biotechnology* 8:833-844) or *Agrobacterium rhizogenes* (Cho et al. (2000) *Planta* 210: 195-204) or other bacterial hosts (Brootghaerts et al. (2005) *Nature* 433:629-633), for example.

In addition, a number of non-stable transformation methods that are well known to those skilled in the art may be desirable for the present invention. Such methods include, but are not limited to, transient expression (Lincoln et al. (1998) *Plant Mol. Biol. Rep.* 16:1-4) and viral transfection (Lacomme et al. (2001), "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The nucleic acid molecules of the present invention may be used to confer the trait of an altered flowering time.

The nucleic acid molecules of the present invention encode appropriate proteins from any organism, but are preferably found in plants, fungi, bacteria or animals.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry. Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, sugarcane, mimosa, Servicea lespedera, corn, wheat, rice, rye, barley, sorghum and grasses such as switch grass, giant reed, Bermuda grass, Johnson grasses or turf grass, millet, hemp, bananas, poplars, eucalyptus trees and conifers. Of interest are plates grown for energy production, so called energy crops, such as broadleaf plants like alfalfa, hemp, Jerusalem artichoke and grasses such as sorgum, switchgrass, Johnson grass and the likes.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of Leads 15, 28, 29, 36, ME04012 and Clone 691319, SEQ ID Nos. 80, 90, 92, 98, 109, and 103, respectively, due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and their Corresponding Nucleotide Sequences The nucleic acid molecules, and nucleotide sequences thereof, of the present invention were identified by use of a variety of screens that are predictive of nucleotide sequences that provide plants with altered size, vegetative growth, growth rate, organ number, plant architecture and/or biomass. One or more of the following screens were, therefore, utilized to identify the nucleotide (and amino acid) sequences of the present invention.

The present invention is further exemplified by the following examples. The examples are not intended to in any way limit the scope of the present application and its uses.

6. Experiments Confirming the Usefulness of the Polynucleotides and Polypeptides of the Invention General Protocols

*Agrobacterium*-Mediated Transformation of *Arabidopsis*

Wild-type *Arabidopsis thaliana* Wassilewskija (WS) plants are transformed with Ti plasmids containing clones in the sense orientation relative to the 35S promoter. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L SunshineMix #5 soil (Sun Gro Horticulture, Ltd., Bellevue, Wash.) is mixed with 16 L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMOCOTE® 14-14-14 (Hummert, Earth City, Mo.) and 1 Tbsp Peters fertilizer 20-20-20 (J. R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C.

Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 μl 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

High-throughput Phenotypic Screening of Misexpression Mutants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

Screening: Screening is routinely performed at four stages: Seedling, Rosette, Flowering, and Senescence.

Seedling—the time after the cotyledons have emerged, but before the $3^{rd}$ true leaf begins to form.

Rosette—the time from the emergence of the $3^{rd}$ true leaf through just before the primary bolt begins to elongate.

Flowering—the time from the emergence of the primary bolt to the onset of senescence (with the exception of noting the flowering time itself, most observations should be made at the stage where approximately 50% of the flowers have opened).

Senescence—the time following the onset of senescence (with the exception of "delayed senescence", most observations should be made after the plant has completely dried). Seeds are then collected.

Screens: Screening for increased size, vegetative growth and/or biomass is performed by taking measurements, specifically $T_2$ measurements were taken as follows:

Days to Bolt=number of days between sowing of seed and emergence of first inflorescence.

Rosette Leaf Number at Bolt=number of rosette leaves present at time of emergence of first inflorescence.

Rosette Area=area of rosette at time of initial inflorescence emergence, using formula $((L \times W)*3.14)/4$.

Height=length of longest inflorescence from base to apex. This measurement was taken at the termination of flowering/onset of senescence.

Primary Inflorescence Thickness=diameter of primary inflorescence 2.5 cm up from base. This measurement was taken at the termination of flowering/onset of senescence.

Inflorescence Number=total number of unique inflorescences. This measurement was taken at the termination of flowering/onset of senescence.

PCR was used to amplify the cDNA insert in one randomly chosen $T_2$ plant. This PCR product was then sequenced to confirm the sequence in the plants.

Results:

Plants transformed with the genes of interest were screened as described above for modulated growth and phenotype characteristics. The observations include those with respect to the entire plant, as well as parts of the plant, such as the roots and leaves. The observations for transformants with each polynucleotide sequence are noted in the Sequence listing for each of the tested nucleotide sequences and the corresponding encoded polypeptide. The modulated characteristics (i.e. observed phenotypes) are noted by an entry in the "miscellaneous features" field for each respective sequence. The "Phenotype" noted in the Sequence Listing for each relevant sequence further includes a statement of the useful utility of that sequence based on the observations.

The observations made for the various transformants can be categorized, depending upon the relevant plant tissue for the observation and the consequent utility/usefulness of the nucleotide sequence/polypeptide used to make that transformant. Table 1 correlates the shorthand notes in the sequence listing to the observations noted for each tranformant (the "description" column), the tissue of the observation, the phenotype thereby associated with the transformant, and the consequent utility/usefulness of the inserted nucleotide sequence and encoded polypeptide (the "translation" column).

For some of the polynucleotides/polypeptides of the invention, the sequence listing further includes (in a "miscellaneous feature" section) an indication of important identified dominant(s) and the corresponding function of the domain or identified by comparison to the publicly available pfam database.

TABLE 1

| TISSUE | PHENOTYPE QUALIFIER | PHENOTYPE | DESCRIPTION | TRANSLATION |
| --- | --- | --- | --- | --- |
| WHOLE PLANT | Senescence Time | Early Senescence | the plant senesces significantly early (note the approximate number of days early it started to senesce in the comments) | Useful for accelerating crop development and harvest |
| INFLORESCENCE | Flowering Time | Early Flowering | the plant flowers significantly early (note the approximate number of days early it flowered in the comments) | Useful for accelerating flowering time |
| INFLORESCENCE | Flowering Time | Late Flowering | the plant flowers significantly late (note the approximate number of days late it flowered in the comments) | Useful for delaying flowering time |
| INFLORESCENCE | Flowering Time | Dtb | days to bolt | Useful for delaying flowering time |

TABLE 1-continued

| TISSUE | PHENOTYPE QUALIFIER | PHENOTYPE | DESCRIPTION | TRANSLATION |
|---|---|---|---|---|
| WHOLE PLANT | Senescence Time | Late Senescence | the plant senesces significantly late (note the approximate number of days late it started to senesce in the comments) | Useful for delaying senescence |
| COTYLEDONS | Silver | Silver | cotyledons have a gray/silver colored surface; This phenotype is often accompanied by a small size mutation, but not always | Useful for drought or stress tolerance |
| WHOLE SEEDLING | Dark Green | Dark Green | plant is visibly darker green | Useful for increasing chlorophyll and photosynthetic capacity |
| WHOLE PLANT | Color | Dark Green | the plant is abnormally dark green | Useful for increasing chlorophyll and photosynthetic capacity |
| WHOLE SEEDLING | High Anthocyanin | High Anthocyanin | the plant is purple in color | Useful for increasing increasing anthocyanin content |
| WHOLE PLANT | Color | High Anthocyanin | the plant is purple in color | Useful for increasing increasing anthocyanin content |
| ROOT | No Growth in Soil | No Growth in Soil | roots grow along the soil surface instead of into the soil | Useful for increasing root growth eg to enhance nutrient uptake |
| ROOT | Other | Other | this correlates with any root mutant phenotypes which do not fit into the above categories (a picture should be taken for documentation) | Useful for increasing root growth eg to enhance nutrient uptake |
| LATERAL ROOTS | Number | Less Lateral Roots | there is an abnormally low number of lateral roots | Useful for increasing root growth eg to enhance nutrient uptake |
| LATERAL ROOTS | Other | Other | this correlates with any lateral root mutant phenotypes which do not fit into the above categories (a picture should be taken for documentation) | Useful for increasing root growth eg to enhance nutrient uptake |
| ROOT | Classic | Classic | there is a lack of lateral roots (buds may appear but do not elongate) | Useful for increasing root growth eg to enhance nutrient uptake |
| ROOT | Dwarf | Dwarf | there is a stunted root system | Useful for increasing root growth eg to enhance nutrient uptake |
| ROOT | Mid-Section | Mid-Section | there are lateral roots in the top and bottom quarters of the whole root, but none in the middle | Useful for increasing root growth eg to enhance nutrient uptake |
| ROOT | Split | Split | appears as "classic" but with two primary roots, both originating from the hypocotyl base | Useful for increasing root growth eg to enhance nutrient uptake |
| ROOT | Other | Other | this correlates with any overall root structure mutant phenotypes which do not fit into the above categories (a picture should be taken for documentation) | Useful for increasing root growth eg to enhance nutrient uptake |
| PRIMARY ROOT | Other | Other | this correlates with any primary root mutant phenotypes which do not fit into the above categories | Useful for increasing root growth eg to enhance nutrient uptake |

TABLE 1-continued

| TISSUE | PHENOTYPE QUALIFIER | PHENOTYPE | DESCRIPTION | TRANSLATION |
|---|---|---|---|---|
| | | | (a picture should be taken for documentation) | |
| ROOT HAIRS | Length | Longer Root Hair | the root hairs are abnormally long | Useful for increasing root growth eg to enhance nutrient uptake |
| ROOT HAIRS | Length | Smaller Root Hair | the root hairs are abnormally short | Useful for increasing root growth eg to enhance nutrient uptake |
| ROOT HAIRS | Number | Less root hairs | there is an abnormally low number of root hairs | Useful for increasing root growth eg to enhance nutrient uptake |
| ROOT HAIRS | Other | Other | this correlates with any root hair mutant phenotypes which do not fit into the above categories (a picture should be taken for documentation) | Useful for increasing root growth eg to enhance nutrient uptake |
| ROOT HAIRS | Bulbous Root Hairs | Bulbous Root Hairs | Bulbous Root Hairs | Useful for increasing root growth eg to enhance nutrient uptake |
| ROOT | Bearded (Nitrogen) | Bearded (Nitrogen) | the lateral roots are long in high nitrogen, and they are short in low nitrogen | Useful for increasing root growth eg to enhance nutrient uptake |
| PRIMARY ROOT | Thickness | Thicker Primary Root | the primary root is abnormally thick | Useful for increasing root growth eg to enhance nutrient uptake |
| WHOLE PLANT | Stress | Root Architecture | Identify plants with increased root mass | Useful for increasing root growth eg to enhance nutrient uptake |
| PRIMARY ROOT | Thickness | Thinner Primary Root | the primary root is abnormally thin | Useful for increasing root growth eg to enhance nutrient uptake |
| PRIMARY ROOT | Wavy | Wavy | there is a consistent and gentle wavy appearance | Useful for increasing root growth eg to enhance nutrient uptake |
| LATERAL ROOTS | Length | Longer Lateral Root | the lateral roots are abnormally long | Useful for increasing root growth eg to enhance nutrient uptake |
| LATERAL ROOTS | Number | More Lateral Roots | there is an abnormally high number of lateral roots | Useful for increasing root growth eg to enhance nutrient uptake |
| ROOT HAIRS | Number | More root hairs | there is an abnormally high number of root hairs | Useful for increasing root growth eg to enhance nutrient uptake Useful for increasing seed carbon or nitrogen |
| SEED | Seed Weight | Weight | weight of seed | Useful for increasing seed weight |
| SILIQUES | Length | Long | siliques are abnormally long (the percent difference in length compared to the control should be noted in the comments) | Useful for increasing seed/fruit yield or modifying fruit content |
| SILIQUES | Length | Short | siliques are abnormally short (the percent difference in length compared to the control should be noted in the comments) | Useful for increasing seed/fruit yield or modifying fruit content |
| SILIQUES | Other | Other | this correlates with any silique mutant phenotypes which do not fit into the above categories (a picture should be taken for documentation) | Useful for increasing seed/fruit yield or modifying fruit content |
| ROSETTE LEAVES | Size | Large | rosette leaves are abnormally large (the percent | Useful for increasing vegetative growth and enhancing foliage |

TABLE 1-continued

| TISSUE | PHENOTYPE QUALIFIER | PHENOTYPE | DESCRIPTION | TRANSLATION |
|---|---|---|---|---|
| | | | difference in size compared to the control should be noted in the comments) | |
| | | | | Useful for making nutraceuticals/pharmaceuticals in plants |
| HYPOCOTYL | Other | Other | this correlates with any hypocotyl mutant phenotypes which do not fit into the above categories (a picture should be taken for documentation) | Useful for making larger plants |
| WHOLE SEEDLING | Other | Other | this correlates with any whole plant mutant phenotypes which do not fit into the above categories (a picture should be taken for documentation) | Useful for making larger plants |
| WHOLE PLANT | Other | Other | this correlates with any whole plant mutant phenotypes which do not fit into the above categories (a picture should be taken for documentation) | Useful for making larger plants |
| CAULINE LEAVES | Petiole Length | Long Petioles | the cauline petioles are abnormally long (the percent difference in size compared to the control should be noted in the comments) | Useful for making larger plants |
| WHOLE SEEDLING | Size | Large | plant is abnormally large (the percent difference in size compared to the control should be noted in the comments) | Useful for making larger plants |
| WHOLE PLANT | Size | Large | plant is abnormally large (the percent difference in size compared to the control should be noted in the comments) | Useful for making larger plants |
| SEED | Lethal | Lethal | the seed is inviable and appears as a small, dark, raisin-like seed in the mature silique | Useful for making lethal plants for genetic confinement systems |
| WHOLE SEEDLING | Germination | No Germination | none of the seed germinates | Useful for making lethal plants for genetic confinement systems |
| WHOLE SEEDLING | Germination | Poor Germination | a portion of the seed never germinates | Useful for making lethal plants for genetic confinement systems |
| WHOLE SEEDLING | Germination | Slow Germination | a portion of the seed germinates significantly later than the rest of the seed in the pot | Useful for making lethal plants for genetic confinement systems |
| ROSETTE LEAVES | Vitrified | Vitrified | leaves are somewhat translucent or ?water soaked? | Useful for making lethal plants for genetic confinement systems |
| CAULINE LEAVES | Vitrified | Vitrified | leaves are somewhat translucent or ?water soaked? | Useful for making lethal plants for genetic confinement systems |

TABLE 1-continued

| TISSUE | PHENOTYPE QUALIFIER | PHENOTYPE | DESCRIPTION | TRANSLATION |
| --- | --- | --- | --- | --- |
| COTYLEDONS | Albino | Opaque Albino | plant is opaque and devoid of pigment | Useful for making lethal plants for genetic confinement systems |
| COTYLEDONS | Albino | Translucent Albino | plant is translucent and devoid of pigment | Useful for making lethal plants for genetic confinement systems |
| WHOLE SEEDLING | Lethal | Seedling Lethal | cotyledons emerge (although they are often small), but then the plant ceases to develop further; No true leaves appear and the plant dies early (These differ from yellow-green lethals in that the cotyledons are wild-type in color and may not look differ | Useful for making lethal plants for genetic confinement systems |
| WHOLE SEEDLING | Lethal | Yellow-Green Lethal | cotyledons are small and pale yellow-green in color, but NOT totally devoid of pigment; In addition to yellow-green cotyledons, these plants produce no or severely reduced size true leaves, which, if present, are also yellow-green; These plants die prem | Useful for making lethal plants for genetic confinement systems |
| WHOLE SEEDLING | Meristem Mutant | Meristem Mutant | this term encompasses a variety of phenotypes, all of which have one thing in common, i.e., they all have something significantly wrong with how the meristem is producing its leaves; Depending on the severity of the phenotype, the plants in this category | Useful for making lethal plants for genetic confinement systems |
| WHOLE SEEDLING | Seedling Defective | Seedling Defective | this term encompasses a variety of phenotypes which share similar characteristics, i.e., they are small, have distorted structures, and are prone to early death; For example, patterning mutants would be a class of mutants which fall under this category | Useful for making lethal plants for genetic confinement systems |
| WHOLE PLANT | Color | Yellow-Green Viable 1 | the leaves and cotyledons are yellow-green in color, but this is not a lethal phenotype | Useful for making lethal plants for genetic confinement systems |
| WHOLE PLANT | Color | Yellow-Green Viable 2 | the leaves are yellow-green in color but the cotyledons are a wild-type green in color | Useful for making lethal plants for genetic confinement systems |
| WHOLE PLANT | Color | Yellow-Green Viable 3 | the leaves start out wild-type green and gradually turn yellow-green in | Useful for making lethal plants for genetic confinement systems |

TABLE 1-continued

| TISSUE | PHENOTYPE QUALIFIER | PHENOTYPE | DESCRIPTION | TRANSLATION |
|---|---|---|---|---|
| WHOLE PLANT | Color | Yellow-Green Viable 4 | color, while the cotyledons stay wild-type green the leaves appear wild-type green, but slowly turn yellow-green over time, while the cotyledons appear and remain yellow-green | Useful for making lethal plants for genetic confinement systems |
| WHOLE PLANT | Stress | Seed Bleaching | Identify plants whose seed coats do not bleach out under long bleach soaking | Useful for making low fiber seeds with increased digestability |
| ROSETTE LEAVES | Fused | Leaf Fused to Inflorescence | the leaf is fused to an inflorescence | Useful for making ornamental plants with flowers and leaves fused |
| ROSETTE LEAVES | Interveinal Chlorosis | Interveinal Chlorosis | the leaf tissue is chlorotic between its veins | Useful for making ornamental plants with modified color |
| CAULINE LEAVES | Interveinal Chlorosis | Interveinal Chlorosis | the leaf tissue is chlorotic between its veins | Useful for making ornamental plants with modified color |
| FLOWER | Organ Morphology | Fused Sepals | the sepals are fused together and won?t open naturally, but the flower is otherwise wild-type | Useful for making ornamental plants with modified flowers |
| FLOWER | Organ Morphology | Narrow Petals | the petals are abnormally narrow | Useful for making ornamental plants with modified flowers |
| FLOWER | Organ Morphology | Narrow Sepals | the sepals are abnormally narrow | Useful for making ornamental plants with modified flowers |
| FLOWER | Organ Morphology | Short Petals | the petals are abnormally short | Useful for making ornamental plants with modified flowers |
| FLOWER | Organ Morphology | Short Sepals | the sepals are abnormally short | Useful for making ornamental plants with modified flowers |
| FLOWER | Size | Large | flower is abnormally large (the percent difference in size compared to the control should be noted in the comments) | Useful for making ornamental plants with modified flowers |
| FLOWER | Size | Small | flower is abnormally small (the percent difference in size compared to the control should be noted in the comments) | Useful for making ornamental plants with modified flowers |
| FLOWER | Other | Other | this correlates with any flower mutant phenotypes which do not fit into the above categories (a picture should be taken for documentation) | Useful for making ornamental plants with modified flowers |
| INFLORESCENCE | Aerial Rosette | Aerial Fosette | rosette forms at or above the first internode | Useful for making ornamental plants with modified flowers |
| INFLORESCENCE | Appearance | Corkscrew Appearance | the inflorescence is really twisted, almost like a corkscrew, but somewhat more irregular | Useful for making ornamental plants with modified flowers |
| INFLORESCENCE | Appearance | Curved Appearance | the inflorescence has a slight, irregular curve upwards, greater than that of the control plants | Useful for making ornamental plants with modified flowers |

TABLE 1-continued

| TISSUE | PHENOTYPE QUALIFIER | PHENOTYPE | DESCRIPTION | TRANSLATION |
| --- | --- | --- | --- | --- |
| INFLORESCENCE | Appearance | Multi-Inflorescence Fusion | the inflorescence is fused to another inflorescence, creating a celery-like appearance | Useful for making ornamental plants with modified flowers |
| INFLORESCENCE | Appearance | Undulate Appearance | the inflorescence is wavy in appearance | Useful for making ornamental plants with modified flowers |
| INFLORESCENCE | Branching | Acauline Branching | first branching is not subtended by a cauline leaf | Useful for making ornamental plants with modified flowers |
| INFLORESCENCE | Wax | Glaucous | inflorescence is abnormally dull in appearance | Useful for making ornamental plants with modified flowers |
| INFLORESCENCE | Wax | Glossy | inflorescence is shiny/glossy in appearance | Useful for making ornamental plants with modified flowers |
| INFLORESCENCE | Other | Other | this correlates with any inflorescence mutant phenotypes which do not fit into the above categories (a picture should be taken for documentation) | Useful for making ornamental plants with modified flowers |
| COTYLEDONS | Asymmetric | Asymmetric | the shape of the cotyledon is asymmetric in reference to the vertical axis | Useful for making ornamental plants with modified foliage |
| ROSETTE LEAVES | Other | Other | this correlates with any leaf mutant phenotypes which do not fit into the above categories (a picture should be taken for documentation) | Useful for making ornamental plants with modified leaves |
| CAULINE LEAVES | Other | Other | this correlates with any cauline mutant phenotypes which do not fit into the above categories (a picture should be taken for documentation) | Useful for making ornamental plants with modified leaves |
| FLOWER | Homeotic Mutant | Homeotic Mutant | the flower has one or more of its organs converted to another type of organ (specific details should be noted in the comments) | Useful for making plants sterile and for genetic confinement |
| FLOWER | Organ Morphology | Aberrant Organ Number | there is an abnormal number of some or all of the flowers organs | Useful for making plants sterile and for genetic confinement |
| FLOWER | Organ Morphology | Short Stamens | the stamens are abnormally short; This often leads to mechanical problems with fertility | Useful for making plants sterile and for genetic confinement |
| FLOWER | Fertility | Aborted fertility | the ovule is unfertilized and appears as a brown or white speck in the mature silique | Useful for making plants sterile and for genetic confinement |
| FLOWER | Fertility | Female-sterile | there is a problem with the ovules such that no fertilization is occurring | Useful for making plants sterile and for genetic confinement |
| FLOWER | Fertility | Male-sterile | there is a problem with the pollen such that no fertilization is occurring | Useful for making plants sterile and for genetic confinement |
| FLOWER | Fertility | Reduced fertility | a reduced number of successful fertilization events, and therefore seeds, | Useful for making plants sterile and for genetic confinement |

TABLE 1-continued

| TISSUE | PHENOTYPE QUALIFIER | PHENOTYPE | DESCRIPTION | TRANSLATION |
|---|---|---|---|---|
| FLOWER | Fertility | Sterile | are being produced by the plant no successful fertilization events, and therefore no seed is being produced by the plant; The reason for this sterility is not known at the time of the observation | Useful for making plants sterile and for genetic confinement |
| FLOWER | Fertility | Other | this correlates with any fertility mutant phenotypes which do not fit into the above categories (a picture should be taken for documentation) | Useful for making plants sterile and for genetic confinement |
| WHOLE PLANT | Stress | Early Flowering | Identify plants that flower early | Useful for making plants that flower early |
| COTYLEDONS | Petiole Length | Long Petioles | the cotyledon petioles are abnormally long (the percent difference in size compared to the control should be noted in the comments) | Useful for making plants that grow and better in shade |
| ROSETTE LEAVES | Petiole Length | Varying Petiole Lengths | the leaf petioles vary in length throughout the rosette | Useful for making plants that grow better in shade |
| ROSETTE LEAVES | Petiole Length | Long Petioles | the leaf petioles are abnormally long (the percent difference in size compared to the control should be noted in the comments) | Useful for making plants that grow better in shade |
| WHOLE PLANT | Stress | | Identify plants able to tolerate high density and no phosphate and nitrogen, possible lead assay for vigor under population density and low nutrient conditions | Useful for making plants tolerant to biotic stress Useful for making plants tolerant to density and low fertilizer |
| WHOLE PLANT | Stress | pH (high) | Identify plants tolerant to high pH, and possibly low phosphate | Useful for making plants tolerant to high pH or low phosphate |
| WHOLE PLANT | Stress | Low Nitrate | Identify plants tolerant to low nitrogen/nitrate growth media | Useful for making plants tolerant to low nitrogen |
| WHOLE PLANT | Stress | LNABA | Identify plants tolerant to low nitrogen and high ABA concentrations | Useful for making plants tolerant to low nitrogen |
| WHOLE PLANT | Stress | No Nitrogen | Identify plants with increased vigor under no nitrogen conditions | Useful for making plants tolerant to low nitrogen |
| WHOLE PLANT | Stress | MSX | Identify plants tolerant to nitrogen assimilation inhibitor, and possibly low nitrogen tolerance and/or seed nitrogen accumulation | Useful for making plants tolerant to low nitrogen |
| WHOLE PLANT | Stress | No N, No PO4 | Identify plants tolerant to no nitrogen and no phosphate growth media | Useful for making plants tolerant to low nitrogen/low phosphate |

TABLE 1-continued

| TISSUE | PHENOTYPE QUALIFIER | PHENOTYPE | DESCRIPTION | TRANSLATION |
|---|---|---|---|---|
| WHOLE PLANT | Stress | Oxidative | Identify plants tolerant to oxidative stress | Useful for making plants tolerant to oxidative stresses |
| ROSETTE LEAVES | Trichomes | Few Trichomes | trichomes are sparse but present on the leaves | Useful for making plants with enhanced chemical composition |
| ROSETTE LEAVES | Trichomes | Glabrous | trichomes are totally absent | Useful for making plants with enhanced chemical composition |
| ROSETTE LEAVES | Trichomes | Abnormal Trichome Shape | the trichomes are abnormally shaped | Useful for making plants with enhanced chemical composition |
| CAULINE LEAVES | Trichomes | Few Trichomes | trichomes are sparse but present on the leaves | Useful for making plants with enhanced chemical composition |
| CAULINE LEAVES | Trichomes | Glabrous | trichomes are totally absent | Useful for making plants with enhanced chemical composition |
| CAULINE LEAVES | Trichomes | Abnormal Trichome Shape | the trichomes are abnormally shaped | Useful for making plants with enhanced chemical composition |
| INFLORESCENCE | Trichomes | Glabrous | trichomes are totally absent | Useful for making plants with enhanced chemical composition |
| INFLORESCENCE | Trichomes | Abnormal Trichome Shape | the trichomes are abnormally shaped | Useful for making plants with enhanced chemical composition |
| ROSETTE LEAVES | Curled | Corkscrew | leaves appear as "Curled 5", with the additional attribute of twisting like a corkscrew, instead of uniformly curling from both sides of the leaf | Useful for making plants with altered leaf shape eg curled leaves |
| ROSETTE LEAVES | Curled | Cup-shaped | leaves are curled up at the leaf margins such that they form a cup or bowl-like shape | Useful for making plants with altered leaf shape eg curled leaves |
| ROSETTE LEAVES | Curled | Curled 1 | leaves are abnormally curled slightly up or down at the leaf margins, but do not fall under the "cup-shaped" description (least severe type) | Useful for making plants with altered leaf shape eg curled leaves |
| ROSETTE LEAVES | Curled | Curled 2 | leaves are abnormally curled up or down at the leaf margins, but do not fall under the "cup-shaped" description (more severe than Curled 1, but less severe than Curled 3) | Useful for making plants with altered leaf shape eg curled leaves |
| ROSETTE LEAVES | Curled | Curled 3 | leaves are abnormally curled up or down at the leaf margins, but do not fall under the "cup-shaped" description (more severe than Curled 2, but less severe than Curled 4) | Useful for making plants with altered leaf shape eg curled leaves |
| ROSETTE LEAVES | Curled | Curled 4 | leaves are abnormally curled/rolled up or down at the leaf margins (more severe than Curled 3, but less severe than Curled 5) | Useful for making plants with altered leaf shape eg curled leaves |
| ROSETTE LEAVES | Curled | Curled 5 | leaves are completely curled/rolled up or down at the leaf margins (most severe type) | Useful for making plants with altered leaf shape eg curled leaves |

TABLE 1-continued

| TISSUE | PHENOTYPE QUALIFIER | PHENOTYPE | DESCRIPTION | TRANSLATION |
|---|---|---|---|---|
| CAULINE LEAVES | Curled | Corkscrew | leaves appear as "Curled 5", with the additional attribute of twisting like a corkscrew, instead of uniformly curling from both sides of the leaf | Useful for making plants with altered leaf shape eg curled leaves |
| CAULINE LEAVES | Curled | Cup-shaped | the cauline leaves are curled up at the leaf margins such that they form a cup or bowl-like shape | Useful for making plants with altered leaf shape eg curled leaves |
| CAULINE LEAVES | Curled | Curled 1 | the cauline leaves are abnormally curled slightly up or down at the leaf margins, but do not fall under the "cup-shaped" description (least severe type) | Useful for making plants with altered leaf shape eg curled leaves |
| CAULINE LEAVES | Curled | Curled 2 | the cauline leaves are abnormally curled up or down at the leaf margins, but do not fall under the "cup-shaped" description (more severe than Curled 1, but less severe than Curled 3) | Useful for making plants with altered leaf shape eg curled leaves |
| CAULINE LEAVES | Curled | Curled 3 | the cauline leaves are abnormally curled up or down at the leaf margins, but do not fall under the "cup-shaped" description (more severe than Curled 2, but less severe than Curled 4) | Useful for making plants with altered leaf shape eg curled leaves |
| CAULINE LEAVES | Curled | Curled 4 | the cauline leaves are abnormally curled/rolled up or down at the leaf margins (more severe than Curled 3, but less severe than Curled 5) | Useful for making plants with altered leaf shape eg curled leaves |
| CAULINE LEAVES | Curled | Curled 5 | the cauline leaves are completely curled/rolled up or down at the leaf margins (most severe type) | Useful for making plants with altered leaf shape eg curled leaves |
| ROSETTE LEAVES | Size | Small | rosette leaves are abnormally small (the percent difference in size compared to the control should be noted in the comments) | Useful for making plants with decreased vegetative growth |
| COTYLEDONS | Wilted | Wilted | cotyledons appear wilted, i.e., they look as though they have suffered from drought conditions | Useful for making plants with enhanced abiotic stress tolerance |
| ROSETTE LEAVES | Wax | Glaucous | leaves are abnormally dull in appearance | Useful for making plants with enhanced abiotic stress tolerance |
| ROSETTE LEAVES | Wax | Glossy | leaves are shiny/glossy in appearance | Useful for making plants with enhanced abiotic stress tolerance |
| CAULINE LEAVES | Wax | Glaucous | leaves are abnormally dull in appearance | Useful for making plants with enhanced abiotic stress tolerance |

TABLE 1-continued

| TISSUE | PHENOTYPE QUALIFIER | PHENOTYPE | DESCRIPTION | TRANSLATION |
|---|---|---|---|---|
| CAULINE LEAVES | Wax | Glossy | leaves are shiny/glossy in appearance | Useful for making plants with enhanced abiotic stress tolerance |
| WHOLE PLANT | Stress | Metabolic Profiling | Identify plants with altered metabolic profiles as defined in 4a | Useful for making plants with enhanced metabolite accumulation |
| WHOLE PLANT | Stress | Plant Architecture | Identify plants with improved architecture | Useful for making plants with enhanced plant architecture |
| WHOLE PLANT | Stress | ABA | Identify plants tolerant to ABA, and possibly drought and/or other stresses | Useful for making plants with enhanced tolerance to drought |
| WHOLE PLANT | Stress | Mannitol | Identify plants tolerant to mannitol, and possibly drought stress | Useful for making plants with enhanced tolerance to drought |
| WHOLE PLANT | Stress | Dessication | Identify plants tolerant to water loss, possibly drought stress tolerant | Useful for making plants with enhanced tolerance to drought |
| WHOLE PLANT | Stress | High Sucrose | Identify plants tolerant to high sucrose conditions (possible Lead assay for C/N partitioning) | Useful for making plants with enhanced tolerance to drought |
| WHOLE PLANT | Stress | Heat | Identify plants with thermotolerance | Useful for making plants with enhanced tolerance to heat |
| WHOLE PLANT | Stress | High Nitrogen | Identify plants tolerant to high nitrogen conditions | Useful for making plants with enhanced tolerance to high nitrogen |
| WHOLE PLANT | Stress | Etiolation | Identify plants with increased vigor in the dark | Useful for making plants with enhanced tolerance to light stress |
| ROSETTE LEAVES | Disorganized Rosette | Disorganized Rosette | rosette leaves do not appear in the normal fashion, i.e., their phyllotaxy may be abnormal or too many leaves may be emerging in comparison to the control | Useful for making plants with increased biomass |
| INFLORESCENCE | Phyllotaxy | Even Phyllotaxy | a phyllotaxy mutant whose new branches emerge at exactly the same height as each other, i.e., there is no internode between them | Useful for making plants with increased biomass |
| COTYLEDONS | Shape | Elliptic Shape | cotyledons are quite narrow and pointed, more so than lanceolate | Useful for making plants with increased biomass and foliage |
| ROSETTE LEAVES | Fused | Leaf Fused to Petiole | the leaf is fused to its petiole | Useful for making plants with increased biomass and foliage |
| ROSETTE LEAVES | Shape | Cordate Shaped | similar to ovate, except the leaf is not rounded at its base | Useful for making plants with increased biomass and foliage |
| ROSETTE LEAVES | Shape | Elliptic Shaped | leaves are quite narrow and pointed, more so that lanceolate | Useful for making plants with increased biomass and foliage |
| ROSETTE LEAVES | Shape | Lanceolate Shaped | leaves are narrow and come to a dull point at the apex | Useful for making plants with increased biomass and foliage |
| ROSETTE LEAVES | Shape | Lobed Shaped | leaves have very deep and rounded serrations, giving an appearance of many lobes forming the margins of the leaves | Useful for making plants with increased biomass and foliage |

TABLE 1-continued

| TISSUE | PHENOTYPE QUALIFIER | PHENOTYPE | DESCRIPTION | TRANSLATION |
|---|---|---|---|---|
| ROSETTE LEAVES | Shape | Oval Shaped | leaves are much rounder than wild-type | Useful for making plants with increased biomass and foliage |
| ROSETTE LEAVES | Shape | Ovate Shaped | leaves are wider at base than at apex, otherwise similar to wild-type | Useful for making plants with increased biomass and foliage |
| ROSETTE LEAVES | Shape | Serrate Margins | leaf margins have little ?teeth? on them, i.e., they are serrated | Useful for making plants with increased biomass and foliage |
| ROSETTE LEAVES | Shape | Trident Shaped | leaves look somewhat like a trident, i.e., they have a sharp point at the apex, and a sharp point on each side | Useful for making plants with increased biomass and foliage |
| ROSETTE LEAVES | Shape | Undulate Shaped | leaves are wavy | Useful for making plants with increased biomass and foliage |
| WHOLE PLANT | Rosette Shape | Bushy Rosette Shaped | the different petioles have very varied liminal angles, giving the plant a very bushy appearance; This is often accompanied by a "Disorganized Rosette" phenotype | Useful for making plants with increased biomass and foliage |
| WHOLE PLANT | Rosette Shape | Flat Rosette Shaped | the petioles have a very small liminal angle, i.e., the rosette appears flat instead of having its usual slight vertical angle | Useful for making plants with increased biomass and foliage |
| WHOLE PLANT | Rosette Shape | Standing Rosette Shaped | the petioles have a very large liminal angle, i.e., it appears as though the leaves are standing up instead of having their usual small vertical angle from the soil | Useful for making plants with increased biomass and foliage |
| CAULINE LEAVES | Fused | Leaf Fused to Inflorescence | the cauline leaf is fused to an inflorescence or branch | Useful for making plants with increased biomass and foliage |
| CAULINE LEAVES | Fused | Leaf Fused to Leaf | the cauline leaf is fused to itself or another cauline leaf | Useful for making plants with increased biomass and foliage |
| CAULINE LEAVES | Shape | Cordate Shaped | similar to ovate, except the leaf is not rounded at its base | Useful for making plants with increased biomass and foliage |
| CAULINE LEAVES | Shape | Elliptic Shaped | leaves are quite narrow and pointed, more so that lanceolate | Useful for making plants with increased biomass and foliage |
| CAULINE LEAVES | Shape | Lanceolate Shaped | leaves are narrow and come to a dull point at the apex | Useful for making plants with increased biomass and foliage |
| CAULINE LEAVES | Shape | Lobed Shaped | leaves have very deep and rounded serrations, giving an appearance of many lobes forming the margins of the leaves | Useful for making plants with increased biomass and foliage |
| CAULINE LEAVES | Shape | Oval Shaped | leaves are much rounder than wild-type | Useful for making plants with increased biomass and foliage |
| CAULINE LEAVES | Shape | Ovate Shaped | leaves are wider at base than at apex, otherwise similar to wild-type | Useful for making plants with increased biomass and foliage |
| CAULINE LEAVES | Shape | Serrate Margins | leaf margins have little ?teeth? on them, i.e., they are serrated | Useful for making plants with increased biomass and foliage |

TABLE 1-continued

| TISSUE | PHENOTYPE QUALIFIER | PHENOTYPE | DESCRIPTION | TRANSLATION |
|---|---|---|---|---|
| CAULINE LEAVES | Shape | Trident Shaped | leaves look somewhat like a trident, i.e., they have a sharp point at the apex, and a sharp point on each side | Useful for making plants with increased biomass and foliage |
| CAULINE LEAVES | Shape | Undulate Shaped | leaves are wavy | Useful for making plants with increased biomass and foliage |
| CAULINE LEAVES | Size | Large | cauline is abnormally large (the percent difference in size compared to the control should be noted in the comments) | Useful for making plants with increased biomass and foliage |
| CAULINE LEAVES | Size | Small | cauline is abnormally small (the percent difference in size compared to the control should be noted in the comments) | Useful for making plants with increased biomass and foliage |
| LATERAL ROOTS | Length | Smaller Lateral Root | the lateral roots are abnormally short | Useful for making plants with increased root growth to prevent lodging or enhance nutrient uptake |
| PRIMARY ROOT | Length | Long Primary Root | the primary root is abnormally long (the percent difference in size compared to the control should be noted in the comments) | Useful for making plants with increased root growth to prevent lodging or enhance nutrient uptake |
| PRIMARY ROOT | Length | Short Primary Root | the primary root is abnormally short (the percent difference in size compared to the control should be noted in the comments) | Useful for making plants with increased root growth to prevent lodging or enhance nutrient uptake |
| WHOLE PLANT | Stress | Plant Size | Identify plants of increased size compared to wild type | Useful for making plants with increased size and biomass |
| WHOLE PLANT | Stress | Starch | Identify plants with increased starch accumulation | Useful for making plants with increased starch content |
| WHOLE PLANT | Stress | Cold Germination | Identify plants that germinate better at cold temperatures | Useful for making plants with increased tolerance to cold stress |
| WHOLE PLANT | Stress | Cold Growth | Identify plants that grow faster at cold temperatures | Useful for making plants with increased tolerance to cold stress |
| WHOLE PLANT | Stress | Soil Drought | Identify plants with increased tolerance to soil drought | Useful for making plants with increased tolerance to drought |
| WHOLE PLANT | Stress | Soil Drought - Desiccation tolerance | Identify plants that are tolerant to low soil moisture and resist wilting | Useful for making plants with increased tolerance to drought |
| WHOLE PLANT | Stress | PEG | Identify plants tolerant to PEG, and possibly drought stress | Useful for making plants with increased tolerance to drought |
| SEED | Size | Large | the seed is abnormally large (the percent difference in size compared to the control should be noted in the comments) | Useful for making plants with larger seeds |

TABLE 1-continued

| TISSUE | PHENOTYPE QUALIFIER | PHENOTYPE | DESCRIPTION | TRANSLATION |
|---|---|---|---|---|
| INFLORESCENCE | Branching | Asecondary Branching | the plant does not form any secondary inflorescences | Useful for making plants with modified flowers |
| SEED | Size | Small | the seed is abnormally small (the percent difference in size compared to the control should be noted in the comments) | Useful for making plants with smaller seeds or no seeds |
| WHOLE PLANT | Stress | C/N Content | Identify plants/seeds with altered carbon/nitrogen levels | Useful for making seeds with altered carbon/nitrogen levels |
| INFLORESCENCE | Internode Length | Short Internode | the internode is abnormally short (the percent difference in length compared to the control should be noted in the comments) | Useful for making shorter plants and plants with modified flowers |
| WHOLE PLANT | Dwarf | Brassino-Steroid Dwarf | these plants are small in stature, dark green, have oval leaves, strong bolts, and are often sterile | Useful for making smaller plants |
| WHOLE PLANT | Dwarf | Misc. Dwarf | these are dwarf plants the do not fall under the brassino-steroid dwarf category | Useful for making smaller plants |
| HYPOCOTYL | Length | Short | hypocotyl is visibly shorter than in wild-type (the percent difference in size compared to the control should be noted in the comments) | Useful for making smaller plants |
| INFLORESCENCE | Height | Short | the inflorescences of the plants are abnormally short (plant height is encompassed under the whole plant size category, but this entry would be used if the height of the plant is abnormal, but is otherwise of normal size) (the percent difference in size | Useful for making smaller plants |
| WHOLE SEEDLING | Size | Small | plant is abnormally small (the percent difference in size compared to the control should be noted in the comments) | Useful for making smaller plants |
| ROSETTE LEAVES | Petiole Length | Short Petioles | the leaf petioles are abnormally short (the percent difference in size compared to the control should be noted in the comments) | Useful for making smaller plants |
| WHOLE PLANT | Size | Small | plant is abnormally small (the percent difference in size compared to the control should be noted in the comments) | Useful for making smaller plants |

TABLE 1-continued

| TISSUE | PHENOTYPE QUALIFIER | PHENOTYPE | DESCRIPTION | TRANSLATION |
|---|---|---|---|---|
| CAULINE LEAVES | Petiole Length | Short Petioles | the cauline petioles are abnormally short (the percent difference in size compared to the control should be noted in the comments) | Useful for making smaller plants |
| INFLORESCENCE | Strength | Strong | the primary inflorescence appears significantly stronger, whether by thickness or rigidity | Useful for making stronger plants |
| INFLORESCENCE | Strength | Weak | the primary inflorescence appears significantly weaker, whether by thickness or rigidity | Useful for making stronger plants |
| INFLORESCENCE | Inflorescence | Thickness | thickness of the primary inflorescence | Useful for making stronger plants |
| HYPOCOTYL | Length | Long | hypocotyl is visibly longer than in wild-type (the percent difference in size compared to the control should be noted in the comments) | Useful for making taller plants |
| INFLORESCENCE | Internode Length | Long Internode | the internode is abnormally long (the percent difference in length compared to the control should be noted in the comments) | Useful for making taller plants and plants with longer flowers |
| INFLORESCENCE | Height | Tall | the inflorescences of the plants are abnormally long (plant height is encompassed under the whole plant size category, but this entry would be used if the height of the plant is abnormal, but is otherwise of normal size) (the percent difference in size | Useful for making taller plants and plants with longer inflorescences |
| SEED | Color | Dark Color | the seed is abnormally dark | Useful for modifying fiber content in seed |
| SEED | Color | Light Color | the seed is abnormally light; Transparent Testa is an example of this phenotype | Useful for modifying fiber content in seed |
| SILIQUES | Shape | Bent | the silique has sharp bend to it part of the way down the length of the silique; this bend can be as much as approaching 90 degrees | Useful for modifying fruit shape, composition and seed yield |
| SILIQUES | Shape | Bulging | the seeds in the silique appears "shrink-wrapped", giving the silique a bulging appearance | Useful for modifying fruit shape, composition and seed yield |
| SILIQUES | Shape | Clubbed | the silique is somewhat bulbous at its terminal end | Useful for modifying fruit shape, composition and seed yield |
| SILIQUES | Shape | Sickle | the silique is curved, much like the blade of a sickle | Useful for modifying fruit shape, composition and seed yield |
| INFLORESCENCE | Branching | No Branching | there is no branching at all | Useful for modifying plant architecture, ie amount of branching |

TABLE 1-continued

| TISSUE | PHENOTYPE QUALIFIER | PHENOTYPE | DESCRIPTION | TRANSLATION |
|---|---|---|---|---|
| INFLORESCENCE | Branching | Horizontal Branching | new branches arise at a 90 degree angle from the bolt they are emerging from | Useful for modifying plant architecture, ie branch angle |
| COTYLEDONS | Horizontally Oblong | Horizontally Oblong | cotyledon is visibly wider than it is long, and it is also symmetrical (or very close to it) when cut along its horizontal axis | Useful for modifying plant architecture, ie leaf structure |
| INFLORESCENCE | Branching | Two Leaf Branching | two cauline leaves subtend branches instead of one | Useful for modifying plant architecture, ie reducing foliage |
| INFLORESCENCE | Branching | Reduced Apical Dominance | the dominance of the primary inflorescence is diminished, with the secondaries appearing as dominant or nearly as dominant | Useful for modifying plant structure, ie increased branching |
| SEED | Seed Arrangement | Stacked Arrangement | the seeds/embryos are stacked one on top of the other within the silique, instead of having the usual side-by-side distribution | Useful for modifying seed content |
| SEED | Other | Other | this correlates with any seed mutant phenotypes which do not fit into the above categories (a picture should be taken for documentation) | Useful for modifying seed content |
| SEED | Shape | Oval Shape | the seeds are much more rounded on the ends, giving the seed a true oval appearance | Useful for modifying seed structure and composition |
| SEED | Shape | Ridged Shape | the seeds have small ridges or bumps on them | Useful for modifying seed structure and composition |
| SEED | Shape | Tapered Shape | the ends of the seeds narrow down to a much sharper point than usual | Useful for modifying seed structure and composition |
| COTYLEDONS | Cotyledon Number | Single Cotyledon | Only one cotyledon appears after germination; This is simply one cotyledon that had formed instead of two, and is not related to the fused phenotype; With this exception, the plant is often otherwise wild-type in appearance | Useful for modifying seed structure and content |
| COTYLEDONS | Cotyledon Number | Tricot | three cotyledons emerge instead of two; With this exception, the plant is often otherwise wild-type in appearance | Useful for modifying seed structure and content |
| COTYLEDONS | Curled | Cup-shaped | cotyledons are curled up at the cotyledon margins such that they form a cup or bowl-like shape | Useful for modifying seed structure and content |
| COTYLEDONS | Curled | Curled 1 | cotyledons are abnormally curled slightly up or down at the cotyledon margins, but do not | Useful for modifying seed structure and content |

TABLE 1-continued

| TISSUE | PHENOTYPE QUALIFIER | PHENOTYPE | DESCRIPTION | TRANSLATION |
|---|---|---|---|---|
| COTYLEDONS | Curled | Curled 2 | fall under the "cup-shaped" description (least severe type) cotyledons are abnormally curled up or down at the cotyledon margins, but do not fall under the "cup-shaped" description (more severe than Curled 1, but less severe than Curled 3) | Useful for modifying seed structure and content |
| COTYLEDONS | Curled | Curled 3 | cotyledons are abnormally curled up or down at the cotyledon margins, but do not fall under the "cup-shaped" description (more severe than Curled 2, but less severe than Curled 4) | Useful for modifying seed structure and content |
| COTYLEDONS | Curled | Curled 4 | cotyledons are abnormally curled/rolled up or down at the cotyledon margins (more severe than Curled 3, but less severe than Curled 5) | Useful for modifying seed structure and content |
| COTYLEDONS | Curled | Curled 5 | cotyledons are completely curled/rolled up or down at the cotyledon margins (most severe type) | Useful for modifying seed structure and content |
| COTYLEDONS | Dimorphic Cotyledons | Dimorphic Cotyledons | one cotyledon is significantly larger than the other | Useful for modifying seed structure and content |
| COTYLEDONS | Fused | Fused 1 | cotyledons are fused to each other, creating one cotyledon structure (least severe type) | Useful for modifying seed structure and content |
| COTYLEDONS | Fused | Fused 2 | cotyledons are fused to each other, creating one cotyledon structure (more severe than Fused 1, but less severe than Fused 3) | Useful for modifying seed structure and content |
| COTYLEDONS | Fused | Fused 3 | cotyledons are fused to each other, creating one cotyledon structure (more severe than Fused 2, but less severe than Fused 4) | Useful for modifying seed structure and content |
| COTYLEDONS | Fused | Fused 4 | cotyledons are fused to each other, creating one cotyledon structure (more severe than Fused 3, but less severe than Fused 5) | Useful for modifying seed structure and content |
| COTYLEDONS | Fused | Fused 5 | cotyledons are fused to each other, creating one cotyledon structure (most severe type) | Useful for modifying seed structure and content |
| COTYLEDONS | Other | Other | this correlates with any cotyledon mutant phenotypes which do not fit into the above categories (a picture | Useful for modifying seed structure and content |

TABLE 1-continued

| TISSUE | PHENOTYPE QUALIFIER | PHENOTYPE | DESCRIPTION | TRANSLATION |
|---|---|---|---|---|
| | | | should be taken for documentation) | |
| ROSETTE LEAVES | Fused | Leaf Fused to Leaf | the leaf is fused to itself or another leaf | Useful for plants with fused leaves eg ornamentals |
| COTYLEDONS | Petiole Length | Short Petioles | the cotyledon petioles are abnormally short (the percent difference in size compared to the control should be noted in the comments) | Useful for shade avoidance and for making smaller plants |
| PRIMARY ROOT | Agravitropic | Agravitropic | the primary root does not appear to have a gravitropic response | |
| PRIMARY ROOT | Kinked | Kinked | there is a sharp bend in the root | |
| ROSETTE LEAVES | Rosette Diameter | Diameter | diameter of rosette | |
| WHOLE PLANT | Plant Weight | Plant Weight | weight of whole plant | |
| WHOLE PLANT | Plant Height | Height | height of whole plant | |
| WHOLE PLANT | Plant DTH | Dth | days to harvest of plant | |
| WHOLE PLANT | Plant Harvest Index | Harvest Index | harvest index of plant | |
| CAULINE LEAVES | Fused | Leaf Fused to Petiole | the cauline leaf is fused to its petiole | |
| N/A | N/A | N/A | N/A | |
| WHOLE PLANT | HERBICIDE SEGREGATION | HERBICIDE SEGREGATION | herbicide segregation ratio | |
| WHOLE PLANT | N/A | No Mutant Phenotype Observed | The plants were screened at all appropriate stages and showed no mutant phenotype, i.e., they looked like normal, wild type *Arabidopsis* plants | |

From the results reported in Table 1 and the Sequence Listing, it can be seen that the nucleotides/polypeptides of the inventions are useful, depending upon the respective individual sequence, to make plants with modified growth and phenotype characteristics, including:
  a. modulated plant size, including increased and decreased height or length;
  b. modulated vegetative growth (increased or decreased);
  c. modulated organ number;
  d. increased biomass;
  e. sterility;
  f. seedling lethality;
  g. accelerated crop development or harvest;
  h. accelerated flowering time;
  i. delayed flowering time;
  j. delayed senescence;
  k. enhanced drought or stress tolerance;
  l. increased chlorophyll and photosynthetic capacity;
  m. increased anthocyanin content;
  n. increased root growth, and increased nutrient uptake;
  o. increased or decreased seed weight or size, increased seed carbon or nitrogen content;
  p. modified, including increased, seed/fruit yield or modified fruit content;
  q. enhanced foliage;
  r. usefulness for making nutratceuticals/pharmaceuticals in plants;
  s. plant lethality;
  t. decrease seed fiber content to provide increased digestability;
  u. modified ornamental appearance with modified leaves, flowers, color or foliage;
  v. modified sterility in plants;
  w. enhanced ability to grow in shade;
  x. enhanced biotic stress tolerance;
  y. increased tolerance to density and low fertilizer;
  z. enhanced tolerance to high or low pH, to low or high nitrogen or phosphate;
  aa. enhanced tolerance to oxidative stress;
  bb. enhanced chemical composition;
  cc. altered leaf shape;
  dd. enhanced abiotic stress tolerance;
  ee. increased tolerance to cold stress;
  ff. increased starch content;
  gg. reduced number or no seeds;
  hh. enhanced plant strength;
  ii. modified flower length;
  jj. longer inflorescences;
  kk. modified seed fiber content;
  ll. modified fruit shape;
  mm. modified fruit composition;
  nn. modified seed yield;
  oo. modified plant architecture, such as modified amount or angle of branching, modified leaf structure, or modified seed structure; and
  pp. enhanced shade avoidance.

EXAMPLE 1

Lead 28-ME04701-Clone 1952-cDNA 13499809 (SEQ ID NO: 90)

Qualitative Analysis of the $T_1$ Plants:

All 10 of the events produced rosettes with more leaves and more inflorescences than the control. The plants were also slightly smaller than the control (Table 1-1). The transgenic "control" was a set of plants expressing a different 35S::cDNA but which were indistinguishable from the untransformed WS wildtype. This method of scoring phenotypes is typical for our large-scale morphological phenotyping project.

TABLE 1-1

Qualitative phenotypes observed in 35S::cDNA 13499809 $T_1$ events

| Event | Increased Rosette Leaf Number, Increased Inflorescence Number, & Slightly Smaller |
|---|---|
| ME04701-01 | x |
| ME04701-02 | x |
| ME04701-03 | x |
| ME04701-04 | x |
| ME04701-05 | x |
| ME04701-06 | x |
| ME04701-07 | x |
| ME04701-08 | x |
| ME04701-09 | x |
| ME04701-10 | x |

Quantitative Analysis of the $T_2$ Plants:

Events ME04701-08 and ME04701-09 were evaluated in greater detail in the $T_2$ generation. These two events were selected because they had the most advantageous phenotypes. Eighteen individuals were sown and observed for both events. The transgenic plants showed an increased number of inflorescences to a 0.05 level of statistical significance (Table 1-2). The $T_2$ plants did not have significantly more leaves than the controls, unlike in the $T_1$. ME04701-08 was slightly later flowering than the control. ME04701-09 had significantly larger rosettes than the control. All plants noted in the table as ME04701-08 and ME04701-09 were segregating progeny of the $T_1$ which exhibited the phenotype of interest. All plants noted in the table as –08 or –09 Control were $T_2$ segregating progeny which did not exhibit the phenotype and did not contain the transgene (internal controls; Table 1-2).

Segregation frequencies of the plants under test suggest that each event contains a single insert, as calculated by a Chi-square test (Table 1-2 and data not shown).

The increase in the inflorescence number for the two events was much less than the increase observed when the 35S promoter was used to express this cDNA (data not shown). This evidence further supports our hypothesis that the degree of expression/dosage of the gene product is highly relevant to the strength of the observed phenotype. By using a promoter with a different expression pattern, we were able to keep the positive phenotype of the previously observed 35S phenotype, while removing the negative aspects of infertility previously observed. Of course, the trade-off is to lessen the positive phenotype, although keeping it significant.

TABLE 1-2

Quantitative phenotypes observed in p326F::cDNA 13499809 $T_2$ events (PIT = Primary Inflorescence Thickness)

| Event/Control | Number of Observations | Rosette Area ($mm^2$) | Number of Leaves | Height (cm) | PIT (mm) | Days to Bolt | Number of Inflorescences |
|---|---|---|---|---|---|---|---|
| ME04701-08 | 14 | 1241.8 | 6.0 | 42.1 | 0.99 | 17.8* | 4.3* |
| -08 Control | 4 | 1419.1 | 5.8 | 38.8 | 1.02 | 16.5 | 2.8 |
| ME04701-09 | 14 | 1620.0* | 5.9 | 40.1 | 1.01 | 16.8 | 4.8* |
| -09 Control | 4 | 996.5 | 6.0 | 40.4 | 0.93 | 16.6 | 2.8 |

*significantly different from control at 0.05 level, via t-test

Although all of the plants in this experiment had fewer inflorescences than the general greenhouse population, the plants were healthy. The transgenics had significantly greater number of inflorescences than the control, so the overall decrease - which was due to greenhouse conditions prevailing at the time of the experiment - in the number of inflorescences did not affect the conclusions of the experiment Lead Summary/Discussion:

Over-expression of Lead 28/cDNA 13499809 with an appropriate promoter results in an increase in the number of inflorescences. As this is a glycine-rich protein (GRP) there is a likely effect on cell wall structure affecting cell expansion or adhesion, different positioning of cell planes, and/or different opportunities for inflorescence initiation. It would be interesting to combine this gene with the gene encoding an unknown protein with an AP2 which also affects plant growth and development.

This polynucleotide/protein can be an especially useful one for controlling the number/rate of cell division in meristems without disturbing overall plant morphology. It can be developed in crops with an appropriate promoter to regulate size and growth rate of many individual organs.

|  |  | Event 1 | Event 4 | Event 5 | Event 7 | Event Average | Percent Increase |
| --- | --- | --- | --- | --- | --- | --- | --- |
| Plant weight | 1952 Transgenic | 1888 | 1423 | 1682 | 1523 | 1629 | 110% |
|  | 1952 Control | 1516 | 1471 | 1383 | 1559 | 1482 |  |
| Fruit weight per plant | 1952 Transgenic | 5892 | 3704 | 5131 | 5814 | 5135 | 105% |
|  | 1952 Control | 4746 | 4826 | 4601 | 5343 | 4879 |  |
| Percent red fruit | 1952 Transgenic | 40.1 | 42.4 | 36.5 | 47.2 | 42 | 107% |
|  | 1952 Control | 42.4 | 46.7 | 28.7 | 37.8 | 39 |  |
| Harvest index | 1952 Transgenic | 75.7% | 72.2% | 75.3% | 79.2% | 76% | 99% |
|  | 1952 Control | 75.8% | 76.6% | 76.9% | 77.4% | 77% |  |

Increased vegetative biomass can give an improved source:sink ratio and improved fixation of carbon to sucrose and starch, leading to improved yield.

More inflorescences gives the opportunity for more flowers and therefore more seeds. The combination of improved biomass and inflorescence number can give a significant improvement in yield.

Tomato Field Trial Results

Clone 1952 was transformed into tomato under the control of the plasmid p326. 4 independent transgenic events were selected for field testing. Results are shown in the following Table 1-3. On the average, there is an increase in total plant weight, fruit weight and percent red fruit per plant. Event 4 did not show an improvement in performance. If event 4 is not considered in the analysis the average plant weight, fruit weight and percent red fruit each increase to approximately 115% of control.

Table 1-3—Results from Tomato Field Trials

EXAMPLE 2

Lead 29-ME04717-Clone 123905-cDNA 12562634 (SEQ ID NO: 921)

Ectopic expression of Ceres cDNA 12562634 under the control of the 326D promoter induces a number of phenotypes including:

Increased number of inflorescences

Continuation of rosette leaf initiation after flowering to generate an overall increased number of leaves.

Misexpression of Ceres cDNA 12562634 can be useful to increase branching and the number of inflorescences. This can have a significant impact on seed number.

Qualitative Analysis of the $T_1$ Plants:

Using the 326D promoter, 9 of the 10 events produced rosettes with more leaves and more inflorescences than the control (Table 1). One of the 9 events also had fertility defects, much like what was seen using 35S::cDNA 12562634. The transgenic "control" was a set of plants expressing different 35S::cDNA constructs and which were indistinguishable from the untransformed WS wildtype. This method of scoring phenotypes is typical for our large-scale morphological phenotyping project.

TABLE 2-1

Qualitative phenotypes observed in p326D::cDNA 12562634 $T_1$ events
(2 events with the most advantageous phenotypes
were chosen for $T_2$ evaluation)

| Event | Increased Rosette Leaf Number & Increased Inflorescence Number | Fertility Defects |
| --- | --- | --- |
| ME04717-02 | x | x |
| ME04717-03 | x |  |
| ME04717-04 | x |  |
| ME04717-05 | x |  |
| ME04717-06 | x |  |
| ME04717-07 | x |  |
| ME04717-08 | x |  |
| ME04717-09 | x |  |
| ME04717-10 | x |  |

Quantitative Analysis of the $T_2$ Plants:

Events ME04717-03 and ME04717-05 were evaluated in greater detail in the $T_2$ generation. Eighteen individuals were sown and observed for both events. The transgenic plants showed an increased number of inflorescences to a 0.05 level of statistical significance. ME04717-03 also had significantly larger rosettes than the control. All plants noted in Table 2-2 as ME04717-03 and ME04717-05 were segregating progeny of the $T_1$ which exhibited the phenotype of interest. All plants noted in the Table 2-2 as −03 or −05 Control were $T_2$ segregating progeny which did not exhibit the phenotype and did not contain the transgene (internal controls; Table 2-2).

Segregation frequencies of the plants under test suggest that each event contains a single insert, as calculated by a chi-square test (data not shown).

It should be noted that the increase in the inflorescence number for the events documented below was less than the increase observed in the 35S::cDNA 12562634 events (data not shown). Other p326D::cDNA 1256263 $T_2$ events, not shown in this report, contained multiple inserts. Some of the $T_2$ progeny of these multiple insert-containing events exhibited some negative effects (fertility defects and dwarfing) similar to the $T_2$ progeny of the 35S::cDNA 12562634 events. This evidence further supports our hypothesis that the degree of expression/dosage of the gene product is highly relevant to the strength of the observed phenotype, By using a new promoter, and creating transgenics with a single insert, we were able to keep the positive phenotype of the previously observed 35S phenotype, while removing the negative aspects previously seen. A consequence of accomplishing this goal is a lessening of the degree of the positive phenotype, although keeping it at a very significant level.

TABLE 2-2

Quantitative phenotypes observed in p326D::cDNA 12562634 T₂ events (PIT = Primary Inflorescence Thickness)

| Event/Control | Number of Observations | Rosette Area (mm²) | Number of Leaves | Height (cm) | PIT (mm) | Days to Bolt | Number of Inflorescences |
|---|---|---|---|---|---|---|---|
| ME04717-03 | 13 | 2701.5* | 7.7* | 35.2 | 0.94 | 18.0 | 8.4* |
| -03 Control | 5 | 1086.9 | 6.6 | 32.7 | 0.99 | 18.6 | 3.8 |
| ME04717-05 | 14 | 1057.6 | 5.7 | 35.0 | 0.91 | 16.1 | 7.3* |
| -05 Control | 4 | 504.6 | 5.0 | 29.3 | 0.71 | 16.0 | 4.0 |

*significantly different from control at 0.05 level, via t-test
The decrease in stature and flowering time is accurate. The plants were healthy, but may have been flowering earlier than other plants grown in the greenhouse at that time. This is especially the case for the flat containing ME04717-05 and its controls. All plants were treated equally within the flat Our goal was only to assay for inflorescence number.

Lead Summary/Discussion:
  Ectopic expression of Ceres cDNA 12562634 under the control of the 326D promoter induces a number of phenotypes including increased number of inflorescences and more leaves.
  Misexpression of Ceres cDNA 12562634 can be useful to increase branching and the number of inflorescences. This can have a significant impact on seed number.
  There is also likely to be a positive impact on harvest index although it has not yet been measured.
  This gene/protein can be an especially useful one for controlling the rate of cell division in the meristems without disturbing overall plant morphology. It can be developed in crops with an appropriate promoter to regulate size and growth rate of many individual organs.
  Increased vegetative biomass can give an improved source:sink ratio and improved fixation of carbon to sucrose and starch, leading to improved yield.
  More inflorescences gives the opportunity for more flowers and therefore more seeds. The combination of improved biomass and inflorescence number can give a significant improvement in yield.

Tomato Yield Trial Results

Gene 123905 was also transformed into tomato under the control of the promoter p326. 4 independent transgenic events were characterized in the field. A number of independent events were originally evaluated and 4 were selected for further analysis based on expression of the gene, presence of a simple insert and the phenotype of the plants observed in the greenhouse. Homozygous T2 seeds were planted in the field in a randomized complete block design. Each event had a corresponding control line. Results of plant weight, the total weight of individual plants, total fruit weight per plant, percent red fruit per plant and harvest index are shown in the Table 2-3 below. The results indicate that events 1 and 21 had substantially reduced leaf mass while retaining yields comparable to controls. Hence, their harvest index improved. These events also had increases in percent red fruit per plant. Event 14 had increased biomass and yield.

TABLE 2-3

Tomato Field Trial Results

| Per plant | | 1 | 14 | 21 | 26 | average |
|---|---|---|---|---|---|---|
| Leaf/stem weight fruit | C5 | 1410.0 | 1537.1 | 1294.4 | 1564.1 | 1451.4 |
| | C5 control | 1866.4 | 1215.9 | 1738.8 | 1766.0 | 1646.8 |
| | C5 | 4300.5 | 4936.5 | 4122.5 | 4159.0 | 4379.6 |

TABLE 2-3-continued

Tomato Field Trial Results

| Per plant | | 1 | 14 | 21 | 26 | average |
|---|---|---|---|---|---|---|
| weight | C5-control | 4293.5 | 4608.5 | 4098.0 | 4877.0 | 4469.3 |
| Percent red fruit | C5 | 35.3 | 33.2 | 56.2 | 36.9 | 40.4 |
| | C5-control | 16.7 | 33.0 | 45.8 | 34.8 | 32.6 |
| Harvest index | C5 | 75% | 76% | 76% | 73% | 75% |
| | C5-control | 70% | 79% | 70% | 73% | 73% |

In summary, tomato plants transformed with gene 123905 tended to have more branches and leaves, and more fruit as compared to control.

Rice Field Trial Results:

Gene 123905 was transformed into rice cultivar Kitaake under the control of p326. Five (5) independent transgenic events were evaluated in the field in a randomized complete block design. The traits evaluated were tillers per plant, days to flowering, leaf angle, plant height, biomass in grams per plant, yield in grams per plant and total plot yield in grams, the results for which are shown below in Tables 2-4, 2-5 and 2-6. Each event resulted in an increase in the number of tillers per plant.

TABLE 2-4

Results from Rice Field Trials

| | Number of plants Plants | Tillers per plant | Days to first flower | Days to mid flower | Approx. leaf angle |
|---|---|---|---|---|---|
| 123905-1 | 1060 | 7.1 | 22 | 32 | 33.1 |
| 123905-4-6 | 200 | 8.2 | 19 | 28 | 45 |
| 123905-8-3 | 650 | 7.4 | 28 | 33 | 32.1 |
| 123905-12-3 | 300 | 8.9 | 22 | 33 | 38.6 |
| Kitaake control | 1200 | 5.4 | 22 | 31 | 31.2 |

Several events showed significant reductions in height. Event 8-3 showed an increase in height, biomass and yield relative to control. While generally lower in yield, and significantly reduced in stature, event 1 and event 12 produce biomass similar to controls indicating an increase in biomass density relative to controls.

TABLE 2-5

Results from Rice Field Trials

| | Plant Height (cm) | Biomass (grams per plant) | Yield (grams per plant) | Total Yield per plot (gms) |
|---|---|---|---|---|
| 123905-1 | 54.0 | 25.3 | 12.52 | 417.0 |
| 123905-4-6 | 37.0 | 19.6 | 7.82 | 116.5 |
| 123905-8-3 | 65.5 | 30.6 | 14.9 | 668.8 |
| 123905-12-3 | 48.8 | 23.3 | 10.02 | 312.3 |
| Kitaake | 61.2 | 26.7 | 13.59 | 537.5 |

Observations on Reduced Stature in Rice

Gene 123905 was transformed into rice cultivar Kitaake under the control of p326. Measurements were conducted to determine which internodes were reduced in length, where internode I is the uppermost internode and internode V is the lowermost internode. In events 1, 4 and 12 which have significantly reduced stature relative to control, internodes III and IV are significantly reduced in length, while internodes I and II are reduced only slightly or not at all.

TABLE 2-6

Results from Rice Field Trials

| | Plant height (cm) | No. panicle | Internode I | Internode II | Internode III | Internode IV | Internode V |
|---|---|---|---|---|---|---|---|
| 123905-1 | 89.0 | 8.8 | 35.2 | 20.0 | 7.9 | 3.0 | 0.1 |
| 123905-4-6 | 68.2 | 18.3 | 30.4 | 16.4 | 4.6 | 1.7 | 0.1 |
| 123905-8-3 | 111.6 | 9.8 | 38.4 | 24.8 | 19.8 | 10.6 | 0.8 |
| 123905-12-3 | 82.6 | 12.2 | 32.4 | 21.4 | 7.0 | 4.1 | 0.3 |
| Kitaake Control | 110.6 | 10.0 | 36.6 | 24.5 | 19.8 | 11.6 | 0.4 |

Observations on Germination in Rice

Transgenic lines 123905-1 and 123905-12-3 germinate 1 to 2 days faster than Kitaake control seed.

EXAMPLE 3

Lead 36-ME03195-Clone 679923-cDNA 13594332 (SEQ ID NO:98)

Clone 679923 in the Ceres soy cDNA library, contains cDNA 13594332, encoding a transcription factor similar to the *Arabidopsis* LEAFY PETIOLE (LEP) gene. This protein sequence contains an AP2 domain. The cDNA was placed into the Ceres Misexpression Pipeline because it was determined to be a putative ortholog of a known *Arabidopsis* gene (LEP).

Qualitative Analysis of the $T_1$ Plants:

All 5 events produced larger rosettes with slightly curled leaves with little to no petiole elongation, and very short inflorescences compared to the controls. These plants were also delayed in flowering time by several days and had no fertility defects (Table 3-1). The transgenic "control" was a set of plants expressing a different 35S::cDNA fusion and which were indistinguishable from the untransformed WS wildtype. This method of scoring phenotypes is typical for our large-scale morphological phenotyping project. After seed collection, it was also apparent that these plants produced a significantly higher number of seeds relative to typical mutants of their height.

TABLE 3-1

Qualitative phenotypes observed in 35S::cDNA 13594332 $T_1$ events

| Event | Large rosettes with curled leaves with short/no petioles, short inflorescences, delayed flowering time |
|---|---|
| ME03195-01 | x |
| ME03195-02 | x |
| ME03195-03 | x |
| ME03195-04 | x |
| ME03195-05 | x |

Quantitative Analysis of the $T_2$ Plants:

The original hypothesis formulated from the $T_1$ observations was that the 35S::cDNA 13594332 plants may have a significantly increased harvest index. Events ME03195-02 and ME03195-04 were evaluated in greater detail in the $T_2$ generation to test this hypothesis. Eighteen individuals were sown and observed for both events. Segregation frequencies of the plants under test suggest that each event contains a single insert, as calculated by a chi-square test (data not shown).

After detailed $T_2$ analyses, we determined the following regarding the transgenics (results below are statistically significant to a 0.05 level or better via t-test unless otherwise noted):

- Flowering time (days to bolt) was 5-8 days later than controls.
- Rosette leaf number at bolt was increased by approximately 2.5 leaves.
- Rosette area was 2-3 times larger than controls.
- Height was approximately ½ that of controls.
- Total seed weight was not significantly different than controls.
- Total plant dry weight was slightly greater for event −04, and no different than the controls for event −02.
- Harvest index was slightly lower than the controls.
- Twice as much seed was produced per unit height of plant than in controls. Details can be found in Tables 3-2 and 3-3.

TABLE 3-2

Quantitative phenotypes observed in p35S::cDNA 13594332 $T_2$ events

| Event/ Control | Number of Observations | Day to Bolt | Number of Leaves | Rosette Area ($mm^2$) | Height (cm) |
|---|---|---|---|---|---|
| ME03195-02 | 12 | 26* | 9.6* | 6735.43* | 18.63* |
| −02 Control | 3 | 18 | 7 | 1802.62 | 42.33 |
| ME03195-04 | 8 | 24.9* | 10.3* | 7758.16* | 25.06* |
| −04 Control | 7 | 19 | 7.7 | 2884.43 | 44.71 |

*significantly different from control at 0.05 level, via t-test

TABLE 3-3

Quantitative phenotypes observed in p35S::cDNA 13594332 T₂ events

| Event/Control | Number of Observations | Seed Weight (g) | Plant Weight (g) | Harvest Index | Seed Weight (g) per Unit Height (cm) |
|---|---|---|---|---|---|
| ME03195-02 | 12 | 0.375 | 0.73 | 53.25* | 0.0204* |
| -02 Control | 3 | 0.376 | 0.58 | 64.47 | 0.0090 |
| ME03195-04 | 8 | 0.431 | 0.8258* | 53.26* | 0.0171* |
| -04 Control | 7 | 0.397 | 0.6119 | 64.90 | 0.0089 |

*significantly different from control at 0.05 level, via t-test

Events -02 and -04 each had three T₂ plants which exhibited a much more severe form of the above-described phenotype. These plants were severely late bolting, had little inflorescence elongation, and were nearly sterile. From other experiments using these plant lines (data not shown), we determined that the detrimental phenotype is due to a dosage/homozygous insert effect, suggesting that hemi/heterozygous plants gave a beneficial trait of increased seed production per unit height, but that the homozygous lines gave the negative phenotype. Our statistical analyses compared the internal controls to the plants which contained the transgene and beneficial phenotype. All transgene-containing plants with the detrimental phenotype were omitted from the statistical analyses in Tables 3-2 and 3-3.

EXAMPLE 4

ME04012-Gemini ID 5000F6 (SEQ ID NO: 109)

ME04012 contains a genomic clone which encodes a putative Cytochrome P450. Plant line ME04012 was being assayed for drought tolerance when it was observed that 15/20 plants in event -03 showed a plant architecture phenotype. 6/15 were a weaker version showing only a wavy stem. 9/15 were strong and showed a wavy stem, decreased height and decreased branch and pedicel angles.

EXAMPLE 5

Lead 15-ME04077-Clone 92459-cDNA 12561537 (SEQ ID NO: 80)

Clone 92459 in the Ceres *Arabidopsis* cDNA library, contains cDNA 12561537, encoding *Arabidopsis* MADS Affecting Flowering 1 (MAF 1). The cDNA was placed into the Ceres Misexpression Pipeline because it is a transcription factor. Transcription factors are of particular interest because they can affect many genes simultaneously, and they therefore have an increased likelihood of producing an altered phenotype in *Arabidopsis* when overexpressed.
    Ectopic expression of Ceres cDNA 12561537 under the control of the 35S promoter induces a number of phenotypes including:
        Taller plants
        Thicker inflorescences
        Larger rosettes
        Increased rosette leaf number
        Delayed flowering
    Misexpression of Ceres cDNA 12561537 can be useful to increase overall plant size/biomass.
Qualitative Analysis of the T₁ Plants:
    All ten events were late flowering, produced larger rosettes with more leaves and tall, thick inflorescences compared to the controls (Table 5-1). The transgenic "control" was a set of different 35S::cDNA expressing plants which were indistinguishable from the =transformed WS wild type. This method of scoring phenotypes is typical for our large-scale morphological phenotyping project.

TABLE 5-1

Qualitative phenotypes observed in 35S::cDNA 12561537 T₁ events

| Event | Increased Rosette Size Increased Rosette Leaf Number | Late Flowering | Tall & Thick |
|---|---|---|---|
| ME04077-01 | X | X | X |
| ME04077-02 | X | X | X |
| ME04077-03 | X | X | X |
| ME04077-04 | X | X | X |
| ME04077-05 | X | X | X |
| ME04077-06 | X | X | X |
| ME04077-07 | X | X | X |
| ME04077-08 | X | X | X |
| ME04077-09 | X | X | X |
| ME04077-10 | X | X | X |

Quantitative Analysis of the T₂ Plants:

Events ME04077-06 and ME04077-10 were evaluated in greater detail in the T₂ generation. Eighteen individuals were sown and observed for event 06, whereas 17 individuals were sown and observed for event 10. The transgenic plants for both events showed increased primary inflorescence thickness, increased number of rosette leaves, a larger rosette, and delay of flowering time to a 0.05 level of statistical significance (Table 5-2). The plants of both events were visibly much taller than the controls, but only event -10 was quantitatively taller to a 0.05 level of statistical significance via t-test. If a greater number of internal controls were available for event -06, this event would very likely fall under the same degree of significance via the same test. Both events had normal fertility. All plants noted in the table as ME04077-06 and ME04077-10 were segregating progeny of the T₁ event which we had confirmed to contain the transgene under test. All plants noted in the table as -06 Control or -10 Control were T₂ segregating progeny which did not contain the transgene under test (internal controls).

Both events produce significantly more seeds than the control, as would be expected for a typical, fertile, late flowering plant.

Event ME04077-06 had 12 transgene-containing plants which exhibited the beneficial phenotype and 3 transgene-containing plants which appeared wild-type (these three were omitted from statistical analyses in Table 5-2). Event ME04077-10 had 9 transgene-containing plants which exhibited the beneficial phenotype and 1 transgene-containing plant which appeared wild-type. Our statistical analyses compared the internal controls to those plants with the beneficial phenotype which contained the transgene.

Segregation frequencies of the transgene under test suggest that each event contains a single insert, as calculated by a Chi-square test. The T₂ seeds segregate 3R:1S for both events (data not shown).

TABLE 5-2

Quantitative phenotypes observed in 35S::cDNA 12561537 T₂ events

| Event/Control | Number of Observations | Rosette Area (mm²) | Number of Leaves | Height (cm) | Primary Inflorescence Thickness (inches) | Days to Bolt |
|---|---|---|---|---|---|---|
| ME04077-06 | 12 | 7302.7* | 15.6* | 72.8 | 0.068* | 23.9 |
| -06 Control | 3 | 1666.3 | 6.7 | 55.9 | 0.046 | 18.3 |
| ME04077-10 | 9 | 9343.9* | 19.6* | 73.0* | 0.086* | 24.4* |
| -10 Control | 7 | 2696.1 | 8.9 | 52.3 | 0.053 | 18.6 |

*significantly different from control at 0.05 level, via t-test

Lead Summary/Discussion:
  The ectopic expression of cDNA 12561537 with a strong constitutive promoter (35S) results in taller plants, with thicker inflorescences, a larger rosette, and more rosette leaves.
  The increase in plant size seen by this expression is accompanied by a delay in flowering time, but no reduction in fertility.
  It can also be a useful gene to increase root growth, given the similar expression pattern in shoot meristems and root tip cells.
  Increased vegetative biomass can give an improved source:sink ratio and improved fixation of carbon to sucrose and starch, leading to improved yield.
  Taller inflorescences give the opportunity for more flowers and therefore more seeds. The combination of improved biomass and inflorescence stature can give a significant improvement in yield.
  Thicker inflorescences may prevent against "snap" against wind, rain or drought.
  Biomass advantage and presumed photosynthesis advantage should be useful in corn and soybean.
  This gene/protein can be an especially useful one for controlling the number/rate of cell division in meristems without disturbing overall plant morphology. It can be developed in crops with an appropriate promoter to regulate size and growth rate of many individual organs. The protein can be useful for creating sturdier stems in corn and preventing against "snap".

Tomato Field Trial Results

This Lead 15 (clone 92459) was transformed into tomato under the control of plasmid p13879. 1 transgenic event was selected for field testing. This event shows an increase in biomass, as shown below in the results of Table 5-3.

TABLE 5-3

Tomato Field Trial Results

| | | Event-13 | Percent Increase |
|---|---|---|---|
| Plant weight | 92459 Transgenic | 2042.54 | 120% |
| | 92459 Control | 1707.50 | |
| Fruit weight per plant | 92459 Transgenic | 4932 | 100% |
| | 92459 Control | 4956 | |
| Percent red fruit | 92459 Transgenic | 28.9 | 93% |
| | 92459 Control | 31.0 | |
| Harvest index | 92459 Transgenic | 71% | 95% |
| | 92459 Control | 74% | |

EXAMPLE 6

Determination of Functional Homolog Sequences

The "Lead" sequences described above in Examples 1-5 are utilized to identify functional homologs of the lead sequences and, together with those sequences, are utilized to determine a consensus sequence for a given group of lead and functional homolog sequences.

A subject sequence is considered a functional homolog of a query sequence if the subject and query sequences encode proteins having a similar function and/or activity. A process known as Reciprocal BLAST (Rivera et al, *Proc. Natl Acad. Sci. USA*, 1998, 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species $S^A$ is BLASTed against all protein sequences from a species of interest. Top hits are determined using an E-value cutoff of $10^{-5}$ and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species $S^A$. A top hit from the forward search that returned a polypeptide from the aforementioned cluster as its best hit is also considered as a potential functional homolog.

Functional homologs are identified by manual inspection of potential functional homolog sequences. Representative functional homologs are shown in FIGS. 1-5. Each Figure represents a grouping of a lead/query sequence aligned with the corresponding identified functional homolog subject sequences. Lead sequences and their corresponding functional homolog sequences are aligned to identify conserved amino acids and to determine a consensus sequence that contains a frequently occurring amino acid residue at particular positions in the aligned sequences, as shown in FIGS. 1-5.

Each consensus sequence then is comprised of the identified and numbered conserved regions or domains, with some of the conserved regions being separated by one or more amino acid residues, represented by a dash (-), between conserved regions.

Useful polypeptides of the inventions, therefore, include each of the lead and functional homolog sequences shown in FIGS. 1-5, as well as the consensus sequences shown in those Figures. The invention also encompasses other useful polypeptides constructed based upon the consensus sequence and the identified conserved regions. Thus, useful polypeptides include those which comprise one or more of the numbered conserved regions in each alignment table in an individual Figure depicted in FIGS. 1-5, wherein the conserved regions may be separated by dashes. Useful polypeptides also include those which comprise all of the numbered conserved regions in an individual alignment table selected from FIGS. 1-5, alternatively comprising all of the numbered conserved regions in an individual alignment table and in the order as depicted in an individual alignment table selected from FIGS. 1-5. Useful polypeptides also include those which comprise all of the numbered conserved regions in an individual alignment table and in the order as depicted in an individual alignment table selected from FIGS. 1-5, wherein the conserved regions are separated by dashes, wherein each dash between two adjacent conserved regions is comprised of the amino acids depicted in the alignment table for lead and/or functional homolog sequences at the positions which define the particular dash. Such dashes in the consensus sequence can be of a length ranging from length of the smallest number of dashes in one of the aligned sequences up to the length of the highest number of dashes in one of the aligned sequences.

Such useful polypeptides can also have a length (a total number of amino acid residues) equal to the length identified for a consensus sequence or of a length ranging from the shortest to the longest sequence in any given family of lead and functional homolog sequences identified in an individual alignment table selected from FIGS. 1-5.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad. Sci. (USA)* 85: 2444.
(11) Yamauchi et al. (1996) *Plant Mol Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA*, 89: 8794-8797.
(18) Hamilton et al. (1996) *Proc. Natl. Acad. Sci. USA*, 93: 9975-9979.
(19) Burke et al. (1987) *Science*, 236:806-812.
(20) Sternberg N. et al. (1990) *Proc Natl Acad Sci USA.*, 87:103-7.
(21) Bradshaw et al. (1995) *Nucl Acids Res*, 23: 4850-4856.
(22) Frischauf et al. (1983) *J. Mol Biol*, 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.*, 22:421.
(29) Christou (1995) *Euphytica*, v. 85, n. 1-3:13-27.
(30) Newell (2000)
(31) Griesbach (1987) *Plant Sci.* 50:69-77.
(32) Fromm et al. (1985) *Proc. Natl. Acad. Sci. USA* 82:5824.
(34) Klein et al. (1987) *Nature* 327:773.
(35) Willmitzer, L. (1993) Transgenic Plants. In: Biotechnology, A Multi-Volume Comprehensive treatise (H. J. Rehm, G. Reed, A. Püler, P. Stadler, eds., Vol. 2, 627-659, VCH Weinheim-New York-Basel-Cambridge).
(36) *Crit. Rev. Plant. Sci.* 4:1-46.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.

What is claimed is:

1. A vector, comprising:
   a) a first nucleic acid comprising a plant promoter of SEQ ID NO: 76; and
   b) a second nucleic acid having a nucleotide sequence having a coding region which encodes a yield associated protein encoding the amino acid sequence of SEQ ID NO: 97 or encoding an amino acid sequence that is at least 95% identical to SEQ ID NO: 97,
   wherein said first and second nucleic acids are operably linked, and
   wherein overexpression of said second nucleic acid in a transgenic plant increases yield of the transgenic plant.

2. The vector according to claim 1, wherein said second nucleic acid sequence is a nucleic acid sequence that encodes the amino acid sequence of SEQ ID NO: 97.

3. A method of increasing yield of a transgenic plant, said method comprising
   (a) introducing into a plant cell a vector according to claim 1;
   (b) generating from said plant cell a transformed plant in which said nucleic acid is expressed; and
   (c) selecting from a plurality of said transformed plants a transformed plant having increased yield as compared to a control plant that does not comprise said nucleic acid.

4. The method of claim 3, wherein said increased yield comprises increased plant size, vegetative growth, organ number, fruit, seed, tillering, and/or biomass.

5. The method of claim 3, wherein said plant cell is a rice plant.

6. The method of claim 5, wherein said rice plant has increased seed yield.

7. A plant cell comprising a vector according to claim 1.

8. A transgenic plant comprising the plant cell of claim 7.

9. Transgenic progeny of the plant of claim 8, wherein said progeny comprises the vector and has increased yield as compared to a control plant that does not comprise said nucleic acid.

10. Transgenic seed from a transgenic plant according to claim 8, wherein the seed comprises the vector.

11. Transgenic vegetative tissue from a transgenic plant according to claim 8 wherein the transgenic vegetative tissue comprises the vector.

12. A food product comprising transgenic vegetative tissue from the transgenic plant of claim 8, wherein the transgenic vegetative tissue comprises the vector.

13. A feed product comprising vegetative tissue from the transgenic plant of claim 8, wherein the transgenic vegetative tissue comprises the vector.

14. A product comprising transgenic vegetative tissue from the transgenic plant of claim 8, wherein the transgenic vegetative tissue comprises the vector, and wherein said product is used for the conversion into fuel or chemical feedstocks.

15. The transgenic plant according to claim 8, which is a rice plant having increased seed yield as compared to a control rice plant that does not comprise said nucleic acid.

16. A method for promoting increased biomass in a plant, said method comprising the steps of:
   (a) transforming a plant with the vector of claim 1;
   (b) expressing said second nucleic acid in said transformed plant; and
   (c) selecting from a plurality of said transformed plants a transformed plant having increased biomass as compared to a plant that has not been transformed with said nucleotide sequence.

17. A method for increasing the biomass of a plant, said method comprising expressing in said plant a nucleic acid molecule having a nucleotide sequence having a coding region which encodes a yield associated protein encoding the amino acid sequence of SEQ ID NO: 97 or comprising an amino acid sequence that is at least 95% identical to SEQ ID NO: 97, wherein said nucleic acid molecule is operably linked to a plant promoter of SEQ ID NO:76.

18. The method according to claim 16, wherein said nucleic acid molecule is a nucleic acid molecule that encodes the amino acid sequence of SEQ ID NO: 97.

19. The method of claim 3, wherein the transformed plants are selected for increased seed yield.

20. The method of claim 3, wherein the transformed plants are selected for increased tillering.

21. The method of claim 3, wherein the transformed plants are selected for increased biomass.

* * * * *

SEQUENCE LISTING

```
<160> NUMBER OF SEQ ID NOS: 222

<210> SEQ ID NO 1
<211> LENGTH: 1823
<212> TYPE: DNA
<213> ORGANISM: Arabidopsis thaliana
<220> FEATURE:
<221> NAME/KEY: misc_feature
```

<222> LOCATION: (1)..(1823)
<223> OTHER INFORMATION: Ceres Promoter 21876

<400> SEQUENCE: 1

```
gtctcttaaa aaggatgaac aaacacgaaa ctggtggatt atacaaatgt cgccttatac      60
atatatcggt tattggccaa aagagctatt ttaccttatg gataatggtg ctactatggt     120
tggagttgga ggtgtagttc aggcttcacc ttctggttta agccctccaa tgggtaatgg     180
taaatttccg gcaaaaggtc ctttgagatc agccatgttt ccaatgttg aggtcttata      240
ttccaagtat gagaaaggta aataaatgc gtttcctata gtggagttgc tagatagtag      300
tagatgttat gggctacgaa ttggtaagag agttcgattt tggactagtc cactcggata     360
cttttttcaat tatggtggtc ctggaggaat ctcttgtgga gtttgatatt tgcgagtata    420
atctttgaac ttgtgtagat tgtacccaaa accgaaaaca tatcctatat aaatttcatt    480
atgagagtaa aattgtttgt tttatgtatc atttctcaac tgtgattgag ttgactattg    540
aaaacatatc ttagataagt ttcgttatga gagttaatga tgattgatga catacacact    600
cctttatgat ggtgattcaa cgttttggag aaaatttatt tataatctct cataaattct    660
ccgttattag ttgaataaaa tcttaaatgt ctcctttaac catagcaaac caacttaaaa    720
atttagattt taaagttaag atggatattg tgattcaacg attaattatc gtaatgcata    780
ttgattatgt aaaataaaat ctaactaccg gaatttattc aataactcca ttgtgtgact    840
gcatttaaat atatgtttta tgtcccatta attaggctgt aatttcgatt tatcaattta    900
tatactagta ttaatttaat tccatagatt tatcaaagcc aactcatgac ggctagggtt    960
ttccgtcacc ttttcgatca tcaagagagt ttttttataa aaaaatttat acaattatac   1020
aatttcttaa ccaaacaaca cataattata agctatttaa catttcaaat tgaaaaaaaa   1080
aatgtatgag aattttgtgg atccattttt gtaattcttt gttgggtaaa ttcacaacca   1140
aaaaaataga aaggcccaaa acgcgtaagg gcaaattagt aaaagtagaa ccacaaagag   1200
aaagcgaaaa ccctagacac ctcgtagcta taagtaccct cgagtcgacc aggattaggg   1260
tgcgctctca tatttctcac attttcgtag ccgcaagact cctttcagat tcttacttgc   1320
aggttagata ttttctctct ttagtgtctc cgatcttcat cttcttatga ttattgtagc   1380
tgtttagggt ttagattctt agttttagct ctatattgac tgtgattatc gcttattctt   1440
tgctgttgtt atactgcttt tgattctcta gctttagatc cgtttactcg tcgatcaata   1500
ttgttcctat tgagtctgat gtataatcct ctgattaatt gatagcgttt agttttgata   1560
tcgtcttcgc atgttttta tcatgtcgat ctgtatctgc tctggttata gttgattctg    1620
atgtatttgg ttggtgatgt tccttagatt tgatatacct gttgtctcgt ggtttgatat   1680
gatagctcaa ctggtgatat gtggtttgt ttcagtggat ctgtgtttga ttatattgtt    1740
gacgttttgg ttgttgtatg gttgatggtt gatgtatttt tgttgattct gatgtttcga   1800
ttttttgtttt tgttttgaca gct                                         1823
```

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0668

<400> SEQUENCE: 2

```
atagagtttt actatgcttt tggaatcttt cttctaatgt gccaactaca gagaaataca      60
tgtattacca ctaggaatcg gaccatatca tagatatcag gattagataa ctagttctcg     120
tcgctatcac ttcgcattaa gttctagtaa ttgttaaaga ttctaatttt ttactaaaca     180
aaaactaaat caacatcaaa tatgcaaagt gtgtgttgtc cacacaagtg actcaaagta     240
tacgcaggtg ggattggacc atattattgc aaatcgtttc cgaaccactc atatttcttt     300 tttctctcc ttttttatc cggagaatta tggaaccact tcatttcaac ttcaaaacta      360 atttttggt tcagtgatca aatacaaaaa aaaaaaaaa gttatagata ttaaatagaa       420
aactattcca atcttaaaaa tacaaatgaa accataattt taatttatac aaaactatttt   480 aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt   660
ttcttctcag ccgtgtgtcc tcctctccta gccgccacat ctcacacact aatgctaacc   720
acgcgatgta accgtaagcg ctgagttttt gcatttcaga tttcacttcc accaaacaaa   780
actcgccacg tcatcaatac gaatcattcc gtataaacgt ctagattctt tacagcctac   840
aatgttctct tctttggtcg gccattattt aacgctttga acctaaatct agcccagcca   900
acgaagaaga cgaagcaaat ccaaaccaaa gttctccatt ttcgtagctt ctttaagctt   960
tttcagtatc atagagacac ttttttttttt ttgattagaa                        1000
```

<210> SEQ ID NO 3
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0535

<400> SEQUENCE: 3

```
ttagtgaaat tatgacatta agtaaggttt tcttagttag ctaatgtatg gctattcaat      60
tgttatgtta ggctatttta gttagtatat gaatttaggc agtctatgca aatgatttcg    120
ttttcatttt ttcatatgta aacatcaaga tcaagtaacg ccattcgagt tgatattttt    180
tttttaaatt agtgtgtgta aattttggac cgcttatttg agtttgctaa tgaagttgca   240
tatatattac gttaaaccat aggcaaacta atttgaaaca tccgattcga tttcctgtaa   300
tttttcttgg ttaattgacc aaaatcaaga tcttcagaaa taaaataaaa gacgaaagaa   360
agctgtcgca aagcagattg tgttaaaaaa aagtggattg ggctcaaacg caacttgtcc   420
agcccgtgac aattacccta tacgcaagta agagtaacgt atcactggca aaagttggta   480
ttagttacga tatctttgtc atgggggcat gcatgggcat ggcttaagag ttaagcctta   540
agaagagtcc cacactcgtg actctcatga tcacttgttg tttcttacgg gcaaatacat   600
ttaactttat tcttcattta ttcacctata ttcttttgga taataacttt tctctatata   660
aaataacaaa catcgtacgt ttcatttatt tacaacaagc gatgagaatt aaaaggagac   720
cttaattgat gatactcttc ttttctctcg gttacaacgg gattattaca gataatgata   780
atctatatgg atgctgacgt ggaaaaacaa aatttggtga aacacgtcaa ttaagcacga   840
cttttccatg gctagtggct aagatcgttt catcacatgg ctatatcata taatacttgg   900
atgaattcaa aataaacgac tgagaaaatg tccacgtcac ggcgcaccgc tttggactta   960
agtctcctat aataaataca acaccaaaca ttgcattcca                        1000
```

<210> SEQ ID NO 4
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0585

<400> SEQUENCE: 4

```
tgaagtcatt taatatgagt ttgacattag gtaaacctaa tctatgagat tatagaatgt      60
agcaaaacta tcaatgtttc ttttccaaaa tattttgtgg ttttctttt tggttcatta     120
tgttttgtta tttgtgaatt attttaatat gaagtaatta tattgatttt atatgatata    180
catattattt tgatataaaa tttaacactt atccattaaa atagcatggg cataatcaaa    240
atcgggacta ttacgatgaa aaagatagtt aaattgtatg ataaaataaa atgtgtaaga    300
ttaaaatttt gggttttaga aaattactaa acaaaatata gacaaagtat gttgactatt    360
atttaaaatt taaatatcat caataagata tagttaaagt cattaagtgt atagcaaaat    420
gaaaattcta agattaaaat tcgattaaaa ttttttttac taaattaaat atttaaaaat    480
agggattatc atttactatt tacaattcta atatcatggg taaaaattga taactttttt    540
taaacccgcc tatctaggtg ggcctaacct agtttactaa ttactatatg attaacttat    600
taccactttt acttcttctt ttttggtcaa attactttat tgttttttat aaagtcaaat    660
tactctttgc attgtaaata atagtagtaa ctaaaatctt aaaacaaaat attcaaccttt   720
tcccattatt ggaatggtaa tgtcttcaac accattgacc aacgttaagg aatgtctttt    780
aatattttg gaacctaaat gctaatactg tataccacaa tcacttatga gtattgaagt     840
tgagatagag gaggtacaag gagaccttat ctgcagaaga caaaaagcca ttttagcaa     900
aactaaagaa agaaaaaaga ttgaaacaca aatatgcgcc actcgtagtc caccctatc     960
tctttggcaa aagccacttc actcttttc cctttttat                            999
```

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0613

<400> SEQUENCE: 5

```
ttaatactaa cattgtagaa agccacaaaa aagaaattga aatgtgagta gatgctgagt      60
cagaggtttg gtcaatacac aacagctaat tgagataata ttatacacgt cacgatgact     120
tgttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactccctt agattttcct aaatttgttt tcctaacttg    300
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaggtca tgcaaaatta tctacgattt atctaaaatt     480
agataaatttg ccatatataa ctattaacta ataatcgatc ctttgatttt tgttttagat    540
aaaacgaaac agctatatct tttttttttg ttatcggatt ttaatcgaat aaaagctgaa    600
```

```
aaataacagt tatatcttct tcttttttaa ctaatgaaac agttatatct taaacaaaca      660
acagaaacag taaatatta atgcaaatcc gcgtcaagag ataaatttta acaaactaat       720
aacaattgag ataagattag cgcaaaagaa actctaatttt tagagcgtgt aaacacaaac    780
acgtcttgaa agtaaacgtg aattacacgc ttctaaaacg agcgtgagtt ttggttataa     840
cgaagatacg gtgaagtgtg acacctttct acgttaattt cagtttgagg acacaactca     900
agttatgttt gatatctaag gacttgcact gtctccaaat ctgcaggaag gacttttttga   960 ttggatcaat ataaatacca tctccattct cgtctccttc                           1000

<210> SEQ ID NO 6
<211> LENGTH: 351
<212> TYPE: DNA
<213> ORGANISM: Arabidopsis thaliana
<220> FEATURE:
<221> NAME/KEY: misc_feature
<222> LOCATION: (1)..(351)
<223> OTHER INFORMATION: Ceres Promoter PT0625

<400> SEQUENCE: 6
gatcatgatc agtttcaact cgctgtgccc acgtgtcgag agatcggcac gtgcctgagc      60
tctcagccgc tcataaatac acttgtttag tagcaacagt atactatagt agtcctctcc     120
tgtttggctt ttagcttgca tcgatggatg gatggatgga tcgcatgaga gggcttcgcg    180
aaggtacgga accttacaca acgcgtgtcc tttctacgtg gccatcgtgt aggcgtctcg     240
ccatgctacg tgtcccggag gatgtctcga tgccaaccct tataaatact gttccattcc     300
aatcccatcg ccacagccag tgcaaatctg atcgatcaag ataatcgagc a             351

<210> SEQ ID NO 7
<211> LENGTH: 1022
<212> TYPE: DNA
<213> ORGANISM: Arabidopsis thaliana
<220> FEATURE:
<221> NAME/KEY: misc_feature
<222> LOCATION: (1)..(1022)
<223> OTHER INFORMATION: Ceres Promoter PT0633

<400> SEQUENCE: 7
cccgatcggc cttaatctga gtcctaaaaa ctgttatact taacagttaa cgcatgatt       60 gatggaggag ccatagatgc aattcaatca aactgaaatt tctgcaagaa tctcaaacac     120
ggagatctca aagtttgaaa gaaaatttat ttcttcgact caaaacaaac ttacgaaatt    180
taggtagaac ttatatacat tatattgtaa tttttttgtaa caaaatgttt ttattattat    240
tatagaattt tactggttaa attaaaaatg aatagaaaag gtgaattaag aggagagagg    300
aggtaaacat tttcttctat ttttttcatat tttcaggata aattattgta aaagtttaca    360
agatttccat ttgactagtg taaatgagga atattctcta gtaagatcat tatttcatct    420
acttctttta tcttctacca gtagaggaat aaacaatatt tagctccttt gtaaatacaa    480
attaattttc gttcttgaca tcattcaatt ttaattttac gtataaaata aaagatcata    540
cctattagaa cgattaagga gaaatacaat tcgaatgaga aggatgtgcc gtttgttata     600
ataaacagcc acacgacgta aacgtaaaat gaccacatga tgggccaata gacatggacc    660
gactactaat aatagtaagt tacattttag gatggaataa atatcatacc gacatcagtt    720
tgaaagaaaa gggaaaaaaa gaaaaaataa ataaaagata tactaccgac atgagttcca    780
aaaagcaaaa aaaagatca agccgacaca gacacgcgta gagagcaaaa tgactttgac     840
gtcacaccac gaaaacagac gcttcatacg tgtccctttta tctctctcag tctctctata    900
```

```
aacttagtga gaccctcctc tgttttactc acaaatatgc aaactagaaa acaatcatca      960
ggaataaagg gtttgattac ttctattgga aagaaaaaaa tctttggaaa aggcctgcag     1020
gg                                                                    1022

<210> SEQ ID NO 8
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0650

<400> SEQUENCE: 8
catacttaat tctaaaaaaa caacacttat agtttataag cagctcttat gataaaaatc       60
tttctgagtt atagctctgt taaacttgta ttcaccccaa aaacggatgt ttcatttctt      120
attttttact tggagtattt tattgtaatt tgtaaaaaaa aatgtaaagt gggggatatc      180
atgaaaaaca acgtcacttt gtttggtcac aatatacatt tgataaaata atggtcgtcg      240
cgtgatttag ttgattttg ttttatcaac cacgtgtttc acttgatgag tagtttatat       300
agttaacatg attcggccac ttcagatttg ggtttgccca catatgacat accgacatag      360
aaggttaaat ccacgtggga aatgccaata ttcaatgttt ggttttcaaa agagaatcat      420
ttctttatat gatctcaaaa gtatggaatt gaaatgacta atgagcacat gcaattggtg      480
ctatcttaaa aaccgaacgt ctttgaattt aatttgtttt tcaccaaagg tacctaatga      540 aacccttttca ttaaaaaata aaggtaacaa acaaaatttt gtattggaaa aaacatttttt    600 tggaatatat aatttggtaa tagaattatg agcaaaaaag aaaaagaaaa gaaagaataa      660
tgagcataat aaagccttta cagtattact aattgggccg agcagttttg ggctcttgat      720
catgtctagt aatcttaaac agacgataaa gttaactgca atttagttgg ttcaggtgag      780
ctaccaaatc caaaaatacg cagattaggt tcaccgtacc ggaacaaacc ggatttatca      840
aaatccttaa gttatacgaa atcacgcttt ccttcgatt tctccgctct tctccactct       900
tcttctctgt tctatcgcag acattttttgt ttatatgcat acataataat aatacactct    960
tgtcaggatt tttgattctc tctttggttt tctcggaaaa                           1000

<210> SEQ ID NO 9
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0660

<400> SEQUENCE: 9
caagtcaagt tccaatattc taaggagaaa taatagtata ctaaacatac attagagagg       60
ttaaacttct ttttggattt aagtgtgtat gcataggcta tttattctta agtataacta      120
ttaactgtag ctagatttat acaagaaata cataaaactt tatgcatgtg aggtagccat      180
gaatatacgt acatgttgca atcgattata catgttgtat ttggatttct ctatacatgt      240
tttaacttgt cattctctaa gtatatacat accattaata ctgtgggcat gagtttatga      300
taagactttt cttttggaga ccagttttgt tttcctttcc acctatatttt gtctataggc     360 ttcacggtac actagtttac aagtgttttt atatgttcta aataaaattg agattttccg      420
```

```
gaacggtatg atctgtttgc aaataaggac gtatatataa cagtatcaaa tatatttgtt      480
gttataaggc aataatatat tttctgagat attgcgtgtt acaaaaaaga aatatttgtt      540
aagaaaaaaa aagatggtcg aaaaagggga gtaggtgggg gcggtcggct tttgattagt      600
aataaaagaa accacacgag tgacctaccg attcgactca acgagtctac cgagctaaca      660
cagattcaac tcgctcgagc ttcgttttat gacaagttgg ttttttttt tttttttaat       720 tttttcatct tcttgggttt ggttgggtca ctcttcaggt caggtgtgta aaaagaaag       780 aaagaaaaga gagattgttg tgttgtaacc cctttgacta aaatctaatg aacttttta      840 acacaacaaa actccttcag atctgaaagg gttcttcttc tctcttagtc tcttcgtcct      900
tttattctcc gtcgtcgttt catgatctga ctctctggtc ttctcttctt cttcttcttc      960
ttctattttt tcttacttcg tcactgttgt gtctgaac                              998
```

```
<210> SEQ ID NO 10
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0665

<400> SEQUENCE: 10
aaaaaggatg ggtaatggga cctatttcc ccaacatccc acatgcacac ttccctctcc       60
attctctcac atttatttct ttcattctaa tttatccatt ccgtgtgtaa catattcact      120
aataatctca tctcactaac tcattcattg attgtgatat gtttatctag aattagtgtt      180
ttaacactgt gtctacatat gatttccttt tcattgtatg tgaacatgtt aactcactaa      240
tcattttgta ttttcgagtt aacatgagtc tccacttcgg tagactaaag taaagatagg      300
tttgagtata ataaagttta aaatttgctt taaaatcaat atttataaat aagttttat      360 cataagtgat ttttgtatgt tatattggac cttgtataaa cagactacag aagaaaatta     420
tttatgagaa cttgtaatgt tagagtggac ctcgtataaa ctaattatgt gggcttttac     480
cataaactat ttatgaaaat tattatggcc cacaccacta taactaaagc ccacatattt     540
agcagcccag tttcattgta agagacatgt tcgctctgga actagaattt tctggttttt      600
gggtatttgt tttcttatgt gtagagaaat gatggtaacg attaaatgtt gtgtattaca     660
atttacaatg gtaagacgat taatatattt acacacaatt ttgttgttgc tgtaacacgt     720
tagtgtgtgt gatgatagaa tttcataaag ctttaactac gaggggcaaa atgttaattc     780
taaatagttg acagcagaaa aagatatgta tacataatat aaggattaaa acgtaaataa     840
taataaataa ggcgagttaa attaaaaccc tgttaaaacc ctagcttgaa acacatgtat     900
aaaaacactt gcgagcgcag cttcatcgcc atcgccattc tctctctcat caaaagcttt     960
tctccttgat tttcgcattc tttagagtct taacgcaaag                          1000
```

```
<210> SEQ ID NO 11
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0672

<400> SEQUENCE: 11
cagccgtaaa tcctccataa atttattttg caagttttgc tcattatata atgagcggaa       60
```

```
tttatgatat aatcgtttgt aataatgtta tgttttgatc aaaatttgaa attaaaagta      120
ggtgagaact tgttatacag tgtagataag gtggatcttg aatataaaaa taaaatttat      180
aagatgtatt taaagcagaa aagcataaaa ctttagataa aataatgtaa aaatgtgtta      240
gcatcaatgt tgggatattg gccgacccga acttaatcaa tgtcggaagc cattacttct      300
ctcccaaaag accttttttcc ttcggagaac taggaacttc ctcactacct ttcgcttaac     360
gtgaaagcca taaatttcat atattcataa aaatcagaaa atctaaaact gtttagtatc      420
acctgttttt ggtatagact attggttttg tgttacttcc taaactatat gatttcgtac      480
ttcattggat cttatagaga tgaatattcg taaaaagata agttatctgg tgaaacgtta     540
cttcagtcat gttgggtcta gattacata ctactatgaa acattttaag ataataatta      600
tcctagccaa ctatatgttc tatattatgg gccaagaaga tatagaacta aaagttcaga     660
atttaacgat ataaattact agtatattct aatacttgaa tgattactgt tttagttgtt    720
tagaataaat agtagcgtgt tggttaagat accatctatc cacatctata tttgtgtggg    780
ttacataaaa tgtacataat attatataca tatatatgta tattttttgat aaagccatat   840 attactcctt gacctctgcc cccatttcct tttactataa ataggaatac tcatgatcct    900
ctaattcagc aatcaacacc aacgaacaca accttttcca aagccaataa taaaagaaca   960
aaagctttta gtttcatcaa agacgaagct gccttagaa                            999

<210> SEQ ID NO 12
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0676

<400> SEQUENCE: 12
aagatagtac agtttcagtg ttttgagaaa aaaagctgaa ctaaaactaa aatgtttaag      60
gacacaatat ttagtttcaa ttagataatt caacagtttg aacaattttt tttttttttt    120
tttgaagtca tttatttata caatgtttta aaacgcatta agcatttagg cagccgacaa    180
acgcctattg tctaactgta aataggcgct tccacttagg ttcatattgc atatttacta    240
tatgtgtata gtgacaaaaa ccaatatttc tcttattttg gatgaaggta tagtagttgt    300
taaatgttca atataattaa gcattaatga caaataaaat aaaattaatt tagttgataa    360
aaagataatc ttataaaaag atcgatgaat agatataatg gttactgaa ttctatagct     420 cttaccttgc acgactatgt cccaaggaga ggaagtacct taactataat tctgaacata   480
attttgtcta tcttggtgag tattatatga cctaaaccct ttaataagaa aaagtataat   540
actggcgtaa cgtaataaat taacacaatc ataagttgtt gacaagcaaa aaaacataca   600
taatttgttt aatgagatat attagttata gttcttatgt caaagtacaa ttatgcctac   660
caaaattaat taatgatttc aacaggaagt ctgagatgat gggccgacgt gtagttacgt   720
ttcttgaatt gtgagagatg gtatttatta tactgaagaa aacattattt actaaataaa    780
ttttcatttc acatcttctg taatcaatgc gggtagatga agaagttgtt aatacgatgg    840
ccaaccatat ggatctcttt tttggcgttt ctatatatag taacctcgac tccaaaggca    900
ttacgtgact caataaaatc aagtcttttg tttccttttta tccaaaaaaa aaaaaagtc    960 ttgtgtttct cttaggttgg ttgagaatca tttcatttca                          1000
```

<210> SEQ ID NO 13
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0678

<400> SEQUENCE: 13

```
aattaaatga aaccgcccct aaattaggag ggatttgggt aagtggtaac acattcactg      60
gaaacatgtg aagaaaggag gatgtcaagt agctgaaaac tcagtatagt aaccaacggc     120
ttctcaccaa cctttcatta ataatttggt catccctata ttttattca acattttgtt     180
tttcaatagc ttagagcacc ttaataccct tcagtgtttt tttataaaaa aaacaaaaat     240
tgggattaat catcaatccc caaatgtaac gtttacttag attatgttca tttttctata     300
cacacaaatc atattctttt gttttaatct tcgaaaaacg agaggacatt aaatacccct     360
aaaaaaggag gggacattac taccaacgta cattaacatg tttgatagca aacgatttat     420
tttgttcgtt ttgaaaaggg gaaagtaatg tgtaaattat gtaaagatta ataaactttt     480
atggtatagt aacattttcg aataataaga gagggaaaac actcgccatt gtcggcaatt     540
tagaaccaat attagaaggg tttttttaga gaaaaaggac ttaaaagttt agagaccta      600
acaacaactt atttagaaat agacatgctt aagttgacaa cagcgagttt attttctata     660
tcgaagaaaa atacgaactt tttcttaatt agatttcgaa tgcatgcact atcgagaatc     720
gaccgtcaca agaaaaaact aatatacata ctgtacatat ctatattcaa tattggtggg     780
gatgggttta atgtgtattt ataattcatg gataaattca cacaataagg tccatgaaac     840
tagaaggtac caaaaataag cattaatgac tctttgccac ttatatatat gattctctca     900
tagtaccatt ttattctccc aaacctatct tcttcttcct ctcttgtctc tctcgctctc     960
tctcttctac attgtttctt gaggtcaatc tattaaaa                            998
```

<210> SEQ ID NO 14
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0683

<400> SEQUENCE: 14

```
gattgaatga tgagtgtgca cccttgtatt actaataaaa aatttagcaa cagttataag      60
ctaacgtcat ccatgagtca ttcattagat tcactatttg cgttctcaaa aatcgaattg     120
ttaaaatttg agaagctcta atatacgagt caatgagatg tggcaaaagc atgtccttga     180
ccataaaatt tcgaggggtc aactcattag ataaggacaa gaatcaacca attgaaggcg     240
tcttctataa caagtttctt tattactaat attaaagtcc aatggggtga ggggagaag      300
aacttaaata aaaggaaata attggtaagt gaataaaatc taaatacgat actagatgat     360
tgatttgtgc tagtgcatgg tattagatca gatatgtgtt actattcgaa ttcaaattgg     420
catattccat gttgttgata agaaaattgt agaagtgtaa aagctgagtt actatattca     480
aactagtggt ttacataaag tgagacaaca actgtttcac aaaaatgact ataaaatagt     540
aagtagtatt aggtcaattg attttaaaat tttaatcaaa ttcaaatttg tgatataatc     600
aaatttgttt atagaaaatg ttaagaaatc aatttttggca gaactaattc agtgagaaac     660
```

```
aatcatttac aaaaacaatt ttaacattat ttaacagtaa gatttgacat ttaacccgtt      720
cgtgtgaacc catcatatct aacatggctc tacccatgac gcctccatgc catggacaat      780
tttgacagat cagaagttct gaacgtggac gaggtaagaa caccatgatg atacgattgg      840
agttagttat gtcgccaccg acatcactgc caatctcatt aataaaagtg gtactaaatc      900
tctaatctct attaactata aatataacaa agaaccaaaa gaaagtttct tatctctctt      960
atctttcata atttccaaga aacacaaacc ttttctacta                          1000
```

<210> SEQ ID NO 15
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0688

<400> SEQUENCE: 15

```
acgttcagag gcatcgcttt tgtacaaatt gaagcgggtt tgttcaatat ttaaaataac       60
acaggaaaca ttcaaatgta ttattgatgt tgcttaggtt tgtgaaatga tatgaaccat      120
atcgtatata ttactagatt tttcttatat gttttaaggg tagtggggct gacctatcat      180
tctgtttggc attaccaatc agactatcag agtattcacc attcaggatt ccataactag      240
aaaaagaagg ggtttacatt ttctcatact gtataatttt ctactatcag agattttatc      300
gattacatta atctcatagt gattattctg atttataaaa aagttgacaa ataattaaa      360 accagtattt tataacaaga ttgtctctct cccatggcca ttattttgac ctctgactta      420
tttaaatctt aattaacagc ataatactgt attaagcgta tttaaatgaa acaaaataaa      480
agaaaaaaag aacaaaacga aagagtggac cacatgcgtg tcaagaaagg ccggtcgtta      540
ccgttaaggt gtgtcgaact gtgattgggc cacgttaacg gcgtatccaa agaaagaaa      600 gggcacgtgt atagatctag gaaaaaagaa agaatggacg gtttagattg tatctaggta      660
ccaggaaatg gaacgtcaca ccaaacggta cgtgtcggat cctgcccgtt gatgctgacg      720
gtcagcaact tccccttatt catgcccccc tgcccgttaa ttacgtgtaa cccttccatg      780
cgaaaatcaa accctttttt ttttttgcgt tcttcttcaa cttttctttt taaatcaaac      840
cttttctttt taaaatcaca ttgcatttcc taacgctcaa caaaatctct ctctactaat      900
atctctctct ctctctctct attgttgaag aagactcata atcggagatt gtttgttttt      960
ggtttgctct gtaaattgga gaagttttgt tagagatcaa                         1000
```

<210> SEQ ID NO 16
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0695

<400> SEQUENCE: 16

```
aacatttcct ttaacttact cttaaatttt aatagtaagt tgatgcatgt tatgttgatc       60
cgtcttgatc acaaatattg ttttatggac gaattctttg acagtaaatg gctatagtga      120
ctcagcttgg agcatcccga tatgaaaaca aagtgcagta ttgtgtcgtg gtcatcacta      180
acgcactttc ctagaactat cgcgcgtgtt tgacctatgc aacacaccag atgtcatgaa      240
```

```
cgtatactta aatagaaaca atgatataga caattggcta tattctgtca tggaacgcaa    300
accggataac atgtctatta gattcatcgg acttgatcat ggttatgtct aatagacga     360 attctttgtt aacgattggt taaaacggct cacgttagag catcctacta tgacttcaaa    420
attgataaat attacatgga aatcacttta attttagtta gaaggtagtt aatttagata    480
ttcttattta ataaattaaa aaatagaaga aaaaagatg agaagagttt tgtttataa      540 aataagaaat atcttttatt gtaattttaa aattaaacaa atttaattta tattaaaatt    600
atctttgttt tattgttaag gcaataatta ttttttggt gggaattgtt aaaacaataa     660
ttagtatact gttaagtggt cctttaataa taagataacg tgatttaaaa aagaacgaga    720
caggctaata tagtagagag gaaaaaatac aatttaggcc aataaagcc caatatagag     780 ttgtgctcaa acacaggtct tcgccagatt cctatgacg ccgtgtgtca atcatgacgc     840
caagtgtcat tcaagaccgt cacgtggcgt tgtttctaca cataggcgat ccatacaaat    900
cagtaacaaa cacgaaaaga gcattcatat gtacgaaagt agaaaagaag agactctttg    960
tgataaaact aagtaagaaa tagcataaaa gtaaaaggga                          1000
```

<210> SEQ ID NO 17
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0708

<400> SEQUENCE: 17

```
gtttccaaaa ctagtattct ttatttgctc tattcattat attttatat ttgtaacgtc      60 ccgaccgtct ttattaggtt tcgacaatca cttctcggaa ggtcgtccat cctgaaatta    120
ctctatccta aacatgttta actataaaat tctctcgaaa cttttgtaac gtatataacc    180
acataaattc tcttaaactt atttgcatac accattatat ttctgaaatc gatatgttac    240
aatattattt aatatttaga ttacttttac tgaatcgaat taaatatcaa atcgaaacaa    300
atctaatcta ccaaaaataa ttttgttata aacatttctt gcctagttct acctcatata    360
cattttagtt aaagaaagaa atcacaacaa ttcccataat tcaataatta aatccacaaa    420
atcttggagt aagtaagaga aataaaaaga tagtatctta acataaacaa ttcaaagatg    480
ctctctcaca caattcacac acacttacaa aacaaaagac agaaacaatg ttttcattca    540
aatcaaaaga agttataaca ctagtacaaa aaaagctcaa attctaatag taactctttt    600
tatttcccaa ttacccaaag attctctctc acttcacaaa actagctttg agagtcgtgt    660
tccacaaaat ccattaaagc tgaaacggtt ttgctcacca ttcaaacaaa tacaaaattg    720
caaaacccca aattataaca aaataatata aaaattaaac cgctaaaaag agtgaaccaa    780
caaaaatcgc cgaatgtgtg tgtaatgaga aaaccgaccc atcatcccaa tcatctcttc    840
ccgtgtcact ctcttcctct cccacgtttc ttctctcttc cctttatggg ttttaacttc    900
tccttcttct tcttcttcaa tcttcagttt tcaaattcaa caacaattca cattttgatt    960
tcttcatcat ctctctctct ctcgcttctc tctcaaatcg                         1000
```

<210> SEQ ID NO 18
<211> LENGTH: 1000
<212> TYPE: DNA
<213> ORGANISM: Arabidopsis thaliana
<220> FEATURE:
<221> NAME/KEY: misc_feature

```
<222> LOCATION: (1)..(1000)
<223> OTHER INFORMATION: Ceres Promoter PT0710

<400> SEQUENCE: 18
tagtgcgcgt ggggagaggg aatggtgaaa ccttagtggt taagttatga ggaaaatgat     60
aaaaggataa aacaatcaaa tgcagcttga aacggccata acataaagta ccttatggtg    120
gtgcgaatat ttttgtgttt ctttcactct tttattgctg aaagctacga cacttgtctt    180
aatatattgt ttccgcaagt cacatgatct acttttttatt taacgtctag aaacgccgag    240
atatatgatg attagtatat cacgtctatg caaattgtta gttcgtgttt ggccaaaaga    300
tatcgagaca tgtctgaaga accgagtctg gttttgagat atttcttcaa gcattactat    360
acaatagaaa aaggagacac gcgaatatga taatagcaaa aggcataaaa aggcgaaaat    420
taaagaaaaa cgtaaagtga tttggcctca atcaacggga acgtatctta attttagagg    480
ttcttctttt acttttgaga cgagagagtt tgcgtctttg cgagctgctt tggttgacta    540
aacattatca tattgaaaac caaaatacaa cggaggaata tttgtcacag tttcactttc    600
acattgtttc cttaacgttt aatcaacctt gttcaaaatt tctatagttg taatcatcat    660
tgtttacaaa attttcgttc aaagatgatt ttaaataaaa ttgtgaaaga aaacctttc    720
tgaaataagg attggatgat agtgttaaaa gaaaaatatg aactgaggca aaaagaggag    780
tggtccccgg aagattgtga aatgtgtcat ctaaaccagc cagacgtagt cacgtgttct    840
ctctagctt atgaacttcc ttagccagca ccatcattgt gattgtagta tatatgtaac    900
cctaccttca tctctcccat tttccattct ccatatagac tcctttacaa tatacaaaac    960
ctatccaaaa gcgaagaagc caagcaaaca tattataaaa                        1000

<210> SEQ ID NO 19
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter PT0723

<400> SEQUENCE: 19
gtcatatctt atcaacacgt caacgatcaa aacctttagc ctattaaatt caacggctta     60
gatcaaaacg aaactaggtg ggtcccactt ttaatatcgt ggctgcataa catttcctcg    120
ataactgaag ccgttgtggt ctttctcaga atctggtgct taaacactct ggtgagttct    180
agtacttctg ctatgatcga tctcattacc atttcttaaa tttctctccc taaatattcc    240
gagttcttga tttttgataa cttcaggttt tctcttttg ataaatctgg tctttccatt    300
ttttttttt tgtggttaat ttagtttcct atgttcttcg attgtattat gcatgatctg    360
tgtttggatt ctgttagatt atgttattgg tgaatatgta tgtgtttttg catgtctggt    420
tttggtctta aaaatgttca aatctgatga tttgattgaa gcttttttag tgttggtttg    480
attcttctca aaactactgt taatttacta tcatgttttc caactttgat tcatgatgac    540
acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt ttgctgattt gcgactgttt cattttttct    780
caaaattgtt ttttgttaag tttatctaac agttatcgtt gtcaaaagtc tctttcattt    840
```

```
tgcaaaatct tcttttttt tttgtttgta actttgtttt ttaagctaca catttagtct    900
gtaaaatagc atcgaggaac agttgtctta gtagacttgc atgttcttgt aacttctatt    960
tgtttcagtt tgttgatgac tgctttgatt ttgtaggtca aa                      1002

<210> SEQ ID NO 20
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter PT0740

<400> SEQUENCE: 20
tgtggccact aaagatttac ccttaaccgg gcccatataa gcccacgtca agtggcgctt     60
atacgctctc cgtaagagag ccaacatttg gtatgtaatg ttgcaaatta ttcttcaaga   120
caataaattc aaatataatt caatattgtc caaatatagt gatgtacttc agttgtgcac   180
atagaaactc cactaaacca acttttagat agatgcattc acaaattttc aacaatgtcg   240
cgaaagtcta atccatcacc agattctaac attttaatta ttatatttaa ctatacatac   300
tctaatcagc atgagtcaaa cgtgtacaat agcccaagca tataataaga ccaaagtcaa   360
actcaaataa atgtctccaa actcaaaact tgaaaagac ctaattatta catggtagat   420
atgactttgt cgacaagtaa accaactaat cctcgaagct accttctctt cccagttatt   480
atgtgtgatc gatttataaa tctcttcttc taataacacc tatattttc ttatgatgtg   540 aataaatata aaacttttaa ctttaaaaca tatttatccg aaatattgca cttagatttc   600
aaatagataa ataatagtac tatctaactg atattgaaaa gacctaacac ggaaaacagt   660
tttataaaaa atcccaaatg tgggtaatta tcttgatttc ttggggaaa cagaaaatgg   720 attaagatta atcggagtcg tgtcaagcag ctcgttaata actgtagcaa gttgactgag   780
taagcatcaa cgtgtcatct ccgtaaagcc cattatttct agtctcgccg cgtcttctct   840
tccacgtagc acttcacttt ttctctcctt ttgtttcctt tggaacacaa acgtttctat   900
ttataggaat aattacgtcg tccgtatctg tgtcggaaca tagatccaaa ttaaaagcga   960
cttacttaat tacatatcgt tcgtgttttt ttcttcaaaa a                       1001

<210> SEQ ID NO 21
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PT0743

<400> SEQUENCE: 21
tcgattggcc cgatcggccc caaaatcaag ctgagccgct tcaaacttca gcttttgaaa     60 tcaccccaa actcatgtcc tcttatcatt ataactaaag gatctttcat tttatttaac   120
tcatcgtctt gcactaccca acccaaaggt tccaactata cccgaagctt tctaaaggtc   180
caaagacttt ttttttcgag ccagactatt caagccaaga aaagccaaac cccacaagcc   240 agtactttc aattccatat tataaaactta tctgtcttgt tttagtccca ctaaaaacaa   300
cagaatttaa tttaggttga gctaaaaccc ttgacaaaag tgtatagtcg tcgattcagt   360
agcacactca tcactcatca gatttgatag ttgacctaaa gtatgactac tccatttcaa   420
ctaacaaatg aaaataaaag agacctaagg gttagaggat tgaaactata ctctcaagtc   480
```

```
ttttatcact aggctactac cagctagtta acttgatgga tttaagcaag aaaacgtaga      540
atttatattc gagcagattg tttagctaaa aaagcttggg tttgaaattg ccttttctcc      600
catataagca cgtcggttcc taaataactc tttctagcgg agagtgtctt tccaataatt      660
taataaaaat ggtgtttgta tatcaaaaaa aaagaaaaa agaaactgat cgagatagaa       720
cgtttgcagt tttataaaca atttaaaaaa caaaaaaaat taaactcaat gtattttta       780 ttaattcaca acaataata aatcatagga tcgaatattt acacggtatc aaaacctact      840
cgccgctact atataaaaat tgaagtcaaa tatcaaccgc aattattaaa ccagcaagac     900
aataattcat aaacttaata taaacataaa taaattaatg ttacacaacg atatatggtg     960
agggttatta ctatcttctt cctctcaaaa cacatctcct aaccttaagc tttagacggc    1020
ctgc                                                                 1024

<210> SEQ ID NO 22
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0758

<400> SEQUENCE: 22
agctagccac atcagtgacc aaaaaagata attaacaaac caaataaaat aacaaatttt      60
gatcatttgg aataaaattt ataaaaggaa cgaaagcgcc ttctcacggg tcccatccat     120
tgaaatatat tctctctttt tgctctatat aataataacg cgtactaatt tgtagtatat     180
attattacaa agtcgatatt tgattgtttt gtgaacgttg atatattaat tttcttggat     240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgattta    480 aatattagtt tttgttgtaa agagatcatt atatatgtct gtaatatttt tatactgagt   540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt   780
ttcgcatgaa aatatgaaag gagagaaatt tattattgtc acttatatat atatacatcg    840
taatcatttt ttcgtgaata attctctctc ccattccatt atttctcagt atctctcttt    900
ctttccctta ctttattgtt gcttttaaac cttcaatttg ctcataaacc aaatatataa    960
tatcaaaaca aacaaacaaa aaatcagaat tcccctaata                         1000

<210> SEQ ID NO 23
<211> LENGTH: 921
<212> TYPE: DNA
<213> ORGANISM: Arabidopsis thaliana
<220> FEATURE:
<221> NAME/KEY: misc_feature
<222> LOCATION: (1)..(921)
<223> OTHER INFORMATION: Ceres Promoter PT0829

<400> SEQUENCE: 23
```

```
aaagttttga attattggga atcaatttcg aagttttgta attctttggg ggctaatagg    60
atattttatt ttcttggttt cgtctattgt tgtttttcta tttatggttg ggcttttaga   120
actctggaca ggcccatgtc atatgttttc ccttctcctt atattttta ttttcattt     180 tgttaaatta atgcataata tccaaaaaca atttaaattt ttgaaggaac cctttagtta   240
cggctccgaa gctttcacaa gtgagaatgt gagatcaaag aaggcaaatg gaggatttta   300
aaagttaaaa tcatcttta tctgcaaaag ttgacaattt ttttgtatca aatctaaatc    360
atcaaactct cttaaactac aagagcataa caacctctat gtaatccatg aaataatctg   420
cttgaaggac ataacataaa tcattatggc tagagtgact aacttcaatc aaatcctctt   480
aactctagct cccttacaat ggtatcgtaa acattatgc attagggatt gttgtcctag    540
gaaaataaaa taaaaatccc cacagaccaa ctaccatttt aacttaaaaa taagcttcgt   600
ccgcgacgaa ttgttttcca tcctaaaaat agaatggtgt aatctgctaa tggtttagtt   660
ccattaactt gcaagttcta ttgaaagcct aaatgtcaat aaagatatta aaattcggag   720
tcaaaagaca aatgaatcaa aagcaacaag acaagtcagc tccattcttc actacccatc   780
ttttacaata aatcatctct cttttcacaa atttcaaact actctcattg cccttagct    840 ttgttataga gccaacacta cagagagact cacacacttg tttcaataat taaatctgaa   900
tttggctctt cttataaact a                                             921

<210> SEQ ID NO 24
<211> LENGTH: 763
<212> TYPE: DNA
<213> ORGANISM: Arabidopsis thaliana
<220> FEATURE:
<221> NAME/KEY: misc_feature
<222> LOCATION: (1)..(763)
<223> OTHER INFORMATION: Ceres Promoter PT0837

<400> SEQUENCE: 24
aactacaagg gagacataat atcaccatct ggttcctgtt atcatctgaa gatttcttgt    60
tttaccttcc agtgataaaa tgatccttat aatacatata gatatattaa attgctgtat   120
tttaagatta tagatatata aggtacatga gagtgtttat ttaaaaaat tcacttggaa    180 ttcatgtttt gtgatacgtt agattggaat ccatttggga aaagaagaat catctgttct   240
tatgtctcaa atttgactt cattcacttt tcttcttgtc ttttaagaaa gcttccacaa    300
tctaactgtt cgatgtgaaa actgagattc gagtaagaaa atgtgaactg tgttatactg   360 tttttttaatt agataattta gattgcactc agataaatta ataacattcc tcgaatactt   420
ttatgtgatt ggatatatta ggtatatctg ccaaccaacc aataaactgc tatgtttaaa   480
caaattaaat aaattagtat atgtttactc aagaataaag aagatagaaa agaaaattct   540
atatgagcta aatttgctgg aggaggcatc ggacgtgggt accagacctt tccaagcaca   600
cgagtagtgc ttagccatgt catgctaaca tacaccattt ggttcataca aaatccaaat   660
caaaatctat ttttaaaatc ttttgcacac gtctttgaaa acacctctc atactatagc    720 tacggaagct tcaatttcaa ggtttgtcta aaagctaacg att                     763

<210> SEQ ID NO 25
<211> LENGTH: 751
<212> TYPE: DNA
<213> ORGANISM: Arabidopsis thaliana
<220> FEATURE:
<221> NAME/KEY: misc_feature
<222> LOCATION: (1)..(751)
<223> OTHER INFORMATION: Ceres Promoter PT0838
```

<400> SEQUENCE: 25

```
atactggtat gcttaaggtt gaagccaaga tctctgtctt acccaagtaa ccactttcta      60
ttagaaggga tcaacactaa gaatatggag atttaagcct aagggctaag gcggttctca     120
acaatacatg atgtgaatac aatcacagac gatttactga ggtttgttga taagatcttg     180
atcagtctct gcatcatctg ttcaacaatc tcaatctttg actgtttgct ttcggagcca     240
taaacagagg aatcccttat tccctgttat aggagcaata caccaagtat tatttccatg     300
gctgaaattc tcttatggaa acctaattgt tccattgaag ctgtaaaatc gaatctggtg     360
aatattctcg agcaaagccg catgctaatt atgtcaattc agaagagttt gattaggaga     420
ctcgaagcga gtttgatgat cttcttgat gttcaactcc gattgtaagg gtataattga      480
cttttcatgt attacggctc caccacctga cactaaggca ctctttgtcc atctcgttgg     540
tatcatcgga ttcggatggt aaaaataaaa agagcagagg aaacttgtta ctcatgcaag     600
cttctcaggt gccacgtcac tccattacgt gtcatcttca cacaccatct cgctcaaaac     660
cgatctcatt tttcaaacct taaaggcaga agcaactgat taagttaaca ctcttgagaa     720
gctctcgatt aagcttgaac ttggaggatc a                                    751
```

<210> SEQ ID NO 26
<211> LENGTH: 669
<212> TYPE: DNA
<213> ORGANISM: Arabidopsis thaliana
<220> FEATURE:
<221> NAME/KEY: misc_feature
<222> LOCATION: (1)..(669)
<223> OTHER INFORMATION: Ceres Promoter PT0848

<400> SEQUENCE: 26

```
tctctttaaa tcagttaact aaccgtttat atatttacga taaggtttga agagattatt      60
gataaaataa tacatttcat aatcccgcgt tcaaccgttt aaagtaacat ttaagttgac     120
tatatctaat ttttttttcca ttaaatatgg agctggtaaa ctttatcaac ttctaaaaag    180
tgtaacaaca aaaattaggt caatcacaat tctgttttttt ttattatttt ggattgactt    240
ccaattgcaa atagtcttag tgatcaccat tatcatacat atatacatca agtaggtttc     300
atcatgatat accacaaagt atttgacaag ccatatggtt ttggatcaaa aagtcggtcc     360
aaaattaatg ttttatgtgc aagaaccgac ccattgtaca cacgtgttaa catcttcaag     420
actttcatct ctattttttct tttggtcatt aagatacccca ttgatccgaa tctgttacat   480
tcccacctac ttttttaatt tttactatcc actccaaatt aaacacaacc gatgattta      540
ataattggaa gcttttaaaa atatttcaaa acaagcctct tgtgtttgt ctatatatat      600
acacgtaata agaaggtgaa tgaatctcac agcttacttg ttctaaggct tccaataacg     660
aaaacagta                                                             669
```

<210> SEQ ID NO 27
<211> LENGTH: 702
<212> TYPE: DNA
<213> ORGANISM: Arabidopsis thaliana
<220> FEATURE:
<221> NAME/KEY: misc_feature
<222> LOCATION: (1)..(702)
<223> OTHER INFORMATION: Ceres Promoter PT0863

<400> SEQUENCE: 27

```
cgggaaacga caatctgatc tctagtccag tcgattggcc cgatcggccg attataaact      60
```

```
tacatgagac aagtataaat aattattata aacttattaa gtttaagatc aaggctttg      120 tgcaatgtat caatgaatgt tagatgtgat atgatgaaag caatgtttta aacacataca      180
tagtcattga tcggaatgtg tgttattaga aatgcatgcc taagccgata gggttatcta      240
tgtttggtct tggacattat agccaaattt cgaatctaat tcttccaata tatatttttt      300 ttttttttgct tagggccact actagtattg cttatcaatt ttaagagctc atgaaaatgc     360
aacaatatag tagttgcaaa tccttgtttc aagagaaatc aaagggccac ttgtgaattg     420
aataataata atatttgcaa ataacctttc actaaaccat accaacaaaa ccacacagat     480
ttggcaaaga cataaccttt gggagacgtg aaaaggctca aaatttgaca attgtcctta     540
caaattcgct cattagtgca attgtgagat ttgtttgcat ccaaatccaa ttcataactc     600
acactcgtct caaattcgaa aaggcctgca gggccagtgc actgggatcc aacaatgtcc     660
tccgactcgt ccaagatcaa gaggaagcgg aaccgcaccg cg                        702

<210> SEQ ID NO 28
<211> LENGTH: 435
<212> TYPE: DNA
<213> ORGANISM: Arabidopsis thaliana
<220> FEATURE:
<221> NAME/KEY: misc_feature
<222> LOCATION: (1)..(435)
<223> OTHER INFORMATION: Ceres Promoter PT0879

<400> SEQUENCE: 28
ttctaggaag actggtcaag ctaagctgtt tctgttttt gttttgtac tttactttt         60 gtttgctagt gggaactggg tttattgggc cttgaagttg ataaaagatg aataaaagac     120
atatcgccta aagcccatat gagaagcaga agacaaaaac ctccaacttt gggcataaat     180
tttgattata gttaaaagtc cagacccaat ttggcacctg gcttagttac gattctaagg     240
catgacacct gcctaatatg tttattacag aaaataaaga gaatcagcta ggtgtccctt     300
attgaacaca ttaacaaact ccaacgacac tacgtgtctt cgtgactctt actatatcca     360
aaaacctata gctaaagctg aattttccat gattagtata gtcccaacca aaaaaatact     420
gaagaaggca taagc                                                     435

<210> SEQ ID NO 29
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres Promoter PT0886

<400> SEQUENCE: 29
agtgtatttg aaaacgacat tgaagaatta atatattttt ttttaatttt agttttttat      60
agtacaaata ttaaaacaaa caatcctacc atatcataac atttgtaaat aacattttaa    120
gttttgtttt gagttttaat taatttttcta tgacaaaaaa atgaagtcaa tagactaagt   180
gaatcatata gtataaataa acacaattta aatagtttca aataaattta gaaagaataa   240
aacaaataga aatcagaagg tgtctgtttc ctcctcgcaa catacgatca aagagaaaca   300 acttgacccct ttacattgct caagagctca tctcttccct ctacaaaaat ggccgcacgt  360
ctccaacctt ctcccaactc cttcttccgc catcatc                             397

<210> SEQ ID NO 30
<211> LENGTH: 1024
```

```
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0007

<400> SEQUENCE: 30
agcagaacaa ctatatttat tgtgtcacat aaatctgaga tcatttataa ccaccaaaga      60
acctatacac agtaaatgac aaatgtatct ccctctatct ctattgccca tatgtagatg     120
ctaaagtaag atttctcttt tttttaatgt acttttttt gtataaagta tattccataa     180
gaaaaaggaa aagcttgttt atggatcaat tgaccccaaa aaagttttt agatcaaagc     240 ccaatataaa aaaaaacac agtagtgaca caaggaact taaataaacc atgaattgat     300
ctataaacag tagagatcga taaggcgaac attttccatg tgaagtgtct tctttcatct     360
ataatatttt tgacatccaa taatttcctc tataatatca ttcacataat tgatagaaac     420
attatgttag aattgtccac atcatttgag ctgtaatata ttctgtttta acaaattata     480
tggtagttgc ttaatcttat gtccatcttc ttctatgcat cgttttcgcg cctagttgtc     540
cagtccattt caactaccta cctctaattc ttatcttaaa acaacatttt ttaatttaag     600
tattatgctc aaagactaac tagatagaaa accgttatta aacattaaac gaattaaaag     660
tcttacatgg aaaatgtagg tttataaacc acgagttatg attgacaata aaaaaaatgc     720
aaatcatcaa tcaaaagaga cttgagtgcg actctatatc aaccattgca attaaaatta     780
tctatcacaa aaattttaga cagattaagt taatttagtc taaattcact aatttatttt     840
ctataattag taattaacta tatttattta tttacacatt ttctgataat ttagaaattt     900
gcatgaataa caaatataag attttggaaa ttagtagcaa atttaattaa taattatttt     960
tgcctaaatg aaccaaacta taaaacctcc acatacacca gtcatcaaat ttacagagac    1020
aaca                                                                 1024

<210> SEQ ID NO 31
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0008

<400> SEQUENCE: 31
ctcgagagat gaagtcttag taatgtttga acaaacaata atcacgtttt ccatcaaatt      60
cgagcattta agtttatat tactacatgc cccaagatga taccgtccat ctcatccgaa     120
aatatttctg aaattgcgct aagacaacaa tgtttgctca aattcgatca tttaaagttt     180
acaaatctct catcaatctt acaaacttct cacactaaac agaggtacat atttcttat     240 aaagacaaaa ggttcgaaca gctggcttct caactcgagt tgtttgtcag ggcctctctt     300
cactaactac aagttggtac ttcaaatatt ggtggctagc ttcacgtgat attgtctaca     360
aattaaaccc atgaaaaagc tgcattaatt gttccaagtg aaccctgagg agtgtcaata     420
gtctttgctt tagtgtgatc attaaaccaa atctctaaat tcctaatttg tactaacatt     480
tggaacgtat ttcctactct tctccctgct ccaactccca aaaataagat tagttagatt     540
tctataacta atatacatgt atactcccaa aaacagtaaa accatattaa taaagctaat     600
tttgcataga tttatttcgg taaaccggcg gttcaagttg gggaaaaaaa agacaaacgg     660
```

-continued

| | | |
|---|---|---|
| tctaaagtca tccaaagaca aaaaaccaaa gacaagttga gagagacgag accaatcaca | 720 | |
| acattgcttc gtagattgcg tgacatcatc cttgacggct actttcattt gtgtcttatt | 780 | |
| tggataaaac gcacgtgttt aattcacgaa ccttcatagc aataagaaat ttccattact | 840 | |
| ttcatatttt caactttttt tattacccat tacatgctta aaatattaat tcacaagtct | 900 | |
| ttgtcaaaat tcaatatttt ccaggttcat gaaccctttt tatctcaatc tactctataa | 960 | |
| tatctcccta taaattacaa caaaacctct ttattttca | 1000 | |

<210> SEQ ID NO 32
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0019

<400> SEQUENCE: 32

| | | |
|---|---|---|
| gatataagta gaatcatttt ttgccgccgt ttctcgctaa cacaccgaaa actgaatcaa | 60 | |
| atctcctagc tcttctacgc aaaatcgagt gcatcgacaa tggcggaacg tggtgtcgaa | 120 | |
| cgtggtggag atcgcggcga tttcggacgt ggattcggtg gtcgcggcgg tggaagaggt | 180 | |
| ggtccgagag gtcgtggtcg ccgtgcaggt cgtgctccag aggaggagaa atgggtgcca | 240 | |
| gtgactaagc ttggtcgtct cgtaaaggaa ggtaagatca caaagattga gcagatctac | 300 | |
| ctccattctc tcccagtcaa ggagtaccag atcatagatt tactcgtcgg tccttcattg | 360 | |
| aaagacgaag tgatgaaaat catgccggtt caaaaacaaa ccagagccgg tcagagaacg | 420 | |
| agattcaagg ccttcatcgt cgtcggagat agtaacggtc acgtcggatt aggagtcaaa | 480 | |
| tgctccaagg aagttgcgac ggcgatcaga ggcgcgatca ttctcgcgaa attgtctgtg | 540 | |
| gttccgatac gaagaggtta ttggggtaac aagattggaa aaccacatac ggttccgtgt | 600 | |
| aaggtaaccg ggaaatgtgg atctgttact gtacgtatgg ttccagctcc gagaggttct | 660 | |
| ggtattgtgg cggctagagt tcctaagaag gttcttcaat tcgctggaat tgatgatgtc | 720 | |
| tttacttctt ctagaggatc caccaaaact cttggaaact tcgtcaaggt atgtactttc | 780 | |
| acaatggctg ttttggtttg atgaactctg aattaggcag tgaaaagta atcattacca | 840 | |
| gttaagtgaa tttatattga agattaggat ttagctgatt gtattggttt gagcatgtga | 900 | |
| gtttgtgttt aagattgctt gaattgaaat gctttaggtt gtttgattac gctaaattct | 960 | |
| gactaatgta attcaaattg ttgttgtttt tttttggtc | 999 | |

<210> SEQ ID NO 33
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0028

<400> SEQUENCE: 33

| | | |
|---|---|---|
| gtcagtgaag tcgattggta gtacttgaaa cacttggttg gtttcatgta tttggcctat | 60 | |
| atataaacaa acatcgtaat tatatacgga ttttttcgg aattttacgc catatctgta | 120 | |
| agtatatata acatgcatgt cgttttcaaa ttcatatgat gaacgatcca cgtaagtgct | 180 | |
| actactccta caatattgca tgagagagat atgtatttat aaatttttatt ttgaagaaga | 240 | |
| aataagaggg aaggttactt gggtggatcg atgtgaaaac aaaagaagaa aaagcgaaac | 300 | |

```
ccactaagcc attacatgat atcgaccttc ttatcttttt cctctttatt ttattttct    360 catcttcttt ttgtcaggac ttttttctac ttaatgaaac ctccaaacta tctaactaat    420
acactcccat gtagaataaa gaaaattata taagatattg ttgatatttt gtaactagaa    480
aatatatttg ctctgtaatt tttcgtaagt taaatcaaca ttttaaagta gaaacaaata    540
ttactgcaaa aagtaggatc attattttg tccaaaatct cagttagcta tagggttgta    600
gtaaaaacaa aacacattct tgatttgccc caaaaaataa agagagagaa gaatattgtt    660
caaaagtggt ctcttctctc tctaattatg ttttcactaa acccaattag attcaaacag    720
tctacaaagt ccaaaagata aacatgggac aacaattcga tgcaaaaaat cctcttttca    780
tgctcttttt ttattctcta gtcttttaaa ttactaataa aaactcacaa atccaccaaa    840
cccattctct acaactcacc ttcatctaga tttaccccact cccaccgaga acacaagaa    900 aaaaaatata catatataaa tatacaagac aacacatgat gctgatgcaa tatacacaac    960
aaagtattaa atcttagata ttgtgggtct cccttttcttc tattcatttt cttattcatt   1020
aaaa                                                                 1024

<210> SEQ ID NO 34
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0039

<400> SEQUENCE: 34
ccgttcgagt atttgaaaat ttcgggtaca cccgcctaaa taggcggacc ttatctagta     60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactctta     300 catggtcaat ctaaatttga taagaaatac gtcacatatt actaagactg atagttttt    360 tgttgtcacc aattatttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggttttttct catttttcc gccatgttaa    840 ccaccggttt aaaaagaccg taacacattg aaagattaat aagggtatat ttgtaattac    900
ggtttgctgg caatttttaa ttattatttt aattagagaa aatagagaag ccctatcaat    960
gtacatggta tatatataaa aggcaaaacc ctagaaaacg atactattcg actcagccgt   1020
cctt                                                                1024

<210> SEQ ID NO 35
<211> LENGTH: 1024
<212> TYPE: DNA
```

<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0050

<400> SEQUENCE: 35

```
aatctgatct ctagtccagt cgattggtac ttgagggaaa catcatattt ttaaaccttg      60
tctcagtaag ctaacacaca ccccttgtga ttacttatcc atgtttatcc acaagaatgc     120
agttggattg agatattttc ttctttgttg aaatcaggcc tcaaggtgtt catgtggtct     180
gcaaaaaaat tcccaaaaat aaagatagtg acatctgaaa tcgataatgg attagacgaa     240
gagtttcgtg ttattccttg gtatgggcgg gtttgggac agatattttg gcacagacga      300
ggactaggcc actgtggtcc tgcagcatta ggtgtccctt ccatgtcctg cattacattt     360
tattgatgga ttcatcaccc tatctactac aacggctaca caaactatga agagttttgt     420
ttactaataa atgcccaagt gaggggtcga tcgaacccgg gacacgtttt tcagtttacc     480
atatagaatt atccttggaa cccttgatac tccatagaac atcaccacct ctgttgtcat     540
ctcaggaatc caggttcaaa cctagtctct ctctccctag tgggaggtat atggccactg     600
ggccaatgat gacaaaatgc aaaaaaaata aaatacattt gggttcatta tctaaaatat     660
ctcttgtgtt tgtaagtttt ggttgcacac tcgtgtggtt gaagtgtgtg tgagaggtac     720
tatacaatac actctgcttt tgttttgtac ctatctcttt ctcttctcca catatccaag     780
actttgggga taaagctgag atcattggtt gccatttggt tgtgtagaag caatcaccca     840
tttgctttat ccgaggttga taaatttcct cgggttctcc ttctgacacg tatgacaaat     900
tctaatagta tattcctcgt agatattacc tatatattct caatagttgc aggtacttaa     960
ggctttgtct tggcatcctc gtcctcttca gcaaaactcg tctctcttgc actccaaaaa    1020
gcaa                                                                 1024
```

<210> SEQ ID NO 36
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0086

<400> SEQUENCE: 36

```
cttatccttt aacaatgaac aggttttag aggtagcttg atgattcctg cacatgtgat       60
cttggcttca ggcttaattt tccaggtaaa gcattatgag atactcttat atctcttaca     120
tacttttgag ataatgcaca agaacttcat aactatatgc tttagtttct gcatttgaca     180
ctgccaaatt cattaatctc taatatcttt gttgttgatc tttggtagac atgggtacta     240
gaaaaagcaa actacaccaa ggtaaaatac ttttgtacaa acataaactc gttatcacgg     300
aacatcaatg gagtgtatat ctaacggagt gtagaaacat ttgattattg caggaagcta     360
tctcaggata ttatcggttt atatggaatc tcttctacgc agagtatctg ttattcccct     420
tcctctagct ttcaatttca tggtgaggat atgcagtttt ctttgtatat cattcttctt     480
cttctttgta gcttggagtc aaaatcggtt ccttcatgta catacatcaa ggatatgtcc     540
ttctgaattt ttatatcttg caataaaaat gcttgtacca attgaaacac cagcttttg      600
agttctatga tcactgactt ggttctaacc aaaaaaaaaa aaatgtttaa tttacatatc     660
taaaagtagg tttagggaaa cctaaacagt aaaatatttg tatattattc gaatttcact    720
```

```
catcataaaa acttaaattg caccataaaa ttttgtttta ctattaatga tgtaatttgt    780
gtaacttaag ataaaaataa tattccgtaa gttaaccggc taaaaccacg tataaaccag    840
ggaacctgtt aaaccggttc tttactggat aaagaaatga agcccatgt agacagctcc     900 attagagccc aaaccctaaa tttctcatct atataaaagg agtgacatta gggttttgt     960 tcgtcctctt aaagcttctc gttttctctg ccgtctctc                           999
```

```
<210> SEQ ID NO 37
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0088

<400> SEQUENCE: 37
```

```
tcgattggga ttactacttc atctagtaag gttctgaaaa cgtttgttgt tgataaggaa     60
gattcgtctc aggttattac tgttgatctt caaggtttgt gattgtgacg cttatacatg    120
tgctgaaact gtggtgttta tttattgaaa acaaaaaaaa agtctctctt gtagtttcat    180
tgtactaaat agaaaacaag aaacgttttt ttctttaatc ttctacattg ataatattgg    240
atcaaaggat tgtttctgca agacacaaca caaacatact tatactagtt tacttctact    300
aagtactaac tacatacccca tacacacact tgcacctaga ctttacttct agacatcatt    360
accctaaggt agaaccaagc ttacaagcaa gttttaccga caactcttac attcaactc     420 tagtctgtag tctttaacgt agacttacta actagtcatt agtggtttaa tttttttaaat    480 tttcatccat atgttttttgt tgtagatata aactaaagtc ggtcacattt aataattgtc    540
attatgtccg cgtaaaagtc aattcagcta ttggacattt atgaaatgta agattttctc    600
tctcatttcc ccgtgcgtga agacatgcat tggtttttct gtaataatca acaaatccaa    660 acccctttc gatctttatt tggacattgt tagagacaaa atttctctat agtcttttc     720 ctaatttgat accatgtttt tgtttctgca caaatttact cactggttta actaactatc    780
cacttattta tgatttttacc attaggcgtc agctagccct agtcaaattt gtaaacaagc    840
caagctatct acataaatcg agatgtcatt aacgttaatc gtcgttaatt cgaattgaa    900 aacatagata gctttagcag tacaatgggc aatggtaaga agaatagcaa aaggcccaat    960
atttggtttg cagaaattaa agccttaaaa aaaagcccac agatatttgt caaagaaccc   1020
taat                                                                1024
```

```
<210> SEQ ID NO 38
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0092

<400> SEQUENCE: 38
```

```
aaagattgag ttgagagaga tggtggagac gcagaacaga caaagggagt ttaccatata     60
gtgctctaaa gggcaatgag attgcagtga tgtggctatc cggggaatca tcgcaggtta    120
ttccttccca tgagcaacaa tcaatggatg ggttccaatt cagaggagaa acagaagaag    180 aaacgttttcc agagaaccac agtagggatt ctcgatcttg cgagttgcag agagcctctg    240
```

```
aaactgcaat agaaaggaca ctgatgaaaa gaacacactg aaggagtatg ccaatcatgt        300
gaaaactcag agcttgtatt ggtcttgtgg ttgatgaagt tctcacaaaa cctttggctt        360
tgaatctccc ctcattagtc atggtgagaa caagaacaag acgagaaaca gacaaagaag        420
atgaaaaaac ttgttggcca gtgttgacta aggggaata gccccagaca taacaaaatt         480
agacttgtcg tacatcttta atattttttt atctgtttct ttgtcctgac gctttcatta       540
ttcctgtgat caattttctc ataccattgg tccatcgtta atcctttctt aatttcattt        600
tctacgtaac atgagaggag accaagtcct atgagaacag ttgacgtaac agtggttgtt       660
aagttaagtt aaaagagga agctagtgag agtgaccgtt aggtagagaa gtgagatctt         720
taaccactct tctttctctc tctctctgct tttttcgtcg tctttcacat ctactgttcg       780
caaactctct tatgcttcca ataatggtga taccaattga gacttgcagg agaatctcct      840
cttctccaca ctctatcaac tggtcagcca tggaatggtc gtttcagttt caatattcct       900
ggattctttt taaggattcc tgtttctctt ctgttcctgg tatattctta acgacgaaat       960
tagtatcgga tcctggtaat acattttgaa gcttttaagt accattgcac tgggatccaa      1020
caat                                                                    1024

<210> SEQ ID NO 39
<211> LENGTH: 1020
<212> TYPE: DNA
<213> ORGANISM: Arabidopsis thaliana
<220> FEATURE:
<221> NAME/KEY: misc_feature
<222> LOCATION: (1)..(1020)
<223> OTHER INFORMATION: Ceres Promoter YP0096

<400> SEQUENCE: 39
gaggtcagtg agtcgattgg tgcaaaattg aaaaattgaa gggtgaaaca aatttaaaga         60
taatatctat taaatcctct aattttaaaa atttagcaaa aattgtattt tcttatggat       120
ctgttagttc acacgtatct taattagtac caaatcatat ctaatgatta gtgataaaac       180
tagttagata tctatatgtg tctttaccat ttaacttgaa tccttcttct tttttttacg      240
taaacaactt gaatccttcg ttaatacata aatttaaagc attttttctt taattctatt     300
gatcggtata tatttactat aagttttagc tcatatgcaa tttcaaatga tatgctttta      360
aattttgtct aggtgtgata gttgtatctt taacataaat cttatagcaa aattatactt     420
gatattctaa atttatctat ttgctcttgt gaacctcata ttagtctaga gaaactttga    480
aatcctttca attagttgta tgtccaatac atttttacta acatttatta gtctttttaa    540

ttaagattat tgttagaaaa aaaaagattt tttaaaaata aataatatgt tttagataca     600
atgtgagtta ggcttcttat atttttaaaa ataaatttat tcatactta aaaatagttt       660 ggaatttcaa tttatttggc tgaataccat aaaatatgtc aaттгaacc ttatacccat      720

tgactatttg gtgttagaaa ccctttaaca aaaaaaaact atttggtgtt agatatcaaa     780

ataaaaaaag tttaaccatt ggtttcttat att gaatt gg ататт gttac atgtatt aaa  840 gtttttttgg tttaatttt g aaacgttgat agaaactatt aagtttaagt ttggtagtat   900

аттттатт gt ggaaaattta att gccatta aatataacgt caactttttt tggtttttt   960

tgagaagtta cgttgtgatt ttgatttcct atataaagt tagattacgt catttttaa    1020

1020

<210> SEQ ID NO 40
<211> LENGTH: 1000
```

```
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0097

<400> SEQUENCE: 40
ttcatcttta tatttaagag tttaaaaact gcaacttttg ttttctttc  actaagtctt      60
atggccacag ttaattaaaa gcagatgaaa ggtggtccaa tggaaaagga gaatgtgatt     120
gggctagttg ggagagttct gatgtctagt gttgggtaca cgtgtccgtc agttacacat     180
agcattaaat cagacggcat gtcattattc aaatctagtt cacatagtac gactaatagc     240
tgataaatta atgattatac agcatatgaa ttatgaattc aaaaaaaaaa aaaaattgaa     300
aatgttaagg agatgctata ttttacaaaa ttcatcgcaa tgctttctac taatttgcta     360
agtggtcttc tccagttagt cttgtcgatt ccaagcgata ttattaaatc ttgaagcatc     420
gctcaaagca ttatagctta agataaccaa attgttatta aaacaccta  gtgaaatttt     480
taaattaaaa caattttgat atctttgtaa tatctaatac tactctttct gtgtctaaaa     540
ggattaattt tcaaaaattt cacacatatt aaaaaaaaaa aaaattact  agctaaacaa     600
ttttcaataa tcataaaaca atagtaactt ataattttt  ttttatttc  aaaatagtcc     660
ttcaagttta caattcattt tagtattata atcaacaaaa tttgtattaa aaagttggaa     720
aattaatctt tgtggaacaa aaaaatctag aaatcatttt ttagaattag agagaggttt     780
gataaaaaaa aataaaaaaa aatagagaga ggtagtacat actaaacgat gtgatactac     840
tattgacaaa atcttaattc tcagtttagt agaataaact agaaggaatg aatgaagtaa     900
atgcgaatcc aactactaac aaaccctact tagtcatcat atttcccat  atgaaatccc     960
tatataaacc catcatcatc tcccactttt ttcatatcca                          1000

<210> SEQ ID NO 41
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0101

<400> SEQUENCE: 41
ttctcgttct ctagaatatt gctggaccgg attaggtcaa tattattggg ccagattaga      60
tattgaattg tcgacgttgc ttacgttacg ttatatcttg tttaagaatt aaacctatcg     120
acttagtctt aattaagaaa acattgcctt aaattctctg gtctgcgacc gttttttga     180
ccgttaaccc ctaattaaag aaacaaaata attatagaaa gagcactgaa atgtgattat     240
tttaacagta ctcttatgag aaaattcgta ctttttagtt tttttttgt  acaaatctct     300
aagaaaaaca ctactactaa ttaagaaacg tttcaaacaa ttttatttc  gttggctcat     360
aatctttctt tctcggtccg ggactaaccg ttggcaaaaa aaaaaaaaaa gttgacaata     420
attattaaag cgtaaatcat acctctcaaa taaaaacttg aatttggaaa caaagacaac     480
taaaaaactc gaatttaaga gaattcctaa atcaagtgaa gtatcatca  cttggtaaaa     540
tttcataacc gttggcttct atttctatgt gtgccttggt ttgcaggaga taatatttca     600
tttccaacca atgatattcg tacacatagt caaacaaatg tttgtctttg ttattatatt     660
gagaaagaaa caagaaagag agagagagat agataagacg aaggaagtga agcttccaag     720
```

-continued

| | |
|---|---|
| cgcccaccgt taaaaatctc gtgtgcaagt ttcaaataca agtggccggt ggtctccata | 780 |
| atttgatcgt catccaatta aaaggaaga aaaagcgtgt tttatacaag aaaactcatt | 840 |
| aaaatagcaa gtctagaaat atctcaacac taatctacca cgtctattac acacacacac | 900 |
| acacacactt gatcttaatt tattttcaag attcaagaaa atacccattc cattaccaca | 960 |
| acttgaccac acgcctatat ataaaacata aaagccctttt cccc | 1004 |

```
<210> SEQ ID NO 42
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0102

<400> SEQUENCE: 42
```

| | |
|---|---|
| atttggttga taacgttttc actcgactaa ttatatactt cagaaggata gtaatagaat | 60 |
| accaaaataa ttaaatgatt ggttagtgcc ttagtgagaa cttttaacc gattctaata | 120 |
| gactaatgat gtagctaagc atttatttgg gatcatcact gtttgaaaac gtgaaatgtg | 180 |
| ataaaagtta tgaaacgatt aaaatataaa ataaccgtac aaaacattat gtaccgtttt | 240 |
| tttctctgtt cttttggcga tttggtttag ttcgttacac tctaaatgtt attgcagata | 300 |
| tatatataat gatgcatttg catctgagga acatataatt ccggttaaca cttccaaatc | 360 |
| ttatatccgt ctaggtaggg atttttataaa tcatttgtgt catcatgcgt tatgcttgtc | 420 |
| ggctttgacc ataacgcaga gatatagaac tagcttttac ttaacttta gatttattat | 480 |
| ttgatctaga gttaagtgga gatatatagt gttttgtta gattattggt ggatgtgaga | 540 |
| gtttgtcttt agtttcaagt tgagaatata aggcaagagg agactctgag gcaatcagag | 600 |
| gttttgattg gcaaaatatc caaaggccc aaaccaagtc gaagcccatc tcgtacaaaa | 660 |
| aaagaaagag atctgtaaga aaaaatattc tttgatattc ttacaaaaat aagtgtaaaa | 720 |
| cttttattag tcaaaatctt caatctttaa aaactctcat cactcctacg aaagcgcgtg | 780 |
| agagttatga gacattcctt aatagcatta ctcacaagtc acaagttcaa aacgtctgac | 840 |
| tgaaacagaa acaagccttt gttgaagtct tgaagaagag acattagtac tcgtcgtata | 900 |
| gccataaaag gtaatatacg aaatttcttc gctaatctct tcaccttcct ctacgcgttt | 960 |
| cactttcact ttataaatcc aaatctccct tcgaaaacat | 1000 |

```
<210> SEQ ID NO 43
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0103

<400> SEQUENCE: 43
```

| | |
|---|---|
| gttttgaaga acaatctgga tcgaaatcta acataaggtc atcgtattca agttacgcag | 60 |
| tcaaggactt gacatcatcc tactctggtc tgaggttacc acttccaaag atgggatttt | 120 |
| tcgactcggt atgcttccta agaaattcgt tttattgaac ctagcaaata tcttgtaatg | 180 |
| taagattcct gagatgatga agaaaaaaca aacttttgtt acagcaggag aacggagaga | 240 |
| aagaaaacag agaaccaaat gctcttgaag caaacagaag aagaagacac aaatccaaac | 300 |
| ttgagacttc ttctacacca gaaaaccgca gcattctggg acaacgcaaa acacgaaagt | 360 |

```
gaaacgggca atgatatata tgtcttgggt gcgttacaag gcatcgtttg caactgttga      420
gttggataag tcaactgtct tcttttcctt tggttgtagt agctgccttt tttttccttt      480
gttgctttaa gaaatagccc gaaaaaaaga atgttctaca tttcggagca gaaaactaac      540
cgaatgagtt tttggtcgga tcatcggatc gatcagatat attttgagtt acgaactgtt      600
ataaaaaaag ccataatttt gtgttgagtt tgcaaaatac cttataactt gttatttgag      660
attgcacctc catatatatt aattcgtaag agtatttatt aagtaagctt tagtataaat      720 cctttttttcc tttaaagtaa gttaatgttc tactaaataa tagtaaagtt gaagaaccgc     780
tccgttttta caccatgcac gtgttatcta acaaagaaaa tatggtacac ctaatggcta      840
atgcaaagga caacacaatg aaactaactt gactctgtgt tatagaaacc catagacatc      900
tgcatacatc ctagtatttg tataaattgg actcaaattc ctgaggacaa tcatagcaaa      960
caatcacatc atcgcaatat acataaacaa aagaggaaga aaaa                      1004
```

<210> SEQ ID NO 44
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0107

<400> SEQUENCE: 44

```
taacaatcct tgggaacatt gcatccatag atatccggtt aagatcgatc tttgaactca      60
taaaaactag tagattggtt ggttggtttc catgtaccag aaggcttacc ctattagttg      120
aaagttgaaa ctttgttccc tactcaattc ctagttgtgt aaatgtatgt atatgtaatg      180
tgtataaaac gtagtactta aatgactagg agtggttctt gagaccgatg agagatggga      240
gcagaactaa agatgatgac ataattaaga acgaatttga aaggctctta ggtttgaatc      300
ctattcgaga atgttttttgt caaagatagt ggcgattttg aaccaaagaa acatttaaa     360 aaatcagtat ccggttacgt tcatgcaaat agaaagtggt ctaggatctg attgtaattt      420
tagacttaaa gagtctctta agattcaatc ctggctgtgt acaaaactac aaataatcta      480
ttttagacta tttgggcctt aactaaactt ccactccatt atttactgag gttagagaat      540
agacttgcga ataaacacat tccccgagaa atactcatga tcccataatt agtcggaggg      600
tatgccaatc agatctaaga acacacattc cctcaaattt taatgcacat gtaatcatag      660
tttagcacaa ttcaaaaata atgtagtatt aaagacagaa atttgtagac ttttttttgg      720
cgttaaaaga agactaagtt tatacgtaca ttttattta agtggaaaac cgaaattttc      780
catcgaaata tatgaattta gtatatatat ttctgcaatg tactattttg ctattttggc      840
aactttcagt ggactactac tttattacaa tgtgtatgga tgcatgagtt tgagtataca      900
catgtctaaa tgcatgcttt gtaaaacgta acgaccaca aaagaggatc catacaaata      960
catctcatag cttcctccat tatttccga cacaaacaga gca                        1003
```

<210> SEQ ID NO 45
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0110

<400> SEQUENCE: 45

```
gggatgcggt tccgcttcct cttgatcttg gacgagtcgg aggacattgt tggatcccag      60
tgcaatggta atataaaaca agaaaacaag agattttata ggacaatcac taaatgacat     120
ttaattgatt aaacatttat tcattaataa ttgtatgtta ctaacttcaa catttaataa     180
ttttgtttaa gatacgttta catcagagac tattaatatt tttacaggtt gtaactttaa     240
actttgtctt gaatcgaaca tgactataga ttttgggcaa acttaaagat aacaacattt     300
ccgttttttt tcaaattatt acaaatcaaa ctgatatatt agacacaaca cgattacacg     360
taatgaaaaa agaaaagat aaaagataa aagaagggat cgattctgtt tggtctggtt      420
tagtgagatt caaagttaag ctcttccttt caagacatgc cttcttaaac cgggaatgtg     480
aacgtttgta atgtagtccg tccagttaat gcttccaaca tcaaatccaa attctctctt     540
ctcgtcctct gacatattct ccattaatct ctggggtatt gctgttatca aatctgtaaa     600
agaaaccaaa aaaaaagat gaaactttg cgggtaccgg ttttgtctgc tctaagaatt       660
agaatgttaa tgagttctgt cttaccttcc accatagaaa gtgtatggct cataaatagt     720
agcaaggtgt ttggcttgtt caacagattt cttgcatata aactttagct tctgcatcat     780
cttactatcc actgaactca taccactcat caacccactc cgttcttgag catctctcca     840
caaatgatcc gagaaatcat caacggaatt gaaaagtttc atcaaacgca ccataatagg     900
atcacccttta gagtccatgc atggagatgt tttgtagtgg ttataaagaa gctccgctaa     960
gtcttcgaaa accagcgggt ttatcgccga agaagcgatc tgatacacgt ttatttcagg    1020
ttcc                                                                 1024
```

<210> SEQ ID NO 46
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0111

<400> SEQUENCE: 46

```
cgattggatt tagtctatac attatagggc gcaagtttgt ggatttaaga attatataaa      60
aacttgaaat atagttttt tatgcattct cctcttgtgt aatacataaa ccaaatgtga     120
gataggttaa tctgtatttc agataatatt aaattccaaa caatattttt acttgttata     180
agaaggcaat taatatctct ctgttaatgg caagtggtac caagtagtat taaactatta     240
atgcaatgga agagtactgt tggaaattat aatcctctat cacacattca aacagatctc     300
ctgaaatctt ctcttccaaa cttgtacttc tctgatccaa atgtaggctc caaaatatag     360
acatttacca tttactaagt ccacaactcc tttcttgtct ccttcaaaaa tgactcttgt     420
gtaaccacca tatgactccg acagttcggc attgccatga tgagagctta aaaattcacc     480
ttcctgagca tttcaagtct tcactccctt agcttgacct gaaccaagat aaaatgcctt     540
tgtcgtcccg taatatccat cctgctttgg acggcatcat agttacattc gatccatcct     600
atttacaatg ttattttagt attaaaaaca tgacaataaa tttgttgtta aacatattca     660
aatacaatat gattggattt ataagtaatt gtaatatgaa atgtccttag taatatgtta     720
aaaaatacat agatacacac acgtactaaa agaggcaacg cgggagatgt cattagagga     780
agaactagga agcagagcgt tcatgcaaaa tgctaccaaa aacgttaatg caatatctca     840
actaatcagc acagtccatt tcatactgag aatgtaaaaa ccaatcagca tcgtccattt     900
```

```
tttcatctaa ttatttgtta actcttaatt ggccacaact tccaaccaca tgacgctctt    960
tctattccct ttatatattc ccatctcaaa tgttcttgga gacacaaaat atcataaaca   1020
tata                                                                1024
```

<210> SEQ ID NO 47
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0115

<400> SEQUENCE: 47

```
gtcgattgga tgatgaacat tctacatata taattattat gtttaagcac ttagacagca     60
taaattcttt ctaattatat aaatctaacc ttgttacatt gtacatctat aaattacttg    120
aagaaataac gagttctatt tcttttttaaa aattaaaaat actataccat atctcagtga    180
ttaagttgaa ccaaaaggta cggaggagaa acaagcattt gattcttcct tattttattt    240
tattcatctc tcactaatga tggtggagaa aaaagaaaa tacctaacaa acaaatatat    300
attgtcatac aaaaatattt ctatattttt agttaattag tttatattcc tcacttttca    360
gggcttatat aagaaagtga gcaaacacaa atcaaaatgc agcagcaaat actatcatca    420
cccatctcct tagttctatt ttataattcc tcttcttttt gttcatagct ttgtaattat    480
agtcttattt ctctttaagg ctcaataaga ggaggtacta ttactacact tctctctact    540
tttacttgta ttttagcatt aaaatcctaa aatccgtttt aaattcaaaa ataaacttag    600
agatgtttaa tctcgattcg gttttttcggc tttaggagaa taattatatg aaattagtat    660
ggatatcttt actagtttcc attcaaatga ttctgatttc aatctaatac tctcactctt    720
taattaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggttttttaa aagaaaaatc taaaactgaa ttatatcgtt taaccaagtt    900
gtaaaagtca taaaacgtag tatcttgtaa atcgctcttc cacggtccaa atagacttct    960
agtaataaac aagtaaaact aattttggtt tcttac                              996
```

<210> SEQ ID NO 48
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0117

<400> SEQUENCE: 48

```
gtcagtgagt cgattggatc acagtccttt atgataaaac aaactcataa ttattccacc     60
gacaacatgc gttttaaatt attttttctt aaattatatt atattatatt gatatcaacc    120
tagctaaaat aattcggatg gcgaaatcgg acaattttta atagaaaaaa tgggtatgaa    180
gatagtctat gattccgttc ttagcgacta gagggacctg ctcaaatctc ccgggtgata    240
cgcgatgtca agctcaatag aaccccacaa ccgacgagac cgagaaatcc ttgatttggg    300
ctagaagatt ttgaaataaa tttaatatat tctaagtaac ttgcttaaat ttttttttcaa    360 actctaaaga cataactaac ataaagtaaa aaaaaaaaag ttaatacatg ggaagaaaaa    420
```

```
aattaaacta atgattagct ctctaacgtg tttaatctcg tatcaagttt tttttaaaa      480 attatattgc tattaaaaca ttgtactatt gtttctattt tgtttagcta ttattcttgt      540
gaaatgaaaa gttgtgttta ttcaattact aaatggcaat atttatcttg gaaaactata      600
cctctaattg gattaggccc tagacatcct ctttagctta ttgacgttaa aattattccc      660
aaaactatta aagtttagta gtttgaaaga tgcatcaaga cctactcaga taggtaaaag      720
tagaaaacta cagttagtgt gattatattt taaaatatat aaaacaatct tattaaacta      780
aatattcaag atatatactc aaatggaaga taaaaacatt tagtctgtta ccactaccag      840
cctagctagt cactaatagt cactttggaa ctgagtagat atttgcatct tgagttacca      900
tggactcaaa agtccaaaaa gagaccccga gtgaaaatgc taccaactta ataacaaaga      960
agcatttaca gcggtcaaaa agtatctata aatgtttaca caacagtagt cataagcacc     1020
attg                                                                  1024

<210> SEQ ID NO 49
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0119

<400> SEQUENCE: 49
taccaaaaat aaggagtttc caaagatgg ttctgatgag aaacagagcc catccctctc        60
cttttcccct tcccatgaaa gaaatcggat ggtcctcctt caatgtcctc cacctactct      120
tctcttcttt ctttttttct ttcttattat taaccattta attaatttcc ccttcaattt      180
cagtttctag ttctgtaaaa agaaaataca catctcactt atagatatcc atatctattt      240
atatgcatgt atagagaata aaaagtgtg agtttctagg tatgttgagt atgtgctgtt       300
tggacaattg ttagatgatc tgtccatttt tttcttttt cttctgtgta taaatatatt      360
tgagcacaaa gaaaaactaa taaccttctg ttttcagcaa gtagggtctt ataaccttca      420
aagaaatatt ccttcaattg aaaacccata aaccaaaata gatattacaa aaggaaagag      480
agatattttc aagaacaaca taattagaaa agcagaagca gcagttaagt ggtactgaga      540
taaatgatat agtttctctt caagaacagt ttctcattac ccaccttctc cttttgctg      600 atctatcgta atcttgagaa ctcaggtaag gttgtgaata ttatgcacca ttcattaacc      660
ctaaaaataa gagatttaaa ataaatgttt cttctttctc tgattcttgt gtaaccaatt      720
catgggtttg atatgtttct tggttattgc ttatcaacaa agagatttga tcattataaa      780
gtagattaat aactcttaaa cacacaaagt ttctttattt tttagttaca tcccaaattc      840
tagaccagaa catggatttg atctatttct tggttatgta ttcttgatca ggaaaaggga      900
tttgatcatc aagattagcc ttctctctct ctctctagat atctttcttg aatttagaaa      960 tcttttattta attatttggt gatgtcatat ataggatcaa                          1000

<210> SEQ ID NO 50
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0120

<400> SEQUENCE: 50
```

| | |
|---|---|
| tagtttttga tttaatctac gttttttctta atcataaatg ggtaattatt agtttttgca | 60 |
| aaatcaaaat ccaaaaattg ttctaaacac tgcaaccatt taaggcctat atcactcaga | 120 |
| aaatttctgg tgggagaact aatcgtttgt cctttctaaa tctcacatat tagaatttag | 180 |
| aattagtgtg ctacataaga atattagttc agctcggaac aactattttt tggtaaaaca | 240 |
| gagaacttaa acaaatgcat tattttatca acatgcattt tgaattgaat ataaaatttc | 300 |
| ataattgtaa agacataaat tacataaaat tttacatgaa aaaatagata tagaaagaaa | 360 |
| atgaaactaa ctgatgatat gctctctaaa ttttttaatc tcataacaag aattcaaatt | 420 |
| aattagttca tattttttggt taatataaca tttacctgtc taagttggaa ctttcatttt | 480 |
| tttctgtttt gtttagtcag tattcttaat gtgaaacgga aagttgaatt tattcaaact | 540 |
| taaattcaat agcattaatt aaaggcgaaa gctattatct ctacatgtgg ttcaaactag | 600 |
| acatccaatt taattagctt attgacgttg aaatgttttc caaaactact atagtttggc | 660 |
| aatttgaaag atgcatcaga actactcaga caggtaaaag tagaacctct agctgtgtga | 720 |
| attgtatgtt agtccataaa gaacatcttg taaacttcat acttaagata tatattacaa | 780 |
| tatatacttg aatggtagat aaaaacgatt agtctgattg ctagcatact cacaactatt | 840 |
| tggaaatgag taagatattg gcattctaga gttactacta tggagacaaa agtcgaataa | 900 |
| aagagacctc acgtgaaaat gttacgagct agtaaaaaaa gcatttacac taacggtaaa | 960 |
| aaaagtatct ataaatgttt acacaaggta gtagtcatt | 999 |

<210> SEQ ID NO 51
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0121

<400> SEQUENCE: 51

| | |
|---|---|
| ttggattttt tttttgttga gtcagcagac catctaatct ctcttttttcc accacagcct | 60 |
| gctttctatg aagcatttgg gcttacggtt gtggaatcaa tgacttgtgc actcccaacg | 120 |
| tttgctacct gtcatggtgg acccgcagag attatcgaaa acggagtttc tgggttccac | 180 |
| attgacccat atcatccaga ccaggttgca gctaccttgg tcagcttctt tgagacctgt | 240 |
| aacaccaatc caaatcattg ggttaaaatc tctgaaggag ggctcaagcg aatctatgaa | 300 |
| aggttggccc attctccttg acaggcttaa caatacaact tgtatcgctt caacaagatg | 360 |
| atggcttaat aaggattttt gcatgtatag gtacacatgg aagaagtact cagagagact | 420 |
| gcttaccctg gctggagtct atgcattctg gaaacatgtg tctaagctcg aaaggagaga | 480 |
| aacacgacgt tacctagaga tgttttactc attgaaattt cgtgatttgg ttagtgtaac | 540 |
| ccactgttat tcttttgatg tctacatcta ctttacttac attattcttt tcttcggttt | 600 |
| gcaggccaat tcaatcccgc tggcaacaga tgagaactga tcatgacagg gtaggatttt | 660 |
| atttcctgca ctttctttag atcttttgtt tgtgttatct tgaataaaaa ttgttgggtt | 720 |
| ttgtttcctt cagtggtttg attttggact tatttgtgtt aatgttgttt tggctgttct | 780 |
| cttaatatca ataacaaata aatttactgg ttggtatcta agatctaaca atagttacta | 840 |
| tttttagagg taaagacacc aaccttgtta tattggtcag agagctaaaa ccttgacttg | 900 |
| ttgggaaaac aaaactctaa tgacagaaaa tctgacatga tgccttataa ttcacagcct | 960 | catgttctac ataaatccta acaatagcac tttgtttct            999

<210> SEQ ID NO 52
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0128

<400> SEQUENCE: 52
gataaactga taatggaaaa gaacaaagaa accagttttt aactatttgc atatgtaatt    60
tatttgttgc aaattatatt tagttaaaat gtttcctcta tttatatata tatatatcag    120
tcaagcacta tgtataagaa atgtcaattt ataaattttt acatgtcctt aacagaaag    180 aaaatgaatt tttacatgtc attcatagag agtcactcgt ttatttctta tatagagaat    240
aacacactca catgcatatg catgcaatat gatacatttt atgacaaaga taatcaacgg    300
aaacggtcaa gacataattt gataaacaac ttgcacgatg cacagatctg atcaaatata    360
taactcttta acatatccaa aatattcaaa agaaaaaact cgatccaaac tagcaacatc    420
acgctcacgc ggtaggctaa aaatttatta atctccaaaa gtctttctta tgaacactgc    480
aaacacaaca acttgaaaag tcatataggt ttagatgatg acgcgtattg gctatcgctt    540
accggagtgg ctcataaata caataaacaa tacgtaaaag tcaaagtcaa atatatttag    600
tcaactataa ccattaatcg ggcaaaacct ttagctgtca aaacaacgtg aaaacgatat    660
ttgtatatat catcaagaat cagtagataa gagaatgatt taatcccctg actattacaa    720
ttttggtgta ataaacagtc tctattggtt tttattcttt gttttaatttt ctcatgacct    780 atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                   1004

<210> SEQ ID NO 53
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0137

<400> SEQUENCE: 53
gtggcacatg ctgaaacccc gagcatctct ccggaagaca cgcgtcgttc gctccaaaga    60
aaacagtcac agctgccgga gaatctccgc cgtcttcttc tgccaccgga aaaactctct    120
ccaccacttt cagtgcccac ctcgtgttat atccactgta tcctcgtagc accatatcag    180
cctaataaaa ttttatgtat caaattttaa gacatagccg aaactacact atactagaca    240
ataataatat gatttgtttc ctgaaaaatt atggtttcat gagaaacatt aatcatctat    300
aaaacaaatt agctatggca tcgaagagtt atcaatcaaa actgatgaat ctttacttaa    360
tatatacaac atatctttac cttgcggcgg agaagatcgg cgagagaagc accccagcca    420
ccgtcactaa aggattcttc agtgatggaa tcaccaaaga gaaaaacctt ccgtctcatc    480
atcttccaca caatctttctt gagaaaatct gagagataag aaaggtgtag tggttttgct    540
gaagtgatcg tgtttgattt agtaaagaaa tgctttattt attgttgggg gaaacataaa    600

```
taaataaagt aaaagtggat gcactaaatg ctttcaccca ctaatcaccg acctttcatg     660
gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                        1001

<210> SEQ ID NO 54
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0143

<400> SEQUENCE: 54
atacaacaga tggcagatat cgagttaaat acgtgaatca gccgttacga tattttaaaa     60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atacttttaa ttttatctgt tgtatgtatt aaggttttgt    360
agctttaaga aaacgcttat aatataaaat aacttctaaa agatatttca tgcgtataca    420
ataaatattt gtgaaaaaac atttcgaaaa cgtgtacaat atataaacta ttgtgttatc    480
ttttgacatt caaacaaatg ttgacaatgt aattttatcc atgatatgat tggccaatta    540
gctgcgaggt aaaaatccgt atacgagtaa aagtaagata aaatttcgca agaagatttt    600
tagcaggaaa tctaagacaa gtgtcatgaa cgtgtcaatc aacaaacgaa aaggagaatt    660
atagaatcca gattcgacgt accacattaa taaatatcaa aacatttat gttattttat    720 ttttgctctg gcagttacac tcttttttcat tgctccaata aaaaaatcac tcgcatgcat    780
gcatatatat acaccatagt aaactccgcc tcttcttcat tttaaaagta tcagtttaca    840
ctgacacaat ccttaactat tttcctttgt tcttcttcat ctttattaca catttttttc    900
aaggtaacaa ataatctttt taagtcactt ttatactctt taaatcttag attgatatat    960
gaatgcatgt taatatttca agatttatag gtctaccaaa c                       1001

<210> SEQ ID NO 55
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0144

<400> SEQUENCE: 55
aaacgttgca agattattga ttgtgagaaa gagtgctcaa ggtagtactg atttctgtaa     60
agctcacggt ggtgggaaac gatgttcttg gggagatggg aaatgtgaga aaatttgcta    120
gaggaaagaa gcggtttatg cgctgcgcat aacactatta tgtctcggga gaacaaagat    180
```

| | |
|---|---|
| ggaagcaaga gcggtttgat tggaccggga ctctttagtg gccttgtttt tggctctact | 240 |
| tctgatcatt ctcagtctgg agctagcgct gtctctgatt gtactgattc tgttgaacga | 300 |
| atacagtttg agaataggca gaagaacaag aagatgatga taccgatgca ggttctagta | 360 |
| ccttcatcaa tgaaatctcc aagtaattca catgaaggag aaacaaacat ctatgacttc | 420 |
| atggttccgg aggagagagt tcacggcggt gggctagtaa tgtctttact tggtggctcc | 480 |
| attgatcgaa actgaaagcc atttatggta aaagtgtcac attctcagca aaaacctgtg | 540 |
| taaagctgta aaatgtgtgg gaatctccga atctgtttgt agccggttac gttatgctgg | 600 |
| atcaaaaact caagatttgt tggatattgt tatgctggat cggtggtgaa accacttccc | 660 |
| ggttgctaaa taaataaacg ttttgtttt ataatctttt tcactaaacg gcagtatggg | 720 |
| cctttagtgg gcttcccttta agcgaccaat acaatcgtcg caccggaatc tactaccatt | 780 |
| tataggttta ttcatgtaaa acctcggaaa atttgagagc cacaacggtc aagagacaaa | 840 |
| aacaacttga agataaaggg ataaggaagg cttcctacat gatggacaac atttcttccc | 900 |
| acacaaattc tcataataaa aatcttataa tacaaatact tacgtcataa tcattcaatc | 960 |
| tagtccccat gttttaaggt cctgtttctt gtctgataca aat | 1003 |

<210> SEQ ID NO 56
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0156

<400> SEQUENCE: 56

| | |
|---|---|
| ttggtttgca ttgtgaagat ttgtattaac tatagaacat tgaattgatg gtgttaagtt | 60 |
| cttacacaag cgtgcttctc ggtttgaact gtttcttttg tatgttgaat cagagcttag | 120 |
| tttataggaa ccagagtatc tacttagtca ttctctgatg ctaagtgcta aggttctacc | 180 |
| tagttgccct ctaggccctt atgttattga taacttatga agctatttga acacttgatt | 240 |
| cttaggagac ctaagttggt acagccagat agagtgtatg ttcttgttct ctatgtgaca | 300 |
| ggatcaagct gccacacata gttcaagggt atgctctgtg tgggtttgct cagattgagg | 360 |
| acaaatctat acaaggaagt agagtctttg acattttgat gttgtatgat aagaagaaga | 420 |
| aaggagagta ataagaaag agaaaaggga aacagaaaca cgtgggagaa catcccaaag | 480 |
| aggaagcaca cgcggatctt catgcaaagc tccccgattc tcccatgtgg tcccttttctc | 540 |
| cctttgtccc cctcctcttt cttctttttct cattttactc cttttttttac cattatacaa | 600 |
| cgaatctttt ttatcataat ttttggttt tggtttatt tccaataaca ctttcttggt | 660 |
| tacttcccat tctcactttt tcatataaga aactcacttt gggaaactta tgtttgagaa | 720 |
| tgacaagtct ttttagagaa agtgatgtaa caaatctaaa gtgattatat aataaccttg | 780 |
| cacaatgttt ttgattttttt gtaagattcg aatattaggt ttattattcg tagggaataa | 840 |
| acttactttc aaaagcgttc ataagttaat actttcatat atgatcataa gtacggacac | 900 |
| tattgttttt tgtttgtttg tgtttattct aaaagaaagt agcttttaat tgaaatgtcc | 960 |
| tcggaggcac agtttaaagt tcgagtgtaa cagtttctaa ggca | 1004 |

<210> SEQ ID NO 57
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0158

<400> SEQUENCE: 57

```
ttattagatt aatagattgc attgcattgc ttgtgctttc aatttacaaa ttgtctccca      60
actccatcga cacatctctt tttgtgtata taagattcag acttgttata ttttttttat    120
aaatatgtta ttagcatctt aagttaaatt gatttttat  atctgcatta aggattacac    180
gactatattt gcgattgtgt gttggttaaa ataaattta  ggattgtctt taactacatt    240
taggattata tgactatatt tggttaaata taaaatctag ctgtgattat tagtattcaa    300
aaataagtag cctaaccaat taaaacaacg gctattgggg caaattagaa catttagtg     360
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt cattttcttt gtttaccatt tttagctaaa ttatttacga ttacaaaga     540
tatcaaagt  tggatcataa tacaatttat agacttactg tagaaaattc gtatgtacaa    600
gtacaacaaa ttcttcataa taaatttga  aaattctatt acaaatgttg taagaaatag    660
aatttgaaat atatataaac taaggagaaa aaaaagaga  acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt ttttttttct tttgtctgaa tggaacaaaa    900
gcatgcgaca tctctgtgtc tttatcttct ctctcctctt cttgaaaaac tgaaccttta    960
attctttctt cacatctcct ttagctttct gaagctgcta                         1000
```

<210> SEQ ID NO 58
<211> LENGTH: 1005
<212> TYPE: DNA
<213> ORGANISM: Arabidopsis thaliana
<220> FEATURE:
<221> NAME/KEY: misc_feature
<222> LOCATION: (1)..(1005)
<223> OTHER INFORMATION: Ceres Promoter YP0188

<400> SEQUENCE: 58

```
gattggtatg aaatttcgga gaccaacaaa aaaaacttta ttgagcttgg agtgaagcta      60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300
attttttgttc ctacgacttt aaacggactt tgcttaagtt gtgtgcatgt aagctcgtcg   360
tccctcgatt gtcatcaaca ttcaccaata tcagcctcta tcacgagt  gaaggtggtg     420
attcggctta atgaaaacag agaaatattt caatatgatt cctattaaat tttaaatctt    480
ttttctcaat ctctagattt tcattaaaag catcatgatt ttttccact  atgttcatat    540
atctctatca cagttttagg tacattgtag aaattggata agatacgtca tacgtctaac    600
atgaatttgg tctagcaagg aaggtttgag ataataagtg aaaagaaaac acaagataat    660
aaattataat ttataaatgc tttatagtat tgaaaaataa gatgatttt  ttttttttta    720
ataccggatt ggctgatcca cttatgatga ctcaaatgtt attaagtttc aagacaattt    780
```

| | |
|---|---|
| atgatgacac aaatcacaat gagtcaatag tagccacgaa gccagaaaaa aaaaatgtac | 840 |
| tacaaaaaga taatgatagt acaaaatgat acgtcgtact gccacatgta cgacacaact | 900 |
| cgattaccaa aaagcagagc catccaacca taaaactcaa aacacacaga ttccactggc | 960 |
| gtgtgctctc ctcacttcac tcgtccttga aacttgaggt actga | 1005 |

<210> SEQ ID NO 59
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190

<400> SEQUENCE: 59

| | |
|---|---|
| taaatagtga cattggtaag aagaaaaaaa acactattaa atagtgaaaa aatggtttat | 60 |
| aactctctta attaacatta cttattattg ctagcaccta aaatctccca caaaatattt | 120 |
| gttgtaaaac acaaatttac aaaatgattt tgttttttaaa ttagtaacac atgttcatat | 180 |
| atacgttaat aagaacatac cctatatgat tttatataaa aaaatttctt tgagacgtct | 240 |
| tattcttttt tctttaataa tatgcaattg tgagagtttg gatttgaatg gtagcattag | 300 |
| aagcaaactt gaaccaaaca tatttcatga agtcaaactt gaaccaatgt gatcactaat | 360 |
| cacagtgttc gcagtgtaag gcatcagaaa atagaagaag gacatagct atgaatcata | 420 |
| taatcttgac acatgtttta taggttttag gtgtgtatgc taacaaaaaa tgagacagct | 480 |
| ttcttctaat agacttaata tttgggctaa atgtaccaca gttgtgaatt tcttacaaaa | 540 |
| atgggccgag ctacaaaaaa ctacaggccc actctcaact cttatcaaac gacagcgttt | 600 |
| tacttttta aaagcacaca cttttgtttt ggtgtcggtg acggtgagtt tcgtccgctc | 660 |
| ttcctttaaa ttgaagcaac ggttttgatc cgatcaaatc caacggtgct gattacacaa | 720 |
| agcccgagac gaaaacgttg actattaagt taggttttaa tctcagccgt taatctacaa | 780 |
| atcaacggtt ccctgtaaaa cgaatcttcc ttccttcttc acttccgcgt cttctctctc | 840 |
| aatcacctca aaaaaatcga tttcatcaaa atattcaccc gcccgaattt gactctccga | 900 |
| tcatcgtctc cgaatctaga tcgacgagat caaaacccta gaaatctaaa tcggaatgag | 960 |
| aaattgattt tgatacgaat tagggatctg tgtgttgagg ac | 1002 |

<210> SEQ ID NO 60
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter YP0212

<400> SEQUENCE: 60

| | |
|---|---|
| agtcgattgg tacactctta atttaattag agtaagagat caacaaaaat atagaatttt | 60 |
| ctttatatcg aagtgctacg accttatata tatagaaaaa aaagcatagg tgaatctcta | 120 |
| aattgagatt gtgctgtagt aaacatatta agttttttagt tttttttaaga aatgaatctt | 180 |
| tttgttgatt aattcaaact agtagtcatt aagattccgg agattccaat ttagaaaagt | 240 |
| caaagattca aagaacaagt ccaggtccac atgttgaatc cgattcatca tccactcatc | 300 |
| cttcatatct tcctccaccg tctccgccca aaaaatcaat aacaataaaa aatcctaaaa | 360 |
| aaacatattt gattttgaaa aaactttatc atatattata ttaattaaat agttatccga | 420 |

```
tgactcatcc tatggtcagg gccttgctgt ctctgacgtc cttaattatc attattttta      480
aatttgtctc tctcagaaaa ttacgccaca atcttcctct ttccctttc cgaaaacagc       540 taatatttgt ggacctaaac taaataacgt agcctctaga ttttatataa ttactaatac      600
tatatgctac tacttgttat tatttactcc aatcatatat gataccaatc aagaatcact      660
acataagtag aaaactttgc aatgagtcca ttaattaaaa ttaagaataa acttaaaatt      720
ttatggtatt ttaagattcc ctttggattg taatgacaag aaatcagcaa attagtcgta      780
actcgtaaga ataaacaaga tcaatttta ctttctttac aaagattccg ttgtaatttt       840
agaaattttt ttttgtcact gttttttat agattaattt atctgcatca atccgattaa       900
gaagtgtaca catgggcatc tatatatatc taacaggtaa aacgtgtatg tacatgcata     960
aggttttacg tgcttctata aatatatgtg gcagt                                995

<210> SEQ ID NO 61
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0214

<400> SEQUENCE: 61
ccagtcgatt ggcgcctcgc atgcctatca tatttaaccg tcaataatgg atttggcggt       60
tttggtaggc cgggtcaacc ggattaaaag aaaacggttt ggagtccttc cttgcaattg      120
aattttcaca cattcgggtt ttgtgatttc tctgtcataa tgggcccggc acatatggtt     180
cataacccat gtgggcctat ggtataattt ttccaattaa aactattgtt aggtcgataa     240
aacaaaaaac aataaaaacg agtggaatac acataccaaa agaatgtga tgaacattag     300 taattttatt ttgatggtta atgaaaaaca aaataaatgc atcttggcat cttccgttgg    360
aaagcgcaaa tagggcagat tttcagacag atatcactat gatgggggt gagagaaaga    420 aaacgaggcg tacctaatgt aacactactt aattagtcgt tagttatagg acttttttt    480 tgtttgggcc tagttatagg atcataaggt aaaaatgaag aatgaatatt agattagtag   540
gagctaatga tggagttaag tatgcacgtg taagaactgg gaagtgaaac ctcctgtatg   600
gtgaagaaac tatacaacaa agccctttgt tggtgtatac gtattaattt ttattctttt   660
atcacaagcg atacgtatct taagacataa taaatatata tcttactcat aataaatatc   720
ttaagatata tatacagtat acacctgtat atatataata aataggcata tagtagaaat   780
taatatgagt tgttgttgtt gcaaatatat aaatcaatca aaagatttaa aacccaccat    840
tcaatcttgg taagtaacga aaaaaaggg aagcaagaag aaccacagaa aaggggcta    900 acaactagac acgtagatct tcatctgccc gtccatctaa cctaccacac tctcatcttc  960
tttttcccgt gtcagtttgt tatataagct ctcactctcc ggtatatttc cccattgcac  1020
tgga                                                                1024

<210> SEQ ID NO 62
<211> LENGTH: 911
<212> TYPE: DNA
<213> ORGANISM: Arabidopsis thaliana
<220> FEATURE:
<221> NAME/KEY: misc_feature
<222> LOCATION: (1)..(911)
<223> OTHER INFORMATION: Ceres Promoter YP0263
```

<400> SEQUENCE: 62

```
atctagctgt ggattccacc aaaattctgg cagggccatg atctaaaaac tgagactgcg      60
cgtgttgttt tgcagtgatt tgtatttcat atttgcacca tcctacacag tccacttggt     120
atcgtaacca acataagga gaacctaatt acattattgt tttaatttcg tcaaactggt     180
ttttaccttt tagttacata gttgattctt catttgtttt agtagttatg gagcacaata     240
atgtgcaaca aagaaagatc atagtggatt aaatatgttga gaggtcagaa attcttggtt     300
aacaaaaaaa agttacaagg actgagattt tgggtgggag aaagccatag cttttaaaac     360
atgattgaac ttaaaagtga tgttatggtt tgagggggaaa aaggttgatg tcaactaaga     420
tagttgaagt aatgtcttaa actaaagtaa accaccggtc caaccgtggt ccggaagcat     480
ctctggtatg atttatccta aaaatcaaaa tagtagaaac atactttaaa tatatacatt     540
gatcggacga aaattgtaaa ctagtatagt ttcaaaaact agttgaacag gttatgtacc     600
ttaaacattt atttcaaact taaacactaa agaacatata tgaatagaag tttatataaa     660
ttactatata tctaccataa atctcttata attatgatgt cacgatgagg aagtgttgaa     720
acgttaaaat gccaaaatat aagcatgcga cggaattttg gcagaagatt gtagagttgt     780
aatctgtcgc aatcattact cgtgctagca ttttcattt tcccttcatt tgtggataac     840
gcacgatata acattctaca caccaacaag attctataaa aacgcaaagg ttgtctccat     900
agaatatcgt c                                                         911
```

<210> SEQ ID NO 63
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0275

<400> SEQUENCE: 63

```
aaacattaat atgtagtaac tatgggcgta tgctttactt tttaaaatgg gcctatgcta      60
taattgaatg acaaggatta aacaactaat aaaattgtag atgggttaag atgacttatt     120
ttttacttac ccaatttata aatgggcttc gatgtactga aatatatcgc gcctattaac     180
gaggccattc aacgaatgtt ttaagggccc tatttcgaca ttttaaagaa cacctaggtc     240
atcattccag aaatggatat tataggattt agataatttc ccacgtttgg tttatttatc     300
tattttttga cgttgaccaa cataatcgtg cccaaccgtt tcacgcaacg aatttatata     360
cgaaatatat atattttca aattaagata ccacaatcaa acagctgtt gattaacaaa     420
gagatttttt tttttggtt ttgagttaca ataacgttag aggataaggt ttcttgcaac     480
gattaggaaa tcgtataaaa taaaatatgt tataattaag tgttttattt tataatgagt     540
attaatataa ataaaacctg caaaggata gggatattga ataataaaga gaaacgaaag     600
agcaattta cttcttata attgaaatta tgtgaatgtt atgtttacaa tgaatgattc     660
atcgttctat atattgaagt aaagaatgag tttattgtgc ttgcataatg acgttaactt     720
cacatataca cttattacat aacatttatc acatgtgcgt ctttttttttt ttttacttg     780
taaaatttcc tcacttttaa gacttttata acaattacta gtaaaataaa gttgcttggg     840
gctacaccct ttctccctcc aacaactcta tttatagata acattatatc aaaatcaaaa     900
catagtccct ttcttctata aaggttttt cacaaccaaa tttccattat aaatcaaaaa     960
ataaaaactt aattagtttt tacagaagaa aagaaaaca                           999
```

<210> SEQ ID NO 64
<211> LENGTH: 981
<212> TYPE: DNA
<213> ORGANISM: Arabidopsis thaliana
<220> FEATURE:
<221> NAME/KEY: misc_feature
<222> LOCATION: (1)..(981)
<223> OTHER INFORMATION: Ceres Promoter YP0285

<400> SEQUENCE: 64

```
gggattatat atgatagacg attgtatttg cgggacattg agatgtttcc gaaaatagtc      60
atcaaatatc aaaccagaat ttgatgtgaa aacactaatt aaaacatata attgacaact     120
agactatatc atttgttaag ttgagcgttg aaagaaaatg aaagagtgta gactgtagta     180
cgtatgagtt tcccaaaaga tggtgcttga atattattgg gaagagactt tggttggttc     240
ggttgaatga agattttac ctgccatgtt gatagagaaa ggcaaataaa tgtaggggtc      300
gatgtctaac gtaaagactg atcaaccaa gagtcctcct cctcgtcttc accaaaaaaa      360
aagagtcctc ctcgtggaaa cttatttctt ctccagccaa gatctcatct catctcttca    420
ctctatgaaa tataaaggaa tcttatggtt tttctaaaaa ctatagtacg tctatatacc    480
aaaggaaaca atataaaatc agttaatctg ataaattttg agtaaataat aaagttaact   540
ttgtacttac ctatatcaaa ctaattcaca aaataaagta ataataacaa agaatttta    600
gtagatccac aatatacaca cacactatga gaaatcataa tagagaattt taatgatttt   660
gtctaactca tagcaacaag tcgctttggc cgagtggtta aggcgtgtgc ctgctaagta    720
catgggctct gcccgcgaga gttcgaatct ctcaggcgac gtttcttttg ttttcggcca    780
taaaggaaaa agcccaatta acacgtctcg cttataagcc cataaagcaa acaatgggct    840
gtctctgtct cactcacaca cgcgttttcc tactttttga ctattttat aaccggcggg    900
tctgacttaa ttagggtttt ctttaataat cagacactct ctcactcgtt tcgtcaacat    960
tgaacacaga caaaaccgcg t                                              981
```

<210> SEQ ID NO 65
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0286

<400> SEQUENCE: 65

```
gaaaacaatc ataggttacg ctattatcat cgaaaggtat gtgatgcata ttcccattga     60
accagatttc catatatttt atttgtaaag tgataatgaa tcacaagatg attcaatatt    120
aaaaatgggt aactcacttt gacgtgtagt acgtggaaga atagttagct atcacgcata    180
catatatcta tgaataagtg tgtatgacat aagaaactaa atatttacc taaagtccag    240
ttactcatac tgatttcatg catatatgta ttatttattt atttttaata aagaagcgat    300
tggtgttttc atagaaatca tgatagattg ataggtattt cagttccaca aatctagatc    360
tgtgtgctat acatgcatgt attaattttt tccccttaaa tcatttcagt tgataatatt    420
gctctttgtt ccaactttag aaaaggtatg aaccaacctg acgattaaca agtaaacatt    480
aattaatctt tatatgagat aaaaccgagg atatatatga ttgtgttgct gtctattgat    540
gatgtgtcga tattatgctt gttgtaccaa tgctcgagcc gagcgtgatc gatgccttga    600
```

-continued

```
caaactatat atgtttcccg aattaattaa gttttgtatc ttaattagaa taacattttt      660
atacaatgta atttctcaag cagacaagat atgtatccta tattaattac tatatatgaa      720
ttgccgggca cctaccagga tgtttcaaat acgagagccc attagtttcc acgtaaatca      780
caatgacgcg acaaaatcta gaatcgtgtc aaaactctat caatacaata atatatattt      840
caagggcaat ttcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                                996
```

<210> SEQ ID NO 66
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0337

<400> SEQUENCE: 66

```
taatttttt atttttggaa ctaacactta ttagtttagg tttccatcac ctatttaatt       60
cgtaattctt atacatgcat ataatagaga tacatatata caaatttatg atcatttttg      120
cacaacatgt gatctcattc attagtatgc attatgcgaa aacctcgacg cgcaaaagac      180
acgtaatagc taataatgtt actcattat aatgattgaa gcaagacgaa acaacaaca       240 tatatatcaa attgtaaact agatatttct taaaagtgaa aaaaacaaa gaaatataaa      300 ggacaatttt gagtcagtct cttaatatta aaacatatat acataaataa gcacaaacgt      360
ggttacctgt cttcatgcaa tgtggacttt agtttatcta atcaaaatca aaataaaagg     420
tgtaatagtt ctcgtcattt ttcaaatttt aaaaatcaga accaagtgat ttttgtttga     480
gtattgatcc attgttttaaa caatttaaca cagtatatac gtctcttgag atgttgacat    540
gatgataaaa tacgagatcg tctccttggtt ttcgaatttt gaactttaat agttttcttt    600
tttagggaaa cttaatagt tgtttatcat aagattagtc acctaatggt tacgttgcag     660
taccgaacca atttttacc cttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgttc atgagccacc tgccacctca    840
ttcacgtcgg tcattttgtc gtttcacggt tcacgctcta gacacgtgct ctgtccccac   900
catgactttc gctgccgact cgcttcgctt tgcaaactca acatgtgtg tatatgtaag     960 tttcatccta ataagcatct cttaccacat taattaaaaa                             1000
```

<210> SEQ ID NO 67
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0356

<400> SEQUENCE: 67

```
ttagttcatt gaaacgtcaa cttttttactt gcaaccactt tgtaggacca ttaactgcaa     60
aataagaatt ctctaagctt cacaaggggt tcgtttggtg ctataaaaac attgttttaa   120
gaactggttt actggttcta taaatctata aatccaaata tgaagtatgg caataataat     180
aacatgttag cacaaaaaat actcattaaa ttcctaccca aaaaaaatct ttatatgaaa    240
```

```
ctaaaactta tatacacaat aatagtgata caaagtaggt cttgatattc aactattcgg     300
gattttctgg tttcgagtaa ttcgtataaa aggtttaaga tctattatgt tcactgaaat     360
cttaactttg ttttgtttcc agttttaact agtagaaatt gaattttta aaaattgtta     420 cttacaataa aatttgaatc aatatcctta atcaaaggat cttaagacta gcacaattaa     480
aacatataac gtagaatatc tgaaataact cgaaatatc tgaactaagt tagtagtttt     540
aaaatataat cccggtttgg accgggcagt atgtacttca atacttgtgg gttttgacga     600
ttttggatcg gattgggcgg gccagccaga ttgatctatt acaaatttca cctgtcaacg     660
ctaactccga acttaatcaa agattttgag ctaaggaaaa ctaatcagtg atcacccaaa     720
gaaaacattc gtgaataatt gtttgctttc catggcagca aaacaaatag acccaaata     780 ggaatgtcaa aaaaagaaa gacacgaaac gaagtagtat aacgtaacac acaaaaataa     840
actagagata ttaaaaacac atgtccacac atggatacaa gagcatttaa ggagcagaag     900
gcacgtagtg gttagaaggt atgtgatata attaatcggc ccaaatagat tggtaagtag     960
tagccgtcta tatcatccat actcatcata acttcaacct                         1000
```

<210> SEQ ID NO 68
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0374

<400> SEQUENCE: 68

```
aagacacccg taaatgttgt catgtagaag aaactagaaa cgttaaacgc atcaaatcaa      60
gaaattaaat tgaaggtaat ttttaacgcc gcctttcaaa tattcttcct aggagaggct     120
acaagacgcg tatttctttc gaattctcca aaccattacc attttgatat ataataccga     180
catgccgttg ataaagtttg tatgcaaatc gttcattggg tatgagcaaa tgccatccat     240
tggttcttgt aattaaatgg tccaaaaata gtttgttccc actactagtt actaatttgt     300
atcactctgc aaaataatca tgatataaac gtatgtgcta tttctaatta aaactcaaaa     360
gtaatcaatg tacaatgcag agatgaccat aaaagaacat taaaacacta cttccactaa     420
atctatgggg tgccttggca aggcaattga ataaggagaa tgcatcaaga tgatatagaa     480
aatgctattc agtttataac attaatgttt tggcggaaaa ttttctatat attagacctt     540
tctgtaaaaa aaaaaaatg atgtagaaaa tgctattatg tttcaaaaat ttcgcactag     600
tataatacgg aacattgtag tttacactgc tcattaccat gaaaccaag gcagtatata     660 ccaacattaa taaactaaat cgcgatttct agcaccccca ttaattaatt ttactattat     720
acattctctt tgcttctcga ataataaac ttctctatat cattctacat aataaataag     780
aaagaaatcg acaagatcta aatttagatc tattcagctt tttcgcctga gaagccaaaa     840
ttgtgaatag aagaaagcag tcgtcatctt cccacgtttg gacgaaataa aacataacaa     900
taataaaata ataatcaaa tatataaatc cctaatttgt ctttattact ccacaatttt     960
ctatgtgtat atatataccc acctctctct tgtgtatttg                         1000
```

<210> SEQ ID NO 69
<211> LENGTH: 998
<212> TYPE: DNA
<213> ORGANISM: Arabidopsis thaliana
<220> FEATURE:

```
<221> NAME/KEY: misc_feature
<222> LOCATION: (1)..(998)
<223> OTHER INFORMATION: Ceres Promoter YP0377

<400> SEQUENCE: 69
tataaaccat tcctataaca ccatatttaa acataacaat gaattgcttg gatttcaaac    60
tttattaaat ttggatttta aattttaatt tgattgaatt ataccccctt aattggataa   120
attcaaatat gtcaactttt tttttgtaag atttttttat ggaaaaaaaa attgattatt   180
cactaaaaag atgacaggtt acttataatt taatatatgt aaaccctaaa agaagaaaa    240
tagtttctgt tttcacttta ggtcttatta tctaaacttc tttaagaaaa tcgcaataaa   300
ttggtttgag ttctaacttt aaacacatta atatttgtgt gctatttaaa aaataattta   360
caaaaaaaaa aacaaattga cagaaaatat caggttttgt aataagatat ttcctgataa   420
atatttaggg aatataacat atcaaaagat tcaaattctg aaaatcaaga atggtagaca   480
tgtgaaagtt gtcatcaata tggtccactt ttctttgctc tataacccaa aattgaccct   540
gacagtcaac ttgtacacgc ggccaaacct ttttataatc atgctattta tttccttcat   600
ttttattcta tttgctatct aactgatttt tcattaacat gataccagaa atgaatttag   660
atggattaat tcttttccat ccacgacatc tggaaacact tatctcctaa ttaaccttac   720
ttttttttta gtttgtgtgc tccttcataa aatctatatt gtttaaaaca aaggtcaata   780
aatataaata tggataagta taataaatct ttattggata tttcttttt  taaaaaagaa   840
ataaatcttt tttggatatt ttcgtggcag catcataatg agagactacg tcgaaaccgc   900
tggcaaccac ttttgccgcg tttaatttct ttctgaggct tatataaata gatcaaaggg   960
gaaagtgaga tataatacag acaaaacaag agaaaaga                          998

<210> SEQ ID NO 70
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0380

<400> SEQUENCE: 70
acaagtacca ttcactttt  tactttcaa  tgtatacaat catcatgtga taaaaaaaa     60
aatgtaacca atcaacacac tgagatacgg ccaaaaaatg gtaatacata aatgtttgta   120
ggttttgtaa tttaaatact ttagttaagt tatgattttta ttattttgc ttatcactta   180
tacgaaatca tcaatctatt ggtatctctt aatcccgctt tttaatttcc accgcacacg   240
caaatcagca aatggttcca gccacgtgca tgtgaccaca tattgtggtc acagtactcg   300
tccttttttt ttcttttgta atcaataaat ttcaatccta aaacttcaca cattgagcac   360
gtcggcaacg ttagctccta aatcataacg agcaaaaaag ttcaaattag ggtatatgat   420
caattgatca tcactacatg tctacataat taatatgtat tcaaccggtc ggtttgttga   480
tactcatagt taagtatata tgtgctaatt agaattagga tgaatcagtt cttgcaaaca   540
actacggttt catataatat gggagtgtta tgtacaaaat gaaagaggat ggatcattct   600
gagatgttat gggctcccag tcaatcatgt tttgctcgca tatgctatct tttgagtctc   660
ttcctaaact catagaataa gcacgttggt ttttccacc  gtcctcctcg tgaacaaaag   720
tacaattaca ttttagcaaa ttgaaaataa ccacgtggat ggaccatatt atatgtgatc   780
atattgcttg tcgtcttcgt tttcttttaa atgtttacac cactacttcc tgacacgtgt   840
```

```
ccctattcac atcatccttg ttatatcgtt ttacttataa aggatcacga acaccaaaac    900
atcaatgtgt acgtcttttg cataagaaga aacagagagc attatcaatt attaacaatt    960
acacaagaca gcgagattgt aaaagagtaa gagagagag                           999

<210> SEQ ID NO 71
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0381

<400> SEQUENCE: 71
cacggtcaaa gtattgctaa catggtcatt acattgaaaa agaaaattaa ttgtctttac     60
tcatgtttat tctatacaaa taaaaatatt aaccaaccat cgcactaaca aaatagaaat    120
cttattctaa tcacttaatt gttgacaatt aaatcattga aaaatacact taaatgtcaa    180
atattcgttt tgcatacttt tcaatttaaa tacatttaaa gttcgacaag ttgcgtttac    240
tatcatagaa aactaaatct cctaccaaag cgaaatgaaa ctactaaagc gacaggcagg    300
ttacataacc taacaaatct ccacgtgtca attaccaaga gaaaaaaaga gaagataagc    360
ggaacacgtg gtagcacaaa aaagataatg tgatttaaat taaaaaacaa aaacaaagac    420
acgtgacgac ctgacgctgc aacatcccac cttacaacgt aataaccact gaacataaga    480
cacgtgtacg atcttgtctt tgttttctcg atgaaaacca cgtgggtgct caaagtcctt    540
gggtcagagt cttccatgat tccacgtgtc gttaatgcac caaacaaggg tactttcggt    600
attttggctt ccgcaaatta gacaaaacag cttttttgttt gattgattt tctcttctct    660 ttttccatct aaattctctt tgggctctta atttcttttt gagtgttcgt tcgagatttg    720
tcggagattt tttcggtaaa tgttgaaatt ttgtgggatt tttttttatt tctttattaa    780 acttttttt attgaattta taaaaaggga aggtcgtcat taatcgaaga aatggaatct    840
tccaaaattt gatattttgc tgttttcttg ggatttgaat tgctctttat catcaagaat    900
ctgttaaaat ttctaatcta aaatctaagt tgagaaaaag agagatctct aatttaaccg    960
gaattaatat tctccgaccg aagttattat gttgcaggct                         1000

<210> SEQ ID NO 72
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0384

<400> SEQUENCE: 72
tttaaaaaat tggataaaac accgataaaa attcacattt gcaaatttta ttcagtcgga     60
atatatattt gaaacaagtt ttgaaatcca ttggacgatt aaaattcatt gttgagagga    120
taaatatgga tttgttcatc tgaaccatgt cgttgattag tgattgacta ccatgaaaaa    180
tatgttatga aaagtataac aacttttgat aaatcacatt tattaacaat aaatcaagac    240
aaaatatgtc aacaataata gtagtagaag atattaattc aaattcatcc gtaacaacaa    300
aaaatcatac cacaattaag tgtacagaaa aaccttttgg atatatttat tgtcgctttt    360
caatgatttt cgtgaaaagg atatatttgt gtaaaataag aaggatcttg acgggtgtaa    420
```

```
aaacatgcac aattcttaat ttagaccaat cagaagacaa cacgaacact tctttattat    480
aagctattaa acaaaatctt gcctattttg cttagaataa tatgaagagt gactcatcag    540
ggagtggaaa atatctcagg atttgctttt agctctaaca tgtcaaacta tctagatgcc    600
aacaacacaa agtgcaaatt cttttaatat gaaaacaaca ataatatttc taatagaaaa    660
ttaaaaaggg aaataaaata ttttttttaaa atatacaaaa gaagaaggaa tccatcatca    720
aagttttata aaattgtaat ataatacaaa cttgtttgct tccttgtctc tccctctgtc    780
tctctcatct ctcctatctt ctccatatat acttcatctt cacacccaaa actccacaca    840
aaatatctct ccctctatct gcaaattttc caaagttgca tcctttcaat ttccactcct    900
ctctaatata attcacattt tcccactatt gctgattcat ttttttttgt gaattatttc    960
aaacccacat aaaaaaatct tgtttaaat ttaaaacca    999
```

```
<210> SEQ ID NO 73
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0385

<400> SEQUENCE: 73
actcaacaat aggacaagcc aaaaaaattc caattattgt gttactctat tcttctaaat     60
ttgaacacta atagactatg acatatgagt ataatgtg aagtcttaag atattttcat    120
gtgggagatg aataggccaa gttggagtct gcaaacaaga agctcttgag ccacgacata    180
agccaagttg atgaccgtaa ttaatgaaac taaatgtgtg tggttatata ttagggaccc    240
atggccatat acacaatttt tgtttctgtc gatagcatgc gtttatatat atttctaaaa    300
aaactaacat atttactgga tttgagttcg aatattgaca ctaatataaa ctacgtacca    360
aactacatat gtttatctat atttgattga tcgaagaatt ctgaactgtt ttagaaaatt    420
tcaatacact taacttcatc ttacaacggt aaaagaaatc accactagac aaacaatgcc    480
tcataatgtc tcgaaccctc aaactcaaga gtatacattt tactagatta gagaatttga    540
tatcctcaag ttgccaaaga attggaagct tttgttacca aacttagaaa cagaagaagc    600
cacaaaaaaa gacaaaggga gttaaagatt gaagtgatgc atttgtctaa gtgtgaaagg    660
tctcaagtct caactttgaa ccataataac attactcaca ctcccttttt ttttcttttt    720
ttttcccaaa gtacccttt taattccctc tataacccac tcactccatt ccctctttct    780
gtcactgatt caacacgtgg ccacactgat gggatccacc tttcctctta cccacctccc    840 ggttatata aacccttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa    998
```

```
<210> SEQ ID NO 74
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0396

<400> SEQUENCE: 74
catagtaaaa gtgaatttaa tcatactaag taaaataaga taaaacatgt tatttgaatt     60
```

```
tgaatatcgt gggatgcgta tttcggtatt tgattaaagg tctggaaacc ggagctccta      120
taacccgaat aaaaatgcat aacatgttct tccccaacga ggcgagcggg tcagggcact      180
agggtcattg caggcagctc ataaagtcat gatcatctag gagatcaaat tgtatgtcgg      240
ccttctcaaa attacctcta agaatctcaa acccaatcat agaacctcta aaagacaaa       300 gtcgtcgctt tagaatgggt tcggtttttg gaaccatatt tcacgtcaat ttaatgttta      360
gtataatttc tgaacaacag aattttggat ttatttgcac gtatacaaat atctaattaa      420
taaggacgac tcgtgactat ccttacatta agtttcactg tcgaaataac atagtacaat      480
acttgtcgtt aatttccacg tctcaagtct ataccgtcat ttacggagaa agaacatctc      540
tgtttttcat ccaaactact attctcactt tgtctatata tttaaaatta agtaaaaaag      600
actcaatagt ccaataaaat gatgaccaaa tgagaagatg gttttgtgcc agattttagg      660
aaaagtgagt caaggtttca catctcaaat ttgactgcat aatcttcgcc attaacaacg      720
gcattatata tgtcaagcca attttccatg ttgcgtactt ttctattgag gtgaaaatat      780
gggtttgttg attaatcaaa gagtttgcct aactaatata actacgactt tttcagtgac      840
cattccatgt aaactctgct tagtgtttca tttgtcaaca atattgtcgt tactcattaa      900
atcaaggaaa aatatacaat tgtataattt tcttatattt taaaattaat tttgatgtat      960
taccccttta taaataggct atcgctacaa caccaataac                            1000

<210> SEQ ID NO 75
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 75
tttcgatcct cttctttttt aggtttcttg atttgatgat cgccgccagt agagccgtcg       60
tcggaagttt cagagattaa aaccatcacc gtgtgagttg gtagcgaatt aacggaaagt      120
ctaagtcaag attttttaaa aagaaattta tgtgtgaaaa gaagccgttg tgtatattta      180
tataatttag aaaatgtttc atcattttaa ttaaaaaatt aataatttgt agaagaaaga      240
agcatttttt atacataaat catttacctt ctttactgtg ttttttcttca cttacttcat      300 ttttactttt ttacaaaaaa gtgaaaagta aattacgtaa ttggtaacat aaattcactt      360
taaatttgca tatgttttgt tttcttcgga aactatatcg aaaagcaaac ggaaagaact      420
tcacaaaaaa ccctagctaa ctaaagacgc atgtgttctt cttattcttc atatatcctc      480
tgtttcttgt gttctgtttt gagtcttaca ttttcaatat ctgactctga ttactatatc      540
taaaagggaa catgaagaac ttgagaccat gttaaactgt acaatgcctt caaacatggc      600
taactaaaga tacattagat ggcttttacag tgtgtaatgc ttattatctt taggtttttt    660
aaatcccttg tattaagtta tttaccaaat tatgttcttg tactgcttat tggcttggtt     720
gttgtgtgct ttgtaaacaa cacctttggc tttatttcat cctttgtaaa cctactggtc    780
tttgttcagc tcctcttgga agtgagtttg tatgcctgga acgggtttta atggagtgtt    840
tatcgacaaa aaaaaaatgt agcttttgaa atcacagaga gtagttttat attcaaatta    900
catgcatgca actaagtagc aacaaagttg atatggccga gttggtctaa ggcgccagat    960
taaggttctg gtccgaaagg gcgtgggttc aaatcccact gtcaacattc tcttttctc   1020
```

```
aaattaatat ttttctgcct caatggttca ggcccaatta tactagacta ctatcgcgac    1080
taaaataggg actagccgaa ttgatccggc ccagtatcag ttgtgtatca ccacgttatt    1140
tcaaatttca aactaaggga taaagatgtc atttgacata tgagatattt ttttgctcca    1200
ctgagatatt tttctttgtc ccaagataaa atatcttttc tcgcatcgtc gtctttccat    1260
ttgcgcatta aaccaaaaag tgtcacgtga tatgtcccca accactacga attttaacta    1320
cagatttaac catggttaaa ccagaattca cgtaaaccga ctctaaacct agaaaatatc    1380
taaaccttgg ttaatatctc agccccctta taaataacga gacttcgtct acatcgttct    1440
acacatctca ctgctcacta ctctcactgt aatcccttag atcttctttt caaatttcac    1500
cattgcactg gatg                                                     1514

<210> SEQ ID NO 76
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 76
gtgggtaaaa gtatccttct ttgtgcattt ggtattttta agcatgtaat aagaaaaacc      60
aaaatagacg gctggtattt aataaaagga gactaatgta tgtatagtat atgatttgtg     120
tggaatataa taaagttgta aaatatagat gtgaagcgag tatctatctt ttgactttca     180
aaggtgatcg atcgtgttct ttgtgatagt tttggtcgtc ggtctacaag tcaacaacca     240
ccttgaagtt ttcgcgtctc ggtttcctct tcgcatctgg tatccaatag catacatata     300
ccagtgcgga aaatggcgaa gactagtggg cttgaaccat aaggtttggc cccaatacgg     360
attccaaaca acaagcctag cgcagtcttt tgggatgcat aagactaaac tgtcgcagtg     420
atagacgtaa gatatatcga cttgattgga atcgtctaag ctaataagtt taccttgacc     480
gtttatagtt gcgtcaacgt ccttatggag attgatgccc atcaaataaa cctgaaaatc     540
catcaccatg accaccataa actcccttgc tgccgctgct ttggcttgag caaggtgttt     600
ccttgtaaag ctccgatctt tggataaagt gttccacttt ttgcaagtag ctctgacccc     660
tctcagagat gtcaccggaa tcttagacag aacctcctct gccaaatcac ttggaagatc     720
ggacaatgtc atcatttttg caggtaattt ctccttcgtt gctgctttgg cttgagcacg     780
gtgcttcttt gtaaagctcc gatctttgga taagagcgga tcggaatcct ctaggaggtg     840
ccagtcccct gacctattaa tttatagaag gttttagtgt attttgttcc aatttcttct     900
ctaacttaac aaataacaac tgcctcatag tcatgggctt caaattttat cgcttggtgt     960
atttcgttat ttgcaaggcc ttggcccatt ttgagcccaa taactaaatc tagccttttc    1020
agaccggaca tgaacttcgc atattggcgt aactgtgcag ttttaccttt ttcggatcag    1080
acaagatcag atttagacca cccaacaata gtcagtcata tttgacaacc taagctagcc    1140
gacactacta aaaagcaaac aaaagaagaa ttctatgttg tcattttacc ggtggcaagt    1200 ggaccccttct ataaaagagt aaagagacag cctgtgtgtg tataatctct aattatgttc    1260
accgacacaa tcacacaaac ccttctctaa tcacacaact tcttcatgat ttacgacatt    1320
aattatcatt aactctttaa attcacttta catgctcaaa aatatctaat ttgcagcatt    1380
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500
```

```
tcttacattt ctagatctaa tctgaaccgt cagatatcta gatctcattg tctgaacaca    1560
gttagatgaa actgggaatg aatctggacg aaattacgat cttacaccaa ccccctcgac    1620
gagctcgtat atataaagct tatacgctcc tccttcacct tcgtactact actaccacca    1680
catttcttta gctcaacctt cattactaat ctccttttaa ggtatgttca cttttcttcg    1740
attcatactt tctcaagatt cctgcatttc tgtagaattt gaaccaagtg tcgattttg     1800 tttgagagaa gtgttgattt atagatctgg ttattgaatc tagattccaa ttttaattg     1860 attcgagttt gttatgtgtg tttatactac ttctcattga tcttgtttga tttctctgct    1920
ctgtattagg tttctttcgt gaatcagatc ggaa                                1954

<210> SEQ ID NO 77
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 77
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catccctttgg taactctcaa gtttaggttg tttgaattgc     300
ctctgttgtg atacttattg tctattgcat caatcttcta atgcaccacc ctagactatt      360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc cattttttg tagtcttgct      720 agttgagata ttacctcttc tcttcaaagt atccttgaac gctcaccggt tatgaaatct     780
ctacactata gctctgtagt cttgctagat agttagttct ttagctctct ttttgtagcc     840
tagttcttta gctctccttt tgtagccttg ctacagagta agatgggata ttacctcctt     900
gaacgctctc cggttatgac caatttgttg tagctccttg taagtagaac ttaggataga    960
gtgagtcaac tttaagaaag aacctagtat gtggcataac cagattgcag gctctgtctc    1020
ggctacagta acgtaactct atagctcttt gttttgttca gaaagaacca gtgattggat    1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct ttttcctttt   1380
gacaacaaca tataaaatca tactcccatt aaaaagattt taatgtaaaa ttctgaatat   1440
aagatatttt ttacaacaac aaccaaaaat atttattttt ttcctttttt acagcaacaa   1500
```

| | |
|---|---|
| gaaggaaaaa cttttttttt tgtcaagaaa aggggagatt atgtaaacag ataaaacagg | 1560 |
| gaaaataact aaccgaactc tcttaattaa catcttcaaa taaggaaaat tatgatccgc | 1620 |
| atatttagga agatcaatgc attaaaacaa cttgcacgtg gaaagagaga ctatacgctc | 1680 |
| cacacaagtt gcactaatgg tacctctcac aaaccaatca aaatactgaa taatgccaac | 1740 |
| gtgtacaaat tagggtttta cctcacaacc atcgaacatt ctcgaaacat tttaaacagc | 1800 |
| ctggcgccat agatctaaac tctcatcgac caatttttga ccgtccgatg gaaactctag | 1860 |
| cctcaaccca aaactctata taaagaaatc ttttccttcg ttattgctta ccaaatacaa | 1920 |
| accctagccg ccttattcgt cttcttcgtt ctctagtttt ttcctcagtc tctgttctta | 1980 |
| gatcccttgt agtttccaaa tcttccgata aggcct | 2016 |

<210> SEQ ID NO 78
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PR0924

<400> SEQUENCE: 78

| | |
|---|---|
| atctataacg agttaacatg ttgccagttt gaatcaagaa gcttggatga tgaatgaatg | 60 |
| gatcggtttg tggtacaatt cttaaaattg tagtagagga gacagagaaa aaacatgata | 120 |
| agactttggt atttacaact tgacggagac aagacagtaa gccaaatctg tcacaaaaac | 180 |
| actcaaactc ttttctcagt gttttgagtt taaagagaga cttattcact tccccttttcg | 240 |
| taacacttat ttgtctccca accaaacagt ttctgtcctt tcccttgtcc tcccacgtgc | 300 |
| atctttatat ctcatgactt ttcgtttcta gatcttgaat aatgtcttag tggattaggt | 360 |
| ttgttgtcgg taaattaggt gaccgttttt ttcttatatt tggaagatcg cgggatgaag | 420 |
| cagatactga gtttcagggc atacacacct aatttgaaaa tcattgttag tccaatttca | 480 |
| ctttaatctt gtttacaaaa aaattgatct gaaaatgttg atgggataag taaaaatgta | 540 |
| agttttgcta gtagtcatga tataataata gcaaaaccag atcaatttg agcaaaagga | 600 |
| agaaacaaaa aacagatcga tcccacgagc aagactaagt gtaaagtggt tcccacaaga | 660 |
| gccatatgga tatggtcctt caacttttaa agcccattac ttcagtggtc gacccgacat | 720 |
| tacgccacga gtagtcacgc acgcacgact ccgttcacgt gacattcacg ttgatatttc | 780 |
| cccctctact ctcttctgct tggttgatct aaaaaacatg aagagaccaa cctaatttca | 840 |
| tattaatata tgatatagac ttcatactca acagtcactt tcgtaatcca aatccatatc | 900 |
| ttacgaaatt agttcttaat aaaggttgtg gattaagtta taatattgtg ttaagagtta | 960 |
| agacacagca tataaccttg taccaacagt gctttattct taaatggaaa caaaacatat | 1020 |
| gtca | 1024 |

<210> SEQ ID NO 79
<211> LENGTH: 857
<212> TYPE: DNA
<213> ORGANISM: Arabidopsis thaliana
<220> FEATURE:
<221> NAME/KEY: misc_feature
<222> LOCATION: (1)..(857)
<223> OTHER INFORMATION: Ceres Promoter PD1367
<220> FEATURE:
<221> NAME/KEY: misc_feature
<222> LOCATION: (116)..(116)
<223> OTHER INFORMATION: n is a, c, t, g, unknown, or other

```
<220> FEATURE:
<221> NAME/KEY: misc_feature
<222> LOCATION: (136)..(136)
<223> OTHER INFORMATION: n is a, c, t, g, unknown, or other
<220> FEATURE:
<221> NAME/KEY: misc_feature
<222> LOCATION: (154)..(154)
<223> OTHER INFORMATION: n is a, c, t, g, unknown, or other
<220> FEATURE:
<221> NAME/KEY: misc_feature
<222> LOCATION: (159)..(159)
<223> OTHER INFORMATION: n is a, c, t, g, unknown, or other
<220> FEATURE:
<221> NAME/KEY: misc_feature
<222> LOCATION: (168)..(168)
<223> OTHER INFORMATION: n is a, c, t, g, unknown, or other
<220> FEATURE:
<221> NAME/KEY: misc_feature
<222> LOCATION: (172)..(172)
<223> OTHER INFORMATION: n is a, c, t, g, unknown, or other
<220> FEATURE:
<221> NAME/KEY: misc_feature
<222> LOCATION: (175)..(175)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<222> LOCATION: (680)..(680)
<223> OTHER INFORMATION: n is a, c, t, g, unknown, or other
<220> FEATURE:
<221> NAME/KEY: misc_feature
<222> LOCATION: (686)..(686)
<223> OTHER INFORMATION: n is a, c, t, g, unknown, or other
<220> FEATURE:
<221> NAME/KEY: misc_feature
<222> LOCATION: (724)..(724)
<223> OTHER INFORMATION: n is a, c, t, g, unknown, or other
<220> FEATURE:
<221> NAME/KEY: misc_feature
<222> LOCATION: (737)..(737)
<223> OTHER INFORMATION: n is a, c, t, g, unknown, or other

<400> SEQUENCE: 79
ttggaattaa ttctgcggcc atggggctgc aggaattcga tggcccgatc ggccacagtt      60 ttctttctc  atcttacaac aagtttccag gaggatagag acataaacga agctcnggat     120
tgtatcgttc tttttnagct tttattcaca tccngaaang tcctgtangt tntangattc     180
tgttatcttg cggttttgag ttaatcagaa acagagtaat caatgtaatg ttgcaggcta     240
gatctttcat ctttggaaat ttgttttttt ctcatgcaat ttctttagct tgaccatgag     300
tgactaaaag atcaatcagt agcaatgatt tgatttggct aagagacatt tgtccacttg     360
gcatcttgat ttggatggtt acaacttgca agacccaatt ggatacttgc tatgacaact     420
ccaactcaag agtgtcgtgt aactaagaac cttgactaat ttgtaatttc aatcccaagt     480
catgttacta tatgttttt  tgtttgtatt attttctctc ctacaattaa gctctttgac     540
gtacgtaatc tccggaacca actcctatat ccaccattta ctccacgttg tctccaatta     600
ttggacgttg aaacttgaca caacgtaaac gtatctacgt ggttgattgt atgtacatat     660
gtacaaacgt acacctttnn tcctncttt cacttcatca cttggcttgt gaattcatta     720
attncctgcg aaggccntgc agggccatca ccactgcagt ggaacaatga agactaatct     780
ttttctcttt ctcatctttt cacttctcct atcattatcc tcggccgaat tcagtaaagg     840
agaagaactt ttcactg                                                    857

<210> SEQ ID NO 80
```

```
<211> LENGTH: 884
<212> TYPE: DNA
<213> ORGANISM: Arabidopsis thaliana
<220> FEATURE:
<221> NAME/KEY: misc_feature
<222> LOCATION: (1)..(884)
<223> OTHER INFORMATION: Ceres CLONE ID no. 92459
<220> FEATURE:
<221> NAME/KEY: misc_feature
<222> LOCATION: (1)..(884)
<223> OTHER INFORMATION: Also Known As Ceres ME LINE ME04077
<220> FEATURE:
<221> NAME/KEY: misc_feature
<222> LOCATION: (1)..(884)
<223> OTHER INFORMATION: Also Known As Ceres LEAD Number 15
<220> FEATURE:
<221> NAME/KEY: CDS
<222> LOCATION: (42)..(663)
<223> OTHER INFORMATION: Referenced by SEQ ID NO: 81

<400> SEQUENCE: 80
aggattaaat tagggcataa cccttatcgg agatttgaag ccatgggaag aagaaaaatc      60
gagatcaagc gaatcgagaa caaaagcagt cgacaagtca ctttctccaa acgacgcaat    120
ggtctcatcg acaaagctcg acaactttcg attctctgtg aatcctccgt cgctgttgtc    180
gtcgtatctg cctccggaaa actctatgac tcttcctccg gtgacgacat ttccaagatc    240
attgatcgtt atgaaataca acatgctgat gaacttagag ccttagatct tgaagaaaaa    300
attcagaatt atcttccaca caaggagtta ctagaaacag tccaaagcaa gcttgaagaa    360
ccaaatgtcg ataatgtaag tgtagattct ctaatttctc tggaggaaca acttgagact    420
gctctgtccg taagtagagc taggaaggca gaactgatga tggagtatat cgagtccctt    480
aaagaaaagg agaaattgct gagagaagag aaccaggttc tggctagcca gatgggaaag    540
aatacgttgc tggcaacaga tgatgagaga ggaatgtttc cgggaagtag ctccggcaac    600
aaaataccgg agactctccc gctgctcaat tagccaccat catcaacggc tgagttttca    660
ccttaaactc aaagcctgat tcataattaa gagaataaat ttgtatatta taaaaagctg    720
tgtaatctca aaccttttat cttcctctag tgtggaattt aaggtcaaaa agaaaacgag    780
aaagtatgga tcagtgttgt acctccttcg gagacaagat cagagtttgt gtgtttgtgt    840
ctgaatgtac ggattggatt tttaaagttg tgctttcttt cttc                     884

<210> SEQ ID NO 81
<211> LENGTH: 206
<212> TYPE: PRT
<213> ORGANISM: Arabidopsis thaliana
<220> FEATURE:
<221> NAME/KEY: misc_feature
<222> LOCATION: (1)..(206)
<223> OTHER INFORMATION: Ceres CLONE ID no. 92459
<220> FEATURE:
<221> NAME/KEY: misc_feature
<222> LOCATION: (1)..(206)
<223> OTHER INFORMATION: Also Known As Ceres CDNA ID no. 23361912
<220> FEATURE:
<221> NAME/KEY: misc_feature
<222> LOCATION: (1)..(206)
<223> OTHER INFORMATION: Also Known As Ceres ME LINE ME04077
<220> FEATURE:
<221> NAME/KEY: misc_feature
<222> LOCATION: (1)..(206)
<223> OTHER INFORMATION: Also Known As Ceres LEAD Number 15
<220> FEATURE:
<221> NAME/KEY: misc_feature
<222> LOCATION: (117)..(166)
<223> OTHER INFORMATION: Pfam Name: K-box; Pfam Description: K-box
      re.g.ion
<220> FEATURE:
```

<221> NAME/KEY: misc_feature
<222> LOCATION: (9)..(59)
<223> OTHER INFORMATION: Pfam Name: SRF-TF; Pfam Description: SRF-type
      transcription factor (DNA-binding and dimerisation domain)
<220> FEATURE:
<221> NAME/KEY: misc_feature
<222> LOCATION:
<223> OTHER INFORMATION: Phenotype: Late Flowering
      Useful for delaying flowering time
<220> FEATURE:
<221> NAME/KEY: misc_feature
<222> LOCATION:
<223> OTHER INFORMATION: Phenotype: Dark Green
      Useful for increasing chlorophyll
      and photosynthetic capacity
<220> FEATURE:
<221> NAME/KEY: misc_feature
<222> LOCATION:
<223> OTHER INFORMATION: Phenotype: Large
      Useful for making larger plants
<220> FEATURE:
<221> NAME/KEY: misc_feature
<222> LOCATION:
<223> OTHER INFORMATION: Phenotype: INFLORESCENCE
      Useful for making ornamental plants
      with modified flowers
<220> FEATURE:
<221> NAME/KEY: misc_feature
<222> LOCATION:
<223> OTHER INFORMATION: Phenotype: CAULINE LEAVES
      Useful for making ornamental plants
      with modified leaves
<220> FEATURE:
<221> NAME/KEY: misc_feature
<222> LOCATION:
<223> OTHER INFORMATION: Phenotype: ROSETTE LEAVES
      Useful for making ornamental plants
      with modified leaves
<220> FEATURE:
<221> NAME/KEY: misc_feature
<222> LOCATION:
<223> OTHER INFORMATION: Phenotype: Serrate Margins
      Useful for making plants with increased biomass
      and foliage
<220> FEATURE:
<221> NAME/KEY: misc_feature
<222> LOCATION:
<223> OTHER INFORMATION: Phenotype: Serrate Margins
      Useful for making plants with increased biomass
      and foliage
<220> FEATURE:
<221> NAME/KEY: misc_feature
<222> LOCATION:
<223> OTHER INFORMATION: Phenotype: Plant Size
      Useful for making plants with increased size
      and biomass
<220> FEATURE:
<221> NAME/KEY: misc_feature
<222> LOCATION:
<223> OTHER INFORMATION: Phenotype: Strong
      Useful for making stronger plants

<400> SEQUENCE: 81

Met Gly Arg Arg Lys Ile Glu Ile Lys Arg Ile Glu Asn Lys Ser Ser
1               5                   10                  15

Arg Gln Val Thr Phe Ser Lys Arg Arg Asn Gly Leu Ile Asp Lys Ala
            20                  25                  30

Arg Gln Leu Ser Ile Leu Cys Glu Ser Ser Val Ala Val Val Val Val
        35                  40                  45

Ser Ala Ser Gly Lys Leu Tyr Asp Ser Ser Ser Gly Asp Asp Ile Ser
    50                  55                  60

Lys Ile Ile Asp Arg Tyr Glu Ile Gln His Ala Asp Glu Leu Arg Ala
65                  70                  75                  80

-continued

```
Leu Asp Leu Glu Glu Lys Ile Gln Asn Tyr Leu Pro His Lys Glu Leu
                85                  90                  95

Leu Glu Thr Val Gln Ser Lys Leu Glu Glu Pro Asn Val Asp Asn Val
            100                 105                 110

Ser Val Asp Ser Leu Ile Ser Leu Glu Glu Gln Leu Glu Thr Ala Leu
            115                 120                 125

Ser Val Ser Arg Ala Arg Lys Ala Glu Leu Met Met Glu Tyr Ile Glu
        130                 135                 140

Ser Leu Lys Glu Lys Glu Lys Leu Leu Arg Glu Glu Asn Gln Val Leu
145                 150                 155                 160

Ala Ser Gln Met Gly Lys Asn Thr Leu Leu Ala Thr Asp Asp Glu Arg
                165                 170                 175

Gly Met Phe Pro Gly Ser Ser Ser Gly Asn Lys Ile Pro Glu Thr Leu
            180                 185                 190

Pro Leu Leu Asn Pro Pro Ser Ser Thr Ala Glu Phe Ser Pro

<210> SEQ ID NO 82
<211> LENGTH: 201
<212> TYPE: PRT
<213> ORGANISM: Brassica rapa subsp. pekinensis
<220> FEATURE:
<221> NAME/KEY: misc_feature
<222> LOCATION: (1)..(201)
<223> OTHER INFORMATION: Public GI no. 71834745
<220> FEATURE:
<221> NAME/KEY: misc_feature
<222> LOCATION: (1)..(201)
<223> OTHER INFORMATION: Functional Homolog of Ceres CLONE ID no. 92459
      at SEQ ID NO. 81
      with e-value of 6.50E-66 and percent identity of 75.2

<400> SEQUENCE: 82

Met Gly Arg Arg Lys Val Glu Ile Lys Leu Ile Glu Asn Lys Ser Ser
1               5                   10                  15

Arg Gln Val Thr Phe Ser Lys Arg Arg Thr Gly Leu Ile Glu Lys Ala
            20                  25                  30

Arg Gln Leu Ser Val Leu Cys Glu Ser Ser Val Ala Val Leu Val Val
        35                  40                  45

Ser Ala Ser Gly Lys Leu Tyr Asn Ser Ser Ser Gly Asp Asn Met Thr
50                  55                  60

Asn Ile Val Asp Arg Tyr Glu Ile Gln His Ala Gly Glu Leu Arg Ser
65                  70                  75                  80

Leu Asp Leu Ala Glu Lys Thr Arg Asn Tyr Leu Pro His Lys Glu Leu
                85                  90                  95

Leu Glu Ser Val Lys Ser Asn Leu Glu Glu Pro Asn Val Asp Ser Val
            100                 105                 110

Ser Val Asp Ser Leu Ile Ser Leu Glu Asp Gln Leu Glu Thr Ala Leu
            115                 120                 125

Ser Ala Thr Arg Ala Arg Lys Thr Glu Leu Thr Met Glu Phe Val Lys
        130                 135                 140

Met Leu Gln Glu Lys Glu Glu Leu Leu Arg Glu Glu Asn Leu Val Leu
145                 150                 155                 160

Val Ser Gln Ile Gly Thr Thr Asn Gly Arg Arg Glu Asn Asn Ser Pro
                165                 170                 175

Val Asn Ser Ser Gly Ile Asn Pro Pro Glu Thr Leu Pro Leu Leu Lys
            180                 185                 190

Val Thr Ser Val Ile Gln Arg Leu Ser
        195                 200
```

```
<210> SEQ ID NO 83
<211> LENGTH: 196
<212> TYPE: PRT
<213> ORGANISM: Brassica napus
<220> FEATURE:
<221> NAME/KEY: misc_feature
<222> LOCATION: (1)..(196)
<223> OTHER INFORMATION: Public GI no. 31580813
<220> FEATURE:
<221> NAME/KEY: misc_feature
<222> LOCATION: (1)..(196)
<223> OTHER INFORMATION: Functional Homolog of Ceres CLONE ID no. 92459
      at SEQ ID NO. 81
      with e-value of 3.09E-59 and percent identity of 67.5

<400> SEQUENCE: 83

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Asn Phe Ser Ala Gly Asp Asn Leu Val
    50                  55                  60

Lys Ile Leu Asp Arg Tyr Gly Lys Gln His Ala Asp Leu Lys Ala
65                  70                  75                  80

Leu Asp Leu Gln Ser Lys Ala Pro Lys Tyr Gly Ser His His Glu Leu
                85                  90                  95

Leu Glu Leu Val Glu Ser Lys Leu Val Glu Ser Asn Ser Asp Val Ser
            100                 105                 110

Val Asp Ser Leu Val Gln Leu Glu Asp His Leu Glu Thr Ala Leu Ser
        115                 120                 125

Val Thr Arg Ala Arg Lys Thr Glu Leu Met Leu Lys Leu Val Asp Ser
130                 135                 140

Leu Lys Glu Lys Glu Lys Leu Leu Lys Glu Glu Asn Gln Gly Leu Ala
145                 150                 155                 160

Ser Gln Met Glu Lys Asn Asn Leu Ala Gly Ala Glu Ala Asp Lys Met
                165                 170                 175

Glu Met Ser Pro Gly Gln Ile Ser Asp Ile Asn Arg Pro Val Thr Leu
            180                 185                 190

Arg Leu Leu Tyr
        195

<210> SEQ ID NO 84
<211> LENGTH: 197
<212> TYPE: PRT
<213> ORGANISM: Brassica oleracea var. capitata
<220> FEATURE:
<221> NAME/KEY: misc_feature
<222> LOCATION: (1)..(197)
<223> OTHER INFORMATION: Public GI no. 34591565
<220> FEATURE:
<221> NAME/KEY: misc_feature
<222> LOCATION: (1)..(197)
<223> OTHER INFORMATION: Functional Homolog of Ceres CLONE ID no. 92459
      at SEQ ID NO. 81
      with e-value of 3.50E-58 and percent identity of 67.0

<400> SEQUENCE: 84

Met Gly Arg Lys Lys Leu Glu Ile Lys Arg Ile Glu Asn Lys Ser Ser
1               5                   10                  15
```

```
Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Asn Phe Ser Ala Gly Asp Asp Leu Val
50                  55                  60

Lys Val Ile Asp Arg Tyr Gly Glu Gln His Ala Asp Asp Arg Lys
65                  70                  75                  80

Ala Leu Asp Leu Gln Ser Glu Ala Pro Lys Tyr Gly Ser His His Glu
                85                  90                  95

Leu Leu Glu Leu Val Glu Ser Lys Leu Val Glu Ser Asn Ser Asp Val
                100                 105                 110

Ser Val Asp Ser Leu Val Gln Leu Glu Asn His Leu Glu Thr Ala Leu
                115                 120                 125

Ser Val Thr Arg Ala Arg Lys Thr Glu Leu Leu Lys Leu Val Asp
                130                 135             140

Ser Leu Lys Glu Lys Gly Lys Leu Leu Lys Glu Glu Asn Gln Gly Leu
145                 150                 155                 160

Ala Ser Gln Met Glu Lys Asn Asn Leu Ala Gly Ala Glu Ala Asp Lys
                165                 170                 175

Met Glu Val Ser Pro Gly Gln Ile Ser Asp Ile Asn Cys Pro Val Thr
                180                 185                 190

Leu Pro Leu Leu Tyr
                195

<210> SEQ ID NO 85
<211> LENGTH: 197
<212> TYPE: PRT
<213> ORGANISM: Brassica napus
<220> FEATURE:
<221> NAME/KEY: misc_feature
<222> LOCATION: (1)..(197)
<223> OTHER INFORMATION: Ceres CLONE ID no. 1065387
<220> FEATURE:
<221> NAME/KEY: misc_feature
<222> LOCATION: (1)..(197)
<223> OTHER INFORMATION: Functional Homolog of Ceres CLONE ID no. 92459
      at SEQ ID NO. 81
      with e-value of 1.30E-60 and percent identity of 67.0

<400> SEQUENCE: 85

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Ser Phe Ser Ser Gly Asp Asn Leu Val
50                  55                  60

Lys Ile Leu Asp Arg Tyr Gly Lys Gln His Asp Asp Leu Lys Ala
65                  70                  75                  80

Leu Asp Arg Gln Ser Lys Ala Leu Asp Cys Gly Ser His His Glu Leu
                85                  90                  95

Leu Glu Leu Val Glu Ser Lys Leu Glu Ser Asn Val Asp Asn Val
                100                 105                 110

Ser Val Gly Ser Leu Val Gln Leu Glu Glu His Leu Glu Asn Ala Leu
                115                 120                 125

Ser Val Thr Arg Ala Arg Lys Thr Glu Leu Met Leu Lys Leu Val Glu
```

```
                130                 135                 140
Asn Leu Lys Glu Lys Glu Lys Leu Leu Glu Glu Asn His Val Leu
145                 150                 155                 160

Ala Ser Gln Met Glu Lys Ser Asn Leu Val Arg Ala Glu Ala Asp Asn
                165                 170                 175

Met Asp Val Ser Pro Gly Gln Ile Ser Asp Ile Asn Leu Pro Val Thr
            180                 185                 190

Leu Pro Leu Leu Asn
        195

<210> SEQ ID NO 86
<211> LENGTH: 197
<212> TYPE: PRT
<213> ORGANISM: Brassica napus
<220> FEATURE:
<221> NAME/KEY: misc_feature
<222> LOCATION: (1)..(197)
<223> OTHER INFORMATION: Public GI no. 17933450
<220> FEATURE:
<221> NAME/KEY: misc_feature
<222> LOCATION: (1)..(197)
<223> OTHER INFORMATION: Functional Homolog of Ceres CLONE ID no. 92459
      at SEQ ID NO. 81
      with e-value of 1.59E-60 and percent identity of 66.8

<400> SEQUENCE: 86

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
                20                  25                  30

Arg Gln Leu Ser Val Leu Cys Asp Ala Ser Val Ala Leu Leu Val Val
            35                  40                  45

Ser Ala Ser Gly Lys Leu Tyr Ser Phe Ser Ser Gly Asp Asn Leu Val
        50                  55                  60

Lys Ile Leu Asp Arg Tyr Gly Lys Gln His Asp Asp Leu Lys Ala
65                  70                  75                  80

Leu Asp Arg Gln Ser Lys Ala Leu Asp Cys Gly Ser His His Glu Leu
                85                  90                  95

Leu Glu Leu Val Glu Ser Lys Leu Glu Glu Ser Asn Val Asp Asn Val
            100                 105                 110

Ser Val Gly Ser Leu Val Gln Leu Glu Glu His Leu Glu Asn Ala Leu
        115                 120                 125

Ser Val Thr Arg Ala Arg Lys Thr Glu Leu Met Leu Lys Leu Val Glu
    130                 135                 140

Asn Leu Lys Glu Lys Glu Lys Leu Leu Glu Glu Asn His Val Leu
145                 150                 155                 160

Ala Ser Gln Met Glu Lys Ser Asn Leu Val Arg Ala Glu Ala Asp Asn
                165                 170                 175

Met Asp Val Ser Pro Gly Gln Ile Ser Asp Ile Asn Leu Pro Val Thr
            180                 185                 190

Leu Pro Leu Leu Asn
        195

<210> SEQ ID NO 87
<211> LENGTH: 196
<212> TYPE: PRT
<213> ORGANISM: Brassica napus
<220> FEATURE:
<221> NAME/KEY: misc_feature
<222> LOCATION: (1)..(196)
```

-continued

```
<223> OTHER INFORMATION: Public GI no. 17933456
<220> FEATURE:
<221> NAME/KEY: misc_feature
<222> LOCATION: (1)..(196)
<223> OTHER INFORMATION: Functional Homolog of Ceres CLONE ID no. 92459
      at SEQ ID NO. 81
      with e-value of 4.99E-59 and percent identity of 66.4

<400> SEQUENCE: 87

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Asn Phe Ser Ala Gly Asp Asp Leu Val
    50                  55                  60

Lys Ile Val Asp Arg Tyr Gly Lys Gln His Ala Asp Asp Arg Lys Ala
65              70                  75                  80

Leu Asp Leu Gln Ser Glu Ala Pro Lys Tyr Gly Ser His His Glu Leu
                85                  90                  95

Leu Glu Leu Val Glu Ser Lys Leu Val Glu Ser Asn Ser Asp Val Ser
            100                 105                 110

Val Asp Ser Leu Val Gln Leu Glu Asn His Leu Glu Thr Ala Leu Ser
        115                 120                 125

Val Thr Arg Ala Arg Lys Thr Glu Leu Leu Leu Lys Leu Val Asp Ser
    130                 135                 140

Leu Lys Glu Lys Glu Lys Leu Leu Lys Glu Glu Asn Gln Gly Leu Ala
145                 150                 155                 160

Ser Gln Met Glu Lys Asn Asn Leu Ala Gly Ala Glu Ala Asp Lys Met
                165                 170                 175

Glu Val Ser Pro Gly Gln Ile Ser Asp Ile Asn Cys Pro Val Thr Leu
            180                 185                 190

Pro Leu Leu Tyr
        195

<210> SEQ ID NO 88
<211> LENGTH: 196
<212> TYPE: PRT
<213> ORGANISM: Brassica napus
<220> FEATURE:
<221> NAME/KEY: misc_feature
<222> LOCATION: (1)..(196)
<223> OTHER INFORMATION: Ceres CLONE ID no. 1091989
<220> FEATURE:
<221> NAME/KEY: misc_feature
<222> LOCATION: (1)..(196)
<223> OTHER INFORMATION: Functional Homolog of Ceres CLONE ID no. 92459
      at SEQ ID NO. 81
      with e-value of 4.99E-59 and percent identity of 66.4

<400> SEQUENCE: 88

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Asn Phe Ser Ala Gly Asp Asp Leu Val
    50                  55                  60
```

```
Lys Ile Val Asp Arg Tyr Gly Lys Gln His Ala Asp Asp Arg Lys Ala
 65                  70                  75                  80

Leu Asp Leu Gln Ser Glu Ala Pro Lys Tyr Gly Ser His His Glu Leu
                 85                  90                  95

Leu Glu Leu Val Glu Ser Lys Leu Val Glu Ser Asn Ser Asp Val Ser
            100                 105                 110

Val Asp Ser Leu Val Gln Leu Glu Asn His Leu Glu Thr Ala Leu Ser
        115                 120                 125

Val Thr Arg Ala Arg Lys Thr Glu Leu Leu Leu Lys Leu Val Asp Ser
    130                 135                 140

Leu Lys Glu Lys Glu Lys Leu Leu Lys Glu Glu Asn Gln Gly Leu Ala
145                 150                 155                 160

Ser Gln Met Glu Lys Asn Asn Leu Ala Gly Ala Glu Ala Asp Lys Met
                165                 170                 175

Glu Val Ser Pro Gly Gln Ile Ser Asp Ile Asn Cys Pro Val Thr Leu
            180                 185                 190

Pro Leu Leu Tyr
            195

<210> SEQ ID NO 89
<211> LENGTH: 196
<212> TYPE: PRT
<213> ORGANISM: Brassica napus
<220> FEATURE:
<221> NAME/KEY: misc_feature
<222> LOCATION: (1)..(196)
<223> OTHER INFORMATION: Public GI no. 17933458
<220> FEATURE:
<221> NAME/KEY: misc_feature
<222> LOCATION: (1)..(196)
<223> OTHER INFORMATION: Functional Homolog of Ceres CLONE ID no. 92459
      at SEQ ID NO. 81
      with e-value of 1.19E-57 and percent identity of 65.6

<400> SEQUENCE: 89

Met Gly Arg Lys Lys Leu Glu Ile Lys Arg Ile Glu Lys Asn Ser Ser
  1               5                  10                  15

Arg Gln Val Thr Phe Cys Lys Arg Arg Asn Gly Leu Ile Glu Lys Ala
             20                  25                  30

Arg Gln Leu Ser Val Leu Cys Glu Ala Ser Val Gly Leu Leu Val Val
         35                  40                  45

Ser Ala Ser Asp Lys Leu Tyr Ser Phe Ser Ser Gly Asp Arg Leu Glu
     50                  55                  60

Lys Ile Leu Asp Arg Tyr Gly Lys Lys His Ala Asp Asp Leu Asn Ala
 65                  70                  75                  80

Leu Asp Leu Gln Ser Lys Ser Leu Asn Tyr Ser Ser His His Glu Leu
                 85                  90                  95

Leu Glu Leu Val Glu Ser Lys Leu Val Glu Ser Ile Asp Asp Val Ser
            100                 105                 110

Val Asp Ser Leu Val Glu Leu Glu Asp His Leu Glu Thr Ala Leu Ser
        115                 120                 125

Val Thr Arg Ala Arg Lys Ala Glu Leu Met Leu Lys Leu Val Glu Ser
    130                 135                 140

Leu Lys Glu Lys Glu Asn Leu Leu Lys Glu Glu Asn Gln Val Leu Ala
145                 150                 155                 160

Ser Gln Ile Glu Lys Lys Asn Leu Glu Gly Ala Glu Ala Asp Asn Ile
                165                 170                 175

Glu Met Ser Ser Gly Gln Ile Ser Asp Ile Asn Leu Pro Val Thr Leu
```

Pro Leu Leu Asn
        195

<210> SEQ ID NO 90
<211> LENGTH: 614
<212> TYPE: DNA
<213> ORGANISM: Arabidopsis thaliana
<220> FEATURE:
<221> NAME/KEY: misc_feature
<222> LOCATION: (1)..(614)
<223> OTHER INFORMATION: Ceres CLONE ID no. 1952
<220> FEATURE:
<221> NAME/KEY: misc_feature
<222> LOCATION: (1)..(614)
<223> OTHER INFORMATION: Also Known As Ceres ME LINE ME04701
<220> FEATURE:
<221> NAME/KEY: misc_feature
<222> LOCATION: (1)..(614)
<223> OTHER INFORMATION: Also Known As Ceres LEAD Number 28
<220> FEATURE:
<221> NAME/KEY: CDS
<222> LOCATION: (30)..(429)
<223> OTHER INFORMATION: Referenced by SEQ ID NO: 91

<400> SEQUENCE: 90

```
ggaagtgaag gaggtatatc cggaggtggt atgtctgggg gcagtggaag taaacacaaa      60
attggaggag gtaaacacgg aggtcttgga ggtaaattcg gaaagaaaag aggcatgtcc     120
ggaagtggag gaggcatgtc aggaagtgaa ggaggtgtgt ctggaagtga aggaagtatg     180
tccggaggtg gtatgtctgg gggtagcgga agtaaacaca aaattggagg aggtaaacac     240
ggaggtctta gaggtaaatt cggaaagaaa agaggtatgt caggaagtga aggaggtatg     300
tctggaagtg aaggaggtgt gtcggaaagt ggtatgtccg ggagtggagg gggtaaacac     360
aaaatcggag gagtaaaaca caaatttgga ggaggtaaac acggaggtgg aggtggccac     420
atggcggagt aaagaacaat ggtcaagttg ttccaacatt aagcagatca ttgtgcatta     480
gttcaagatt gtatgattgg gaaagtaaaa gaaagaaaaa atattttcta ataagtttta     540
tgtttatatg taatgttgaa tctgattatt atgataaaaa gacataaatg tgatacaatg     600
tttattttaa gagc                                                      614
```

<210> SEQ ID NO 91
<211> LENGTH: 133
<212> TYPE: PRT
<213> ORGANISM: Arabidopsis thaliana
<220> FEATURE:
<221> NAME/KEY: misc_feature
<222> LOCATION: (1)..(133)
<223> OTHER INFORMATION: Ceres CLONE ID no. 1952
<220> FEATURE:
<221> NAME/KEY: misc_feature
<222> LOCATION: (1)..(133)
<223> OTHER INFORMATION: Also Known As Ceres ME LINE ME04701
<220> FEATURE:
<221> NAME/KEY: misc_feature
<222> LOCATION: (1)..(133)
<223> OTHER INFORMATION: Also Known As Ceres LEAD Number 28
<220> FEATURE:
<221> NAME/KEY: misc_feature
<222> LOCATION:
<223> OTHER INFORMATION: Phenotype: INFLORESCENCE
      Useful for making ornamental plants
      with modified flowers
<220> FEATURE:
<221> NAME/KEY: misc_feature
<222> LOCATION:
<223> OTHER INFORMATION: Phenotype: ROSETTE LEAVES
      Useful for making ornamental plants

```
        with modified leaves
<220> FEATURE:
<221> NAME/KEY: misc_feature
<222> LOCATION:
<223> OTHER INFORMATION: Phenotype: Plant Architecture
        Useful for making plants
        with enhanced plant architecture
<220> FEATURE:
<221> NAME/KEY: misc_feature
<222> LOCATION:
<223> OTHER INFORMATION: Phenotype: Disorganized Rosette
        Useful for making plants
        with increased biomass
<220> FEATURE:
<221> NAME/KEY: misc_feature
<222> LOCATION:
<223> OTHER INFORMATION: Phenotype: Lanceolate Shaped
        Useful for making plants with increased biomass
        and foliage

<400> SEQUENCE: 91

Met Ser Gly Gly Ser Gly Ser Lys His Lys Ile Gly Gly Lys His
1               5                   10                  15

Gly Gly Leu Gly Gly Lys Phe Gly Lys Lys Arg Gly Met Ser Gly Ser
            20                  25                  30

Gly Gly Gly Met Ser Gly Ser Glu Gly Gly Val Ser Gly Ser Glu Gly
        35                  40                  45

Ser Met Ser Gly Gly Gly Met Ser Gly Ser Gly Ser Lys His Lys
    50                  55                  60

Ile Gly Gly Gly Lys His Gly Gly Leu Arg Gly Lys Phe Gly Lys Lys
65              70                  75                  80

Arg Gly Met Ser Gly Ser Glu Gly Gly Met Ser Gly Ser Glu Gly Gly
                85                  90                  95

Val Ser Glu Ser Gly Met Ser Gly Ser Gly Gly Lys His Lys Ile
            100                 105                 110

Gly Gly Gly Lys His Lys Phe Gly Gly Lys His Gly Gly Gly
        115                 120                 125

Gly His Met Ala Glu

<210> SEQ ID NO 92
<211> LENGTH: 1383
<212> TYPE: DNA
<213> ORGANISM: Arabidopsis thaliana
<220> FEATURE:
<221> NAME/KEY: misc_feature
<222> LOCATION: (1)..(1383)
<223> OTHER INFORMATION: Ceres CLONE ID no. 123905
<220> FEATURE:
<221> NAME/KEY: misc_feature
<222> LOCATION: (1)..(1383)
<223> OTHER INFORMATION: Also Known As Ceres ME LINE ME04717
<220> FEATURE:
<221> NAME/KEY: misc_feature
<222> LOCATION: (1)..(1383)
<223> OTHER INFORMATION: Also Known As Ceres LEAD Number 29
<220> FEATURE:
<221> NAME/KEY: CDS
<222> LOCATION: (119)..(920)
<223> OTHER INFORMATION: Referenced by SEQ ID NO: 93

<400> SEQUENCE: 92
caaaaacaca aacaaaactc atattttcaa tctccaggtg ctttacacca acagagtcgc      60
aagaaaacaa aaaccaaaact cggatttagt ttgacagaag aaggaatcga gagtcgggta   120
tgcattatcc taacaacaga accgaattcg tcggagctcc agccccaacc cggtatcaaa    180
aggagcagtt gtcaccggag caagagcttt cagttattgt ctctgctttg caacacgtga    240
```

```
tctcagggga aaacgaaacg gcgccgtgtc agggttttc cagtgacagc acagtgataa      300
gcgcgggaat gcctcggttg gattcagaca cttgtcaagt ctgtaggatc gaaggatgtc      360
tcggctgtaa ctactttttc gcgccaaatc agagaattga aaagaatcat caacaagaag      420
aagagattac tagtagtagt aacagaagaa gagagagctc tcccgtggcg aagaaagcgg      480
aaggtggcgg gaaaatcagg aagaggaaga acaagaagaa tggttacaga ggagttaggc      540
aaagaccttg gggaaaattt gcagctgaga tcagagatcc taaaagagcc acacgtgttt      600
ggcttggtac tttcgaaacc gccgaagatg cggctcgagc ttatgatcga gccgcgattg      660
gattccgtgg gccaagggct aaactcaact tccccttttgt ggattacacg tcttcagttt      720
catctcctgt tgctgctgat gatataggag caaatgcaag tgcaagcgcc agtgtgagcg      780
ccacagattc agttgaagca gagcaatgga acggaggagg aggggattgc aatatggagt      840
ggatgaatat gatgatgatg atggattttg ggaatggaga ttcttcagat tcaggaaata      900
caattgctga tatgttccag tgataaatga gctctttctt gttggcgttt tttggagtta      960
agtgcaagaa gagattgaca ctgtggcttg tttaaagtga acaagaacaa gaaagcatgt     1020
aattagtagt ctcattcttt tgtttgtggt caattctatg tttatctcat ataaaatctg     1080
agttaaacct atctgaggag agagtaaata aagaggttaa gaaacccaac attggtctga     1140
attataaacg taagtgtcaa cgttgtttat aaaggagaaa actataattg gtgacaaaag     1200
acataaagaa aagatgtcta ctcctacaaa gcatcgcgtg cagctattcg acaaacaatg     1260
gcatctccca gagaggaaat tccgagctct tggctagtta tcttgtaatg ctgaaaacat     1320
gaatgtattt gagtttattt ctgtaacatt ggaagcgaaa taaaagggtt atcaactgtt     1380
acc                                                                    1383

<210> SEQ ID NO 93
<211> LENGTH: 267
<212> TYPE: PRT
<213> ORGANISM: Arabidopsis thaliana
<220> FEATURE:
<221> NAME/KEY: misc_feature
<222> LOCATION: (1)..(267)
<223> OTHER INFORMATION: Ceres CLONE ID no. 123905
<220> FEATURE:
<221> NAME/KEY: misc_feature
<222> LOCATION: (1)..(267)
<223> OTHER INFORMATION: Also Known As Ceres ME LINE ME04717
<220> FEATURE:
<221> NAME/KEY: misc_feature
<222> LOCATION: (1)..(267)
<223> OTHER INFORMATION: Also Known As Ceres LEAD Number 29
<220> FEATURE:
<221> NAME/KEY: misc_feature
<222> LOCATION: (134)..(197)
<223> OTHER INFORMATION: Pfam Name: AP2; Pfam Description: AP2 domain
<220> FEATURE:
<221> NAME/KEY: misc_feature
<222> LOCATION:
<223> OTHER INFORMATION: Phenotype: INFLORESCENCE
      Useful for making ornamental plants
      with modified flowers
<220> FEATURE:
<221> NAME/KEY: misc_feature
<222> LOCATION:
<223> OTHER INFORMATION: Phenotype: ROSETTE LEAVES
      Useful for making ornamental plants
      with modified leaves
<220> FEATURE:
<221> NAME/KEY: misc_feature
<222> LOCATION:
<223> OTHER INFORMATION: Phenotype: Plant Architecture
      Useful for making plants
``` with enhanced plant architecture
<220> FEATURE:
<221> NAME/KEY: misc_feature
<222> LOCATION:
<223> OTHER INFORMATION: Phenotype: Disorganized Rosette
      Useful for making plants
      with increased biomass
<220> FEATURE:
<221> NAME/KEY: misc_feature
<222> LOCATION:
<223> OTHER INFORMATION: Phenotype: Lanceolate Shaped
      Useful for making plants with increased biomass
      and foliage
<220> FEATURE:
<221> NAME/KEY: misc_feature
<222> LOCATION:
<223> OTHER INFORMATION: Phenotype: Short
      Useful for making shorter plants
<220> FEATURE:
<221> NAME/KEY: misc_feature
<222> LOCATION:
<223> OTHER INFORMATION: Phenotype: Reduced Apical Dominance
      Useful for modifying plant structure, i.e. increased
      branching
<220> FEATURE:
<221> NAME/KEY: misc_feature
<222> LOCATION:
<223> OTHER INFORMATION: Phenotype: Reduced fertility
      Useful for sterility, genetic confinement systems

<400> SEQUENCE: 93

Met His Tyr Pro Asn Asn Arg Thr Glu Phe Val Gly Ala Pro Ala Pro
1               5                   10                  15

Thr Arg Tyr Gln Lys Glu Gln Leu Ser Pro Glu Gln Glu Leu Ser Val
            20                  25                  30

Ile Val Ser Ala Leu Gln His Val Ile Ser Gly Glu Asn Glu Thr Ala
        35                  40                  45

Pro Cys Gln Gly Phe Ser Ser Asp Ser Thr Val Ile Ser Ala Gly Met
    50                  55                  60

Pro Arg Leu Asp Ser Asp Thr Cys Gln Val Cys Arg Ile Glu Gly Cys
65                  70                  75                  80

Leu Gly Cys Asn Tyr Phe Phe Ala Pro Asn Gln Arg Ile Glu Lys Asn
                85                  90                  95

His Gln Gln Glu Glu Glu Ile Thr Ser Ser Asn Arg Arg Arg Arg Glu
            100                 105                 110

Ser Ser Pro Val Ala Lys Lys Ala Glu Gly Gly Lys Ile Arg Lys
        115                 120                 125

Arg Lys Asn Lys Lys Asn Gly Tyr Arg Gly Val Arg Gln Arg Pro Trp
    130                 135                 140

Gly Lys Phe Ala Ala Glu Ile Arg Asp Pro Lys Arg Ala Thr Arg Val
145                 150                 155                 160

Trp Leu Gly Thr Phe Glu Thr Ala Glu Asp Ala Ala Arg Ala Tyr Asp
                165                 170                 175

Arg Ala Ala Ile Gly Phe Arg Gly Pro Arg Ala Lys Leu Asn Phe Pro
            180                 185                 190

Phe Val Asp Tyr Thr Ser Ser Val Ser Ser Pro Val Ala Ala Asp Asp
        195                 200                 205

Ile Gly Ala Asn Ala Ser Ala Ser Ala Ser Val Ser Ala Thr Asp Ser
    210                 215                 220

Val Glu Ala Glu Gln Trp Asn Gly Gly Gly Asp Cys Asn Met Glu
225                 230                 235                 240

Trp Met Asn Met Met Met Met Met Asp Phe Gly Asn Gly Asp Ser Ser
                245                 250                 255

Asp Ser Gly Asn Thr Ile Ala Asp Met Phe Gln

<210> SEQ ID NO 94
<211> LENGTH: 229
<212> TYPE: PRT
<213> ORGANISM: Populus balsamifera subsp. trichocarpa
<220> FEATURE:
<221> NAME/KEY: misc_feature
<222> LOCATION: (1)..(229)
<223> OTHER INFORMATION: 1460991
<220> FEATURE:
<221> NAME/KEY: misc_feature
<222> LOCATION: (1)..(229)
<223> OTHER INFORMATION: Functional Homolog of Ceres CLONE ID no. 123905
      at SEQ ID NO. 93 with e-value of 2.10E-35 and percent
      identity of 59.8

<400> SEQUENCE: 94

Met Val Ala Ala Leu Lys Asn Val Val Ser Gly Thr Ala Ser Met Asp
1               5                   10                  15

Phe Ser Arg Glu Met Asn Ser Ile Asn Met Pro Ile Ile Thr Ser His
            20                  25                  30

Pro Gln Phe Gly Ser Ala Ser Asn Asn Gly Asn Gly Phe Cys Asn Ser
        35                  40                  45

Ile Leu Pro Pro Ser Ser Asp Leu Asp Thr Cys Gly Val Cys Lys Ile
    50                  55                  60

Lys Gly Cys Leu Gly Cys Asn Phe Phe Pro Pro Asn Gln Glu Asp Lys
65                  70                  75                  80

Lys Asp Asp Lys Lys Gly Lys Arg Lys Arg Val Lys Lys Asn Tyr Arg
                85                  90                  95

Gly Val Arg Gln Arg Pro Trp Gly Lys Trp Ala Ala Glu Ile Arg Asp
            100                 105                 110

Pro Arg Lys Ala Ala Arg Val Trp Leu Gly Thr Phe Asn Thr Ala Glu
        115                 120                 125

Glu Ala Ala Arg Ala Tyr Asp Lys Ala Ala Ile Asp Phe Arg Gly Pro
    130                 135                 140

Arg Ala Lys Leu Asn Phe Pro Phe Pro Asp Ser Gly Ile Ala Ser Phe
145                 150                 155                 160

Glu Glu Ser Lys Glu Lys Gln Glu Lys Gln Gln Glu Ile Ser Glu Lys
                165                 170                 175

Arg Ser Glu Phe Glu Thr Glu Thr Gly Lys Asp Asn Glu Phe Leu Asp
            180                 185                 190

Asn Ile Val Asp Glu Glu Leu Gln Glu Trp Met Ala Met Ile Met Asp
        195                 200                 205

Phe Gly Asn Gly Gly Ser Ser Asn Ser Ser Gly Thr Ala Ser Ala Ala
    210                 215                 220

Ala Thr Ile Gly Phe
225

<210> SEQ ID NO 95
<211> LENGTH: 256
<212> TYPE: PRT
<213> ORGANISM: Zea mays
<220> FEATURE:
<221> NAME/KEY: misc_feature
<222> LOCATION: (1)..(256)
<223> OTHER INFORMATION: Ceres CLONE ID no. 1494990
<220> FEATURE:
<221> NAME/KEY: misc_feature
<222> LOCATION: (1)..(256)
<223> OTHER INFORMATION: Functional Homolog of Ceres CLONE ID no. 123905 at SEQ ID NO. 93 with e-value of 4.19E-37 and percent
identity of 49.2

<400> SEQUENCE: 95

Met Glu Ala Ser Arg Gln Tyr Met Ile Arg Phe Asp Gly His Phe Glu
1               5                   10                  15

Glu Gly Pro Ser Ser Ala Ala Glu Pro Pro Gln Pro Phe Ala Ser
            20                  25                  30

Arg Ala Phe Ser Pro Glu Gln Glu Gln Ser Val Met Val Ala Ala Leu
        35                  40                  45

Leu His Val Val Ser Gly Tyr Ala Thr Pro Ala Pro Asp Leu Phe Phe
50                  55                  60

Pro Ala Gly Lys Glu Ala Cys Thr Ala Cys Gly Val Asp Gly Cys Leu
65                  70                  75                  80

Gly Cys Glu Phe Phe Gly Ala Glu Ala Gly Arg Ala Val Ala Ala Ser
                85                  90                  95

Asp Ala Pro Arg Ala Ala Thr Ala Gly Gly Pro Gln Arg Arg Arg
            100                 105                 110

Asn Lys Lys Ser Gln Tyr Arg Gly Val Arg Gln Arg Pro Trp Gly Lys
            115                 120                 125

Trp Ala Ala Glu Ile Arg Asp Pro Arg Arg Ala Val Arg Val Trp Leu
130                 135                 140

Gly Thr Phe Asp Thr Ala Glu Asp Ala Ala Arg Ala Tyr Asp Arg Ala
145                 150                 155                 160

Ala Val Lys Phe Arg Gly Pro Arg Ala Lys Leu Asn Phe Ser Phe Pro
                165                 170                 175

Glu Gln His Leu Arg Asp Asp Ser Gly Asn Ala Ala Ala Lys Ser Asp
            180                 185                 190

Ala Cys Ser Pro Ser Pro Ser Pro Arg Ser Ala Glu Glu Glu Thr
            195                 200                 205

Gly Asp Leu Leu Trp Asp Gly Leu Val Asp Leu Met Lys Leu Asp Glu
210                 215                 220

Ser Asp Leu Cys Leu Leu Leu Pro Val Asp Asn Thr Leu Asp Lys Phe
225                 230                 235                 240

His Ala Pro Gly Gln Arg Arg Ser Gly Ser Gly Val Pro Leu Cys Tyr
                245                 250                 255

<210> SEQ ID NO 96
<211> LENGTH: 266
<212> TYPE: PRT
<213> ORGANISM: Triticum aestivum
<220> FEATURE:
<221> NAME/KEY: misc_feature
<222> LOCATION: (1)..(266)
<223> OTHER INFORMATION: Ceres CLONE ID no. 634402
<220> FEATURE:
<221> NAME/KEY: misc_feature
<222> LOCATION: (1)..(266)
<223> OTHER INFORMATION: Functional Homolog of Ceres CLONE ID no. 123905
      at SEQ ID NO. 93 with e-value of 1.80E-36 and percent
      identity of 45.0

<400> SEQUENCE: 96

Met Thr Phe Ser Val Ser Pro Ala Thr Gly Ala Ser Gln Glu Tyr Met
1               5                   10                  15

Ile Arg Phe Asp Gly His Phe Glu Asp Pro Ser Ser Ala Ala Ala Ser
            20                  25                  30

Ala Glu Pro Pro Leu Pro Phe Ala Gly Arg Ala Phe Ser Pro Gln Gln
        35                  40                  45

```
Glu Gln Ser Ala Met Val Ala Ala Leu Leu His Val Ser Gly Tyr
     50                  55                  60

Thr Thr Pro Ala Pro Asp Leu Phe Phe Pro Ala Arg Lys Glu Ala Cys
 65                  70                  75                  80

Thr Ala Cys Gly Met Asp Gly Cys Leu Gly Cys Glu Phe Phe Gly Ala
                 85                  90                  95

Glu Ala Gly Arg Ala Val Ala Ala Ser Asp Ala Pro Arg Ala Pro Ala
            100                 105                 110

Ala Gly Gly Pro Gln Arg Arg Arg Asn Lys Lys Asn Gln Tyr Arg
        115                 120                 125

Gly Val Arg Gln Arg Pro Trp Gly Lys Trp Ala Ala Glu Ile Arg Asp
    130                 135                 140

Pro Arg Arg Ala Val Arg Val Trp Leu Gly Thr Phe Asp Thr Ala Glu
145                 150                 155                 160

Asp Ala Ala Arg Ala Tyr Asp Arg Ala Ala Val Glu Phe Arg Gly Pro
                165                 170                 175

Arg Ala Lys Leu Asn Phe Ser Phe Pro Glu Gln Gln Gln Gln Gln Leu
            180                 185                 190

Gly Gly Ser Gly Asn Ala Ala Lys Ser Asp Ala Cys Ser Pro Ser
        195                 200                 205

Pro Ser Pro Arg Ser Ala Asp Glu Asp Glu Thr Gly Asp Leu Leu Trp
210                 215                 220

Asp Gly Leu Val Asp Leu Met Lys Leu Asp Glu Ser Asp Leu Cys Leu
225                 230                 235                 240

Leu Leu Pro Val Asp Asn Thr Asp Lys Phe His Ile Glu Gly Lys Arg
                245                 250                 255

Arg Ser Gly Ser Gly Val Pro Leu Cys Tyr
            260                 265

<210> SEQ ID NO 97
<211> LENGTH: 274
<212> TYPE: PRT
<213> ORGANISM: Oryza sativa subsp. japonica
<220> FEATURE:
<221> NAME/KEY: misc_feature
<222> LOCATION: (1)..(274)
<223> OTHER INFORMATION: Public GI no. 51536200
<220> FEATURE:
<221> NAME/KEY: misc_feature
<222> LOCATION: (1)..(274)
<223> OTHER INFORMATION: Functional Homolog of Ceres CLONE ID no. 123905
      at SEQ ID NO. 93 with e-value of 3.09E-34 and percent
      identity of 43.4

<400> SEQUENCE: 97

Met Thr Lys Lys Val Ile Pro Ala Met Ala Ala Arg Gln Asp Ser
 1               5                  10                  15

Cys Lys Thr Lys Leu Asp Glu Arg Gly Gly Ser His Gln Ala Pro Ser
                20                  25                  30

Ser Ala Arg Trp Ile Ser Ser Glu Gln Glu His Ser Ile Ile Val Ala
            35                  40                  45

Ala Leu Arg Tyr Val Val Ser Gly Cys Thr Thr Pro Pro Glu Ile
     50                  55                  60

Val Thr Val Ala Cys Gly Glu Ala Cys Ala Leu Cys Gly Ile Asp Gly
 65                  70                  75                  80

Cys Leu Gly Cys Asp Phe Phe Gly Ala Glu Ala Ala Gly Asn Glu Glu
                 85                  90                  95
```

```
Ala Val Met Ala Thr Asp Tyr Ala Ala Ala Ala Ala Ala Ala Val
            100                 105                 110

Ala Gly Gly Ser Gly Lys Arg Val Arg Arg Arg Lys Lys Asn
        115                 120                 125

Val Tyr Arg Gly Val Arg His Arg Pro Trp Gly Lys Trp Ala Ala Glu
    130                 135                 140

Ile Arg Asp Pro Arg Arg Ala Val Arg Lys Trp Leu Gly Thr Phe Asp
145                 150                 155                 160

Thr Ala Glu Glu Ala Arg Ala Tyr Asp Arg Ala Ala Leu Glu Phe
                165                 170                 175

Arg Gly Ala Arg Ala Lys Leu Asn Phe Pro Cys Ser Glu Pro Leu Pro
                180                 185                 190

Met Pro Ser Gln Arg Asn Gly Asn Gly Gly Asp Ala Val Thr Ala Ala
            195                 200                 205

Thr Thr Thr Ala Glu Gln Met Thr Pro Thr Leu Ser Pro Cys Ser Ala
210                 215                 220

Asp Ala Glu Glu Thr Thr Thr Pro Val Asp Trp Gln Met Gly Ala Asp
225                 230                 235                 240

Glu Ala Gly Ser Asn Gln Leu Trp Asp Gly Leu Gln Asp Leu Met Lys
                245                 250                 255

Leu Asp Glu Ala Asp Thr Trp Phe Pro Pro Phe Ser Gly Ala Ala Ser
                260                 265                 270

Ser Phe

<210> SEQ ID NO 98
<211> LENGTH: 541
<212> TYPE: DNA
<213> ORGANISM: Glycine max
<220> FEATURE:
<221> NAME/KEY: misc_feature
<222> LOCATION: (1)..(541)
<223> OTHER INFORMATION: Ceres CLONE ID no. 679923
<220> FEATURE:
<221> NAME/KEY: misc_feature
<222> LOCATION: (1)..(541)
<223> OTHER INFORMATION: Also Known As Ceres ME LINE ME03195
<220> FEATURE:
<221> NAME/KEY: misc_feature
<222> LOCATION: (1)..(541)
<223> OTHER INFORMATION: Also Known As Ceres LEAD Number 36
<220> FEATURE:
<221> NAME/KEY: CDS
<222> LOCATION: (24)..(456)
<223> OTHER INFORMATION: Referenced by SEQ ID NO: 99

<400> SEQUENCE: 98
gctcaagttt ccaagaccaa gccaatggaa aacctttcac cattgattta caaaaacccc      60
attagaagaa cttctaggcg atctacaatg tatcttggtg tgagaaaaag gccatgggga     120
agatatgctg ctgagattag gaacccatac accaaagaga gacactggct aggcacattt     180
gacactgctg aagaggctgc tatagcttat gatctttcat ctatcaagat ttgtggcatt     240
aatgctcgaa ctaattttca ctacccttt gtgtctcttc caccacttcc tatgtcgtca     300
ttgcctcctc caccgccacc gccgacccca gagttggatc caagtgttga agtttgtcta     360
gagatgatga atgctgcttc ttacgatggt gatgatgaat ctcttgttat tgcttccatt     420
ttgcaaagtt tttctaattc tggtaactgt tcttttagt ttttggttcc aatgaggcta      480
tggcctgcct cttatcaaat caataattct attttttc tttgcaaaaa aaaaaaaaa     540 a                                                                     541
```

```
<210> SEQ ID NO 99
<211> LENGTH: 144
<212> TYPE: PRT
<213> ORGANISM: Glycine max
<220> FEATURE:
<221> NAME/KEY: misc_feature
<222> LOCATION: (1)..(144)
<223> OTHER INFORMATION: Ceres CLONE ID no. 679923
<220> FEATURE:
<221> NAME/KEY: misc_feature
<222> LOCATION: (1)..(144)
<223> OTHER INFORMATION: Also Known As Ceres ME LINE ME03195
<220> FEATURE:
<221> NAME/KEY: misc_feature
<222> LOCATION: (1)..(144)
<223> OTHER INFORMATION: Also Known As Ceres LEAD Number 36
<220> FEATURE:
<221> NAME/KEY: misc_feature
<222> LOCATION: (21)..(84)
<223> OTHER INFORMATION: Pfam Name: AP2; Pfam Description: AP2 domain
<220> FEATURE:
<221> NAME/KEY: misc_feature
<222> LOCATION:
<223> OTHER INFORMATION: Phenotype: Late Flowering
      Useful for delaying flowering time
<220> FEATURE:
<221> NAME/KEY: misc_feature
<222> LOCATION:
<223> OTHER INFORMATION: Phenotype: Large
      Useful for making ornamental plants
      with modified flowers
<220> FEATURE:
<221> NAME/KEY: misc_feature
<222> LOCATION:
<223> OTHER INFORMATION: Phenotype: ROSETTE LEAVES
      Useful for making ornamental plants
      with modified leaves
<220> FEATURE:
<221> NAME/KEY: misc_feature
<222> LOCATION:
<223> OTHER INFORMATION: Phenotype: Curled 1
      Useful for making plants
      with altered leaf shape e.g. curled leaves
<220> FEATURE:
<221> NAME/KEY: misc_feature
<222> LOCATION:
<223> OTHER INFORMATION: Phenotype: Plant Architecture
      Useful for making plants
      with enhanced plant architecture
<220> FEATURE:
<221> NAME/KEY: misc_feature
<222> LOCATION:
<223> OTHER INFORMATION: Phenotype: Short
      Useful for making shorter plants
<220> FEATURE:
<221> NAME/KEY: misc_feature
<222> LOCATION:
<223> OTHER INFORMATION: Phenotype: Short Petioles
      Useful for making smaller plants
<220> FEATURE:
<221> NAME/KEY: misc_feature
<222> LOCATION:
<223> OTHER INFORMATION: Phenotype: Strong
      Useful for making stronger plants

<400> SEQUENCE: 99

Met Glu Asn Leu Ser Pro Leu Ile Tyr Lys Asn Pro Ile Arg Arg Thr
1               5                   10                  15

Ser Arg Arg Ser Thr Met Tyr Leu Gly Val Arg Lys Arg Pro Trp Gly
            20                  25                  30

Arg Tyr Ala Ala Glu Ile Arg Asn Pro Tyr Thr Lys Glu Arg His Trp
        35                  40                  45

Leu Gly Thr Phe Asp Thr Ala Glu Glu Ala Ala Ile Ala Tyr Asp Leu
    50                  55                  60
```

-continued

```
Ser Ser Ile Lys Ile Cys Gly Ile Asn Ala Arg Thr Asn Phe His Tyr
 65                  70                  75                  80

Pro Phe Val Ser Leu Pro Pro Leu Pro Met Ser Ser Leu Pro Pro Pro
             85                  90                  95

Pro Pro Pro Pro Thr Pro Glu Leu Asp Pro Ser Val Glu Val Cys Leu
            100                 105                 110

Glu Met Met Asn Ala Ala Ser Tyr Asp Gly Asp Glu Ser Leu Val
        115                 120                 125

Ile Ala Ser Ile Leu Gln Ser Phe Ser Asn Ser Gly Asn Cys Ser Phe
        130                 135                 140
```

<210> SEQ ID NO 100
<211> LENGTH: 129
<212> TYPE: PRT
<213> ORGANISM: Populus balsamifera subsp. trichocarpa
<220> FEATURE:
<221> NAME/KEY: misc_feature
<222> LOCATION: (1)..(129)
<223> OTHER INFORMATION: 1479788
<220> FEATURE:
<221> NAME/KEY: misc_feature
<222> LOCATION: (1)..(129)
<223> OTHER INFORMATION: Functional Homolog of Ceres CLONE ID no. 679923
      at SEQ ID NO. 99 with e-value of 3.80E-36 and percent
      identity of 69.0

<400> SEQUENCE: 100

```
Met Glu Asn Phe Pro Pro Leu Leu Tyr Arg Asn Pro Lys Arg Ser Ser
  1               5                  10                  15

Arg Gln Ser Ser Arg Tyr Leu Gly Val Arg Arg Arg Pro Trp Gly Arg
             20                  25                  30

Tyr Ala Ala Glu Ile Arg Asn Pro Tyr Thr Lys Glu Arg His Trp Leu
         35                  40                  45

Gly Thr Phe Asp Thr Ala Glu Glu Ala Ala Val Ala Tyr Asp Leu Ser
     50                  55                  60

Ser Ile Ser Phe Ser Gly Ile Glu Arg Ala Arg Thr Asn Phe Tyr Tyr
 65                  70                  75                  80

Pro Phe Phe Ala His Pro Ser Pro Ser Gln Glu Ala Pro Pro Pro Pro
             85                  90                  95

Leu Pro Pro Pro Glu Met Glu Lys Gly Asp Gln Leu Gly Met Glu Asp
            100                 105                 110

Val Asp Gly Asn Asn Ala Leu Glu Ile Leu Lys Ala Gly Asn Gly
        115                 120                 125

Lys
```

<210> SEQ ID NO 101
<211> LENGTH: 143
<212> TYPE: PRT
<213> ORGANISM: Populus balsamifera subsp. trichocarpa
<220> FEATURE:
<221> NAME/KEY: misc_feature
<222> LOCATION: (1)..(143)
<223> OTHER INFORMATION: 1533259
<220> FEATURE:
<221> NAME/KEY: misc_feature
<222> LOCATION: (1)..(143)
<223> OTHER INFORMATION: Functional Homolog of Ceres CLONE ID no. 679923
      at SEQ ID NO. 99 with e-value of 3.49E-42 and percent
      identity of 66.6

<400> SEQUENCE: 101

```
Met Glu Asn Phe Pro Pro Leu Leu Tyr Arg Asn Pro Lys Arg Ser Ser
```

```
                1               5                  10                  15
        Arg Gln Ser Ser Arg Tyr Leu Gly Val Arg Arg Pro Trp Gly Arg
                        20                  25                  30
        Tyr Ala Ala Glu Ile Arg Asn Pro Tyr Thr Lys Glu Arg His Trp Leu
                        35                  40                  45
        Gly Thr Phe Asp Thr Ala Glu Glu Ala Ala Val Ala Tyr Asp Leu Ser
                50                  55                  60
        Ser Ile Ser Phe Ser Gly Ile Glu Arg Ala Arg Thr Asn Phe Tyr Tyr
        65                  70                  75                  80
        Pro Phe Phe Ala His Pro Ser Pro Ser Gln Glu Ala Pro Pro Pro
                        85                  90                  95
        Leu Pro Pro Pro Glu Met Glu Lys Gly Asp Gln Leu Gly Met Glu Asp
                        100                 105                 110
        Val Gly Thr Thr Gln Asp Glu Ser Ile Val Ile Ala Ser Ile Leu
                        115                 120                 125
        Gln Ser Phe Cys Gln Ser Thr Ser Tyr Ser Phe His Pro Gln Ile
                        130                 135                 140
```

<210> SEQ ID NO 102
<211> LENGTH: 175
<212> TYPE: PRT
<213> ORGANISM: Oryza sativa subsp. japonica
<220> FEATURE:
<221> NAME/KEY: misc_feature
<222> LOCATION: (1)..(175)
<223> OTHER INFORMATION: Public GI no. 50941583
<220> FEATURE:
<221> NAME/KEY: misc_feature
<222> LOCATION: (1)..(175)
<223> OTHER INFORMATION: Functional Homolog of Ceres CLONE ID no. 679923
      at SEQ ID NO. 99 with e-value of 1.20E-32 and percent
      identity of 65.8

<400> SEQUENCE: 102

```
        Met Ala Asp Ala Ala Glu Gln His His Arg Gln Glu Thr Ala Ala
        1               5                   10                  15
        Ala Thr Thr Thr Pro Gln Gln Met Met Met Arg Arg Arg Ala Arg
                        20                  25                  30
        Ala Ser Ser Glu Tyr Leu Gly Val Arg Arg Pro Trp Gly Arg Tyr
                        35                  40                  45
        Ala Ala Glu Ile Arg Asn Pro Tyr Thr Lys Glu Arg His Trp Leu Gly
                        50                  55                  60
        Thr Phe Asp Thr Ala Glu Glu Ala Ala Val Ala Tyr Asp Leu Ser Ala
        65                  70                  75                  80
        Ile Ser Ile Ser Gly Ala Ala Ala Arg Thr Asn Phe Leu Tyr Pro
                        85                  90                  95
        Asp Met His His His Pro Ser Pro Gln His Ala Leu Ser Pro
                        100                 105                 110
        Ala Val Pro Pro Pro Pro Pro Pro Ser Pro Leu Tyr Asp
                        115                 120                 125
        Asp Asp Tyr Leu Ser Pro Ala Ala Glu Glu Val Glu Ala Gly
                        130                 135                 140
        Asp Asp Glu Ser Leu Thr Ile Ala Thr Ile Leu Gln Ser Phe Gln Tyr
        145                 150                 155                 160
        Gln Gln Ser Val Pro Pro Ala Ser Ser Gly Ser Met Phe Tyr Tyr
                        165                 170                 175
```

<210> SEQ ID NO 103

```
<211> LENGTH: 1681
<212> TYPE: DNA
<213> ORGANISM: Glycine max
<220> FEATURE:
<221> NAME/KEY: misc_feature
<222> LOCATION: (1)..(1681)
<223> OTHER INFORMATION: Ceres CLONE ID no. 691319
<220> FEATURE:
<221> NAME/KEY: misc_feature
<222> LOCATION: (1)..(1681)
<223> OTHER INFORMATION: Also Known As Ceres ME LINE ME05057
<220> FEATURE:
<221> NAME/KEY: misc_feature
<222> LOCATION: (1)..(1681)
<223> OTHER INFORMATION: Also Known As Ceres ME LINE ME09233
<220> FEATURE:
<221> NAME/KEY: CDS
<222> LOCATION: (111)..(1470)
<223> OTHER INFORMATION: Referenced by SEQ ID NO: 104

<400> SEQUENCE: 103
```

| | | |
|---|---|---|
| aaaagggtgt ccaaagaagg aatcacacaa gagaaatttt gggtggatct tggtaattta | 60 |
| aatttggtcc aaaatagta agaaaaaaaa accatagttc atttaatttt catgtccttg | 120 |
| ctaacggtgg cgcaccaaag ggggtcaggt gagtttatcc ggttcacgga aagtcatggc | 180 |
| ggtggtggcg atgacgtcag tggtgacggt gaacatggtt gtggacatga tgatggaagt | 240 |
| ggtgctggag gttcactagg gttgaatttt aaccaagtga tgcaacaagg tgaggtgaca | 300 |
| atgcaaggtg gttcattggt ttcagggtat aacaggggtg atccagagtt gagagaaata | 360 |
| gtttcagctt tgacacacgt ggtgtcttca gggtctggcc agaggagcac cgaattgacc | 420 |
| cagcaaagtg gttttcctat gatgtctgct tcttctcttt cacgtttgtc tgctttctct | 480 |
| tcttcttctc cttctccttc ttctggagcc tcttggggttg ccacaaaag aggcagagaa | 540 |
| gaagaagaga atagtacttc acataacttg atgcaacaac aacaacaaag tgctccaaga | 600 |
| ctcttcagaa acattggtga cttcatggtg ccttctcaag gagactcatc atcagtgaca | 660 |
| gaagaagccc ccacctccac aactacaact gtaaccgccg tcactgaaaa cccaccagga | 720 |
| ggtggggaaa ggaggagaaa gtacagagga gtgaggcaga ggccatgggg aaaatgggca | 780 |
| gcagaaatcc gtgatccaca caaagcagca agagtttggc taggcacatt tgacacagaa | 840 |
| gaagcagcag caagagccta tgatgaagct gcattgaggt tcagaggcaa cagagcaaag | 900 |
| cttaacttcc ctgaaaatgt aagagcagtt ccacccattc aaccttttca agccaccact | 960 |
| aggctaaccg tttctgattc caccacctct caattccggc cactctccgc ggtggcgcca | 1020 |
| cccttcattc agcagccaca gattcagggc tcctctgact tgatcagaga ctacttgcaa | 1080 |
| tactctcagc ttctacagag tgattttcaa cagcaacaaa tacaacaaca acagcagcag | 1140 |
| cagcggcagc agcagcagcg gcagcggcag cagcggcagc agcagcagca acaacaacaa | 1200 |
| caaccatcta gtttgcttca gcagttgtac tataatgcac aatttgcttc acttcaatca | 1260 |
| ccttcaatgc tatcatcatc tccttcattt tcttcttctg tgtctccagc accattccca | 1320 |
| ttattcacaa cctctgcttc tttccccttg ttttcaagtc aacaaatggg ctatttccag | 1380 |
| ccaccggaaa gccgcaatcc cgctggcggc gtgccggagt tccaacgtc cacatggtcg | 1440 |
| gataccagta gccagccacc accttctggt tgatacagtg ttttagtttc cttcatattt | 1500 |
| tccttttttct tttttcttc tttcattctt agcataaaaa aaaagactt gttatactta | 1560 |
| tttctttttt caagggtgaa actatgatat agtttttttt aagtatttt ggtactattc | 1620 |
| tcgtatcaga attagagttt cagtaattta tgttgatatt caatacaaat ctttattatg | 1680 |
| t | 1681 |

```
<210> SEQ ID NO 104
<211> LENGTH: 453
<212> TYPE: PRT
<213> ORGANISM: Glycine max
<220> FEATURE:
<221> NAME/KEY: misc_feature
<222> LOCATION: (1)..(453)
<223> OTHER INFORMATION: Ceres CLONE ID no. 691319
<220> FEATURE:
<221> NAME/KEY: misc_feature
<222> LOCATION: (1)..(453)
<223> OTHER INFORMATION: Also Known As Ceres ME LINE ME05057
<220> FEATURE:
<221> NAME/KEY: misc_feature
<222> LOCATION: (1)..(453)
<223> OTHER INFORMATION: Also Known As Ceres ME LINE ME09233
<220> FEATURE:
<221> NAME/KEY: misc_feature
<222> LOCATION: (209)..(272)
<223> OTHER INFORMATION: Pfam Name: AP2; Pfam Description: AP2 domain
<220> FEATURE:
<221> NAME/KEY: misc_feature
<222> LOCATION:
<223> OTHER INFORMATION: Phenotype: ROSETTE LEAVES
      Useful for making ornamental plants
      with modified leaves
<220> FEATURE:
<221> NAME/KEY: misc_feature
<222> LOCATION:
<223> OTHER INFORMATION: Phenotype: Disorganized Rosette
      Useful for making plants
      with increased biomass
<220> FEATURE:
<221> NAME/KEY: misc_feature
<222> LOCATION:
<223> OTHER INFORMATION: Phenotype: Lanceolate Shaped
      Useful for making plants with increased biomass
      and foliage
<220> FEATURE:
<221> NAME/KEY: misc_feature
<222> LOCATION:
<223> OTHER INFORMATION: Phenotype: Short
      Useful for making shorter plants

<400> SEQUENCE: 104

Met Ser Leu Leu Thr Val Ala His Gln Arg Gly Ser Gly Glu Phe Ile
1               5                   10                  15

Arg Phe Thr Glu Ser His Gly Gly Gly Asp Asp Val Ser Gly Asp
            20                  25                  30

Gly Glu His Gly Cys Gly His Asp Asp Gly Ser Gly Ala Gly Gly Ser
        35                  40                  45

Leu Gly Leu Asn Phe Asn Gln Val Met Gln Gln Gly Glu Val Thr Met
    50                  55                  60

Gln Gly Gly Ser Leu Val Ser Gly Tyr Asn Arg Gly Asp Pro Glu Leu
65                  70                  75                  80

Arg Glu Ile Val Ser Ala Leu Thr His Val Val Ser Gly Ser Gly
                85                  90                  95

Gln Arg Ser Thr Glu Leu Thr Gln Gln Ser Gly Phe Pro Met Met Ser
                100                 105                 110

Ala Ser Ser Leu Ser Arg Leu Ser Ala Phe Ser Ser Ser Pro Ser
            115                 120                 125

Pro Ser Ser Gly Ala Ser Trp Val Gly His Lys Arg Gly Arg Glu Glu
        130                 135                 140

Glu Glu Asn Ser Thr Ser His Asn Leu Met Gln Gln Gln Gln Ser
145                 150                 155                 160

Ala Pro Arg Leu Phe Arg Asn Ile Gly Asp Phe Met Val Pro Ser Gln
```

```
                165                 170                 175
Gly Asp Ser Ser Ser Val Thr Glu Glu Ala Pro Thr Ser Thr Thr Thr
            180                 185                 190
Thr Val Thr Ala Val Thr Glu Asn Pro Pro Gly Gly Gly Glu Arg Arg
        195                 200                 205
Arg Lys Tyr Arg Gly Val Arg Gln Arg Pro Trp Gly Lys Trp Ala Ala
    210                 215                 220
Glu Ile Arg Asp Pro His Lys Ala Ala Arg Val Trp Leu Gly Thr Phe
225                 230                 235                 240
Asp Thr Glu Glu Ala Ala Arg Ala Tyr Asp Glu Ala Ala Leu Arg
            245                 250                 255
Phe Arg Gly Asn Arg Ala Lys Leu Asn Phe Pro Glu Asn Val Arg Ala
        260                 265                 270
Val Pro Pro Ile Gln Pro Phe Gln Ala Thr Thr Arg Leu Thr Val Ser
    275                 280                 285
Asp Ser Thr Thr Ser Gln Phe Arg Pro Leu Ser Ala Val Ala Pro Pro
290                 295                 300
Phe Ile Gln Gln Pro Gln Ile Gln Gly Ser Ser Asp Leu Ile Arg Asp
305                 310                 315                 320
Tyr Leu Gln Tyr Ser Gln Leu Leu Gln Ser Asp Phe Gln Gln Gln Gln
            325                 330                 335
Ile Gln Gln Gln Gln Gln Gln Arg Gln Gln Gln Arg Gln Arg
        340                 345                 350
Gln Gln Arg Gln Gln Gln Gln Gln Gln Gln Pro Ser Ser Leu
    355                 360                 365
Leu Gln Gln Leu Tyr Tyr Asn Ala Gln Phe Ala Ser Leu Gln Ser Pro
370                 375                 380
Ser Met Leu Ser Ser Ser Pro Ser Phe Ser Ser Ser Val Ser Pro Ala
385                 390                 395                 400
Pro Phe Pro Leu Phe Thr Thr Ser Ala Ser Phe Pro Leu Phe Ser Ser
            405                 410                 415
Gln Gln Met Gly Tyr Phe Gln Pro Pro Glu Ser Arg Asn Pro Ala Gly
        420                 425                 430
Gly Val Pro Glu Phe Pro Thr Ser Thr Trp Ser Asp Thr Ser Ser Gln
    435                 440                 445
Pro Pro Pro Ser Gly
```

<210> SEQ ID NO 105
<211> LENGTH: 398
<212> TYPE: PRT
<213> ORGANISM: Populus balsamifera subsp. trichocarpa
<220> FEATURE:
<221> NAME/KEY: misc_feature
<222> LOCATION: (1)..(398)
<223> OTHER INFORMATION: 1443093
<220> FEATURE:
<221> NAME/KEY: misc_feature
<222> LOCATION: (1)..(398)
<223> OTHER INFORMATION: Functional Homolog of Ceres CLONE ID no. 691319
    at SEQ ID NO. 104 with e-value of 3.19E-73 and percent
    identity of 56.0

<400> SEQUENCE: 105

```
Met Gly Tyr Ser Ser Ser Thr Glu Met Ser Met Val Ser Glu Leu Thr
1               5                   10                  15
His Val Val Ser Gly Gln Arg Gly Ser Thr Ser Asp Trp Gly Ser Tyr
            20                  25                  30
```

```
Gly Ala Val Gly Leu Gly Ala Thr Ile Thr Ser Asn Phe Gly Gln
         35                  40                  45

Ala Ala Pro Gly Ser Asn Thr Ser Thr Pro Ala Ser Pro Pro Leu Ser
 50                      55                  60

Ala Tyr Ser Ser Thr Ser Gly Ser Gly Leu Trp Ile Gly Gln Lys Arg
 65                  70                  75                  80

Gly Arg Glu Glu Ala Gly Ala Ala Gln Leu Met Glu Ser Leu
                 85                  90                  95

Pro Arg Val Tyr Arg Gly Phe Asn Asp Phe Arg Ser Ser Gln Gly Asp
             100                 105                 110

Ser Ser Ser Ser Gly Ala Thr Ala Thr Glu Glu Val Ser Ala Ser Thr
         115                 120                 125

Ile Val Ile Pro Thr Thr Thr Pro Ser Thr Thr Ala Thr Pro Ser
130                 135                 140

Ser Glu Ile Ala Ser Leu Glu Glu Thr Gly Glu Gln Arg Arg Arg Tyr
145                 150                 155                 160

Arg Gly Val Arg Gln Arg Pro Trp Gly Lys Trp Ala Ala Glu Ile Arg
                 165                 170                 175

Asp Pro His Lys Ala Ala Arg Val Trp Leu Gly Thr Phe Asp Thr Ala
             180                 185                 190

Glu Ala Ala Ala Arg Ala Tyr Asp Asp Ala Ala Leu Arg Phe Arg Gly
         195                 200                 205

Asn Arg Ala Lys Leu Asn Phe Pro Glu Asn Val Arg Leu Leu Pro Ala
    210                 215                 220

Gln Thr Gln Asn Val Thr Ala Ser Gln Val Pro Ile Ser His Ser Gln
225                 230                 235                 240

Leu Ser Ser His Leu Gln Leu Gln Pro Ile Ser Ser Pro Arg Gln Gln
                 245                 250                 255

Ala Gln Arg Pro Gln Ala Pro Ala Pro Ala Leu Phe Gln Ser Gln Ala
             260                 265                 270

Asp Ile Ile Arg Asp Tyr Trp Glu Tyr Ser Gln Leu Leu Gln Ser Ser
         275                 280                 285

Gly Glu Phe His His His Gln Gln Gln Gln Gln Gln Gln Gln Gln Pro
    290                 295                 300

Ser Ser Leu Leu Gln Pro Met Phe Tyr Asn Pro Gln Val Ala Ser Leu
305                 310                 315                 320

Gln Ser Ser Ala Leu Thr Ser Leu Ser Ser Thr Ser Val Ser Ser
                 325                 330                 335

Leu Ala Ala Ile Ser Ser Gly Ser Ser Pro Ser Thr Phe Ser Pro Ser
             340                 345                 350

Ala Ser Ser Phe Pro Leu Leu Phe Ala Gly Gln Gln Leu Gly Tyr Phe
         355                 360                 365

Arg Pro Pro Gln Asn Gln Asn Pro Ala Ser Gly Ser Asp Phe Pro Val
    370                 375                 380

Pro Pro Trp Thr Asp Ser Ser His Asn Pro Ser Ser Ser Gly
385                 390                 395

<210> SEQ ID NO 106
<211> LENGTH: 393
<212> TYPE: PRT
<213> ORGANISM: Populus balsamifera subsp. trichocarpa
<220> FEATURE:
<221> NAME/KEY: misc_feature
<222> LOCATION: (1)..(393)
<223> OTHER INFORMATION: 1452324
<220> FEATURE:
```

<221> NAME/KEY: misc_feature
<222> LOCATION: (1)..(393)
<223> OTHER INFORMATION: Functional Homolog of Ceres CLONE ID no. 691319
at SEQ ID NO. 104 with e-value of 1.69E-67 and percent
identity of 54.8

<400> SEQUENCE: 106

```
Met Gly Tyr Ser Ser Ala Glu Met Ser Ala Met Val Ser Ala Leu
1               5                   10                  15

Thr His Val Val Ser Gly His Arg Gly Ser Thr Ser Asp Trp Gly Ser
            20                  25                  30

Tyr Gly Ala Ser Gly Leu Gly Gly Ala Thr Ile Thr Ser Thr Ile Val
            35                  40                  45

Gln Ala Ala Pro Gly Ser Asn Thr Ser Pro Ala Ser Pro Ser Leu Ser
50                  55                  60

Ala Tyr Ser Ser Thr Ser Gly Gly Ser Trp Ile Gly Gln Lys Arg
65                  70                  75                  80

Gly Arg Glu Lys Glu Ala Gly Ala Ala Ala Gln Leu Lys Glu Ser Leu
            85                  90                  95

Pro Arg Val His Arg Gly Phe Asp Asp Phe Arg Ser Ser Leu Gly Asp
            100                 105                 110

Ser Pro Ser Ser Gly Ala Thr Ala Thr Glu Glu Val Ser Ala Ser Thr
        115                 120                 125

Leu Val Phe Ser Thr Thr Ala Thr Pro Ser Thr Thr Ala Thr Pro Ser
130                 135                 140

Ser Glu Thr Ala Ser Leu Gly Glu Thr Gly Glu Arg Lys Arg Arg Tyr
145                 150                 155                 160

Arg Gly Val Arg Gln Arg Pro Trp Gly Lys Trp Ala Ala Glu Ile Arg
                165                 170                 175

Asp Pro His Lys Ala Ala Arg Val Trp Leu Gly Thr Phe Glu Thr Ala
            180                 185                 190

Glu Ala Ala Ala Arg Ala Tyr Asp Glu Ala Ala Leu Arg Phe Arg Gly
        195                 200                 205

Ser Arg Ala Lys Leu Asn Phe Pro Glu Asn Ala Arg Leu Leu Pro Ala
210                 215                 220

Gln Met Gln Asn Val Thr Ala Ser Gln Val Pro Ile Ser Arg Ser Gln
225                 230                 235                 240

Leu Pro Ser His His Gln Leu Gln Ser Ile Ser Ser Pro Arg Gln Gln
                245                 250                 255

Ala Gln Arg Pro Gln Val Pro Ala Pro Ala Leu Phe Gln Ser Gln Pro
            260                 265                 270

Asp Ile Ile Arg Asp Tyr Trp Glu Tyr Ser Gln Leu Leu Gln Ser Ser
        275                 280                 285

Gly Asp Phe His Gly Gln Gln Pro Pro Ser Asn Leu Leu Glu
290                 295                 300

Gln Met Phe Tyr Asn Pro Gln Leu Ala Ser Leu Gln Ser Ser Thr Leu
305                 310                 315                 320

Ser Ser Leu Pro Ser Ser Thr Ser Gly Ser Ser Phe Ala Ala Ile Pro
                325                 330                 335

Ser Gly Ser Ile Ser Ser Thr Leu Ser Pro Ser Ala Ser Ser Phe Pro
            340                 345                 350

Leu Leu Phe Ala Gly Gln Gln Leu Gly Tyr Phe Arg Pro Pro Glu Asn
        355                 360                 365

Gln Asn Pro Ala Ala Gly Ser Asp Phe Pro Val Pro Trp Thr Asp
370                 375                 380
```

Cys Ser Arg Arg Pro Ser Ser Thr Gly
385                 390

<210> SEQ ID NO 107
<211> LENGTH: 877
<212> TYPE: DNA
<213> ORGANISM: Arabidopsis thaliana
<220> FEATURE:
<221> NAME/KEY: misc_feature
<222> LOCATION: (1)..(877)
<223> OTHER INFORMATION: Ceres CLONE ID no. 98850
<220> FEATURE:
<221> NAME/KEY: CDS
<222> LOCATION: (47)..(626)
<223> OTHER INFORMATION: Referenced by SEQ ID NO: 108

<400> SEQUENCE: 107

```
agattaggat taaattaggg cataacccctt atcggagatt tgaagccatg ggaagaagaa    60
aaatcgagat caagcgaatc gagaacaaaa gcagtcgaca agtcactttc tccaaacgac   120
gcaatggtct catcgacaaa gctcgacaac tttcgattct ctgtgaatcc tccgtcgctg   180
ttgtcgtcgt atctgcctcc ggaaaactct atgactcttc ctccggtgac gagatagaag   240
cgctgttcaa gccggagaaa cctcaatgtt ttgaactcga tcttgaagaa aaaattcaga   300
attatcttcc acacaaggag ttactagaaa cagtccaaag caagcttgaa gaaccaaatg   360
tcgataatgt aagtgtagat tctctaattt ctctggagga acaacttgag actgctctgt   420
ccgtaagtag agctaggaag gcagaactga tgatggagta tatcgagtcc cttaaagaaa   480
aggagaaatt gctgagagaa gagaaccagg ttctggctag ccagatggga aagaatacgt   540
tgctggcaac agatgatgag agaggaatgt tccgggaag tagctccggc aacaaaatac   600
cggagactct cccgctgctc aattagccac catcatcaac ggctgagttt tcaccttaaa   660
ctcaaagcct gattcataat taagagaata aatttgtata ttataaaaag ctgtgtaatc   720
tcaaacccttt tatcttcctc tagtgtggaa tttaaggtca aaaagaaaac gagaaagtat   780
ggatcagtgt tgtacctcct tcggagacaa gatcagagtt tgtgtgtttg tgtctgaatg   840
tacggattgg atttttaaag ttgtgctttc tttctcc                            877
```

<210> SEQ ID NO 108
<211> LENGTH: 192
<212> TYPE: PRT
<213> ORGANISM: Arabidopsis thaliana
<220> FEATURE:
<221> NAME/KEY: misc_feature
<222> LOCATION: (1)..(192)
<223> OTHER INFORMATION: Ceres CLONE ID no. 98850
<220> FEATURE:
<221> NAME/KEY: misc_feature
<222> LOCATION: (69)..(162)
<223> OTHER INFORMATION: Pfam Name: K-box; Pfam Description: K-box
    re.g.ion
<220> FEATURE:
<221> NAME/KEY: misc_feature
<222> LOCATION: (9)..(59)
<223> OTHER INFORMATION: Pfam Name: SRF-TF; Pfam Description: SRF-type
    transcription factor (DNA-binding and dimerisation domain)

<400> SEQUENCE: 108

Met Gly Arg Arg Lys Ile Glu Ile Lys Arg Ile Glu Asn Lys Ser Ser
1               5                   10                  15

Arg Gln Val Thr Phe Ser Lys Arg Arg Asn Gly Leu Ile Asp Lys Ala
            20                  25                  30

Arg Gln Leu Ser Ile Leu Cys Glu Ser Ser Val Ala Val Val Val Val

|  |  |  |  |  | 35 |  |  |  |  | 40 |  |  |  |  | 45 |  |
|---|---|---|---|---|---|---|---|---|---|---|---|---|---|---|---|---|

Ser Ala Ser Gly Lys Leu Tyr Asp Ser Ser Gly Asp Glu Ile Glu
 50                  55                  60

Ala Leu Phe Lys Pro Glu Lys Pro Gln Cys Phe Glu Leu Asp Leu Glu
 65                  70                  75                  80

Glu Lys Ile Gln Asn Tyr Leu Pro His Lys Glu Leu Leu Glu Thr Val
                 85                  90                  95

Gln Ser Lys Leu Glu Glu Pro Asn Val Asp Asn Val Ser Val Asp Ser
             100                 105                 110

Leu Ile Ser Leu Glu Glu Gln Leu Glu Thr Ala Leu Ser Val Ser Arg
         115                 120                 125

Ala Arg Lys Ala Glu Leu Met Met Glu Tyr Ile Glu Ser Leu Lys Glu
130                 135                 140

Lys Glu Lys Leu Leu Arg Glu Glu Asn Gln Val Leu Ala Ser Gln Met
145                 150                 155                 160

Gly Lys Asn Thr Leu Leu Ala Thr Asp Asp Glu Arg Gly Met Phe Pro
                165                 170                 175

Gly Ser Ser Ser Gly Asn Lys Ile Pro Glu Thr Leu Pro Leu Leu Asn
            180                 185                 190

```
<210> SEQ ID NO 109
<211> LENGTH: 1614
<212> TYPE: DNA
<213> ORGANISM: Arabidopsis thaliana
<220> FEATURE:
<221> NAME/KEY: misc_feature
<222> LOCATION: (1)..(1614)
<223> OTHER INFORMATION: Ceres cDNA ID no. 36533702
<220> FEATURE:
<221> NAME/KEY: misc_feature
<222> LOCATION: (1)..(1614)
<223> OTHER INFORMATION: Also Known As Ceres ME LINE ME04012
<220> FEATURE:
<221> NAME/KEY: CDS
<222> LOCATION: (14)..(1523)
<223> OTHER INFORMATION: Referenced by SEQ ID NO: 110

<400> SEQUENCE: 109
```

| | | | | |
|---|---|---|---|---|
| aaacactttc | atacatgagc | aatattcaag | aaatggagat | gatattgatg | gtctctttgt |   60 |
| gcttaacgac | cctcattacc | cttttcttgc | ttaaacaatt | cctcaaacga | accgccaaca |  120 |
| aagtgaactt | accaccatct | ccatggaggc | ttccgttgat | tggtaacctc | accagctta  |  180 |
| gcctccaccc | tcaccgttcc | ctccattccc | taagccttcg | gtacggacca | ctcatgctcc |  240 |
| ttcattttgg | ccgtgtcccc | atactcgtag | tatcctccgg | ggaagcagct | caagaggtat |  300 |
| tgaaaacaca | cgatcttaag | tttgccaacc | gcccgagatc | aaaagccgtt | catgggctta |  360 |
| tgaatggggg | gcgtgatgtg | gtgtttggtc | cctatggaga | atattggaga | cagatgaaga |  420 |
| gtgtatgcat | tctcaatctg | ctcacgaaca | aaatggttgc | gtcctttgag | aagataagag |  480 |
| aagaagagct | aaatgaaatg | atcaagaagc | tggagaaagc | aagttcttct | tcttcgtcag |  540 |
| aaaatctgag | cgaactcttt | gttactctcc | caagcgatgt | tacgagtaga | attgccttgg |  600 |
| gaagaaaaca | tagtgaggac | gaaaccgcaa | gggatctcaa | gaagcgagtg | aggcagatca |  660 |
| tggagctttt | aggcgagttc | ccaatcgggg | actatgtccc | ggctttggca | tggatagaca |  720 |
| ggatcaacgg | tttcaatgct | agaataaagg | aagtaagtca | agggtttagc | gatcttatgg |  780 |
| acaaagtggt | gcaagaacat | ttagaggcag | gtaatcataa | agaggacttt | gtcgatatac |  840 |
| tgttatcaat | cgaaagcgag | aagagtattg | gattccaagc | tcaaagagac | gacatcaaat |  900 |

-continued

```
tcatgatatt ggatatgttt ataggaggga cgtcaacaag ttcaactcta ctagaatgga    960
taatgacgga gctgatcaga aatccaaatg ttatgaagaa actccaagac gagattcggt   1020
caaccattag gccacatggt tcatacataa aagaaaaaga tgttgaaaat atgaaatact   1080
tgaaagccgt gattaaagag gtgtttcggg tgcatcctcc tcttccacta atacttccca   1140
gattattaag tgaagatgtc aaagtaaagg gatataacat agccgcagga accgaggtga   1200
taatcaatgc ttgggccatc caaagagacc ccgcgatatg gggaccggat gcagaagaat   1260
tcaaaccaga aagacattta gattcaactt tggattatca tggaaaagat ttaaacttca   1320
tcccattcgg atcagggaga aggatttgtc cagggataaa tcttgctttg ggtttggtag   1380
aggtgacagt ggccaacctt gtaggccgat tgactggag ggccgaggct ggaccaaatg   1440
gggatcaacc tgatctaact gaagcttttg gtctcgatgt ttgccgaaag ttccctctca   1500
ttgcatttcc atcttccgtt atttaaaatg tttctctttt tatctttta cttgttatgc   1560 acttaattaa taagaagcat tgtaagatat aataaaatcc ttcattttag aaaa         1614
```

<210> SEQ ID NO 110
<211> LENGTH: 503
<212> TYPE: PRT
<213> ORGANISM: Arabidopsis thaliana
<220> FEATURE:
<221> NAME/KEY: misc_feature
<222> LOCATION: (1)..(503)
<223> OTHER INFORMATION: Ceres CDNA ID no. 36533702
<220> FEATURE:
<221> NAME/KEY: misc_feature
<222> LOCATION: (1)..(503)
<223> OTHER INFORMATION: Also Known As Ceres ME LINE ME04012
<220> FEATURE:
<221> NAME/KEY: misc_feature
<222> LOCATION: (40)..(498)
<223> OTHER INFORMATION: Pfam Name: p450; Pfam Description: Cytochrome
      P450
<220> FEATURE:
<221> NAME/KEY: misc_feature
<222> LOCATION:
<223> OTHER INFORMATION: Phenotype: Dark Green
      Useful for increasing chlorophyll
      and photosynthetic capacity

<400> SEQUENCE: 110

```
Met Ser Asn Ile Gln Glu Met Glu Met Ile Leu Met Val Ser Leu Cys
1               5                   10                  15

Leu Thr Thr Leu Ile Thr Leu Phe Leu Leu Lys Gln Phe Leu Lys Arg
            20                  25                  30

Thr Ala Asn Lys Val Asn Leu Pro Pro Ser Pro Trp Arg Leu Pro Leu
        35                  40                  45

Ile Gly Asn Leu His Gln Leu Ser Leu His Pro His Arg Ser Leu His
    50                  55                  60

Ser Leu Ser Leu Arg Tyr Gly Pro Leu Met Leu Leu His Phe Gly Arg
65                  70                  75                  80

Val Pro Ile Leu Val Val Ser Ser Gly Glu Ala Ala Gln Glu Val Leu
                85                  90                  95

Lys Thr His Asp Leu Lys Phe Ala Asn Arg Pro Arg Ser Lys Ala Val
            100                 105                 110

His Gly Leu Met Asn Gly Gly Arg Asp Val Val Phe Gly Pro Tyr Gly
        115                 120                 125

Glu Tyr Trp Arg Gln Met Lys Ser Val Cys Ile Leu Asn Leu Leu Thr
    130                 135                 140

Asn Lys Met Val Ala Ser Phe Glu Lys Ile Arg Glu Glu Glu Leu Asn
```

```
                145                 150                 155                 160
        Glu Met Ile Lys Lys Leu Glu Lys Ala Ser Ser Ser Ser Ser Ser Glu
                        165                 170                 175

Asn Leu Ser Glu Leu Phe Val Thr Leu Pro Ser Asp Val Thr Ser Arg
                        180                 185                 190

Ile Ala Leu Gly Arg Lys His Ser Glu Asp Thr Ala Arg Asp Leu
                        195                 200                 205

Lys Lys Arg Val Arg Gln Ile Met Glu Leu Leu Gly Glu Phe Pro Ile
                210                 215                 220

Gly Asp Tyr Val Pro Ala Leu Ala Trp Ile Asp Arg Ile Asn Gly Phe
        225                 230                 235                 240

Asn Ala Arg Ile Lys Glu Val Ser Gln Gly Phe Ser Asp Leu Met Asp
                        245                 250                 255

Lys Val Val Gln Glu His Leu Glu Ala Gly Asn His Lys Glu Asp Phe
                        260                 265                 270

Val Asp Ile Leu Leu Ser Ile Glu Ser Glu Lys Ser Ile Gly Phe Gln
                        275                 280                 285

Ala Gln Arg Asp Asp Ile Lys Phe Met Ile Leu Asp Met Phe Ile Gly
                        290                 295                 300

Gly Thr Ser Thr Ser Ser Thr Leu Leu Glu Trp Ile Met Thr Glu Leu
        305                 310                 315                 320

Ile Arg Asn Pro Asn Val Met Lys Lys Leu Gln Asp Glu Ile Arg Ser
                        325                 330                 335

Thr Ile Arg Pro His Gly Ser Tyr Ile Lys Glu Lys Asp Val Glu Asn
                        340                 345                 350

Met Lys Tyr Leu Lys Ala Val Ile Lys Glu Val Phe Arg Val His Pro
                        355                 360                 365

Pro Leu Pro Leu Ile Leu Pro Arg Leu Leu Ser Glu Asp Val Lys Val
                        370                 375                 380

Lys Gly Tyr Asn Ile Ala Ala Gly Thr Glu Val Ile Ile Asn Ala Trp
        385                 390                 395                 400

Ala Ile Gln Arg Asp Pro Ala Ile Trp Gly Pro Asp Ala Glu Glu Phe
                        405                 410                 415

Lys Pro Glu Arg His Leu Asp Ser Thr Leu Asp Tyr His Gly Lys Asp
                        420                 425                 430

Leu Asn Phe Ile Pro Phe Gly Ser Gly Arg Arg Ile Cys Pro Gly Ile
                        435                 440                 445

Asn Leu Ala Leu Gly Leu Val Glu Val Thr Val Ala Asn Leu Val Gly
                        450                 455                 460

Arg Phe Asp Trp Arg Ala Glu Ala Gly Pro Asn Gly Asp Gln Pro Asp
        465                 470                 475                 480

Leu Thr Glu Ala Phe Gly Leu Asp Val Cys Arg Lys Phe Pro Leu Ile
                        485                 490                 495

Ala Phe Pro Ser Ser Val Ile

<210> SEQ ID NO 111
<211> LENGTH: 503
<212> TYPE: PRT
<213> ORGANISM: Arabidopsis thaliana
<220> FEATURE:
<221> NAME/KEY: misc_feature
<222> LOCATION: (1)..(503)
<223> OTHER INFORMATION: Public GI no. 42569483
<220> FEATURE:
<221> NAME/KEY: misc_feature
<222> LOCATION: (1)..(503)
```

US 9,914,935 B2
221                                                                          222
-continued
<223> OTHER INFORMATION: Functional Homolog of Ceres CDNA ID no.
      36533702 at SEQ ID NO. 110 with e-value of 1.49E-242 and percent
      identity of 89.4

<400> SEQUENCE: 111

Met Ser Asn Ile Gln Glu Met Glu Met Ile Leu Ser Ile Ser Leu Cys
1               5                   10                  15

Leu Thr Thr Leu Ile Thr Leu Leu Leu Arg Arg Phe Leu Lys Arg
                20                  25                  30

Thr Ala Thr Lys Val Asn Leu Pro Pro Ser Pro Trp Arg Leu Pro Val
            35                  40                  45

Ile Gly Asn Leu His Gln Leu Ser Leu His Pro His Arg Ser Leu Arg
        50                  55                  60

Ser Leu Ser Leu Arg Tyr Gly Pro Leu Met Leu His Phe Gly Arg
65                  70                  75                  80

Val Pro Ile Leu Val Val Ser Ser Gly Glu Ala Ala Gln Glu Val Leu
                85                  90                  95

Lys Thr His Asp His Lys Phe Ala Asn Arg Pro Arg Ser Lys Ala Val
            100                 105                 110

His Gly Leu Met Asn Gly Gly Arg Asp Val Val Phe Ala Pro Tyr Gly
        115                 120                 125

Glu Tyr Trp Arg Gln Met Lys Ser Val Cys Ile Leu Asn Leu Leu Thr
130                 135                 140

Asn Lys Met Val Glu Ser Phe Glu Lys Val Arg Glu Asp Glu Val Asn
145                 150                 155                 160

Ala Met Ile Glu Lys Leu Glu Lys Ala Ser Ser Ser Ser Ser Ser Glu
                165                 170                 175

Asn Leu Ser Glu Leu Phe Ile Thr Leu Pro Ser Asp Val Thr Ser Arg
            180                 185                 190

Val Ala Leu Gly Arg Lys His Ser Glu Asp Glu Thr Ala Arg Asp Leu
        195                 200                 205

Lys Lys Arg Val Arg Gln Ile Met Glu Leu Leu Gly Glu Phe Pro Ile
210                 215                 220

Gly Glu Tyr Val Pro Ile Leu Ala Trp Ile Asp Gly Ile Arg Gly Phe
225                 230                 235                 240

Asn Asn Lys Ile Lys Glu Val Ser Arg Gly Phe Ser Asp Leu Met Asp
                245                 250                 255

Lys Val Val Gln Glu His Leu Glu Ala Ser Asn Asp Lys Ala Asp Phe
            260                 265                 270

Val Asp Ile Leu Leu Ser Ile Glu Lys Asp Lys Asn Ser Gly Phe Gln
        275                 280                 285

Val Gln Arg Asn Asp Ile Lys Phe Met Ile Leu Asp Met Phe Ile Gly
290                 295                 300

Gly Thr Ser Thr Thr Ser Thr Leu Leu Glu Trp Thr Met Thr Glu Leu
305                 310                 315                 320

Ile Arg Ser Pro Lys Ser Met Lys Lys Leu Gln Asp Glu Ile Arg Ser
                325                 330                 335

Thr Ile Arg Pro His Gly Ser Tyr Ile Lys Glu Lys Val Glu Asn
            340                 345                 350

Met Lys Tyr Leu Lys Ala Val Ile Lys Glu Val Leu Arg Leu His Pro
        355                 360                 365

Ser Leu Pro Met Ile Leu Pro Arg Leu Leu Ser Glu Asp Val Lys Val
370                 375                 380

Lys Gly Tyr Asn Ile Ala Ala Gly Thr Glu Val Ile Ile Asn Ala Trp

-continued

```
385                 390                 395                 400
Ala Ile Gln Arg Asp Thr Ala Ile Trp Gly Pro Asp Ala Glu Glu Phe
                405                 410                 415

Lys Pro Glu Arg His Leu Asp Ser Gly Leu Asp Tyr His Gly Lys Asn
            420                 425                 430

Leu Asn Tyr Ile Pro Phe Gly Ser Gly Arg Arg Ile Cys Pro Gly Ile
                435                 440                 445

Asn Leu Ala Leu Gly Leu Ala Glu Val Thr Val Ala Asn Leu Val Gly
450                 455                 460

Arg Phe Asp Trp Arg Val Glu Ala Gly Pro Asn Gly Asp Gln Pro Asp
465                 470                 475                 480

Leu Thr Glu Ala Ile Gly Ile Asp Val Cys Arg Lys Phe Pro Leu Ile
                485                 490                 495

Ala Phe Pro Ser Ser Val Val
                500

<210> SEQ ID NO 112
<211> LENGTH: 497
<212> TYPE: PRT
<213> ORGANISM: Arabidopsis thaliana
<220> FEATURE:
<221> NAME/KEY: misc_feature
<222> LOCATION: (1)..(497)
<223> OTHER INFORMATION: Public GI no. 2880054
<220> FEATURE:
<221> NAME/KEY: misc_feature
<222> LOCATION: (1)..(497)
<223> OTHER INFORMATION: Functional Homolog of Ceres cDNA ID no.
      36533702 at SEQ ID NO. 110 with e-value of 1.69E-239 and percent
      identity of 89.3

<400> SEQUENCE: 112

Met Glu Met Ile Leu Ser Ile Ser Leu Cys Leu Thr Thr Leu Ile Thr
1               5                   10                  15

Leu Leu Leu Leu Arg Arg Phe Leu Lys Arg Thr Ala Thr Lys Val Asn
                20                  25                  30

Leu Pro Pro Ser Pro Trp Arg Leu Pro Val Ile Gly Asn Leu His Gln
            35                  40                  45

Leu Ser Leu His Pro His Arg Ser Leu Arg Ser Leu Ser Leu Arg Tyr
50                  55                  60

Gly Pro Leu Met Leu Leu His Phe Gly Arg Val Pro Ile Leu Val Val
65                  70                  75                  80

Ser Ser Gly Glu Ala Ala Gln Glu Val Leu Lys Thr His Asp His Lys
                85                  90                  95

Phe Ala Asn Arg Pro Arg Ser Lys Ala Val His Gly Leu Met Asn Gly
            100                 105                 110

Gly Arg Asp Val Val Phe Ala Pro Tyr Gly Glu Tyr Trp Arg Gln Met
        115                 120                 125

Lys Ser Val Cys Ile Leu Asn Leu Leu Thr Asn Lys Met Val Glu Ser
    130                 135                 140

Phe Glu Lys Val Arg Glu Asp Glu Val Asn Ala Met Ile Glu Lys Leu
145                 150                 155                 160

Glu Lys Ala Ser Ser Ser Ser Ser Glu Asn Leu Ser Glu Leu Phe
                165                 170                 175

Ile Thr Leu Pro Ser Asp Val Thr Ser Arg Val Ala Leu Gly Arg Lys
            180                 185                 190

His Ser Glu Asp Glu Thr Ala Arg Asp Leu Lys Lys Arg Val Arg Gln
        195                 200                 205
```

```
Ile Met Glu Leu Leu Gly Glu Phe Pro Ile Gly Tyr Val Pro Ile
    210                 215                 220

Leu Ala Trp Ile Asp Gly Ile Arg Gly Phe Asn Asn Lys Ile Lys Glu
225                 230                 235                 240

Val Ser Arg Gly Phe Ser Asp Leu Met Asp Lys Val Val Gln Glu His
                245                 250                 255

Leu Glu Ala Ser Asn Asp Lys Ala Asp Phe Val Asp Ile Leu Leu Ser
            260                 265                 270

Ile Glu Lys Asp Lys Asn Ser Gly Phe Gln Val Gln Arg Asn Asp Ile
        275                 280                 285

Lys Phe Met Ile Leu Asp Met Phe Ile Gly Gly Thr Ser Thr Thr Ser
290                 295                 300

Thr Leu Glu Trp Thr Met Thr Glu Leu Ile Arg Ser Pro Lys Ser
305                 310                 315                 320

Met Lys Lys Leu Gln Asp Glu Ile Arg Ser Thr Ile Arg Pro His Gly
                325                 330                 335

Ser Tyr Ile Lys Glu Lys Glu Val Glu Asn Met Lys Tyr Leu Lys Ala
            340                 345                 350

Val Ile Lys Glu Val Leu Arg Leu His Pro Ser Leu Pro Met Ile Leu
        355                 360                 365

Pro Arg Leu Leu Ser Glu Asp Val Lys Val Lys Gly Tyr Asn Ile Ala
370                 375                 380

Ala Gly Thr Glu Val Ile Ile Asn Ala Trp Ala Ile Gln Arg Asp Thr
385                 390                 395                 400

Ala Ile Trp Gly Pro Asp Ala Glu Glu Phe Lys Pro Glu Arg His Leu
                405                 410                 415

Asp Ser Gly Leu Asp Tyr His Gly Lys Asn Leu Asn Tyr Ile Pro Phe
            420                 425                 430

Gly Ser Gly Arg Arg Ile Cys Pro Gly Ile Asn Leu Ala Leu Gly Leu
        435                 440                 445

Ala Glu Val Thr Val Ala Asn Leu Val Gly Arg Phe Asp Trp Arg Val
450                 455                 460

Glu Ala Gly Pro Asn Gly Asp Gln Pro Asp Leu Thr Glu Ala Ile Gly
465                 470                 475                 480

Ile Asp Val Cys Arg Lys Phe Pro Leu Ile Ala Phe Pro Ser Ser Val
                485                 490                 495

Val

<210> SEQ ID NO 113
<211> LENGTH: 497
<212> TYPE: PRT
<213> ORGANISM: Arabidopsis thaliana
<220> FEATURE:
<221> NAME/KEY: misc_feature
<222> LOCATION: (1)..(497)
<223> OTHER INFORMATION: Public GI no. 22329490
<220> FEATURE:
<221> NAME/KEY: misc_feature
<222> LOCATION: (1)..(497)
<223> OTHER INFORMATION: Functional Homolog of Ceres cDNA ID no.
      36533702 at SEQ ID NO. 110 with e-value of 1.49E-233 and percent
      identity of 86.6

<400> SEQUENCE: 113

Met Glu Met Thr Leu Met Val Ser Leu Cys Leu Thr Thr Leu Leu Thr
1               5                   10                  15

Leu Leu Leu Leu Lys Lys Phe Leu Lys Arg Thr Ala Lys Lys Val Asn
```

```
                    20                  25                  30
Leu Pro Pro Ser Pro Trp Arg Ile Pro Val Ile Gly Asn Leu His Gln
            35                  40                  45
Leu Ser Leu His Pro His Arg Ser Leu His Ser Leu Ser Leu Arg Tyr
        50                  55                  60
Gly Pro Leu Met Leu Leu His Phe Gly Arg Val Pro Ile Leu Val Val
65                  70                  75                  80
Ser Ser Ser Glu Ala Ala His Glu Ile Leu Lys Thr His Asp Leu Lys
                85                  90                  95
Phe Ala Asn Arg Pro Lys Ser Lys Ala Val His Gly Leu Met Asn Gly
            100                 105                 110
Gly Arg Asp Val Val Phe Gly Pro Tyr Gly Glu Tyr Trp Arg Gln Met
        115                 120                 125
Lys Ser Val Cys Ile Leu Asn Leu Leu Thr Asn Lys Met Val Ala Ser
        130                 135                 140
Phe Glu Lys Val Arg Glu Glu Val Asn Ala Met Met Glu Lys Leu
145                 150                 155                 160
Glu Lys Ala Ser Cys Ser Ser Ser Ala Glu Asn Leu Ser Glu Leu Phe
                165                 170                 175
Val Thr Leu Thr Ser Asp Val Thr Ser Arg Val Ser Leu Gly Lys Lys
            180                 185                 190
Tyr Trp Glu Asp Glu Thr Ala Gly Gly Leu Lys Lys Arg Val Arg Gln
        195                 200                 205
Ile Met Glu Leu Leu Arg Glu Phe Pro Ile Gly Asp Tyr Val Pro Ala
        210                 215                 220
Leu Ala Trp Ile Asp Arg Ile Asn Gly Phe Asn Ser Lys Ile Val Glu
225                 230                 235                 240
Val Ser Arg Ala Tyr Ser Asp Leu Met Glu Lys Val Val Gln Glu His
                245                 250                 255
Leu Glu Ala Gly Glu His Lys Ala Asp Phe Val Asn Ile Leu Leu Ser
            260                 265                 270
Ile Glu Lys Glu Lys Asn Asn Gly Phe Lys Val Gln Arg Asn Asp Ile
        275                 280                 285
Lys Phe Met Ile Leu Asp Met Phe Ile Gly Gly Ile Ser Thr Ser Ser
        290                 295                 300
Thr Leu Leu Glu Trp Ile Met Thr Glu Leu Ile Arg Asn Pro Glu Cys
305                 310                 315                 320
Met Lys Lys Leu Gln Asn Glu Ile Arg Ser Thr Ile Arg Pro His Gly
                325                 330                 335
Ser Tyr Ile Lys Glu Lys Glu Val Glu Asn Met Arg Tyr Leu Lys Ala
            340                 345                 350
Val Ile Lys Glu Val Phe Arg Val His Pro Pro Leu Pro Leu Ile Leu
        355                 360                 365
Pro Arg Leu Leu Thr Glu Asp Val Lys Val Lys Gly Tyr Asp Ile Ala
        370                 375                 380
Ala Gly Thr Glu Val Leu Ile Asn Ala Trp Ser Ile His Arg Asp Pro
385                 390                 395                 400
Ala Ile Trp Gly Pro Asp Ala Glu Glu Phe Lys Pro Gly Arg His Leu
                405                 410                 415
Asp Ser Thr Leu Asp Tyr His Gly Gln Asp Leu Lys Tyr Ile Pro Phe
            420                 425                 430
Gly Ser Gly Arg Arg Ile Cys Pro Gly Ile Asn Leu Ala Met Gly Leu
        435                 440                 445
```

```
Val Glu Val Thr Leu Ala Asn Leu Val Gly Arg Phe Asp Trp Ser Val
        450                 455                 460

Asp Pro Gly Pro Asn Gly Asp Gln Pro Asp Leu Ala Glu Asp Phe Gly
465                 470                 475                 480

Leu Asp Val Cys Arg Lys Asn Pro Leu Ile Ala Phe Pro Ser Ser Val
                485                 490                 495

Ala

<210> SEQ ID NO 114
<211> LENGTH: 477
<212> TYPE: PRT
<213> ORGANISM: Arabidopsis thaliana
<220> FEATURE:
<221> NAME/KEY: misc_feature
<222> LOCATION: (1)..(477)
<223> OTHER INFORMATION: Public GI no. 4835796
<220> FEATURE:
<221> NAME/KEY: misc_feature
<222> LOCATION: (1)..(477)
<223> OTHER INFORMATION: Functional Homolog of Ceres CDNA ID no.
      36533702 at SEQ ID NO. 110 with e-value of 9.10E-218 and percent
      identity of 86.1

<400> SEQUENCE: 114

Met Glu Met Thr Leu Met Val Ser Leu Cys Leu Thr Thr Leu Leu Thr
1               5                   10                  15

Leu Leu Leu Leu Lys Lys Phe Leu Lys Arg Thr Ala Lys Lys Val Asn
                20                  25                  30

Leu Pro Pro Ser Pro Trp Arg Ile Pro Val Ile Gly Asn Leu His Gln
            35                  40                  45

Leu Ser Leu His Pro His Arg Ser Leu His Ser Leu Ser Leu Ser Glu
        50                  55                  60

Ala Ala His Glu Ile Leu Lys Thr His Asp Leu Lys Phe Ala Asn Arg
65                  70                  75                  80

Pro Lys Ser Lys Ala Val His Gly Leu Met Asn Gly Gly Arg Asp Val
                85                  90                  95

Val Phe Gly Pro Tyr Gly Glu Tyr Trp Arg Gln Met Lys Ser Val Cys
            100                 105                 110

Ile Leu Asn Leu Leu Thr Asn Lys Met Val Ala Ser Phe Glu Lys Val
        115                 120                 125

Arg Glu Glu Glu Val Asn Ala Met Met Glu Lys Leu Glu Lys Ala Ser
    130                 135                 140

Cys Ser Ser Ser Ala Glu Asn Leu Ser Glu Leu Phe Val Thr Leu Thr
145                 150                 155                 160

Ser Asp Val Thr Ser Arg Val Ser Leu Gly Lys Lys Tyr Trp Glu Asp
                165                 170                 175

Glu Thr Ala Gly Gly Leu Lys Lys Arg Val Arg Gln Ile Met Glu Leu
            180                 185                 190

Leu Arg Glu Phe Pro Ile Gly Asp Tyr Val Pro Ala Leu Ala Trp Ile
        195                 200                 205

Asp Arg Ile Asn Gly Phe Asn Ser Lys Ile Val Glu Val Ser Arg Ala
    210                 215                 220

Tyr Ser Asp Leu Met Glu Lys Val Val Gln Glu His Leu Glu Ala Gly
225                 230                 235                 240

Glu His Lys Ala Asp Phe Val Asn Ile Leu Leu Ser Ile Glu Lys Glu
                245                 250                 255

Lys Asn Asn Gly Phe Lys Val Gln Arg Asn Asp Ile Lys Phe Met Ile
```

```
                260                 265                 270
Leu Asp Met Phe Ile Gly Gly Ile Ser Thr Ser Ser Thr Leu Leu Glu
            275                 280                 285

Trp Ile Met Thr Glu Leu Ile Arg Asn Pro Glu Cys Met Lys Lys Leu
        290                 295                 300

Gln Asn Glu Ile Arg Ser Thr Ile Arg Pro His Gly Ser Tyr Ile Lys
305                 310                 315                 320

Glu Lys Glu Val Glu Asn Met Arg Tyr Leu Lys Ala Val Ile Lys Glu
                325                 330                 335

Val Phe Arg Val His Pro Pro Leu Pro Leu Ile Leu Pro Arg Leu Leu
            340                 345                 350

Thr Glu Asp Val Lys Val Lys Gly Tyr Asp Ile Ala Ala Gly Thr Glu
        355                 360                 365

Val Leu Ile Asn Ala Trp Ser Ile His Arg Asp Pro Ala Ile Trp Gly
    370                 375                 380

Pro Asp Ala Glu Glu Phe Lys Pro Glu Arg His Leu Asp Ser Thr Leu
385                 390                 395                 400

Asp Tyr His Gly Gln Asp Leu Lys Tyr Ile Pro Phe Gly Ser Gly Arg
                405                 410                 415

Arg Ile Cys Pro Gly Ile Asn Leu Ala Met Gly Leu Val Glu Val Thr
            420                 425                 430

Leu Ala Asn Leu Val Gly Arg Phe Asp Trp Ser Val Asp Pro Gly Pro
        435                 440                 445

Asn Gly Asp Gln Pro Asp Leu Ala Glu Asp Phe Gly Leu Asp Val Cys
    450                 455                 460

Arg Lys Asn Pro Leu Ile Ala Phe Pro Ser Ser Val Ala
465                 470                 475

<210> SEQ ID NO 115
<211> LENGTH: 509
<212> TYPE: PRT
<213> ORGANISM: Nepeta racemosa
<220> FEATURE:
<221> NAME/KEY: misc_feature
<222> LOCATION: (1)..(509)
<223> OTHER INFORMATION: Public GI no. 3582021
<220> FEATURE:
<221> NAME/KEY: misc_feature
<222> LOCATION: (1)..(509)
<223> OTHER INFORMATION: Functional Homolog of Ceres cDNA ID no.
      36533702 at SEQ ID NO. 110 with e-value of 3.60E-113 and percent
      identity of 46.3

<400> SEQUENCE: 115

Met Val Ser Leu Ser Tyr Phe Leu Ile Ala Leu Leu Cys Thr Leu Pro
1               5                   10                  15

Phe Leu Leu Phe Leu Asn Lys Trp Arg Arg Ser Tyr Ser Gly Lys Thr
            20                  25                  30

Pro Pro Pro Ser Pro Pro Lys Leu Pro Val Ile Gly Asn Leu His Gln
        35                  40                  45

Leu Gly Leu Tyr Pro His Arg Tyr Leu Gln Ser Leu Ser Arg Arg Tyr
    50                  55                  60

Gly Pro Leu Met Gln Leu His Phe Gly Ser Val Pro Val Leu Val Ala
65                  70                  75                  80

Ser Ser Pro Glu Ala Ala Arg Glu Ile Met Lys Asn Gln Asp Ile Val
                85                  90                  95

Phe Ser Asn Arg Pro Lys Met Ser Ile Ala Asn Arg Leu Phe Phe Asn
            100                 105                 110
```

```
Asn Arg Asp Val Ala Phe Thr Gln Tyr Gly Glu Tyr Trp Arg Gln Ile
            115                 120                 125

Arg Ser Ile Cys Val Leu Gln Leu Leu Ser Asn Lys Arg Val Gln Ser
        130                 135                 140

Phe Arg Arg Val Arg Glu Glu Thr Ser Ile Met Val Glu Lys Ile
145                 150                 155                 160

Met Gln Leu Gly Ser Ser Ser Thr Pro Val Asn Leu Ser Glu Leu
                165                 170                 175

Leu Leu Ser Leu Thr Asn Asp Val Val Cys Arg Val Thr Leu Gly Lys
            180                 185                 190

Lys Tyr Gly Gly Gly Asn Gly Ser Glu Glu Val Asp Lys Leu Lys Glu
        195                 200                 205

Met Leu Thr Glu Ile Gln Asn Leu Met Gly Ile Ser Pro Val Trp Glu
    210                 215                 220

Phe Ile Pro Trp Leu Asn Trp Thr Arg Arg Phe Asp Gly Val Asp Gln
225                 230                 235                 240

Arg Val Asp Arg Ile Val Lys Ala Phe Asp Gly Phe Leu Glu Ser Val
                245                 250                 255

Ile Gln Glu His Lys Glu Arg Asp Gly Asp Lys Asp Gly Asp Gly Asp
            260                 265                 270

Gly Ala Leu Asp Phe Val Asp Ile Leu Leu Gln Phe Gln Arg Glu Asn
        275                 280                 285

Lys Asn Arg Ser Pro Val Glu Asp Asp Thr Val Lys Ala Leu Ile Leu
    290                 295                 300

Asp Met Phe Val Ala Gly Thr Asp Thr Thr Ala Thr Ala Leu Glu Trp
305                 310                 315                 320

Ala Val Ala Glu Leu Ile Lys Asn Pro Arg Ala Met Lys Arg Leu Gln
                325                 330                 335

Asn Glu Val Arg Glu Val Ala Gly Ser Lys Ala Glu Ile Glu Glu Glu
            340                 345                 350

Asp Leu Glu Lys Met Pro Tyr Leu Lys Ala Ser Ile Lys Glu Ser Leu
        355                 360                 365

Arg Leu His Val Pro Val Leu Leu Val Pro Arg Glu Ser Thr Arg
    370                 375                 380

Asp Thr Asn Val Leu Gly Tyr Asp Ile Ala Ser Gly Thr Arg Val Leu
385                 390                 395                 400

Ile Asn Ala Trp Ala Ile Ala Arg Asp Pro Ser Val Trp Glu Asn Pro
                405                 410                 415

Glu Glu Phe Leu Pro Glu Arg Phe Leu Asp Ser Ser Ile Asp Tyr Lys
            420                 425                 430

Gly Leu His Phe Glu Leu Leu Pro Phe Gly Ala Gly Arg Arg Gly Cys
        435                 440                 445

Pro Gly Ala Thr Phe Ala Val Ala Ile Asp Glu Leu Ala Leu Ala Lys
    450                 455                 460

Leu Val His Lys Phe Asp Phe Gly Leu Pro Asn Gly Ala Arg Met Glu
465                 470                 475                 480

Glu Leu Asp Met Ser Glu Thr Ser Gly Met Thr Val His Lys Lys Ser
                485                 490                 495

Pro Leu Leu Leu Leu Pro Ile Pro His His Ala Ala Pro
            500                 505

<210> SEQ ID NO 116
<211> LENGTH: 494
```

```
<212> TYPE: PRT
<213> ORGANISM: Ammi majus
<220> FEATURE:
<221> NAME/KEY: misc_feature
<222> LOCATION: (1)..(494)
<223> OTHER INFORMATION: Public GI no. 46947673
<220> FEATURE:
<221> NAME/KEY: misc_feature
<222> LOCATION: (1)..(494)
<223> OTHER INFORMATION: Functional Homolog of Ceres CDNA ID no.
      36533702 at SEQ ID NO. 110 with e-value of 1.10E-102 and percent
      identity of 46.0

<400> SEQUENCE: 116

Met Lys Met Leu Glu Gln Asn Pro Gln Tyr Leu Tyr Phe Phe Ser Leu
1               5                   10                  15

Phe Leu Val Thr Ile Phe Leu Tyr Lys Trp Leu Thr Leu Lys Lys Thr
            20                  25                  30

Pro Leu Lys Asn Leu Pro Pro Ser Pro Pro Gln Tyr Pro Ile Ile Gly
        35                  40                  45

Asn Leu His Gln Ile Gly Pro Asp Pro Gln Ala Ser Leu Arg Asp Leu
    50                  55                  60

Ala Gln Lys Tyr Gly Pro Leu Met Phe Leu Lys Phe Gly Thr Val Pro
65                  70                  75                  80

Val Leu Val Val Ser Ser Ala Asp Ala Ala Arg Glu Ala Leu Lys Thr
                85                  90                  95

His Asp Leu Val Phe Ala Asp Arg Pro Tyr Ser Val Ala Asn Lys
            100                 105                 110

Ile Phe Tyr Asn Gly Lys Asp Met Val Phe Ala Arg Tyr Thr Glu Tyr
        115                 120                 125

Trp Arg Gln Val Lys Ser Ile Cys Val Thr Gln Leu Leu Ser Asn Lys
130                 135                 140

Arg Val Asn Ser Phe His Tyr Val Arg Glu Glu Val Asp Leu Leu
145                 150                 155                 160

Val Gln Asn Leu Glu Asn Ser His Ser Lys Val Ala Asn Leu Thr Glu
                165                 170                 175

Leu Leu Ile Glu Val Thr Gly Asn Val Val Cys Arg Val Ser Val Gly
            180                 185                 190

Ser Gly Asp Lys Val Asp Ser Tyr Lys Ile Leu Ile Leu Glu Ile Met
        195                 200                 205

Asp Met Leu Gly Tyr Ser Arg Ser Ile Glu Asp Phe Phe Pro Leu Leu
    210                 215                 220

Gly Trp Val Asp Trp Leu Thr Gly Leu Arg Gly Lys Val Ala Glu Ala
225                 230                 235                 240

Ala Lys Gly Val Asp Thr Phe Leu Glu Gly Val Leu Lys Glu His Leu
                245                 250                 255

Ser Thr Thr Gly Ser Lys Tyr Asn Asp Phe Val Ser Ile Leu Leu Glu
            260                 265                 270

Ile Gln Glu Ala Asp Ala Gly Ser Ser Met Asp Asn Glu Cys Ile Lys
        275                 280                 285

Ser Leu Ile Trp Asp Met Leu Gly Ala Gly Thr Glu Thr Ile Ser Thr
    290                 295                 300

Ala Leu Glu Trp Thr Leu Ala Ala Leu Ile Lys Asn Pro Asp Ala Met
305                 310                 315                 320

Phe Lys Leu Gln Asn Glu Val Arg Glu Ile Gly Lys Gly Lys Ser Lys
                325                 330                 335

Ile Ser Glu Ala Asp Leu Val Lys Met Asn Tyr Leu Gln Ala Val Met
```

-continued

```
                  340                 345                 350
Lys Glu Ser Met Arg Leu Tyr Phe Thr Ala Pro Leu Leu Val Pro Arg
            355                 360                 365

Glu Ala Arg Gln Asp Ile Lys Phe Met Gly Tyr Asp Ile Ser Ser Gly
        370                 375                 380

Thr Gln Val Leu Ile Asn Ala Trp Ala Ile Ala Arg Asp Pro Leu Leu
385                 390                 395                 400

Trp Asp Lys Pro Glu Glu Phe Arg Pro Glu Arg Phe Leu Asn Ser Pro
                405                 410                 415

Ile Asp Tyr Lys Gly Phe His Tyr Glu Phe Leu Pro Phe Gly Ala Gly
            420                 425                 430

Arg Arg Gly Cys Pro Gly Ile Gln Phe Ala Met Cys Ile Asn Glu Leu
        435                 440                 445

Val Val Ala Asn Leu Val His Lys Phe Asn Phe Glu Leu Pro Asp Gly
    450                 455                 460

Lys Arg Leu Glu Asp Leu Asp Met Thr Ala Ala Ser Gly Ile Thr Leu
465                 470                 475                 480

Arg Lys Lys Ser Pro Leu Leu Val Val Ala Arg Pro His Val
                485                 490

<210> SEQ ID NO 117
<211> LENGTH: 471
<212> TYPE: PRT
<213> ORGANISM: Persea americana
<220> FEATURE:
<221> NAME/KEY: misc_feature
<222> LOCATION: (1)..(471)
<223> OTHER INFORMATION: Public GI no. 117188
<220> FEATURE:
<221> NAME/KEY: misc_feature
<222> LOCATION: (1)..(471)
<223> OTHER INFORMATION: Functional Homolog of Ceres cDNA ID no.
      36533702 at SEQ ID NO. 110 with e-value of 3.09E-107 and percent
      identity of 45.9

<400> SEQUENCE: 117

Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Lys Pro Asn Leu Pro
            20                  25                  30

Pro Ser Pro Pro Asn Leu Pro Ile Ile Gly Asn Leu His Gln Leu Gly
        35                  40                  45

Asn Leu Pro His Arg Ser Leu Arg Ser Leu Ala Asn Glu Leu Gly Pro
    50                  55                  60

Leu Ile Leu Leu His Leu Gly His Ile Pro Thr Leu Ile Val Ser Thr
65                  70                  75                  80

Ala Glu Ile Ala Glu Glu Ile Leu Lys Thr His Asp Leu Ile Phe Ala
                85                  90                  95

Ser Arg Pro Ser Thr Thr Ala Ala Arg Arg Ile Phe Tyr Asp Cys Thr
            100                 105                 110

Asp Val Ala Phe Ser Pro Tyr Gly Glu Tyr Trp Arg Gln Val Arg Lys
        115                 120                 125

Ile Cys Val Leu Glu Leu Leu Ser Ile Lys Arg Val Asn Ser Tyr Arg
    130                 135                 140

Ser Ile Arg Glu Glu Glu Val Gly Leu Met Met Glu Arg Ile Ser Gln
145                 150                 155                 160

Ser Cys Ser Thr Gly Glu Ala Val Asn Leu Ser Glu Leu Leu Leu Leu
                165                 170                 175
```

Leu Ser Ser Gly Thr Ile Thr Arg Val Ala Phe Gly Lys Lys Tyr Glu
            180                 185                 190

Gly Glu Glu Glu Arg Lys Asn Lys Phe Ala Asp Leu Ala Thr Glu Leu
        195                 200                 205

Thr Thr Leu Met Gly Ala Phe Phe Val Gly Asp Tyr Phe Pro Ser Phe
    210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp Asp His Leu
                245                 250                 255

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
        275                 280                 285

Leu Asn Arg Asn Asn Leu Lys Ala Val Ile Leu Asp Met Phe Ser Gly
    290                 295                 300

Gly Thr Asp Thr Thr Ala Val Thr Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Glu Asp Leu His Gln Leu
            340                 345                 350

His Tyr Leu Lys Leu Ile Ile Lys Glu Thr Leu Arg Leu His Pro Val
        355                 360                 365

Ala Pro Leu Leu Val Pro Arg Glu Ser Thr Arg Asp Val Val Ile Arg
    370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
            420                 425                 430

Leu Ile Pro Phe Gly Ala Gly Arg Arg Gly Cys Pro Gly Ile Ala Phe
        435                 440                 445

Gly Ile Ser Ser Val Glu Ile Ser Leu Ala Asn Leu Leu Tyr Trp Phe
    450                 455                 460

Asn Trp Glu Leu Pro Gly Ile
465                 470

<210> SEQ ID NO 118
<211> LENGTH: 529
<212> TYPE: PRT
<213> ORGANISM: Oryza sativa subsp. japonica
<220> FEATURE:
<221> NAME/KEY: misc_feature
<222> LOCATION: (1)..(529)
<223> OTHER INFORMATION: Public GI no. 34904242
<220> FEATURE:
<221> NAME/KEY: misc_feature
<222> LOCATION: (1)..(529)
<223> OTHER INFORMATION: Functional Homolog of Ceres CDNA ID no.
      36533702 at SEQ ID NO. 110 with e-value of 2.70E-99 and percent
      identity of 45.5

<400> SEQUENCE: 118

Met Ala Val Ser Leu Val Val Val Val Val Val Val Ile Ala Ile Val
1               5                   10                  15

-continued

```
Val Pro Leu Leu Tyr Leu Val Leu Leu Pro Ala Trp Lys Pro Ala Arg
             20                  25                  30

Arg Asp Asp Gly Asp Gly Gly Met Arg Arg Leu Pro Pro Ser Pro
         35                  40                  45

Pro Trp Gly Leu Pro Leu Leu Gly His Leu His Leu Leu Gly Ala Leu
     50                  55                  60

Pro His Arg Ala Leu Arg Ser Leu Ala Ala His Gly Pro Val Leu
 65              70                  75                  80

Leu Leu Arg Leu Gly Arg Val Pro Val Val Val Ser Ser Ala Ala
                 85                  90                  95

Ala Ala Glu Glu Val Met Arg Thr Arg Asp Leu Glu Phe Ala Ser Arg
             100                 105                 110

Pro Arg Val Ala Met Ala Glu Arg Leu Leu Tyr Gly Gly Arg Asp Val
             115                 120                 125

Ala Phe Ala Pro Tyr Gly Glu Tyr Trp Arg Gln Thr Arg Arg Ile Cys
         130                 135                 140

Val Val His Leu Leu Ser Ala Arg Arg Val Leu Ser Phe Arg Arg Val
 145                 150                 155                 160

Arg Glu Glu Glu Ala Ala Ala Leu Val Ala Arg Val Arg Ala Ala Gly
             165                 170                 175

Gly Ala Val Asp Leu Val Glu His Leu Thr Ala Tyr Ser Asn Thr Val
             180                 185                 190

Val Ser Arg Ala Val Phe Gly Asp Glu Ser Ala Arg Gly Leu Tyr Gly
         195                 200                 205

Asp Val Asp Arg Gly Arg Val Leu Arg Lys Leu Phe Asp Asp Phe Val
 210                 215                 220

Glu Leu Leu Gly Gln Glu Pro Met Gly Glu Leu Leu Pro Trp Leu Gly
 225                 230                 235                 240

Trp Val Asp Ala Leu Asn Gly Met Glu Val Lys Val Gln Arg Thr Phe
                 245                 250                 255

Glu Ala Leu Asp Gly Ile Leu Glu Lys Val Ile Asp Asp His Arg Arg
             260                 265                 270

Arg Arg Arg Glu Val Gly Arg Gln Met Asp Asp Gly Gly Gly Gly Asp
         275                 280                 285

His Arg Asp Phe Val Asp Val Leu Leu Asp Val Asn Glu Thr Asp Met
 290                 295                 300

Asp Ala Gly Val Gln Leu Gly Thr Ile Glu Ile Lys Ala Ile Ile Leu
 305                 310                 315                 320

Asp Met Phe Ala Ala Gly Thr Asp Thr Thr Thr Val Ile Glu Trp
             325                 330                 335

Ala Met Ala Glu Leu Ile Thr His Pro Asp Ala Met Arg Asn Ala Gln
             340                 345                 350

Asp Glu Ile Lys Ala Val Val Gly Ile Thr Ser His Ile Thr Glu Asp
         355                 360                 365

His Leu Asp Arg Leu Pro Tyr Leu Lys Ala Val Leu Lys Glu Thr Leu
 370                 375                 380

Arg Leu His Pro Pro Leu Pro Leu Leu Val Pro His Glu Pro Ser Ser
 385                 390                 395                 400

Asp Thr Lys Ile Leu Gly Tyr Ser Ile Pro Ala Cys Thr Arg Ile Val
                 405                 410                 415

Ile Asn Ala Trp Thr Ile Gly Arg Asp Gln Ala Thr Trp Gly Glu His
             420                 425                 430

Ala Glu Glu Phe Ile Pro Glu Arg Phe Leu Glu Ser Gly Leu Asp Tyr
```

```
                435                 440                 445
Ile Gly Gln Asp Phe Val Leu Val Pro Phe Gly Ala Gly Arg Arg Gly
    450                 455                 460

Cys Pro Gly Val Gly Phe Ala Val Gln Ala Met Glu Met Ala Leu Ala
465                 470                 475                 480

Ser Leu Leu Tyr Asn Phe Asp Trp Glu Thr Arg Val Val Asp Arg Arg
                485                 490                 495

Ser Glu Phe Gly Thr Ser Ser Leu Asp Met Ser Glu Met Asn Gly Leu
            500                 505                 510

Ser Val Arg Leu Lys Tyr Gly Leu Pro Leu Ile Ala Ile Ser Arg Phe
        515                 520                 525

Pro

<210> SEQ ID NO 119
<211> LENGTH: 482
<212> TYPE: PRT
<213> ORGANISM: Triticum aestivum
<220> FEATURE:
<221> NAME/KEY: misc_feature
<222> LOCATION: (1)..(482)
<223> OTHER INFORMATION: Ceres CLONE ID no. 921721
<220> FEATURE:
<221> NAME/KEY: misc_feature
<222> LOCATION: (1)..(482)
<223> OTHER INFORMATION: Functional Homolog of Ceres CDNA ID no.
      36533702 at SEQ ID NO. 110 with e-value of 6.10E-102 and percent
      identity of 45.2

<400> SEQUENCE: 119

Met Glu Gly Arg Arg His Leu Pro Pro Ser Pro Arg Gly Leu Pro Leu
1               5                   10                  15

Leu Gly His Leu His Leu Leu Gly Ser Leu Pro His Arg Ala Leu Arg
            20                  25                  30

Ser Leu Ala Ala Ala His Gly Pro Val Leu Leu Arg Leu Gly Arg
        35                  40                  45

Val Pro Ala Val Val Val Ser Ser Pro Ala Ala Glu Glu Val Met
    50                  55                  60

Arg Ala Arg Asp Leu Ala Phe Ala Ser Arg Pro Arg Ser Ala Met Ala
65                  70                  75                  80

Asp Arg Leu Leu Tyr Gly Arg Asp Val Ala Phe Ala Pro Tyr Gly Glu
                85                  90                  95

Tyr Trp Arg Gln Ala Arg Arg Val Cys Val Val His Leu Leu Ser Pro
            100                 105                 110

Leu Arg Ile Leu Ser Phe Arg Gly Val Arg Glu Glu Glu Ala Ala Ala
        115                 120                 125

Leu Val Glu Arg Val Arg Gly Ala Ala Ala Gly Ala Ala Val Asp
    130                 135                 140

Leu Cys Glu Leu Leu Val Ala Tyr Ala Asn Thr Val Val Ser Arg Ala
145                 150                 155                 160

Ala Phe Gly Asp Asp Ser Ala Arg Gly Leu Tyr Glu Glu Gly Asn Lys
                165                 170                 175

Glu Arg Glu Leu Arg Lys Val Phe Asn Asp Phe Gln Glu Leu Leu Gly
            180                 185                 190

Thr Ala Pro Leu Gly Glu Leu Leu Pro Trp Leu Gly Trp Leu Asp Ala
        195                 200                 205

Val Arg Gly Met Glu Gly Lys Ile Arg Arg Thr Phe Lys Ala Leu Asp
    210                 215                 220
```

```
Gly Val Leu Glu Lys Val Ile Gly Asp His Arg Arg Arg Gln Ala
225                 230                 235                 240

Gly Gln Gln Thr Gly Asp Asp Gly Asp His Arg Asp Phe Val Asp
            245                 250                 255

Val Leu Leu Asp Val Ser Asp Thr Asp Glu Ala Gly Met Arg Leu
        260                 265                 270

Ser Thr Thr Glu Ile Lys Ala Ile Ile Leu Asp Met Phe Ala Ala Gly
    275                 280                 285

Thr Asp Thr Thr Ser Thr Ala Met Glu Trp Ala Met Ala Glu Val Ile
290                 295                 300

Thr His Pro Asp Ser Met Arg Lys Leu Gln Asp Glu Leu Arg Ala Ala
305                 310                 315                 320

Val Gly Gly Ser Gly His Val Ile Thr Glu Asp His Ile Asp Lys Leu
            325                 330                 335

His Tyr Leu Lys Ala Val Val Lys Glu Thr Leu Arg Leu His Pro Pro
        340                 345                 350

Ile Pro Leu Leu Val Pro Arg Glu Pro Gln Asp Asp Ala Glu Ile Leu
    355                 360                 365

Gly His His Val Pro Ala Gly Thr Arg Val Val Ile Asn Ala Trp Ala
370                 375                 380

Val Gly Arg Asp Pro Ala Ala Trp Glu Arg Ala Glu Glu Phe Val Pro
385                 390                 395                 400

Glu Arg Phe Leu Asp Gly Ala Val Asp Tyr Lys Gly Gln Asp Phe Gln
            405                 410                 415

Leu Ile Pro Phe Gly Ala Gly Arg Arg Gly Cys Pro Gly Val Gly Phe
        420                 425                 430

Ala Ala Ala Thr Val Glu Met Ala Leu Ala Ser Leu Met Tyr His Phe
            435                 440                 445

Asp Trp Glu Pro Ala Gly Ala Ser Leu Asp Met Arg Glu Val Asn Gly
    450                 455                 460

Leu Ala Val His Leu Lys Ser Gly Leu Pro Leu Val Ala Lys Leu Arg
465                 470                 475                 480

Phe Arg

<210> SEQ ID NO 120
<211> LENGTH: 515
<212> TYPE: PRT
<213> ORGANISM: Triticum aestivum
<220> FEATURE:
<221> NAME/KEY: misc_feature
<222> LOCATION: (1)..(515)
<223> OTHER INFORMATION: Ceres CLONE ID no. 703961
<220> FEATURE:
<221> NAME/KEY: misc_feature
<222> LOCATION: (1)..(515)
<223> OTHER INFORMATION: Functional Homolog of Ceres CDNA ID no.
      36533702 at SEQ ID NO. 110 with e-value of 6.10E-102 and percent
      identity of 45.2

<400> SEQUENCE: 120

Met Ala Val Ser Pro Leu Ala Leu Val Leu Leu Leu Ala Phe Ala
1               5                   10                  15

Val Ser Leu Leu Tyr Ile Leu Arg Arg Pro Ala Pro Leu Arg Ser Gly
            20                  25                  30

Ser Asp Gly Gly Arg Arg His Leu Pro Pro Ser Pro Arg Gly Leu Pro
        35                  40                  45

Leu Leu Gly His Leu His Leu Leu Gly Ser Leu Pro His Arg Ala Leu
    50                  55                  60
```

```
Arg Ser Leu Ala Ala Ala His Gly Pro Val Leu Leu Arg Leu Gly
 65                  70                  75                  80

Arg Val Pro Ala Val Val Ser Ser Pro Ala Ala Glu Glu Val
             85                  90                  95

Met Arg Ala Arg Asp Leu Ala Phe Ala Ser Arg Pro Arg Ser Ala Met
            100                 105                 110

Ala Asp Arg Leu Leu Tyr Gly Arg Asp Val Ala Phe Ala Pro Tyr Gly
            115                 120                 125

Glu Tyr Trp Arg Gln Ala Arg Arg Val Cys Val Val His Leu Leu Ser
130                 135                 140

Pro Leu Arg Ile Leu Ser Phe Arg Gly Val Arg Glu Glu Glu Ala Ala
145                 150                 155                 160

Ala Leu Val Glu Arg Val Arg Gly Ala Ala Gly Gly Ala Ala Val
                165                 170                 175

Asp Leu Cys Glu Leu Leu Val Ala Tyr Ala Asn Thr Val Val Ser Arg
            180                 185                 190

Ala Ala Phe Gly Asp Asp Ser Ala Arg Gly Leu Tyr Glu Glu Gly Asn
            195                 200                 205

Lys Glu Arg Glu Leu Arg Lys Val Phe Asn Asp Phe Gln Glu Leu Leu
210                 215                 220

Gly Thr Ala Pro Leu Gly Glu Leu Leu Pro Trp Leu Gly Trp Leu Asp
225                 230                 235                 240

Ala Val Arg Gly Met Glu Gly Lys Ile Arg Arg Thr Phe Lys Ala Leu
                245                 250                 255

Asp Gly Val Leu Glu Lys Val Ile Gly Asp His Arg Arg Arg Gln
            260                 265                 270

Ala Gly Gln Gln Thr Gly Asp Asp Gly Gly Asp His Arg Asp Phe Val
            275                 280                 285

Asp Val Leu Leu Asp Val Ser Asp Thr Asp Glu Ala Gly Met Arg
290                 295                 300

Leu Ser Thr Thr Glu Ile Lys Ala Ile Ile Leu Asp Met Phe Ala Ala
305                 310                 315                 320

Gly Thr Asp Thr Thr Ser Thr Ala Met Glu Trp Ala Met Ala Glu Val
                325                 330                 335

Ile Thr His Pro Asp Ser Met Arg Lys Leu Gln Asp Glu Leu Arg Ala
            340                 345                 350

Ala Val Gly Gly Ser Gly His Val Ile Thr Glu Asp His Ile Asp Lys
            355                 360                 365

Leu His Tyr Leu Lys Ala Val Val Lys Glu Thr Leu Arg Leu His Pro
370                 375                 380

Pro Ile Pro Leu Leu Val Pro Arg Glu Pro Gln Asp Asp Ala Glu Ile
385                 390                 395                 400

Leu Gly His His Val Pro Ala Gly Thr Arg Val Val Ile Asn Ala Trp
                405                 410                 415

Ala Val Gly Arg Asp Pro Ala Ala Trp Glu Arg Ala Glu Glu Phe Val
            420                 425                 430

Pro Glu Arg Phe Leu Asp Gly Ala Val Asp Tyr Lys Gly Gln Asp Phe
            435                 440                 445

Gln Leu Ile Pro Phe Gly Ala Gly Arg Arg Gly Cys Pro Gly Val Gly
450                 455                 460

Phe Ala Ala Ala Thr Val Glu Met Ala Leu Ala Ser Leu Met Tyr His
465                 470                 475                 480
```

```
Phe Asp Trp Glu Pro Ala Gly Ala Ser Leu Asp Met Arg Glu Val Asn
                485                 490                 495

Gly Leu Ala Val His Leu Lys Ser Gly Leu Pro Leu Val Ala Lys Leu
            500                 505                 510

Arg Phe Arg
        515

<210> SEQ ID NO 121
<211> LENGTH: 502
<212> TYPE: PRT
<213> ORGANISM: Persea americana
<220> FEATURE:
<221> NAME/KEY: misc_feature
<222> LOCATION: (1)..(502)
<223> OTHER INFORMATION: Public GI no. 25282608
<220> FEATURE:
<221> NAME/KEY: misc_feature
<222> LOCATION: (1)..(502)
<223> OTHER INFORMATION: Functional Homolog of Ceres CDNA ID no.
      36533702 at SEQ ID NO. 110 with e-value of 3.69E-111 and percent
      identity of 45.2

<400> SEQUENCE: 121

Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Pro Asn Leu Pro
            20                  25                  30

Pro Ser Pro Asn Leu Pro Ile Ile Gly Asn Leu His Gln Leu Gly
        35                  40                  45

Asn Leu Pro His Arg Ser Leu Arg Ser Leu Ala Asn Glu Leu Gly Pro
50                  55                  60

Leu Ile Leu Leu His Leu Gly His Ile Pro Thr Leu Ile Val Ser Thr
65                  70                  75                  80

Ala Glu Ile Ala Glu Glu Ile Leu Lys Thr His Asp Leu Ile Phe Ala
                85                  90                  95

Ser Arg Pro Ser Thr Thr Ala Ala Arg Arg Ile Phe Tyr Asp Cys Thr
            100                 105                 110

Asp Val Ala Phe Ser Pro Tyr Gly Glu Tyr Trp Arg Gln Val Arg Lys
        115                 120                 125

Ile Cys Val Leu Glu Leu Leu Ser Ile Lys Arg Val Asn Ser Tyr Arg
    130                 135                 140

Ser Ile Arg Glu Glu Glu Val Gly Leu Met Met Glu Arg Ile Ser Gln
145                 150                 155                 160

Ser Cys Ser Thr Gly Glu Ala Val Asn Leu Ser Glu Leu Leu Leu Leu
                165                 170                 175

Leu Ser Ser Gly Thr Ile Thr Arg Val Ala Phe Gly Lys Lys Tyr Glu
            180                 185                 190

Gly Glu Glu Glu Arg Lys Asn Lys Phe Ala Asp Leu Ala Thr Glu Leu
        195                 200                 205

Thr Thr Leu Met Gly Ala Phe Phe Val Gly Asp Tyr Phe Pro Ser Phe
    210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp His Leu
                245                 250                 255

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
```

-continued

```
                275                 280                 285
Leu Asn Arg Asn Asn Leu Lys Ala Val Ile Leu Asp Met Phe Ser Gly
        290                 295                 300

Gly Thr Asp Thr Thr Ala Val Thr Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Asp Leu His Gln Leu
                340                 345                 350

His Tyr Leu Lys Leu Ile Ile Lys Glu Thr Leu Arg Leu His Pro Val
        355                 360                 365

Ala Pro Leu Leu Val Pro Arg Glu Ser Thr Arg Asp Val Val Ile Arg
        370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
                420                 425                 430

Leu Ile Pro Phe Gly Ala Gly Arg Arg Gly Cys Pro Gly Ile Ala Phe
        435                 440                 445

Gly Ile Ser Ser Val Glu Ile Ser Leu Ala Asn Leu Leu Tyr Trp Phe
        450                 455                 460

Asn Trp Glu Leu Pro Gly Asp Leu Thr Lys Glu Asp Leu Asp Met Ser
465                 470                 475                 480

Glu Ala Val Gly Ile Thr Val His Met Lys Phe Pro Leu Gln Leu Val
                485                 490                 495

Ala Lys Arg His Leu Ser
            500
```

<210> SEQ ID NO 122
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 122

```
Pro Phe Ala Ser Arg
1               5
```

<210> SEQ ID NO 123
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 123

```
Phe Ser Pro Glu Gln Glu
1               5
```

<210> SEQ ID NO 124
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 124

Ser Val Met Val Ala Ala Leu
1               5

<210> SEQ ID NO 125
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 125

His Val Val Ser Gly
1               5

<210> SEQ ID NO 126
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 126

Thr Pro Ala Pro
1

<210> SEQ ID NO 127
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 127

Val Cys Gly Ile Asp Gly Cys Leu Gly Cys
1               5                   10

<210> SEQ ID NO 128
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 128

Phe Phe Gly Ala Glu Ala
1               5

<210> SEQ ID NO 129
<211> LENGTH: 9
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 129

Ala Gly Gly Lys Gln Arg Arg Arg Arg
1               5

<210> SEQ ID NO 130

```
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 130

Asn Lys Lys Asn
1

<210> SEQ ID NO 131
<211> LENGTH: 44
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 131

Tyr Arg Gly Val Arg Gln Arg Pro Trp Gly Lys Trp Ala Ala Glu Ile
1               5                   10                  15

Arg Asp Pro Arg Arg Ala Val Arg Val Trp Leu Gly Thr Phe Asp Thr
            20                  25                  30

Ala Glu Asp Ala Ala Arg Ala Tyr Asp Arg Ala Ala
        35                  40

<210> SEQ ID NO 132
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 132

Glu Phe Arg Gly Pro Arg Ala Lys Leu Asn Phe
1               5                   10

<210> SEQ ID NO 133
<211> LENGTH: 16
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 133

Met Leu Trp Asp Gly Met Val Asp Leu Met Lys Leu Asp Glu Ser Asp
1               5                   10                  15

<210> SEQ ID NO 134
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 1

<400> SEQUENCE: 134

Gly Ser Gly Val
1

<210> SEQ ID NO 135
<211> LENGTH: 4
<212> TYPE: PRT
<213> ORGANISM: Artificial sequence
```

```
<220> FEATURE:
<221> NAME/KEY: misc_feature
<223> OTHER INFORMATION: Part of Consensus Sequence For FIGURE 2

<400> SEQUENCE: 135

Met Glu Asn Phe
1

<210> SEQ ID NO 136
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 136

Pro Leu Leu Tyr Arg Asn Pro
1               5

<210> SEQ ID NO 137
<211> LENGTH: 54
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 137

Arg Ser Ser Arg Gln Ser Ser Arg Tyr Leu Gly Val Arg Arg Pro
1               5                   10                  15

Trp Gly Arg Tyr Ala Ala Glu Ile Arg Asn Pro Tyr Thr Lys Glu Arg
            20                  25                  30

His Trp Leu Gly Thr Phe Asp Thr Ala Glu Glu Ala Ala Val Ala Tyr
        35                  40                  45

Asp Leu Ser Ser Ile Ser
    50

<210> SEQ ID NO 138
<211> LENGTH: 13
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 138

Ser Gly Ile Glu Arg Ala Arg Thr Asn Phe Tyr Tyr Pro
1               5                   10

<210> SEQ ID NO 139
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 139

Phe Phe Ala His Pro Ser Pro
1               5

<210> SEQ ID NO 140
<211> LENGTH: 4
<212> TYPE: PRT
<213> ORGANISM: Artificial sequence
```

```
<220> FEATURE:
<221> NAME/KEY: misc_feature
<223> OTHER INFORMATION: Part of Consensus Sequence For FIGURE 2

<400> SEQUENCE: 140

Gln Glu Ala Leu
1

<210> SEQ ID NO 141
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 141

Pro Pro Pro Pro
1

<210> SEQ ID NO 142
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 142

Glu Lys Gly Asp Gln Leu Gly
1               5

<210> SEQ ID NO 143
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 143

Met Glu Asp Val
1

<210> SEQ ID NO 144
<211> LENGTH: 15
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 2

<400> SEQUENCE: 144

Gly Asp Asp Glu Ser Leu Val Ile Ala Ser Ile Leu Gln Ser Phe
1               5                   10                  15

<210> SEQ ID NO 145
<211> LENGTH: 35
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 145

Lys Leu Glu Ile Lys Arg Ile Glu Asn Lys Ser Ser Arg Gln Val Thr
1               5                   10                  15
```

-continued

```
Phe Ser Lys Arg Arg Asn Gly Leu Ile Glu Lys Ala Arg Gln Leu Ser
        20                  25                  30

Val Leu Cys
        35

<210> SEQ ID NO 146
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 146

Leu Val Val Ser Ala Ser Gly Lys Leu Tyr Asn
1               5                   10

<210> SEQ ID NO 147
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 147

Lys Ile Ile Asp Arg Tyr
1               5

<210> SEQ ID NO 148
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 148

Ala Leu Asp Leu Gln
1               5

<210> SEQ ID NO 149
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 149

Glu Leu Leu Glu
1

<210> SEQ ID NO 150
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 150

Val Glu Ser Lys Leu
1               5

<210> SEQ ID NO 151
<211> LENGTH: 6
```

```
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 151

Val Ser Val Asp Ser Leu
1               5

<210> SEQ ID NO 152
<211> LENGTH: 16
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 152

Leu Glu Thr Ala Leu Ser Val Thr Arg Ala Arg Lys Thr Glu Leu Met
1               5                   10                  15

<210> SEQ ID NO 153
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 153

Val Asp Ser Leu Lys Glu Lys Glu Lys Leu Leu
1               5                   10

<210> SEQ ID NO 154
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 154

Glu Glu Asn Gln
1

<210> SEQ ID NO 155
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 155

Leu Ala Ser Gln Met
1               5

<210> SEQ ID NO 156
<211> LENGTH: 8
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 156

Lys Asn Asn Leu Ala Gly Ala Glu
```

```
1               5

<210> SEQ ID NO 157
<211> LENGTH: 8
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 157

Asp Lys Met Glu Met Ser Pro Gly
1               5

<210> SEQ ID NO 158
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 3

<400> SEQUENCE: 158

Thr Leu Pro Leu Leu Tyr
1               5

<210> SEQ ID NO 159
<211> LENGTH: 9
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 159

Ala Leu Met Val Leu Leu Ile Ala Leu
1               5

<210> SEQ ID NO 160
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 160

Leu Leu Phe Leu
1

<210> SEQ ID NO 161
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 161

Asn Leu Pro Pro Ser
1               5

<210> SEQ ID NO 162
<211> LENGTH: 11
<212> TYPE: PRT
<213> ORGANISM: Artificial sequence
<220> FEATURE:
<221> NAME/KEY: misc_feature
```

```
<223> OTHER INFORMATION: Part of Consensus Sequence For FIGURE 4

<400> SEQUENCE: 162

Leu Pro Leu Ile Gly Asn Leu His Gln Leu Gly
1               5                   10

<210> SEQ ID NO 163
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 163

Leu Pro His Arg Ser Leu Arg Ser Leu Ala
1               5                   10

<210> SEQ ID NO 164
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 164

Tyr Gly Pro Leu Met Leu Leu
1               5

<210> SEQ ID NO 165
<211> LENGTH: 17
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 165

Gly Arg Val Pro Val Leu Val Val Ser Ser Ala Glu Ala Ala Glu Glu
1               5                   10                  15

Val

<210> SEQ ID NO 166
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 166

Asp Leu Val Phe Ala Ser Arg Pro Arg Ser
1               5                   10

<210> SEQ ID NO 167
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 167

Met Ala Asn Arg Leu
1               5
```

<210> SEQ ID NO 168
<211> LENGTH: 19
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 168

Tyr Asn Gly Arg Asp Val Ala Phe Ala Pro Tyr Gly Glu Tyr Trp Arg
1               5                   10                  15

Gln Val Arg

<210> SEQ ID NO 169
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 169

Ile Cys Val Leu
1

<210> SEQ ID NO 170
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 170

Leu Leu Ser Asn Lys Arg Val
1               5

<210> SEQ ID NO 171
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 171

Ser Phe Arg Arg Val Arg Glu Glu Glu Val
1               5                   10

<210> SEQ ID NO 172
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 172

Ala Ser Ser Ser
1

<210> SEQ ID NO 173
<211> LENGTH: 8
<212> TYPE: PRT
<213> ORGANISM: Artificial sequence
<220> FEATURE:
<221> NAME/KEY: misc_feature

```
<223> OTHER INFORMATION: Part of Consensus Sequence For FIGURE 4

<400> SEQUENCE: 173

Ala Val Asn Leu Ser Glu Leu Leu
1               5

<210> SEQ ID NO 174
<211> LENGTH: 8
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 174

Asn Asp Val Val Ser Arg Val Ala
1               5

<210> SEQ ID NO 175
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 175

Gly Lys Lys Tyr Ala
1               5

<210> SEQ ID NO 176
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 176

Leu Lys Lys Leu
1

<210> SEQ ID NO 177
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 177

Glu Ile Met Glu Leu Leu Gly
1               5

<210> SEQ ID NO 178
<211> LENGTH: 8
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 178

Ile Pro Trp Leu Gly Trp Val Asp
1               5

<210> SEQ ID NO 179
```

```
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 179

Leu Asn Gly Met
1

<210> SEQ ID NO 180
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 180

Lys Ala Leu Asp Gly
1               5

<210> SEQ ID NO 181
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 181

Leu Glu Lys Val Ile Gln
1               5

<210> SEQ ID NO 182
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 182

Asp Phe Val Asp
1

<210> SEQ ID NO 183
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 183

Ala Gly Met Gln Leu
1               5

<210> SEQ ID NO 184
<211> LENGTH: 25
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 184
```

```
Ile Leu Asp Met Phe Ala Ala Gly Thr Asp Thr Thr Ser Thr Ala Leu
1               5                   10                  15

Glu Trp Ala Met Ala Glu Leu Ile Lys
            20                  25

<210> SEQ ID NO 185
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 185

Pro Asp Ala Met
1

<210> SEQ ID NO 186
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 186

Lys Leu Gln Asp Glu Ile Arg Ala Val Val Gly
1               5                   10

<210> SEQ ID NO 187
<211> LENGTH: 25
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 187

His Tyr Leu Lys Ala Val Ile Lys Glu Thr Leu Arg Leu His Pro Pro
1               5                   10                  15

Leu Pro Leu Leu Val Pro Arg Glu Ser
            20                  25

<210> SEQ ID NO 188
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 188

Asp Val Lys Ile Leu Gly Tyr
1               5

<210> SEQ ID NO 189
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 189

Ala Gly Thr Arg Val
1               5
```

```
<210> SEQ ID NO 190
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 190

Ile Asn Ala Trp Ala Ile Gly Arg Asp Pro Ala
1               5                   10

<210> SEQ ID NO 191
<211> LENGTH: 15
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 191

Glu Asn Ala Glu Glu Phe Leu Pro Glu Arg Phe Leu Asp Ser Ser
1               5                   10                  15

<210> SEQ ID NO 192
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 192

Asp Tyr Lys Gly Gln Asp Phe
1               5

<210> SEQ ID NO 193
<211> LENGTH: 14
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 193

Leu Ile Pro Phe Gly Ala Gly Arg Arg Gly Cys Pro Gly Ile
1               5                   10

<210> SEQ ID NO 194
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 194

Phe Ala Val Ala
1

<210> SEQ ID NO 195
<211> LENGTH: 14
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4
```

```
-continued

<400> SEQUENCE: 195

Ala Leu Ala Asn Leu Val Tyr Lys Phe Asp Trp Glu Leu Pro
1               5                   10

<210> SEQ ID NO 196
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 196

Leu Asp Met Ser Glu Ala
1               5

<210> SEQ ID NO 197
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 197

Gly Leu Thr Val His
1               5

<210> SEQ ID NO 198
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 4

<400> SEQUENCE: 198

Pro Leu Leu Leu Val Ala Lys
1               5

<210> SEQ ID NO 199
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 199

Met Gly Tyr Ser Ser Ser Ala Glu Met Ser
1               5                   10

<210> SEQ ID NO 200
<211> LENGTH: 24
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 200

Met Val Ser Glu Leu Thr His Val Val Ser Gly His Arg Gly Ser Thr
1               5                   10                  15

Ser Asp Trp Gly Ser Tyr Gly Ala
            20
```

```
<210> SEQ ID NO 201
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 201

Gly Ala Thr Ile Thr Ser
1               5

<210> SEQ ID NO 202
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 202

Gln Ala Ala Pro
1

<210> SEQ ID NO 203
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 203

Gly Ser Asn Thr
1

<210> SEQ ID NO 204
<211> LENGTH: 4
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 204

Pro Ala Ser Pro
1

<210> SEQ ID NO 205
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 205

Leu Ser Ala Tyr Ser Ser Thr Ser Gly Ser
1               5                   10

<210> SEQ ID NO 206
<211> LENGTH: 18
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 206
```

-continued

Gly Ser Trp Ile Gly Gln Lys Arg Gly Arg Glu Glu Ala Gly Ala
1               5                   10                  15

Ala Ala

<210> SEQ ID NO 207
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 207

Glu Ser Leu Pro Arg Val
1               5

<210> SEQ ID NO 208
<211> LENGTH: 21
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 208

Ser Ser Gln Gly Asp Ser Ser Ser Gly Ala Thr Ala Thr Glu Glu
1               5                   10                  15

Val Ser Ala Ser Thr
            20

<210> SEQ ID NO 209
<211> LENGTH: 14
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 209

Thr Thr Thr Thr Pro Ser Thr Thr Ala Thr Pro Ser Ser Glu
1               5                   10

<210> SEQ ID NO 210
<211> LENGTH: 74
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 210

Glu Thr Gly Glu Arg Arg Arg Arg Tyr Arg Gly Val Arg Gln Arg Pro
1               5                   10                  15

Trp Gly Lys Trp Ala Ala Glu Ile Arg Asp Pro His Lys Ala Ala Arg
            20                  25                  30

Val Trp Leu Gly Thr Phe Asp Thr Ala Glu Ala Ala Ala Arg Ala Tyr
        35                  40                  45

Asp Glu Ala Ala Leu Arg Phe Arg Gly Asn Arg Ala Lys Leu Asn Phe
    50                  55                  60

Pro Glu Asn Val Arg Leu Leu Pro Ala Gln
65                  70

<210> SEQ ID NO 211

-continued

```
<211> LENGTH: 11
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 211

Gln Asn Val Thr Ala Ser Gln Val Pro Ile Ser
1               5                   10

<210> SEQ ID NO 212
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 212

Ser Gln Leu Ser Ser His
1               5

<210> SEQ ID NO 213
<211> LENGTH: 12
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 213

Ile Ser Ser Pro Arg Gln Gln Ala Gln Arg Pro Gln
1               5                   10

<210> SEQ ID NO 214
<211> LENGTH: 9
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 214

Pro Ala Pro Ala Leu Phe Gln Ser Gln
1               5

<210> SEQ ID NO 215
<211> LENGTH: 16
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 215

Asp Ile Ile Arg Asp Tyr Trp Glu Tyr Ser Gln Leu Leu Gln Ser Ser
1               5                   10                  15

<210> SEQ ID NO 216
<211> LENGTH: 22
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 216
```

-continued

```
Gln Gln Gln Gln Gln Gln Gln Gln Pro Ser Ser Leu Leu Gln Gln
1               5                   10                  15

Met Phe Tyr Asn Pro Gln
            20

<210> SEQ ID NO 217
<211> LENGTH: 6
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 217

Ala Ser Leu Gln Ser Ser
1               5

<210> SEQ ID NO 218
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 218

Ser Leu Ser Ser Ser Thr Ser
1               5

<210> SEQ ID NO 219
<211> LENGTH: 7
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 219

Ala Ala Ile Ser Ser Gly Ser
1               5

<210> SEQ ID NO 220
<211> LENGTH: 32
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 220

Pro Ser Thr Leu Ser Pro Ser Ala Ser Ser Phe Pro Leu Leu Phe Ala
1               5                   10                  15

Gly Gln Gln Leu Gly Tyr Phe Arg Pro Pro Glu Asn Gln Asn Pro Ala
            20                  25                  30

<210> SEQ ID NO 221
<211> LENGTH: 10
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 221

Ser Asp Phe Pro Val Pro Pro Trp Thr Asp
1               5                   10
```

```
<210> SEQ ID NO 222
<211> LENGTH: 5
<212> TYPE: PRT
<213> ORGANISM: Artificial sequence
<220> FEATURE:
<221> NAME/KEY: misc_feature
<223> OTHER INFORMATION: Part of Consensus Sequence For FIGURE 5

<400> SEQUENCE: 222

Pro Ser Ser Ser Gly
1               5
```